United States Patent
McGowan et al.

(10) Patent No.: US 10,100,064 B2
(45) Date of Patent: Oct. 16, 2018

(54) PURINE INHIBITORS OF HUMAN PHOSPHATIDYLINOSITOL 3-KINASE DELTA

(71) Applicant: Merck Sharp & Dohme Corp., Rahway, NJ (US)

(72) Inventors: Meredeth Ann McGowan, Boston, MA (US); Kin Chiu Fong, Shanghai (CN); Neville John Anthony, Northborough, MA (US); Hua Zhou, Boston, MA (US); Jason D. Katz, Boston, MA (US); Lihu Yang, Edison, NJ (US); Chaomin Li, Boston, MA (US); Yuan Tian, Shanghai (CN); Changwei Mu, Beijing (CN); Baijun Ye, Beijing (CN); Feng Shi, Beijing (CN); Xiaoli Zhao, Beijing (CN); Jianmin Fu, Beijing (CN); Yabin Li, Beijing (CN)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 15/318,483

(22) PCT Filed: Jun. 9, 2015

(86) PCT No.: PCT/CN2015/081059
§ 371 (c)(1),
(2) Date: Dec. 13, 2016

(87) PCT Pub. No.: WO2016/004807
PCT Pub. Date: Jan. 14, 2016

(65) Prior Publication Data
US 2017/0114078 A1 Apr. 27, 2017

(30) Foreign Application Priority Data

Jun. 13, 2014 (WO) ................ PCT/CN2014/079835

(51) Int. Cl.
*C07D 473/30* (2006.01)
*C07D 473/34* (2006.01)
*C07D 519/00* (2006.01)
*A61K 31/52* (2006.01)

(52) U.S. Cl.
CPC ............ *C07D 519/00* (2013.01); *A61K 31/52* (2013.01); *C07D 473/30* (2013.01); *C07D 473/34* (2013.01)

(58) Field of Classification Search
CPC .... A61K 31/52; C07D 473/30; C07D 473/34; C07D 519/00
See application file for complete search history.

(56) References Cited

FOREIGN PATENT DOCUMENTS

| CN | 102838600 A | 12/2012 |
| WO | WO2009146406 A1 | 12/2009 |
| WO | WO2012007493 A1 | 1/2012 |
| WO | WO2012064973 A1 | 5/2012 |
| WO | WO2014075393 A1 | 5/2014 |

OTHER PUBLICATIONS

STN database, answer 3 of 13, (RN# 1394705-04-4, Sep. 18, 2012), downloaded Jun. 14, 2017, p. 1.*
Google Patents, English Translation of CN102838600, 16 pages.
Supplementary European Search Report for 15819372.2, dated Oct. 9, 2017, 5 pages.

* cited by examiner

*Primary Examiner* — Susanna Moore
(74) *Attorney, Agent, or Firm* — Patricia A. Shatynski; John C. Todaro

(57) ABSTRACT

The instant invention provides compounds of formula (I) which are PI3K-delta inhibitors, and as such are useful for the treatment of PI3K-delta-mediated diseases such as inflammation, asthma, COPD and cancer.

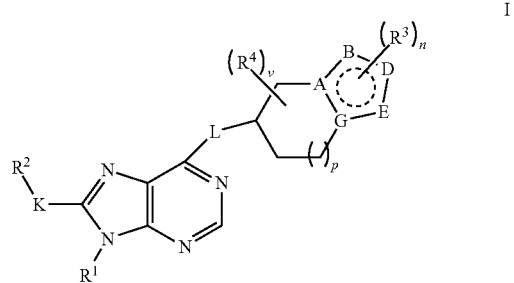

11 Claims, No Drawings

PURINE INHIBITORS OF HUMAN PHOSPHATIDYLINOSITOL 3-KINASE DELTA

CROSS REFERENCE TO RELATED APPLICATIONS

This application is a U.S. National Phase application under 35 U.S.C. § 371 of PCT Application No. PCT/CN2015/081059, filed Jun. 9, 2015 which claims priority under 35 U.S.C. § 119(e) from PCT/CN2014/079835, filed on Jun. 13, 2014.

BACKGROUND OF THE INVENTION

Compounds are provided that inhibit phosphatidylinositol 3-kinase delta isoform (PI3K-delta) activity, including compounds that selectively inhibit PI3K-delta activity. The invention provides methods of using PI3K-delta inhibitory compounds to inhibit PI3K-delta mediated processes in vitro and in vivo.

Methods of inhibiting PI3K-delta activity, and methods of treating diseases, such as disorders of immunity and inflammation, in which PI3K-delta plays a role in leukocyte function are disclosed. Methods of using PI3K-delta inhibitory compounds to inhibit cancer cell growth or proliferation are also provided. Preferably, the methods employ active agents that selectively inhibit PI3K-delta, while not significantly inhibiting activity of other PI3K isoforms.

SUMMARY OF THE INVENTION

The present invention provides novel compounds which are inhibitors of phosphoinosititde 3-kinases delta (PI3K-delta). The invention also provides a method for the treatment and prevention of PI3K-delta-mediated diseases and disorders using the novel compounds, as well as pharmaceutical compositions containing the compounds.

DETAILED DESCRIPTION OF THE INVENTION

The present invention provides compounds of formula I or pharmaceutically acceptable salts or stereoisomers thereof:

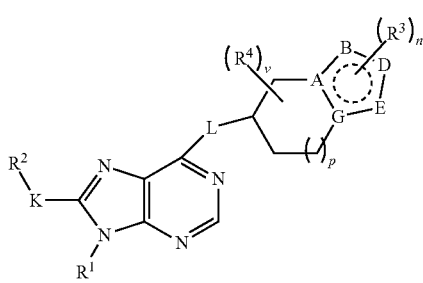

I

A, B, D, E and G are independently selected from carbon and nitrogen, wherein at least two of A, B, D, E and G are carbon and wherein A, B, D, E and G form an aromatic ring;

$R^1$ is selected from hydrogen, $C_{1-5}$alkyl, and —($C_{0-3}$alkyl) $C_{3-4}$cycloalkyl, wherein $R^1$ is optionally substituted by 0, 1, 2, 3, or 4 groups independently selected from hydrogen, fluoro, chloro, methyl, $C_{1-3}$haloalkyl, amino, $O(C=O)R^a$, $O(C=O)OR^a$ and $NH(C=O)R^a$;

$R^a$ is independently selected from $C_{1-3}$alkyl, $C_{1-3}$haloalkyl, and —($C_{0-3}$alkyl)$C_{3-4}$cycloalkyl;

$R^2$ is selected from hydrogen, halogen, $C_{1-10}$alkyl, $C_{3-12}$ cycloalkyl, $C_{3-12}$heterocycloalkyl, $C_{1-10}$ heteroalkyl, $C_{2-10}$alkenyl, $C_{1-6}$haloalkyl, aryl, and heteroaryl, wherein $R^2$ is substituted with 0, 1, 2, 3, or 4 $R^6$ substituents;

$R^4$ is selected from halogen, $C_{1-10}$alkyl, $C_{2-10}$alkynyl, and $C_{1-10}$ alkoxy, wherein $R^4$ is substituted with 0, 1, 2, 3, or 4 substituents selected from OH, halogen, and —$CO_2H$;

n is 0, 1, 2, or 3;

v is 0, 1, 2, or 3;

p is 0 or 1;

L is selected from —O—, —NH—, and —N($C_{1-3}$alkyl)-;

K is selected from a bond, NH, O, C(O), $CH_2$, N($C_{1-5}$)alkyl, —C(O)N($R^b$)—$(CH_2)_m$—, S, $SO_2$, and $C_{2-10}$ alkynylene;

$R^b$ is H or $C_{1-10}$ alkyl, m is 0, 1, 2, or 3;

$R^3$ is independently selected from:
halogen,
$C_{1-10}$ alkyl(oxy)$_{0-1}$(carbonyl)$_{0-1}C_{0-10}$ alkyl,
$C_{2-10}$ alkenyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
aryl $C_{2-10}$ alkynyl(oxy)$_{0-1}$(carbonyl)$_{0-1}C_{0-10}$ alkyl,
$C_{3-12}$ cycloalkyl$C_{0-10}$ alkyl(oxy)$_{0-1}$(carbonyl)$_{0-1}C_{0-10}$ alkyl,
heteroaryl $C_{0-10}$ alkyl(oxy)$_{0-1}$ (carbonyl)$_{0-1}C_{0-10}$ alkyl,
$(C_{3-12})$heterocycloalkyl $C_{0-10}$ alkyl(oxy)$_{0-1}$(carbonyl)$_{0-1}$ $C_{0-10}$ alkyl,
$(C_{1-10}$ alkyl)$_{1-2}$ amino$C_{0-10}$ alkyl,
amino$C_{0-10}$ alkyl,
$C_{1-10}$ alkyl(carbonyl)$_{0-1}$oxy$C_{0-10}$ alkyl,
$C_{1-10}$ heteroalkyl(carbonyl)$_{0-1}$oxy$C_{0-10}$ alkyl,
$C_{1-10}$ heteroalkyl(carbonyl)$_{0-1}$ oxy$C_{0-10}$ alkyl,
aryl $C_{0-10}$ alkyl (carbonyl)$_{0-1}$oxy$C_{0-10}$ alkyl,
$(C_{3-12})$cycloalkyl $C_{0-10}$ alkyl(carbonyl)$_{0-1}$ oxy$C_{0-10}$ alkyl,
heteroaryl$C_{0-10}$ alkyl(carbonyl)$_{0-1}$ oxy$C_{0-10}$ alkyl,
$(C_{3-12})$heterocycloalkyl $C_{0-10}$ alkyl(carbonyl)$_{0-1}$ oxy$C_{0-10}$ alkyl,
$C_{0-10}$ alkylamino(carbonyl)$_{0-1}C_{0-10}$ alkyl,
$(C_{1-10}$ alkyl)$_{1-2}$amino$C_{0-10}$ alkyl carbonyl$C_{1-10}$ alkyl,
$(C_{1-10})$heteroalkylamino(carbonyl)$_{0-1}C_{0-10}$ alkyl,
$C_{3-12}$ cycloalkyl $C_{0-10}$ alkylamino(carbonyl)$_{0-1}C_{0-10}$ alkyl,
aryl $C_{0-10}$alkylamino(carbonyl)$_{0-1}C_{0-10}$ alkyl,
heteroaryl$C_{0-10}$alkylamino(carbonyl)$_{0-1}C_{0-10}$ alkyl,
$(C_{3-12})$heterocycloalkyl$C_{1-10}$ alkylamino(carbonyl)$_{0-1}$ $C_{0-10}$ alkyl,
$C_{1-10}$ alkylcarbonylamino$C_{0-10}$ alkyl,
$C_{1-10}$ heteroalkylcarbonylamino$C_{1-10}$ alkyl,
$C_{3-12}$ cycloalkyl $C_{0-10}$ alkylcarbonylamino$C_{0-10}$ alkyl,
aryl $C_{0-10}$ alkylcarbonylamino$C_{1-10}$ alkyl,
heteroaryl $C_{0-10}$ alkylcarbonylamino$C_{0-10}$ alkyl,
$(C_{3-12})$heterocycloalkyl $C_{0-10}$ alkylcarbonylamino$C_{0-10}$ alkyl,
—$CO_2(C_{0-10}$ alkyl),
—($C_{0-10}$ alkyl)$CO_2H$,
Oxo (=O),
$C_{0-10}$ alkylsulfonyl$C_{0-10}$ alkyl,
$C_{1-10}$ heteroalkylsulfonyl$C_{1-10}$ alkyl,
$(C_{3-12})$cycloalkyl$C_{0-10}$alkylsulfonyl$C_{0-10}$ alkyl,
$(C_{3-12})$cycloheteroalkyl$C_{0-10}$alkylsulfonyl$C_{0-10}$ alkyl,
heteroaryl$C_{0-10}$ alkylsulfonyl$C_{0-10}$ alkyl,
aryl$C_{0-10}$ alkylsulfonyl$C_{0-10}$ alkyl,
—$SO_2N(C_{1-6}$ alkyl)$_{0-2}$, —SO₂CF₃,
—SO₂CF₂H,
amino,
hydroxy,
(C$_{1-10}$ alkyl)OH,
C$_{0-10}$ alkoxy,
cyano,
C$_{1-6}$alkylcyano, and
C$_{1-6}$haloalkyl;
wherein R$^3$ is each substituted with 0, 1, 2, 3, or 4 R$^5$ substituents and each R$^5$ is independently selected from:
halogen,
C$_{1-10}$ alkyl(oxy)$_{0-1}$(carbonyl)$_{0-1}$C$_{0-10}$ alkyl,
C$_{1-10}$ heteroalkyl(oxy)$_{0-1}$ (carbonyl)$_{0-1}$C$_{0-10}$ alkyl,
aryl C$_{0-10}$ alkyl(oxy)$_{0-1}$(carbonyl)$_{0-1}$C$_{0-10}$ alkyl,
C$_{3-12}$ cycloalkyl C$_{0-10}$ alkyl(oxy)$_{0-1}$(carbonyl)$_{0-1}$C$_{1-10}$ alkyl,
heteroaryl C$_{0-10}$ alkyl(oxy)$_{0-1}$ (carbonyl)$_{0-1}$C$_{0-10}$ alkyl,
(C$_{3-12}$)heterocycloalkyl C$_{0-10}$ alkyl(oxy)$_{0-1}$(carbonyl)$_{0-1}$C$_{0-10}$ alkyl,
C$_{1-10}$ alkylamino(carbonyl)$_{0-1}$C$_{0-10}$ alkyl,
C$_{3-12}$ cycloalkyl C$_{0-10}$ alkylamino(carbonyl)$_{0-1}$C$_{0-10}$ alkyl,
aryl C$_{0-10}$ alkylamino(carbonyl)$_{0-1}$C$_{0-10}$ alkyl,
heteroaryl C$_{0-10}$ alkylamino(carbonyl)$_{0-1}$C$_{0-10}$ alkyl,
(C$_{3-12}$)heterocycloalkyl C$_{0-10}$ alkylamino(carbonyl)$_{0-1}$C$_{0-10}$ alkyl,
C$_{0-10}$ alkylsulfonylC$_{0-10}$ alkyl,
(C$_{3-12}$)cycloalkylC$_{0-10}$alkylsulfonylC$_{0-10}$ alkyl,
(C$_{3-12}$)cycloheteroalkylC$_{0-10}$alkylsulfonylC$_{0-10}$ alkyl,
heteroarylC$_{0-10}$ alkylsulfonylC$_{0-10}$ alkyl,
arylC$_{0-10}$ alkylsulfonylC$_{0-10}$ alkyl,
—CO₂(C$_{0-10}$ alkyl),
—(C$_{0-10}$ alkyl)CO₂H,
Oxo (═O),
—SO₂N(C$_{1-6}$alkyl)$_{1-2}$,
—SO₂C$_{1-6}$alkyl,
—SO₂CF₃,
—SO₂CF₂H,
amino,
(C$_{0-10}$ alkyl)$_{1-2}$ amino,
hydroxy,
(C$_{1-10}$ alkyl)OH,
C$_{1-10}$ alkoxy,
cyano, and
C$_{1-6}$haloalkyl;
R$^6$ is independently selected from:
halogen,
C$_{1-10}$ alkyl(oxy)$_{0-1}$(carbonyl)$_{0-1}$C$_{0-10}$ alkyl,
C$_{1-10}$ haloalkyl(oxy)$_{0-1}$(carbonyl)$_{0-1}$C$_{0-10}$ alkyl,
C$_{1-10}$ heteroalkyl(oxy)$_{0-1}$(carbonyl)$_{0-1}$C$_{0-10}$ alkyl,
aryl C$_{0-10}$ alkyl(oxy)$_{0-1}$(carbonyl)$_{0-1}$C$_{0-10}$ alkyl,
C$_{3-12}$ cycloalkyl C$_{0-10}$ alkyl(oxy)$_{0-1}$(carbonyl)$_{0-1}$C$_{0-10}$ alkyl,
heteroaryl C$_{0-10}$ alkyl(oxy)$_{0-1}$(carbonyl)$_{0-1}$C$_{0-10}$ alkyl,
(C$_{3-12}$)heterocycloalkyl C$_{0-10}$ alkyl(oxy)$_{0-1}$ (carbonyl)$_{0-1}$C$_{0-10}$ alkyl,
C$_{0-10}$ alkyl(oxy)$_{0-1}$ carbonylaminoC$_{0-10}$ alkyl,
C$_{0-10}$ alkylamino(oxy)$_{0-1}$ carbonylC$_{0-10}$ alkyl,
(C$_{1-10}$)heteroalkylamino(oxy)$_{01}$(carbonyl)$_{0-1}$C$_{0-10}$ alkyl,
C$_{3-12}$ cycloalkylamino(oxy)$_{0-1}$ (carbonyl)$_{0-1}$C$_{0-10}$ alkyl,
aryl C$_{0-10}$ alkylamino(oxy)$_{0-1}$(carbonyl)$_{0-1}$C$_{0-10}$ alkyl,
heteroaryl C$_{0-10}$ alkylamino(oxy)$_{0-1}$(carbonyl)$_{0-1}$C$_{0-10}$ alkyl,
(C$_{3-12}$)heterocycloalkylamino(oxy)$_{0-1}$(carbonyl)$_{0-1}$C$_{0-10}$ alkyl,
—CO₂(C$_{0-10}$ alkyl),
—(C$_{0-10}$ alkyl)CO₂H,
oxo (═O),
C$_{0-10}$ alkylsulfonylC$_{0-10}$ alkyl,
C$_{1-10}$ heteroalkylsulfonylC$_{0-10}$ alkyl,
(C$_{3-12}$)cycloalkylC$_{0-10}$alkylsulfonylC$_{0-10}$ alkyl,
(C$_{3-12}$)cycloheteroalkylC$_{0-10}$alkylsulfonylC$_{0-10}$ alkyl,
heteroarylC$_{0-10}$ alkylsulfonylC$_{0-10}$ alkyl,
arylC$_{0-10}$ alkylsulfonylC$_{0-10}$ alkyl,
—SO₂NH₂,
—SO₂NH(C$_{1-10}$ alkyl),
—SO₂N(C$_{1-10}$ alkyl)$_2$,
—SO₂CF₃,
—SO₂CF₂H,
amino,
(C$_{1-10}$ alkyl)$_{1-2}$ amino,
-(oxy)$_{0-1}$ (carbonyl)$_{0-1}$N(C$_{0-10}$ alkyl)$_{1-2}$
hydroxy,
(C$_{1-10}$ alkyl)OH,
C$_{1-10}$ alkoxy,
(C$_{1-10}$ alkyl)cyano,
cyano, and
C$_{1-6}$haloalkyl; and
wherein R$^5$ and R$^6$ are each independently substituted with 0, 1, 2, or 3 R$^7$ substituents and each R$^7$ substituent is independently selected from hydroxy, (C$_{1-6}$)alkyl, (C$_{1-6}$) alkoxy, (C$_{5-6}$)aryl, (C$_{5-6}$)heteroaryl, (C$_{1-10}$ alkyl)OH, halogen, CO₂H, —(C$_{0-6}$)alkylCN, —O(C═O)C$_1$-C$_6$ alkyl, —(C═O)OC$_1$-C$_6$ alkyl, NO₂, trifluoromethoxy, trifluoroethoxy, trifluoromethyl, trifluoroethyl, —N—C(O)O(C$_{0-6}$)alkyl, C$_{1-10}$ alkylsulfonyl, oxo (O═), aminosulfonyl, —SO₂N(C$_{1-6}$alkyl)$_{1-2}$, —SO₂C$_{1-6}$alkyl, —SO₂CF₃, —SO₂CF₂H, —C$_{1-10}$ alkylsulfinyl, —O$_{(0-1)}$(C$_{1-10}$)haloalkyl, amino(C$_{1-6}$alkyl)$_{1-2}$ and NH₂.

Representative compounds of the instant invention include, but are not limited to, the following compounds and their pharmaceutically acceptable salts and their stereoisomers thereof:

N-(3-cyclopropyl-5,6,7,8-tetrahydro[1,2,4]triazolo[4,3-a]pyridin-6-yl)-9-ethyl-8-(2-methylpyrimidin-5-yl)-9H-purin-6-amine;

9-ethyl-8-(2-methylpyrimidin-5-yl)-N-[3-phenyl-5,6,7,8-tetrahydro[1,2,4]triazolo[4,3-a]pyridin-6-yl]-9H-purin-6-amine;

9-ethyl-N-[3-(1-methylethyl)-5,6,7,8-tetrahydro[1,2,4]triazolo[4,3-a]pyridin-6-yl]-8-(2-methylpyrimidin-5-yl)-9H-purin-6-amine;

9-ethyl-N-[3-ethyl-5,6,7,8-tetrahydro[1,2,4]triazolo[4,3-a]pyridin-6-yl]-8-(2-methylpyrimidin-5-yl)-9H-purin-6-amine;

8-(difluoromethyl)-9-ethyl-N-[3-(1-methylethyl)-5,6,7,8-tetrahydro[1,2,4]triazolo[4,3-a]pyridin-6-yl]-9H-purin-6-amine;

N-(3-cyclopropyl-5,6,7,8-tetrahydro[1,2,4]triazolo[4,3-a]pyridin-6-yl)-9-ethyl-8-(1-phenyl-1H-pyrazol-4-yl)-9H-purin-6-amine;

N-(3-cyclopropyl-5,6,7,8-tetrahydro[1,2,4]triazolo[4,3-a]pyridin-6-yl)-9-ethyl-8-[6-(trifluoromethyl)pyridin-3-yl]-9H-purin-6-amine;

N-(3-cyclopropyl-5,6,7,8-tetrahydro[1,2,4]triazolo[4,3-a]pyridin-6-yl)-9-ethyl-8-(5-fluoro-6-methoxypyridin-3-yl)-9H-purin-6-amine;

N-(3-cyclopropyl-5,6,7,8-tetrahydro[1,2,4]triazolo[4,3-a]pyridin-6-yl)-9-ethyl-8-(6-methoxypyridin-3-yl)-9H-purin-6-amine;

N-(3-cyclopropyl-5,6,7,8-tetrahydro[1,2,4]triazolo[4,3-a]pyridin-6-yl)-8-[6-(difluoromethoxy)pyridin-3-yl]-9-ethyl-9H-purin-6-amine;

N-(3-cyclopropyl-5,6,7,8-tetrahydro[1,2,4]triazolo[4,3-a]
pyridin-6-yl)-9-ethyl-8-(6-methoxy-5-methylpyridin-3-
yl)-9H-purin-6-amine;
N-(3-cyclopropyl-5,6,7,8-tetrahydro[1,2,4]triazolo[4,3-a]
pyridin-6-yl)-9-ethyl-8-[4-(trifluoromethoxy)phenyl]-
9H-purin-6-amine;
N-(3-cyclopropyl-5,6,7,8-tetrahydro[1,2,4]triazolo[4,3-a]
pyridin-6-yl)-9-ethyl-8-(1-ethyl-5-methyl-1H-pyrazol-4-
yl)-9H-purin-6-amine;
9-ethyl-N-[3-(1-methylethyl)-5,6,7,8-tetrahydro[1,2,4]tri-
azolo[4,3-a]pyridin-6-yl]-8-[6-(trifluoromethyl)pyridin-
3-yl]-9H-purin-6-amine;
9-ethyl-N-[3-(1-methylethyl)-5,6,7,8-tetrahydro[1,2,4]tri-
azolo[4,3-a]pyridin-6-yl]-8-[4-(trifluoromethyl)phenyl]-
9H-purin-6-amine;
9-ethyl-8-(5-fluoro-6-methoxypyridin-3-yl)-N-[3-(1-methy-
lethyl)-5,6,7,8-tetrahydro[1,2,4]triazolo[4,3-a]pyridin-6-
yl]-9H-purin-6-amine;
8-(5-chloro-6-methoxypyridin-3-yl)-9-ethyl-N-[3-(1-
methylethyl)-5,6,7,8-tetrahydro[1,2,4]triazolo[4,3-a]pyri-
din-6-yl]-9H-purin-6-amine;
9-ethyl-N-[3-(1-methylethyl)-5,6,7,8-tetrahydro[1,2,4]tri-
azolo[4,3-a]pyridin-6-yl]-8-(1-phenyl-1H-pyrazol-4-yl)-
9H-purin-6-amine;
8-[4-(difluoromethyl)phenyl]-9-ethyl-N-[3-(1-methyl-
ethyl)-5,6,7,8-tetrahydro[1,2,4]triazolo[4,3-a]pyridin-6-
yl]-9H-purin-6-amine;
9-ethyl-N-[3-(1-methylethyl)-5,6,7,8-tetrahydro[1,2,4]tri-
azolo[4,3-a]pyridin-6-yl]-8-[4-(trifluoromethyl)-1H-imi-
dazol-1-yl]-9H-purin-6-amine;
N-[3-cyclopropyl-5,6,7,8-tetrahydro[1,2,4]triazolo[4,3-a]
pyridin-6-yl]-9-ethyl-8-iodo-9H-purin-6-amine;
N-(3-cyclopropyl-5,6,7,8-tetrahydro[1,2,4]triazolo[4,3-a]
pyridin-6-yl)-9-ethyl-8-[4-(trifluoromethyl)phenyl]-9H-
purin-6-amine;
N-[3-cyclopropyl-5,6,7,8-tetrahydro[1,2,4]triazolo[4,3-a]
pyridin-6-yl]-9-ethyl-8-[6-(methylsulfonyl)pyridin-3-yl]-
9H-purin-6-amine;
6-{[3-cyclopropyl-5,6,7,8-tetrahydro[1,2,4]triazolo[4,3-a]
pyridin-6-yl]oxy}-9-ethyl-8-(2-methylpyrimidin-5-yl)-
9H-purine;
9-ethyl-6-{[3-(1-methylethyl)-5,6,7,8-tetrahydro[1,2,4]tri-
azolo[4,3-a]pyridin-6-yl]oxy}-8-(2-methylpyrimidin-5-
yl)-9H-purine;
6-{[3-cyclobutyl-5,6,7,8-tetrahydro[1,2,4]triazolo[4,3-a]
pyridin-6-yl]oxy}-9-ethyl-8-(2-methylpyrimidin-5-yl)-
9H-purine;
9-ethyl-6-{[3-(1-methylethyl)-5,6,7,8-tetrahydro[1,2,4]tri-
azolo[4,3-a]pyridin-6-yl]amino}-N-(2,2,2-trifluoro-
ethyl)-9H-purine-8-carboxamide;
N-[3-cyclopropyl-6,7-dihydro-5H-pyrrolo[2,1-c][1,2,4]tri-
azol-6-yl]-9-ethyl-8-(2-methylpyrimidin-5-yl)-9H-purin-
6-amine;
tert-butyl 3-cyclopropyl-5-{[9-ethyl-8-(2-methylpyrimidin-
5-yl)-9H-purin-6-yl]amino}-4,5,6,7-tetrahydro-1H-inda-
zole-1-carboxylate;
N-[3-cyclopropyl-4,5,6,7-tetrahydro-1H-indazol-5-yl]-9-
ethyl-8-(2-methylpyrimidin-5-yl)-9H-purin-6-amine;
N-{1-[2-(dimethylamino)ethyl]-3-(1-methylethyl)-4,5,6,7-
tetrahydro-1H-indazol-5-yl}-9-ethyl-8-(2-methylpyrimi-
din-5-yl)-9H-purin-6-amine;
9-ethyl-N-[3-(-methylethyl)-4,5,6,7-tetrahydro-1H-indazol-
5-yl]-8-(2-methylpyrimidin-5-yl)-9H-purin-6-amine;
9-ethyl-N-[5-methyl-3-(1-methylethyl)-4,5,6,7-tetrahydro-
1H-indazol-5-yl]-8-(2-methylpyrimidin-5-yl)-9H-purin-
6-amine;
9-ethyl-N-[3-(1-methylethyl)-4,5,6,7-tetrahydro-1H-inda-
zol-5-yl]-8-[4-(trifluoromethyl)phenyl]-9H-purin-6-
amine;
8-(difluoromethyl)-9-ethyl-N-[3-(1-methylethyl)-4,5,6,7-
tetrahydro-1H-indazol-5-yl]-9H-purin-6-amine;
9-ethyl-N-[3-(1-methylethyl)-1-propyl-4,5,6,7-tetrahydro-
1H-indazol-5-yl]-8-(2-methylpyrimidin-5-yl)-9H-purin-
6-amine;
2-[5-{[9-ethyl-8-(2-methylpyrimidin-5-yl)-9H-purin-6-yl]
amino}-3-(1-methylethyl)-4,5,6,7-tetrahydro-1H-inda-
zol-1-yl]ethanol;
N-[1-acetyl-3-(1-methylethyl)-4,5,6,7-tetrahydro-1H-inda-
zol-5-yl]-9-ethyl-8-(2-methylpyrimidin-5-yl)-9H-purin-
6-amine;
9-ethyl-N-[3-(1-methylethyl)-1-(phenylcarbonyl)-4,5,6,7-
tetrahydro-1H-indazol-5-yl]-8-(2-methylpyrimidin-5-yl)-
9H-purin-6-amine;
N-{1-[(dimethylamino)acetyl]-3-(1-methylethyl)-4,5,6,7-
tetrahydro-1H-indazol-5-yl}-9-ethyl-8-(2-methylpyrimi-
din-5-yl)-9H-purin-6-amine;
N-[1-(3,3-dimethylbutanoyl)-3-(1-methylethyl)-4,5,6,7-tet-
rahydro-1H-indazol-5-yl]-9-ethyl-8-(2-methylpyrimidin-
5-yl)-9H-purin-6-amine;
tert-butyl 5-{[9-ethyl-8-(2-methylpyrimidin-5-yl)-9H-pu-
rin-6-yl]amino}-3-(1-methylethyl)-4,5,6,7-tetrahydro-
1H-indazole-1-carboxylate;
ethyl 5-{[9-ethyl-8-(2-methylpyrimidin-5-yl)-9H-purin-6-
yl]amino}-3-(1-methylethyl)-4,5,6,7-tetrahydro-1H-inda-
zole-1-carboxylate;
1-methylethyl 5-{[9-ethyl-8-(2-methylpyrimidin-5-yl)-9H-
purin-6-yl]amino}-3-(1-methylethyl)-4,5,6,7-tetrahydro-
1H-indazole-1-carboxylate;
methyl 5-{[9-ethyl-8-(2-methylpyrimidin-5-yl)-9H-purin-6-
yl]amino}-3-(1-methylethyl)-4,5,6,7-tetrahydro-1H-inda-
zole-1-carboxylate;
2,2,2-trifluoro-1,1-dimethylethyl 5-{[9-ethyl-8-(2-methyl-
pyrimidin-5-yl)-9H-purin-6-yl]amino}-3-(1-methyl-
ethyl)-4,5,6,7-tetrahydro-1H-indazole-1-carboxylate;
N-tert-butyl-5-{[9-ethyl-8-(2-methylpyrimidin-5-yl)-9H-
purin-6-yl]amino}-3-(1-methylethyl)-4,5,6,7-tetrahydro-
1H-indazole-1-carboxamide;
9-ethyl-N-[3-(1-methylethyl)-1-pyridin-2-yl-4,5,6,7-tetra-
hydro-1H-indazol-5-yl]-8-(2-methylpyrimidin-5-yl)-9H-
purin-6-amine;
9-ethyl-N-[3-(1-methylethyl)-1-(methylsulfonyl)-4,5,6,7-
tetrahydro-1H-indazol-5-yl]-8-(2-methylpyrimidin-5-yl)-
9H-purin-6-amine;
9-ethyl-N-[2-methyl-3-(1-methylethyl)-4,5,6,7-tetrahydro-
2H-indazol-5-yl]-8-(2-methylpyrimidin-5-yl)-9H-purin-
6-amine;
9-ethyl-N-[1-methyl-3-(1-methylethyl)-4,5,6,7-tetrahydro-
1H-indazol-5-yl]-8-(2-methylpyrimidin-5-yl)-9H-purin-
6-amine;
N-(1-benzyl-1,4,5,6-tetrahydrocyclopenta[c]pyrazol-5-yl)-
9-ethyl-8-(2-methylpyrimidin-5-yl)-9H-purin-6-amine;
6-[(1,3-diethyl-4,5,6,7-tetrahydro-1H-indazol-5-yl)oxy]-9-
ethyl-8-(2-methylpyrimidin-5-yl)-9H-purine;
N-[3-cyclopropyl-5,6,7,8-tetrahydroimidazo[1,5-a]pyridin-
6-yl]-9-ethyl-8-(2-methylpyrimidin-5-yl)-9H-purin-6-
amine;
9-ethyl-N-[3-(1-methylethyl)-5,6,7,8-tetrahydroimidazo[1,
5-a]pyridin-6-yl]-8-(2-methylpyrimidin-5-yl)-9H-purin-
6-amine;
N-(3-cyclopropyl-5,6,7,8-tetrahydroimidazo[1,2-a]pyridin-
6-yl)-9-ethyl-8-(2-methylpyrimidin-5-yl)-9H-purin-6-
amine;

9-ethyl-N-[3-(1-methylethyl)-5,6,7,8-tetrahydroimidazo[1,2-a]pyridin-6-yl]-8-(2-methylpyrimidin-5-yl)-9H-purin-6-amine;

9-ethyl-6-[(3-ethyl-6,7-dihydro-5H-pyrrolo[1,2-a]imidazol-6-yl)oxy]-8-(2-methylpyrimidin-5-yl)-9H-purine;

N-(1-cyclopropyl-4,5,6,7-tetrahydro-1H-benzimidazol-6-yl)-9-ethyl-8-(2-methylpyrimidin-5-yl)-9H-purin-6-amine;

N-(1-cyclopropyl-4,5,6,7-tetrahydro-1H-benzimidazol-6-yl)-9-ethyl-8-[6-(trifluoromethyl)pyridin-3-yl]-9H-purin-6-amine;

N-(1-cyclopropyl-4,5,6,7-tetrahydro-1H-benzimidazol-6-yl)-9-ethyl-8-[4-(trifluoromethyl)phenyl]-9H-purin-6-amine;

N-(1-cyclopropyl-4,5,6,7-tetrahydro-1H-benzimidazol-6-yl)-8-(difluoromethyl)-9-ethyl-9H-purin-6-amine;

N-(1-cyclopropyl-2-methyl-4,5,6,7-tetrahydro-1H-benzimidazol-6-yl)-9-ethyl-8-(2-methylpyrimidin-5-yl)-9H-purin-6-amine;

N-(1-cyclopropyl-2-ethyl-4,5,6,7-tetrahydro-1H-benzimidazol-6-yl)-9-ethyl-8-(2-methylpyrimidin-5-yl)-9H-purin-6-amine;

6-[(1-cyclopropyl-4,5,6,7-tetrahydro-1H-benzimidazol-6-yl)amino]-9-ethyl-N-(2,2,2-trifluoroethyl)-9H-purine-8-carboxamide;

N-[1-cyclopropyl-2-(difluoromethyl)-4,5,6,7-tetrahydro-1H-benzimidazol-6-yl]-9-ethyl-8-(2-methylpyrimidin-5-yl)-9H-purin-6-amine;

N-(2-chloro-1-cyclopropyl-4,5,6,7-tetrahydro-1H-benzimidazol-6-yl)-9-ethyl-8-(2-methylpyrimidin-5-yl)-9H-purin-6-amine;

9-ethyl-N-[1-(-3-methoxycyclobutyl)-4,5,6,7-tetrahydro-1H-benzimidazol-6-yl]-8-(2-methylpyrimidin-5-yl)-9H-purin-6-amine;

9-ethyl-N-[1-(1-methylethyl)-4,5,6,7-tetrahydro-1H-benzimidazol-6-yl]-8-(2-methylpyrimidin-5-yl)-9H-purin-6-amine;

9-ethyl-N-[4-methyl-1-(1-methylethyl)-4,5,6,7-tetrahydro-1H-benzimidazol-6-yl]-8-(2-methylpyrimidin-5-yl)-9H-purin-6-amine;

9-ethyl-N-[5-methyl-1-(1-methylethyl)-4,5,6,7-tetrahydro-1H-benzimidazol-6-yl]-8-(2-methylpyrimidin-5-yl)-9H-purin-6-amine;

9-ethyl-N-[7-methyl-1-(1-methylethyl)-4,5,6,7-tetrahydro-1H-benzimidazol-6-yl]-8-(2-methylpyrimidin-5-yl)-9H-purin-6-amine; and 9-ethyl-N-[1-(1-methylethyl)-5,6,7,8-tetrahydroimidazo[1,5-a]pyridin-7-yl]-8-(2-methylpyrimidin-5-yl)-9H-purin-6-amine.

The invention also encompasses pharmaceutical compositions containing a compound of formula I, and methods for treatment or prevention of PI3K-delta mediated diseases using compounds of formula I.

One aspect of the present invention is to provide compounds that can inhibit the biological activity of human PI3K-delta. Another aspect of the invention is to provide methods of selectively modulating human PI3K-delta activity and thereby promoting medical treatment of diseases mediated by PI3K-delta dysfunction.

In one embodiment of the invention, the compounds of formula I inhibit PI3K-delta activity in biochemical and cell-based assays and to exhibit therapeutic activity in medical conditions in which PI3K-delta activity is excessive or undesirable.

The invention is described using the following definitions unless otherwise indicated.

"Acyl" means a —C(O)R radical Where R is optionally substituted alkyl, alkenyl, cycloalkyl, heterocycloalkyl, aryl heteroaryl, etc.

"Acylamino" means a —NRR' radical where R is H, OH, or alkoxy and R' is acyl, as defined herein.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

The term "alkyl" refers to an aliphatic hydrocarbon group which may be straight or branched and having the indicated number of carbon atoms. Non-limiting examples of alkyl groups include methyl, ethyl, propyl, isopropyl, butyl, s- and t-butyl, pentyl, hexyl, and the like.

The term "heteroalkyl" refers to an alkyl group where 1, 2, or 3 of the carbon atoms are each independently replaced by a heteroatom independently selected from N, O, or S.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkynyl" refers to an aliphatic hydrocarbon group containing at least one carbon-carbon triple bond and which may be straight or branched and having the indicated number of carbon atoms. Non-limiting examples of suitable alkynyl groups include ethynyl, propynyl, 2-butynyl and 3-methylbutynyl.

"Alkoxy" refers to an alkyl-O— group in which the alkyl group is as described above. $C_{1-6}$alkoxy, for example, includes methoxy, ethoxy, propoxy, isopropoxy, and the like. "Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

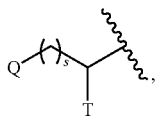

wherein s is an integer equal to zero, 1 or 2, the structure is

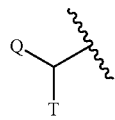

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and polycarbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

"Carboxy" refers to the functional group —C(O)OR, for example: ethylcarboxy is

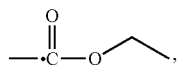

phenylcarboxy is

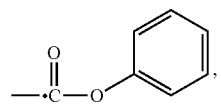

and cyclopropycarboxy is

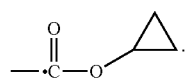

"Carboxyalkyl" refers to an alkyl group substituted with at least one, specifically one or two, —C(O)OH group(s).

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

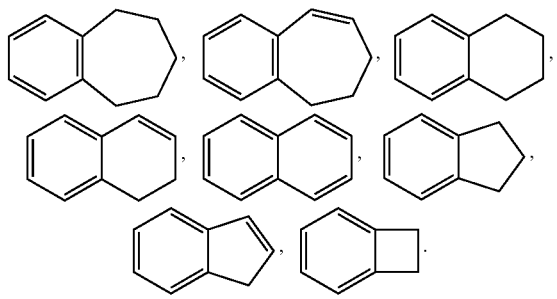

"Cyanoalkyl" refers to an alkyl group as described above in which one hydrogen atom has been replaced by a cyano group. Examples include $CH_2CN$, $CH_2CH_2CN$ and $CH(CN)CH_3$.

"Cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro[2.2]pentane), or are bridged groups (e.g., norbornane). Additional examples within the above meaning include, but are not limited to, cyclopropane, cyclobutane, cyclopentane, cyclohexane, perhydroindan, decalin, spiro[4.5]decane, spiro[2.5]oxtyl, bicyclo[2.2.2]octane, and the like.

"Heterocycloalkyl" refers to a "cycloalkyl" wherein one or more of the carbon atoms are replaced by at least one heteroatom, such as, for example, 1 to 4 heteroatoms selected from nitrogen, oxygen, and sulfur.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$haloalkyl, for example, includes —$CF_3$, —$CF_2CF_3$, $CHFCH_3$, and the like.

"Heterocycle", "heterocyclic" or "heterocyclyl" represents a monocyclic or bicyclic 3-12 membered ring system in which at least one ring is non-aromatic (saturated or partially unsaturated) and containing at least one heteroatom selected from O, S and N. In a bicyclic ring system, the second ring may be a heteroaryl, heterocycle or a saturated, partially unsaturated or aromatic carbocycle, and the point (s) of attachment to the rest of the molecule may be on either ring. "Heterocyclyl" therefore includes heteroaryls, as well as dihydro and tetrahydro analogs thereof. Attachment of a heterocyclyl substituent can occur via a carbon atom or via a heteroatom.

Examples of heterocycles (heterocyclyl) include, but are not limited to, azetidinyl, pyrrolidinyl, piperidinyl, piperazinyl, morpholinyl, thiamorpholinyl, tetrahydrofuranyl, dihydrofuranyl, tetrahydrothienyl, tetrahydropyranyl, dihydropyranyl, dihydroimidazolyl, dihydroindolyl, 1,2,3,4-tetrahydroisoquinolinyl, 5,6,7,8-tetrahydroimidazo[1,2-a]pyrazine, 2,3-dihydrobenzofuranyl, benzo-1,4-dioxanyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

Saturated heterocyclics form a subset of the heterocycles; i.e., the terms "saturated heterocyclic and heterocycloalkyl" generally refers to a heterocycle as defined above in which the entire ring system (whether mono- or poly-cyclic) is saturated. The term "saturated heterocyclic ring" refers to a 3- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, azetidinyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles. The term "heteroaromatic ring" (alternatively "heteroaryl") refers a 5- or 6-membered monocyclic aromatic ring or a 7- to 12-membered bicyclic which consists of carbon atoms and one or more heteroatoms selected from N, O and S. For a bicyclic heteroaryl only one of the rings need to be heteroaromatic, the second ring may be a heteroaromatic or an aromatic, saturated, or partially unsatuated carbocycle, and the point(s) of attachment to the rest of the molecule may be on either ring. In the case of substituted heteroaryl rings containing at least one nitrogen atom (e.g., pyridine), such substitutions can be those resulting in N-oxide formation. Examples of heteroaryl include, but are not limited to, furanyl, thienyl (or thiophenyl), pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]pyrimidinyl, 5,6-dihydropyrrolo[1,2-b]pyrazolyl, pyrrolo[3,2-c]pyridinyl, pyrrolo[2,3-b]pyridinyl, pyrazolo[3,4-b]pyridinyl, 4,5,6,7-tetrahydro-1H-benzimidazolyl, thieno[2,3-b]pyrrolyl, furopyridine and thienopyridine.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxin 1 (i.e.,

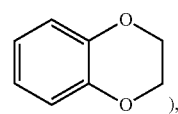), imidazo(2,1-b)(1,3) thiazole, (i.e.,

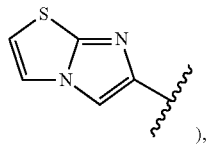), and benzo-1,3-dioxolyl (i.e.,

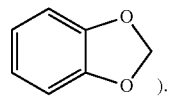).

In certain contexts herein,

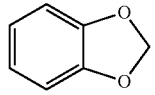

is alternatively referred to as phenyl having as a substituent methylenedioxy attached to two adjacent carbon atoms.

"Heteroalicyclic" group refers to a monocyclic or fused ring of 3 to 12 ring atoms containing one, or more heteroatoms in the ring.

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

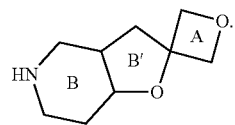

In one embodiment, all rings of the spirocyclyl system are saturated, such as spiro[2.5]octyl. In another embodiment, the individual rings of the spirocyclyl system are selected from both saturated and unsaturated rings.

For example a heteroalicyclic spirocyclyl or "spiroheterocyclic ring," as used herein, refers to a bicyclic heterocyclic ring as defined above wherein the two rings are joined through a common ring carbon atom. In one embodiment, a spiroheterocyclic ring is a 3- to 12-membered ring system containing one to three heteroatoms, e.g., one to two heteroatoms, selected from the group consisting of N and O. Non-limiting examples of spiroheterocyclic rings include azaspiro[2.4]heyptyl, 1,9-diazaspiro[5.5]undecane; 2,8-diazaspiro[5.5]undecane; 2,8-diazaspiro[4.5]decane; 1,7-diazaspiro[4.4]nonane; 1,7-diazaspiro[4.5]decane; 2,7-diazaspiro[4.5]decane, 1-oxa-8-azaspiro[5.5]undecane; 2-oxa-7-azaspiro[4.5]decane; 1-oxa-7-azaspiro[4.5]decane; 1,4-dioxa-7-azaspiro[4.5]decane; 1,4-dioxa-8-azaspiro[4.5]decane, and 1,4-dioxaspiro[4.5]decane.

Non-limiting examples of a carbocyclic spirocyclyl systems comprising include: spiro[2.2]pentane, spiro[cylclobutane-1,2'-indene], spiro[4.4]nonane, and spiro[4.5]decane.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation from a reaction mixture to a useful degree of purity, and formulation into an efficacious therapeutic agent.

The term "oxy" means an oxygen (O) atom. The term "thio" means a sulfur (S) atom. The term "oxo" means "=O". The term "carbonyl" means "C=O."

Structural representations of compounds having substituents terminating with a methyl group may display the terminal methyl group either using the characters "$CH_3$", e.g. "—$CH_3$" or using a straight line representing the presence of the methyl group, e.g. "-", i.e.,

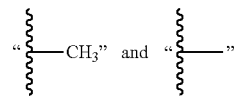

have equivalent meanings.

For variable definitions containing terms having repeated terms, e.g., $(CR_iR_j)_r$, where r is the integer 2, $R_i$ is a defined variable, and $R_j$ is a defined variable, the value of $R_i$ may differ in each instance in which it occurs, and the value of $R_j$ may differ in each instance in which it occurs. For example, if $R_i$ and $R_j$ are independently selected from the group consisting of methyl, ethyl, propyl and butyl, then $(CR_iR_j)_2$ can be

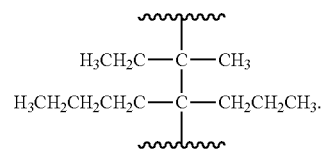

In one embodiment of the invention, $R^1$ is selected from hydrogen, $C_{1-5}$alkyl, and —$(C_{0-3}$alkyl$)C_{3-4}$cycloalkyl, wherein $R^1$ is optionally substituted by 0, 1, 2, 3, or 4 groups independently selected from hydrogen, fluoro, chloro, methyl, $C_{1-3}$haloalkyl, amino, $O(C=O)R^a$, $O(C=O)OR^a$ and $NH(C=O)R^a$.

In another embodiment of the invention, $R^1$ is hydrogen or $C_{1-5}$alkyl, wherein $R^1$ is optionally substituted by 0, 1, 2, 3, or 4 groups independently selected from hydrogen, fluoro, chloro, methyl, $C_{1-3}$haloalkyl, amino, $O(C=O)R^a$, $O(C=O)OR^a$ and $NH(C=O)R^a$.

In another embodiment of the invention, $R^1$ is $C_{1-5}$alkyl, optionally substituted by 0, 1, 2, 3, or 4 groups independently selected from hydrogen, fluoro, chloro, methyl, $C_{1-3}$haloalkyl, amino, $O(C=O)R^a$, $O(C=O)OR^a$ and $NH(C=O)R^a$.

In yet another variant of this embodiment, $R^1$ is methyl, ethyl, propyl, isopropyl, butyl, isobutyl, pentyl, or isopentyl, wherein $R^1$ is optionally substituted by 0, 1, 2, 3, or 4 groups independently selected from hydrogen, fluoro, chloro, methyl, $C_{1-3}$haloalkyl, amino, $O(C=O)R^a$, $O(C=O)OR^a$ and $NH(C=O)R^a$. In yet another embodiment, $R^1$ is ethyl.

In one embodiment of the invention, $R^a$ is independently selected from and $C_{1-3}$alkyl and $C_{1-3}$haloalkyl. In one variant of this invention, $R^a$ is $C_{1-3}$alkyl.

In one embodiment of the invention, K is selected from a bond, NH, $N(C_{1-5})$alkyl, —C(O)N($R^b$)—$(CH_2)_m$—, S, $SO_2$, and $C_{2-10}$ alkynylene.

In another embodiment of the invention, K is selected from a bond, NH, O, C(O), $CH_2$, —C(O)N($R^b$)—$(CH_2)_m$—, S, and $SO_2$. In a variant of this embodiment, K is selected from a bond, NH, $CH_2$, and —C(O)N($R^b$)—$(CH_2)_m$—. In one embodiment, $R^b$ is H or $C_{1-3}$ alkyl. In another embodiment, $R^b$ is H.

In one embodiment of the invention, L is selected from —O—, —NH—, and —N(C1-3alkyl)-. In a variant of this embodiment, L is —NH— or —O—. In another variant, L is —N(C1-3alkyl)-.

In one embodiment, n is 0, 1, or 2. In a variant of this embodiment, n is 0. In yet another embodiment, n is 1. In yet another embodiment, n is 2. In yet another embodiment of the invention, n is 3.

In one embodiment, v is 0, 1, 2 or 3. In a variant of this embodiment, v is 0, 1 or 2. In yet another embodiment, v is 1.

In one embodiment, p is 0. In another embodiment of the invention p, is 1.

In one embodiment of the invention, m is 0 or 1. In another embodiment, m is 0. In yet another embodiment, m is 1.

In one embodiment of the invention, K is a bond, methylene, or —C(O)NH—.

In one embodiment of the invention, $R^2$ is selected from hydrogen, halogen, $C_{1-10}$alkyl, $C_{3-12}$ cycloalkyl, $C_{3-12}$heterocycloalkyl, $C_{1-10}$ heteroalkyl, aryl, $C_{1-6}$haloalkyl, and heteroaryl, wherein $R^2$ is substituted with 0, 1, 2, 3, or 4 $R^6$ substituents.

In another embodiment of the invention, $R^2$ is selected from hydrogen, halogen, aryl, $C_{1-6}$haloalkyl, and heteroaryl, wherein $R^2$ is substituted with 0, 1, 2, 3, or 4 $R^6$ substituents. In another embodiment of the invention, $R^2$ is hydrogen.

In another embodiment of the invention, $R^2$ is selected from pyridinyl, pyrimidinyl, fluoro, pyrazolyl, phenyl, imidazolyl, iodo, and trifluoroethyl, wherein $R^2$ is substituted with 0, 1, 2, 3, or 4 $R^6$ substituents.

In one embodiment of the invention, $R^3$ is selected from: halogen, $C_{1-10}$ alkyl(oxy)$_{0-1}$(carbonyl)$_{0-1}$C$_{0-10}$ alkyl, aryl $C_{0-10}$ alkyl(oxy)$_{0-1}$(carbonyl)$_{0-1}$C$_{0-10}$ alkyl, $C_{3-12}$ cycloalkylC$_{0-10}$ alkyl(oxy)$_{0-1}$(carbonyl)$_{0-1}$C$_{0-10}$ alkyl, heteroaryl $C_{0-10}$ alkyl(oxy)$_{0-1}$(carbonyl)$_{0-1}$C$_{0-10}$ alkyl, $(C_{3-12})$heterocycloalkyl $C_{0-10}$ alkyl(oxy)$_{0-1}$(carbonyl)$_{0-1}$C$_{0-10}$ alkyl, $(C_{1-10}$ alkyl$)_{1-2}$ aminoC$_{0-10}$ alkyl, aminoC$_{0-10}$ alkyl, $C_{1-10}$alkyl(carbonyl)$_{0-1}$ oxyC$_{0-10}$ alkyl, aryl C$_{0-10}$ alkyl (carbonyl)$_{0-1}$oxyC$_{0-10}$ alkyl, $(C_{3-12})$cycloalkyl C$_{0-10}$ alkyl(carbonyl)$_{0-1}$oxyC$_{0-10}$ alkyl, heteroarylC$_{0-10}$ alkyl(carbonyl)$_{0-1}$oxyC$_{0-10}$ alkyl, $(C_{3-12})$heterocycloalkyl C$_{0-10}$ alkyl(carbonyl)$_{0-1}$oxyC$_{0-10}$ alkyl, C$_{0-10}$ alkylamino(carbonyl)$_{0-1}$C$_{0-10}$ alkyl, $(C_{1-10}$ alkyl$)_{1-2}$aminoC$_{0-10}$ alkyl carbonylC$_{0-10}$ alkyl, $C_{3-12}$ cycloalkyl C$_{0-10}$ alkylamino(carbonyl)$_{0-1}$C$_{0-10}$ alkyl, aryl C$_{0-10}$alkylamino(carbonyl)$_{0-1}$C$_{0-10}$ alkyl, heteroarylC$_{0-10}$alkylamino(carbonyl)$_{0-1}$C$_{0-10}$ alkyl, $(C_{3-12})$heterocycloalkylC$_{0-10}$alkylamino(carbonyl)$_{0-1}$C$_{0-10}$ alkyl, $C_{1-10}$ alkylcarbonylaminoC$_{0-10}$ alkyl, $C_{1-10}$ heteroalkylcarbonylaminoC$_{0-10}$ alkyl, $C_{3-12}$ cycloalkyl C$_{0-10}$ alkylcarbonylaminoC$_{0-10}$ alkyl, aryl C$_{0-10}$ alkylcarbonylaminoC$_{0-10}$ alkyl, heteroaryl C$_{0-10}$ alkylcarbonylaminoC$_{0-10}$ alkyl, $(C_{3-12})$heterocycloalkyl C$_{0-10}$ alkylcarbonylaminoC$_{0-10}$ alkyl, —CO$_2$(C$_{0-10}$ alkyl), —(C$_{0-10}$ alkyl)CO$_2$H, Oxo (═O), C$_{0-10}$ alkylsulfonylC$_{0-10}$ alkyl, —SO$_2$N(C$_{1-6}$ alkyl)$_{0-2}$, amino, hydroxy, (C$_{1-10}$ alkyl)OH, C$_{0-10}$ alkoxy, and C$_{1-6}$haloalkyl, wherein $R^3$ is each substituted with 0, 1, 2, 3, or 4 $R^5$ substituents.

In one embodiment of the invention, $R^3$ is selected from: halogen, $C_{1-10}$ alkyl(oxy)$_{0-1}$(carbonyl)$_{0-1}$C$_{0-10}$ alkyl, aryl $C_{0-10}$ alkyl(oxy)$_{0-1}$(carbonyl)$_{0-1}$C$_{0-10}$ alkyl, $C_{3-12}$ cycloalkylC$_{0-10}$ alkyl(oxy)$_{0-1}$(carbonyl)$_{0-1}$C$_{0-10}$ alkyl, heteroaryl $C_{0-10}$ alkyl(oxy)$_{0-1}$ (carbonyl)$_{0-1}$C$_{0-10}$ alkyl, (C$_{1-10}$ alkyl)$_{1-2}$ aminoC$_{0-10}$ alkyl, C$_{0-10}$ alkylamino(carbonyl)$_{0-1}$C$_{0-10}$ alkyl, (C$_{1-10}$ alkyl)$_{1-2}$aminoC$_{0-10}$ alkyl carbonylC$_{0-10}$ alkyl, C$_{0-10}$ alkylsulfonylC$_{0-10}$ alkyl, (C$_{1-10}$ alkyl)OH, and C$_{1-6}$haloalkyl, wherein $R^3$ is each substituted with 0, 1, 2, 3, or 4 $R^5$ substituents.

In yet another embodiment of the invention, $R^3$ is selected from: cyclopropyl, phenyl, isopropyl, ethyl, cyclobutyl, (dimethylamino)ethyl, methylcarbonyl, 2,2-dimethylpropylcarbonyl, tert-butyloxycarbonyl, tert-butylaminocarbonyl, isopropyloxycarbonyl, pyridyl, methylsulfonyl, methyl, benzyl, ethyl, propyl, hydroxyethyl, methylcarbonyl, phenylcarbonyl, (dimethylamino)methylcarbonyl, ethoxycarbonyl, 1-methylethylcarboxy, methoxycarbonyl, chloro, methoxycyclobutyl, and difluoromethyl, wherein $R^3$ is each substituted with 0, 1, 2, 3, or 4 $R^5$ substituents.

In one embodiment, $R^4$ is selected from halogen, $C_{1-10}$alkyl, $C_{2-10}$alkynyl, and $C_{1-10}$ alkoxy, wherein $R^4$ is substituted with 0, 1, 2, 3, or 4 substituents selected from OH, halogen, and —CO$_2$H.

In another embodiment, $R^4$ is halogen, or $C_{1-10}$alkyl, wherein $R^4$ is substituted with 0, 1, 2, 3, or 4 substituents selected from OH, halogen, and —CO$_2$H. In a variant of this embodiment, $R^4$C$_{1-10}$alkyl, wherein $R^4$ is substituted with 0, 1, 2, 3, or 4 substituents selected from OH, halogen, and —CO$_2$H.

In alternative embodiment, $R^4$ is chloro, fluoro, bromo, methyl, ethyl, iso-propyl, propyl, butyl, iso-butyl, tert-butyl, or pentyl, wherein $R^4$ is substituted with 0, 1, 2, 3, or 4 substituents selected from OH, halogen, and —CO$_2$H. In a variant of this embodiment, $R^4$ is methyl.

In one embodiment of the invention,

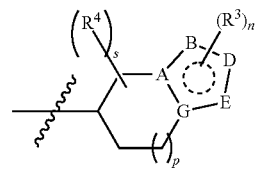

is selected from:

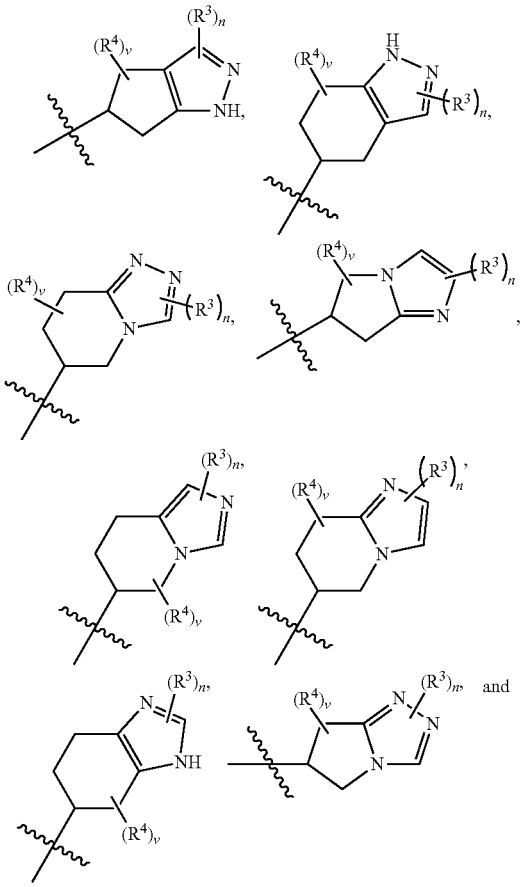

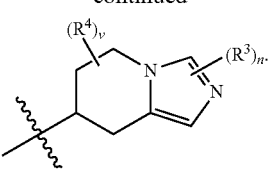

In another embodiment,

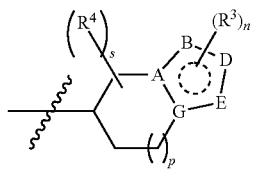

is selected from:

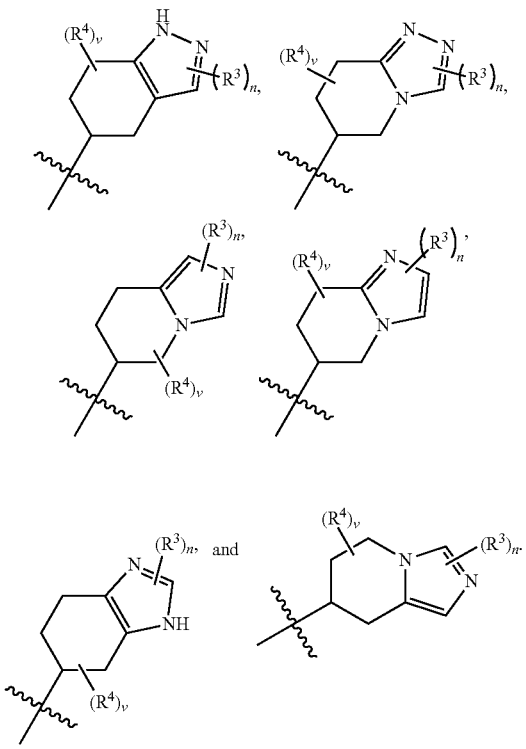

In another embodiment,

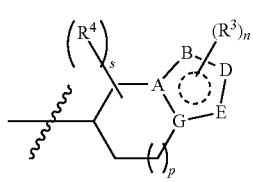

is selected from:

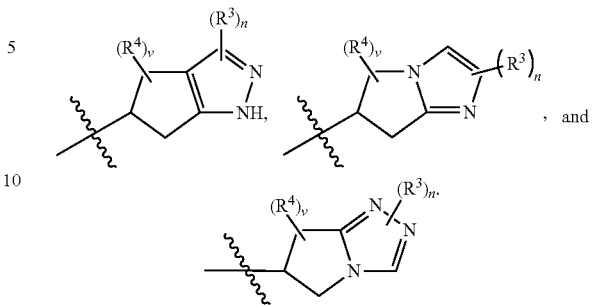

In one embodiment of the invention, $R^5$ is independently selected from: halogen, $C_{1-10}$ alkyl(oxy)$_{0-1}$(carbonyl)$_{0-1}$ $C_{0-10}$ alkyl, $C_{1-10}$ heteroalkyl(oxy)$_{0-1}$ (carbonyl)$_{0-1}C_{0-10}$ alkyl, aryl $C_{0-10}$ alkyl(oxy)$_{0-1}$(carbonyl)$_{0-1}C_{0-10}$ alkyl, $C_{3-12}$ cycloalkyl $C_{0-10}$ alkyl(oxy)$_{0-1}$(carbonyl)$_{0-1}$ $C_{0-10}$ alkyl, heteroaryl $C_{0-10}$ alkyl(oxy)$_{0-1}$ (carbonyl)$_{0-1}C_{0-10}$ alkyl, $(C_{3-12})$ heterocycloalkyl $C_{0-10}$ alkyl(oxy)$_{0-1}$(carbonyl)$_{0-1}C_{0-10}$ alkyl, $C_{1-10}$ alkylamino(carbonyl)$_{0-1}C_{0-10}$ alkyl, $C_{3-12}$ cycloalkyl $C_{0-10}$ alkylamino(carbonyl)$_{0-1}C_{0-10}$ alkyl, aryl $C_{0-10}$ alkylamino(carbonyl)$_{0-1}C_{0-10}$ alkyl, heteroaryl $C_{0-10}$ alkylamino(carbonyl)$_{0-1}C_{0-10}$ alkyl, $(C_{3-12})$heterocycloalkyl $C_{0-10}$ alkylamino(carbonyl)$_{0-1}C_{0-10}$ alkyl, $C_{0-10}$ alkylsulfonyl$C_{0-10}$ alkyl, $(C_{3-12})$cycloalkyl$C_{0-10}$alkylsulfonyl$C_{0-10}$ alkyl, $(C_{3-12})$cycloheteroalkyl$C_{0-10}$alkylsulfonyl$C_{0-10}$ alkyl, heteroaryl$C_{0-10}$ alkylsulfonyl$C_{0-10}$ alkyl, aryl$C_{0-10}$ alkylsulfonyl$C_{0-10}$ alkyl, —CO$_2$(C$_{0-10}$ alkyl), —(C$_{0-10}$ alkyl)CO$_2$H, Oxo (=O), —SO$_2$N(C$_{1-6}$alkyl)$_{1-2}$, —SO$_2$C$_{1-6}$alkyl, —SO$_2$CF$_3$, —SO$_2$CF$_2$H, amino, (C$_{0-10}$ alkyl)$_{1-2}$ amino, hydroxy, (C$_{1-10}$ alkyl)OH, C$_{1-10}$ alkoxy, cyano, and C$_{1-6}$haloalkyl; wherein $R^5$ is substituted with 0, 1, 2, or 3 $R^7$.

In another embodiment, $R^5$ is selected from: halogen, $C_{1-10}$ alkyl(oxy)$_{0-1}$ (carbonyl)$_{0-1}C_{0-10}$ alkyl, $C_{3-12}$ cycloalkyl $C_{0-10}$ alkyl(oxy)$_{0-1}$(carbonyl)$_{0-1}C_{0-10}$ alkyl, heteroaryl $C_{0-10}$ alkyl(oxy)$_{0-1}$(carbonyl)$_{0-1}C_{0-10}$ alkyl, $(C_{3-12})$heterocycloalkyl $C_{0-10}$ alkyl(oxy)$_{0-1}$(carbonyl)$_{0-1}C_{0-10}$ alkyl, $C_{1-10}$ alkylamino(carbonyl)$_{0-1}C_{0-10}$ alkyl, $C_{3-12}$ cycloalkyl $C_{0-10}$ alkylamino(carbonyl)$_{0-1}C_{0-10}$ alkyl, $(C_{3-12})$heterocycloalkyl $C_{0-10}$ alkylamino(carbonyl)$_{0-1}C_{0-10}$ alkyl, $C_{0-10}$ alkylsulfonyl$C_{0-10}$ alkyl, —CO$_2$(C$_{0-10}$ alkyl), —(C$_{0-10}$ alkyl)CO$_2$H, Oxo (=O), —SO$_2$N(C$_{1-6}$alkyl)$_{1-2}$, —SO$_2$C$_{1-6}$alkyl, —SO$_2$CF$_3$, —SO$_2$CF$_2$H, amino, (C$_{0-10}$ alkyl)$_{1-2}$ amino, hydroxy, (C$_{1-10}$ alkyl)OH, C$_{1-10}$ alkoxy, cyano, and C$_{1-6}$haloalkyl; wherein $R^5$ is substituted with 0, 1, 2, or 3 $R^7$.

In another embodiment, $R^5$ is trifluoromethyl or methoxy.

In one embodiment, $R^6$ is independently selected from: halogen, $C_{1-10}$ alkyl(oxy)$_{0-1}$(carbonyl)$_{0-1}C_{0-10}$ alkyl, $C_{1-10}$ haloalkyl(oxy)$_{0-1}$ (carbonyl)$_{0-1}C_{0-10}$ alkyl, aryl $C_{0-10}$ alkyl (oxy)$_{0-1}$(carbonyl)$_{0-1}C_{0-10}$ alkyl, heteroaryl $C_{0-10}$ alkyl (oxy)$_{0-1}$(carbonyl)$_{0-1}C_{0-10}$ alkyl, $C_{0-10}$ alkyl(oxy)$_{0-1}$carbonylamino$C_{0-10}$ alkyl, $C_{0-10}$ alkylamino(oxy)$_{0-1}$carbonyl $C_{0-10}$ alkyl, $(C_{1-10})$heteroalkylamino(oxy)$_{0-1}$ (carbonyl)$_{0-1}$ $C_{0-10}$ alkyl, —CO$_2$(C$_{0-10}$ alkyl), —(C$_{0-10}$ alkyl)CO$_2$H, oxo (=O), $C_{0-10}$ alkylsulfonyl$C_{0-10}$ alkyl, $(C_{3-12})$cycloalkyl $C_{0-10}$alkylsulfonyl$C_{0-10}$ alkyl, $(C_{3-12})$cycloheteroalkyl $C_{0-10}$alkylsulfonyl$C_{0-10}$ alkyl, heteroaryl$C_{0-10}$ alkylsulfonyl$C_{0-10}$ alkyl, aryl$C_{0-10}$ alkylsulfonyl$C_{0-10}$ alkyl, —SO$_2$NH$_2$, —SO$_2$NH(C$_{1-10}$ alkyl), —SO$_2$N(C$_{1-10}$ alkyl)$_2$, amino, (C$_{1-10}$ alkyl)$_{1-2}$ amino, -(oxy)$_{0-1}$(carbonyl)$_{0-1}$N(C$_{0-10}$ alkyl)$_{1-2}$, hydroxy, (C$_{1-10}$ alkyl)OH, C$_{1-10}$ alkoxy, and C$_{1-6}$haloalkyl, wherein $R^6$ is substituted with 0, 1, 2, or 3 $R^7$.

In another embodiment, $R^6$ is independently selected from: halogen, $C_{1-10}$ alkyl(oxy)$_{0-1}$(carbonyl)$_{0-1}C_{0-10}$ alkyl, $C_{1-10}$ haloalkyl(oxy)$_{0-1}$(carbonyl)$_{0-1}C_{0-10}$ alkyl, aryl $C_{0-10}$ alkyl(oxy)$_{0-1}$(carbonyl)$_{0-1}$C$_{0-10}$ alkyl, heteroaryl C$_{0-10}$ alkyl (oxy)$_{0-1}$ (carbonyl)$_{0-1}$C$_{0-10}$ alkyl, C$_{0-10}$ alkyl(oxy)$_{0-1}$carbonylaminoC$_{0-10}$ alkyl, C$_{0-10}$ alkylamino(oxy)$_{0-1}$ carbonyl C$_{0-10}$ alkyl, —CO$_2$(C$_{0-10}$ alkyl), —(C$_{0-10}$ alkyl)CO$_2$H, oxo (=O), C$_{0-10}$ alkylsulfonylC$_{0-10}$ alkyl, —SO$_2$NH$_2$, —SO$_2$N(C$_{1-10}$ alkyl)$_2$, amino, (C$_{1-10}$ alkyl)$_{1-2}$ amino, -(oxy)$_{0-1}$ (carbonyl)$_{0-1}$N(C$_{0-10}$ alkyl)$_{1-2}$, hydroxy, (C$_{1-10}$ alkyl)OH, C$_{1-10}$ alkoxy, and C$_{1-6}$haloalkyl, wherein R$^6$ is substituted with 0, 1, 2, or 3 R$^7$.

In yet another embodiment, R$^6$ is selected from: halogen, aryl C$_{0-10}$ alkyl(oxy)$_{0-1}$(carbonyl)$_{0-1}$C$_{0-10}$ alkyl, heteroaryl C$_{0-10}$ alkyl(oxy)$_{0-1}$(carbonyl)$_{0-1}$C$_{0-10}$ alkyl, and C$_{1-6}$haloalkyl, wherein R$^6$ is substituted with 0, 1, 2, or 3 R$^7$.

In one embodiment of the invention, R$^6$ is selected from: methyl, phenyl, trifluoromethyl, methoxy, fluoro, ethyl, chloro, difluoromethyl, methylsulfonyl, and trifluoroethyl, wherein R$^6$ is substituted with 0, 1, 2, or 3 R$^7$.

In one embodiment, R$^7$ substituent is independently selected from hydroxy, (C$_{1-6}$)alkyl, (C$_{1-6}$)alkoxy, (C$_{5-6}$)aryl, (C$_{5-6}$)heteroaryl, halogen, CO$_2$H, trifluoromethoxy, trifluoroethoxy, trifluoromethyl, trifluoroethyl, amino(C$_{1-6}$ alkyl)$_{1-2}$ and NH$_2$.

In yet another embodiment, R$^7$ is independently selected halogen, CO$_2$H, and NH$_2$. In a variant of this embodiment, R$^7$ is fluoro.

In one embodiment of the invention includes the following compounds and their pharmaceutically acceptable salts thereof:

9-ethyl-N-[3-(1-methylethyl)-5,6,7,8-tetrahydro[1,2,4]triazolo[4,3-a]pyridin-6-yl]-8-(2-methylpyrimidin-5-yl)-9H-purin-6-amine;

(S)-9-ethyl-N-[3-(1-methylethyl)-5,6,7,8-tetrahydro[1,2,4]triazolo[4,3-a]pyridin-6-yl]-8-(2-methylpyrimidin-5-yl)-9H-purin-6-amine;

(R)-9-ethyl-N-[3-(1-methylethyl)-5,6,7,8-tetrahydro[1,2,4]triazolo[4,3-a]pyridin-6-yl]-8-(2-methylpyrimidin-5-yl)-9H-purin-6-amine;

8-(difluoromethyl)-9-ethyl-N-[3-(1-methylethyl)-5,6,7,8-tetrahydro[1,2,4]triazolo[4,3-a]pyridin-6-yl]-9H-purin-6-amine;

(S)-8-(difluoromethyl)-9-ethyl-N-[3-(1-methylethyl)-5,6,7,8-tetrahydro[1,2,4]triazolo[4,3-a]pyridin-6-yl]-9H-purin-6-amine;

(R)-8-(difluoromethyl)-9-ethyl-N-[3-(1-methylethyl)-5,6,7,8-tetrahydro[1,2,4]triazolo[4,3-a]pyridin-6-yl]-9H-purin-6-amine;

N-(3-cyclopropyl-5,6,7,8-tetrahydro[1,2,4]triazolo[4,3-a]pyridin-6-yl)-8-[6-(difluoromethoxy)pyridin-3-yl]-9-ethyl-9H-purin-6-amine;

(S)—N-(3-cyclopropyl-5,6,7,8-tetrahydro[1,2,4]triazolo[4,3-a]pyridin-6-yl)-8-[6-(difluoromethoxy)pyridin-3-yl]-9-ethyl-9H-purin-6-amine;

(R)—N-(3-cyclopropyl-5,6,7,8-tetrahydro[1,2,4]triazolo[4,3-a]pyridin-6-yl)-8-[6-(difluoromethoxy)pyridin-3-yl]-9-ethyl-9H-purin-6-amine;

9-ethyl-N-[3-(1-methylethyl)-5,6,7,8-tetrahydro[1,2,4]triazolo[4,3-a]pyridin-6-yl]-8-[6-(trifluoromethyl)pyridin-3-yl]-9H-purin-6-amine;

(S)-9-ethyl-N-[3-(1-methylethyl)-5,6,7,8-tetrahydro[1,2,4]triazolo[4,3-a]pyridin-6-yl]-8-[6-(trifluoromethyl)pyridin-3-yl]-9H-purin-6-amine;

(R)-9-ethyl-N-[3-(1-methylethyl)-5,6,7,8-tetrahydro[1,2,4]triazolo[4,3-a]pyridin-6-yl]-8-[6-(trifluoromethyl)pyridin-3-yl]-9H-purin-6-amine;

9-ethyl-N-[(6S)-3-(1-methylethyl)-5,6,7,8-tetrahydro[1,2,4]triazolo[4,3-a]pyridin-6-yl]-8-[4-(trifluoromethyl)phenyl]-9H-purin-6-amine;

(S)-9-ethyl-N-[(6S)-3-(1-methylethyl)-5,6,7,8-tetrahydro[1,2,4]triazolo[4,3-a]pyridin-6-yl]-8-[4-(trifluoromethyl)phenyl]-9H-purin-6-amine;

(R)-9-ethyl-N-[(6S)-3-(1-methylethyl)-5,6,7,8-tetrahydro[1,2,4]triazolo[4,3-a]pyridin-6-yl]-8-[4-(trifluoromethyl)phenyl]-9H-purin-6-amine;

9-ethyl-6-{[3-(1-methylethyl)-5,6,7,8-tetrahydro[1,2,4]triazolo[4,3-a]pyridin-6-yl]oxy}-8-(2-methylpyrimidin-5-yl)-9H-purine;

(S)-9-ethyl-6-{[3-(1-methylethyl)-5,6,7,8-tetrahydro[1,2,4]triazolo[4,3-a]pyridin-6-yl]oxy}-8-(2-methylpyrimidin-5-yl)-9H-purine;

(R)-9-ethyl-6-{[3-(1-methylethyl)-5,6,7,8-tetrahydro[1,2,4]triazolo[4,3-a]pyridin-6-yl]oxy}-8-(2-methylpyrimidin-5-yl)-9H-purine;

N-{1-[2-(dimethylamino)ethyl]-3-(1-methylethyl)-4,5,6,7-tetrahydro-1H-indazol-5-yl}-9-ethyl-8-(2-methylpyrimidin-5-yl)-9H-purin-6-amine;

(S)—N-{1-[2-(dimethylamino)ethyl]-3-(1-methylethyl)-4,5,6,7-tetrahydro-1H-indazol-5-yl}-9-ethyl-8-(2-methylpyrimidin-5-yl)-9H-purin-6-amine;

(R)—N-{1-[2-(dimethylamino)ethyl]-3-(1-methylethyl)-4,5,6,7-tetrahydro-1H-indazol-5-yl}-9-ethyl-8-(2-methylpyrimidin-5-yl)-9H-purin-6-amine;

9-ethyl-N-[3-(1-methylethyl)-4,5,6,7-tetrahydro-1H-indazol-5-yl]-8-[4-(trifluoromethyl)phenyl]-9H-purin-6-amine;

(R)-9-ethyl-N-[3-(1-methylethyl)-4,5,6,7-tetrahydro-1H-indazol-5-yl]-8-[4-(trifluoromethyl)phenyl]-9H-purin-6-amine;

(S)-9-ethyl-N-[3-(1-methylethyl)-4,5,6,7-tetrahydro-1H-indazol-5-yl]-8-[4-(trifluoromethyl)phenyl]-9H-purin-6-amine 9-ethyl-N-[5-methyl-3-(1-methylethyl)-4,5,6,7-tetrahydro-1H-indazol-5-yl]-8-(2-methylpyrimidin-5-yl)-9H-purin-6-amine;

(S)-9-ethyl-N-[5-methyl-3-(1-methylethyl)-4,5,6,7-tetrahydro-1H-indazol-5-yl]-8-(2-methylpyrimidin-5-yl)-9H-purin-6-amine;

(R)-9-ethyl-N-[5-methyl-3-(1-methylethyl)-4,5,6,7-tetrahydro-1H-indazol-5-yl]-8-(2-methylpyrimidin-5-yl)-9H-purin-6-amine;

9-ethyl-N-[3-(1-methylethyl)-4,5,6,7-tetrahydro-1H-indazol-5-yl]-8-[4-(trifluoromethyl)phenyl]-9H-purin-6-amine;

(S)-9-ethyl-N-[3-(1-methylethyl)-4,5,6,7-tetrahydro-1H-indazol-5-yl]-8-[4-(trifluoromethyl)phenyl]-9H-purin-6-amine;

(R)-9-ethyl-N-[3-(1-methylethyl)-4,5,6,7-tetrahydro-1H-indazol-5-yl]-8-[4-(trifluoromethyl)phenyl]-9H-purin-6-amine;

2-[5-{[9-ethyl-8-(2-methylpyrimidin-5-yl)-9H-purin-6-yl]amino}-3-(1-methylethyl)-4,5,6,7-tetrahydro-1H-indazol-1-yl]ethanol;

(S)-2-[5-{[9-ethyl-8-(2-methylpyrimidin-5-yl)-9H-purin-6-yl]amino}-3-(1-methylethyl)-4,5,6,7-tetrahydro-1H-indazol-1-yl]ethanol;

(R)-2-[5-{[9-ethyl-8-(2-methylpyrimidin-5-yl)-9H-purin-6-yl]amino}-3-(1-methylethyl)-4,5,6,7-tetrahydro-1H-indazol-1-yl]ethanol;

N-(3-cyclopropyl-5,6,7,8-tetrahydroimidazo[1,2-a]pyridin-6-yl)-9-ethyl-8-(2-methylpyrimidin-5-yl)-9H-purin-6-amine;

(S)—N-(3-cyclopropyl-5,6,7,8-tetrahydroimidazo[1,2-a]pyridin-6-yl)-9-ethyl-8-(2-methylpyrimidin-5-yl)-9H-purin-6-amine;

(R)—N-(3-cyclopropyl-5,6,7,8-tetrahydroimidazo[1,2-a]pyridin-6-yl)-9-ethyl-8-(2-methylpyrimidin-5-yl)-9H-purin-6-amine;
9-ethyl-N-[3-(1-methylethyl)-5,6,7,8-tetrahydroimidazo[1,2-a]pyridin-6-yl]-8-(2-methylpyrimidin-5-yl)-9H-purin-6-amine;
(S)-9-ethyl-N-[3-(1-methylethyl)-5,6,7,8-tetrahydroimidazo[1,2-a]pyridin-6-yl]-8-(2-methylpyrimidin-5-yl)-9H-purin-6-amine;
(R)-9-ethyl-N-[3-(1-methylethyl)-5,6,7,8-tetrahydroimidazo[1,2-a]pyridin-6-yl]-8-(2-methylpyrimidin-5-yl)-9H-purin-6-amine;
N-(1-cyclopropyl-4,5,6,7-tetrahydro-1H-benzimidazol-6-yl)-9-ethyl-8-[6-(trifluoromethyl)pyridin-3-yl]-9H-purin-6-amine;
(S)—N-(1-cyclopropyl-4,5,6,7-tetrahydro-1H-benzimidazol-6-yl)-9-ethyl-8-[6-(trifluoromethyl)pyridin-3-yl]-9H-purin-6-amine;
(R)—N-(1-cyclopropyl-4,5,6,7-tetrahydro-1H-benzimidazol-6-yl)-9-ethyl-8-[6-(trifluoromethyl)pyridin-3-yl]-9H-purin-6-amine;
6-[(1-cyclopropyl-4,5,6,7-tetrahydro-1H-benzimidazol-6-yl)amino]-9-ethyl-N-(2,2,2-trifluoroethyl)-9H-purine-8-carboxamide;
(R)-6-[(1-cyclopropyl-4,5,6,7-tetrahydro-1H-benzimidazol-6-yl)amino]-9-ethyl-N-(2,2,2-trifluoroethyl)-9H-purine-8-carboxamide;
(S)-6-[(1-cyclopropyl-4,5,6,7-tetrahydro-1H-benzimidazol-6-yl)amino]-9-ethyl-N-(2,2,2-trifluoroethyl)-9H-purine-8-carboxamide;
N-[1-cyclopropyl-2-(difluoromethyl)-4,5,6,7-tetrahydro-1H-benzimidazol-6-yl]-9-ethyl-8-(2-methylpyrimidin-5-yl)-9H-purin-6-amine;
(S)—N-[1-cyclopropyl-2-(difluoromethyl)-4,5,6,7-tetrahydro-1H-benzimidazol-6-yl]-9-ethyl-8-(2-methylpyrimidin-5-yl)-9H-purin-6-amine;
(R)—N-[1-cyclopropyl-2-(difluoromethyl)-4,5,6,7-tetrahydro-1H-benzimidazol-6-yl]-9-ethyl-8-(2-methylpyrimidin-5-yl)-9H-purin-6-amine;
9-ethyl-N-[1-(cis-3-methoxycyclobutyl)-4,5,6,7-tetrahydro-1H-benzimidazol-6-yl]-8-(2-methylpyrimidin-5-yl)-9H-purin-6-amine;
(S)-9-ethyl-N-[1-(cis-3-methoxycyclobutyl)-4,5,6,7-tetrahydro-1H-benzimidazol-6-yl]-8-(2-methylpyrimidin-5-yl)-9H-purin-6-amine;
(R)-9-ethyl-N-[1-(cis-3-methoxycyclobutyl)-4,5,6,7-tetrahydro-1H-benzimidazol-6-yl]-8-(2-methylpyrimidin-5-yl)-9H-purin-6-amine;
9-ethyl-N-[7-methyl-1-(1-methylethyl)-4,5,6,7-tetrahydro-1H-benzimidazol-6-yl]-8-(2-methylpyrimidin-5-yl)-9H-purin-6-amine;
9-ethyl-N-[(6S, 7S)-7-methyl-1-(1-methylethyl)-4,5,6,7-tetrahydro-1H-benzimidazol-6-yl]-8-(2-methylpyrimidin-5-yl)-9H-purin-6-amine; and
9-ethyl-N-[(6R, 7R)-7-methyl-1-(1-methylethyl)-4,5,6,7-tetrahydro-1H-benzimidazol-6-yl]-8-(2-methylpyrimidin-5-yl)-9H-purin-6-amine.

Yet another embodiment of the invention includes compounds or their pharmaceutically acceptable salts thereof selected from:
9-ethyl-N-[3-(1-methylethyl)-5,6,7,8-tetrahydro[1,2,4]triazolo[4,3-a]pyridin-6-yl]-8-(2-methylpyrimidin-5-yl)-9H-purin-6-amine;
8-(difluoromethyl)-9-ethyl-N-[3-(1-methylethyl)-5,6,7,8-tetrahydro[1,2,4]triazolo[4,3-a]pyridin-6-yl]-9H-purin-6-amine;
N-(3-cyclopropyl-5,6,7,8-tetrahydro[1,2,4]triazolo[4,3-a]pyridin-6-yl]-8-[6-(difluoromethoxy)pyridin-3-yl]-9-ethyl-9H-purin-6-amine;
9-ethyl-N-[3-(1-methylethyl)-5,6,7,8-tetrahydro[1,2,4]triazolo[4,3-a]pyridin-6-yl]-8-[6-(trifluoromethyl)pyridin-3-yl]-9H-purin-6-amine;
9-ethyl-N-[(6S)-3-(1-methylethyl)-5,6,7,8-tetrahydro[1,2,4]triazolo[4,3-a]pyridin-6-yl]-8-[4-(trifluoromethyl)phenyl]-9H-purin-6-amine;
9-ethyl-6-{[3-(1-methylethyl)-5,6,7,8-tetrahydro[1,2,4]triazolo[4,3-a]pyridin-6-yl]oxy}-8-(2-methylpyrimidin-5-yl)-9H-purine;
N-{1-[2-(dimethylamino)ethyl]-3-(1-methylethyl)-4,5,6,7-tetrahydro-1H-indazol-5-yl}-9-ethyl-8-(2-methylpyrimidin-5-yl)-9H-purin-6-amine;
9-ethyl-N-[3-(1-methylethyl)-4,5,6,7-tetrahydro-1H-indazol-5-yl]-8-[4-(trifluoromethyl)phenyl]-9H-purin-6-amine;
9-ethyl-N-[5-methyl-3-(1-methylethyl)-4,5,6,7-tetrahydro-1H-indazol-5-yl]-8-(2-methylpyrimidin-5-yl)-9H-purin-6-amine;
9-ethyl-N-[3-(1-methylethyl)-4,5,6,7-tetrahydro-1H-indazol-5-yl]-8-[4-(trifluoromethyl)phenyl]-9H-purin-6-amine;
2-[5-{[9-ethyl-8-(2-methylpyrimidin-5-yl)-9H-purin-6-yl]amino}-3-(1-methylethyl)-4,5,6,7-tetrahydro-1H-indazol-1-yl]ethanol;
N-(3-cyclopropyl-5,6,7,8-tetrahydroimidazo[1,2-a]pyridin-6-yl)-9-ethyl-8-(2-methylpyrimidin-5-yl)-9H-purin-6-amine;
9-ethyl-N-[3-(1-methylethyl)-5,6,7,8-tetrahydroimidazo[1,2-a]pyridin-6-yl]-8-(2-methylpyrimidin-5-yl)-9H-purin-6-amine;
N-(1-cyclopropyl-4,5,6,7-tetrahydro-1H-benzimidazol-6-yl)-9-ethyl-8-[6-(trifluoromethyl)pyridin-3-yl]-9H-purin-6-amine;
6-[(1-cyclopropyl-4,5,6,7-tetrahydro-1H-benzimidazol-6-yl)amino]-9-ethyl-N-(2,2,2-trifluoroethyl)-9H-purine-8-carboxamide;
N-[1-cyclopropyl-2-(difluoromethyl)-4,5,6,7-tetrahydro-1H-benzimidazol-6-yl]-9-ethyl-8-(2-methylpyrimidin-5-yl)-9H-purin-6-amine;
9-ethyl-N-[1-(cis-3-methoxycyclobutyl)-4,5,6,7-tetrahydro-1H-benzimidazol-6-yl]-8-(2-methylpyrimidin-5-yl)-9H-purin-6-amine; and
9-ethyl-N-[7-methyl-1-(1-methylethyl)-4,5,6,7-tetrahydro-1H-benzimidazol-6-yl]-8-(2-methylpyrimidin-5-yl)-9H-purin-6-amine.

"Patient" for the purposes of the present invention includes humans and other animals, particularly mammals and other organisms. Thus the methods are applicable to both human therapy and veterinary applications.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —$(CR_3R_3)_2$—, each occurrence of the two $R_3$ groups may be the same or different. As used herein, unless explicitly stated to the contrary, each reference to a specific compound of the present invention or a generic formula of compounds of the present invention is intended to include the compound (s) as well as pharmaceutically acceptable salts thereof.

Optical Isomers—Diastereomers—Geometric Isomers—Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the class of compounds without specific stereochemistry. When the compounds of the present invention contain one chiral center, the term "stereoisomer" includes both enantiomers and mixtures of enantiomers, such as the specific 50:50 mixture referred to as racemic mixtures.

In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereomeric compound is named using an "and" in the stereomeric designation, for example, (S and R)—N-[1-(3,3-dimethylbutanoyl)-3-(1-methylethyl)-4,5,6,7-tetrahydro-1H-indazol-5-yl]-9-ethyl-8-(2-methylpyrimidin-5-yl)-9H-purin-6-amine, the "and" indicates a racemic mixture of the enantiomers. That is, the individual enantiomers were not individually isolated.

When the stereomeric nomenclature includes "or", for example, (S or R)-9-ethyl-N-[5-methyl-3-(1-methylethyl)-4,5,6,7-tetrahydro-1H-indazol-5-yl]-8-(2-methylpyrimidin-5-yl)-9H-purin-6-amine, the "or" indicates that chiral resolution of racemate into individual enantiomers was accomplished but the actual optical activity of the specific enantiomer was not determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I, subsets thereof, embodiments thereof, as well as specific compounds are meant to also include the pharmaceutically acceptable salts.

Furthermore, some of the crystalline forms for compounds of the present invention may exist as polymorphs and as such all forms are intended to be included in the present invention.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-(C1-C2)alkyl and piperidino-, pyrrolidino- or morpholino$(C_2-C_3)$alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$ alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$alkyl and Y$^3$ is $(C_1-C_6)$alkyl, carboxy $(C_1-C_6)$alkyl, amino$(C_1-C_4)$alkyl or mono-N- or di-N,N—$(C_1-C_6)$alkylaminoalkyl, —C(Y$^4$)Y$^5$ wherein Y$^4$ is H or methyl and Y$^5$ is mono-N- or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Additionally, the present invention is meant to include in compounds of generic Formula I, all suitable replacements of sp3 orbital carbons to sp3 Si as can readily be invisoned by one of ordinary skill in the art.

Utilities

Compounds of the Invention have activity for PI3K-delta. Compounds of this invention have been tested using the assays described in the Biological Examples and have been determined to be inhibitors of PI3K-delta. Suitable in vitro assays for measuring PI3K-delta activity and the inhibition thereof by compounds are known in the art. For further details of an in vitro assay for measuring PI3K-delta see the Biological Examples herein. Cell-based assays for measurement of in vitro efficacy in treatment of cancer are known in the art. In addition, assays are described in the Biological Examples provided herein.

Suitable in vivo models for cancer are known to those of ordinary skill in the art. See for example, international patent application published as WO 2012/037226 for further details of in vivo models for prostate adenocarcinoma, glioblastoma, lung carcinoma, and melanoma. Following the examples disclosed herein, as well as that disclosed in the art, a person of ordinary skill in the art can determine the activity of a compound of this invention.

Compounds of Formula I are useful for treating diseases, including autoimmune disorders, inflammatory diseases, and cancers, which are listed below.

Cancers:

Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplasia syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

Autoimmune Diseases:

Hashimoto's thyroiditis, systemic lupus erythematosus (SLE), Goodpasture's syndrome, pemphigus, receptor autoimmune diseases, Basedow's disease (Graves' disease), myasthernia gravis, insulin resistant diseases, autoimmune hemolytic anemia, autoimmune thrombocytopenic purpura, autoimmune encephalomyelitis, rheumatism, rheumatoid arthritis, scleroderma, mixed connective tissue disease, polymyositis, pernicious anemia, idiopathic Addison's disease, some types of infertility, glomerulonephritis, bullous pemphigus, Sjogren's syndrome, some types of diabetes, adrenergic agent resistance, chronic active hepatitis, primary biliary cirrhosis, endocrine failure, vitiligo, angiitis, post-cardiac surgery syndrome, urticaria, atopic dermatiti and multiple sclerosis, autoimmune polyglandular disease (also known as autoimmune polyglandular syndrome), autoimmune alopecia; pernicious anemia; vitiligo; autoimmune hypopituatarism, and Guillain-Barre syndrome.

Inflammatory Diseases:

asthma, allergic rhinitis, psoriasis, inflammatory arthritis, rheumatoid arthritis, psoriatic arthritis or osteoarthritis, irritable bowel syndrome, ulcerative colitis, Crohn's disease, respiratory allergies (asthma, hay fever, allergic rhinitis) or skin allergies, scleracierma, mycosis fungoides, acute inflammatory responses (such as acute respiratory distress syndrome and ishchemia/reperfusion injury), dermatomyositis, alopecia greata, chronic actinic dermatitis, eczema, Behcet's disease, Pustulosis palmoplanteris, Pyoderma gangrenum, Sezary's syndrome, atopic dermatitis, systemic sclerosis, and morphea.

Central Nervous System Disorders:

multiple sclerosis, schizophrenia

Thus, in one embodiment, the invention provides a method of inhibiting PI3K-delta comprising contacting the PI3K-delta with an effective amount of a compound as disclosed herein.

In one embodiment, the compounds of the instant invention are selective PI3K-delta inhibitors relative to PI3K-alpha. The determination of relative selectivity for a given compound of PI3K-delta inhibition is defined as the relative ratio of the (PI3K-alpha $IC_{50}$ value/PI3K-delta $IC_{50}$ value) is at least 2. In yet another embodiment, for a given compound, the relative ratios of the (PI3K-alpha $IC_{50}$ value/PI3K-delta $IC_{50}$ value) is at least 4.

In another embodiment, the invention provides a method of treating a PI3K-delta modulated disease comprising administering to a mammal in need of such treatment a therapeutically effective amount of a compound as disclosed herein.

In another embodiment, the invention provides a method of treating cancer disease mediated by PI3K-delta comprising administering to a mammal in need of such treatment a therapeutically effective amount of a compound as disclosed herein.

Compounds of the invention are also useful as inhibitors of PI3K-delta in vivo for studying the in vivo role of PI3K-delta in biological processes, including the diseases described herein. Accordingly, the invention also comprises a method of inhibiting PI3K-delta in vivo comprising administering a compound or composition of the invention to a mammal.

Accordingly, another aspect of the present invention provides a method for the treatment or prevention of a PI3K-delta mediated disease or disorder comprising administering to a mammal in need thereof a therapeutically effective amount of a compound of formula I. In one embodiment such diseases include asthma and rheumatoid arthritis.

Another aspect of the present invention provides for the use of a compound of formula I in the manufacture of a medicament for the treatment or prevention of a PI3K-delta mediated diseases or disorder.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 milligram of active agent per kilogram body weight of a mammal (mg/kg) to about 100 mg/kg, typically, between 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.01 mg to 10 g of active agent compounded with an appropriate and convenient amount of carrier material which may vary from about 5 to about 99.95 percent of the total composition. Dosage unit forms will generally contain between from about 0.1 mg to about 0.5 g of an active ingredient, typically 0.5 mg, 1 mg, 2 mg, 5 mg, 10 mg, 25 mg, 50 mg, 100 mg, 200 mg, 400 mg, or 500 mg.

If formulated as a fixed dose, such combination products employ the compounds of this invention within the dosage range described above and the other pharmaceutically acceptable agent(s) when a combination formulation is inappropriate.

The final dosage regimen will be determined by the attending physician in view of good medical practice, considering various factors that modify the action of drugs, e.g., the agent's specific activity, the identity and severity of the disease state, the responsiveness of the patient, the age, condition, body weight, sex, and diet of the patient, and the severity of any infection. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, can be preferred for continuous infusion.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or *arachis* oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI)

which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 m to about 10 µm; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especiallylactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferablylies between 60 microns and 1000 microns. The relativelylarge size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

In certain embodiments, a compound of Formula I is combined in a pharmaceutical combination formulation, or dosing regimen as combination therapy, with one or more other therapeutic agent that has anti-inflammatory or anti-hyperproliferative properties or that is useful for treating an inflammation, immune-response disorder, or hyperproliferative disorder (e.g., cancer). The other therapeutic agent of the pharmaceutical combination formulation or dosing regimen preferably has complementary activities to the compound of Formula I such that they do not adversely affect each other. Such agents are suitably present in combination in amounts that are effective for the purpose intended.

In one embodiment of the invention, the compound of Formula I, or a stereoisomer, tautomer, or pharmaceutically acceptable salt or prodrug thereof, may be co-administered with one or more other therapeutic agents for the treatment and prevention of PI3Kdelta mediated diseases. Thus in another aspect the present invention provides pharmaceutical compositions for treating PI3Kdelta mediated diseases comprising a therapeutically effective amount of a compound of Formula I and one or more other therapeutic agents.

In one embodiment for example, for the treatment of the inflammatory diseases rheumatoid arthritis, psoriasis, inflammatory bowel disease, COPD, asthma and allergic rhinitis a compound of formula I may be combined with other therapeutic agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclidinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

In another embodiment of the invention, the compounds of Formula I, or a stereoisomer, tautomer, or pharmaceutically acceptable salt or prodrug thereof, may be employed alone or in combination with other therapeutic agents for the treatment of hyperproliferative disorders (e.g., cancer) including standard chemotherapy regimens, and anti-CD20 monoclonal antibodies, rituximab, bendamustine, ofatumumab, fludarabine, lenalidomide, and/or bortezomib.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active therapeutic agents simultaneously exert their biological activities.

SCHEMES AND EXAMPLES

The abbreviations used herein have the following tabulated meanings. Abbreviations not tabulated below have their meanings as commonly used unless specifically stated otherwise.

Abbreviations Used in the Description of Compound Preparation

| BINAP | 2,2'-bis(diphenylphosphino)-1,1'-binaphthalene |
| Boc | tert-butoxycarbamate |
| BSA | N-trimethylsilyl-1-trimethylsilyloxyethanimine |
| Cbz | benzyl chloroformate |
| DBU | 1,8-diazabicyclo[5.4.0]undec-7-ene |
| DCE | 1,2-dichloroethane |
| DCM | Dichloromethane |
| DIAD | diisopropyl azidocarboxylate |
| DIEA | N,N-diisopropylethylamine |
| DMA | Dimethylacetamide |
| DMAP | Dimethylaminopyridine |
| DME | Dimethoxyethane |
| DMF | Dimethylformamide |
| DMSO | dimethyl sulfoxide |
| DPPA | diphenylphosphoryl azide |
| dppf | 1,1-bis(diphenylphosphino)ferrocene |
| EI | electron ionization |
| EtOAc (EA) | ethyl acetate |
| HATU | 1-[bis(dimethylamino)methylene]-1H-1,2,3-triazolo[4,5-b]pyridinium 3-oxid-hexafluorophosphate |
| HPLC | high performance liquid chromatography |
| i-PrOH | 2-propanol |
| LC/MS | liquid chromatography coupled to mass spectrometer |
| LDA | lithium diisopropylamide |
| LHMDS | lithium hexamethyldisilazide |
| MeCN | Acetonitrile |
| MeOH | Methanol |
| MS | mass spectrum (data) |
| NCS | N-chlorosuccinamide |
| NMP | n-methylpyrrolidone |
| NMR | nuclear magnetic resonance (data) |
| Pd(dppf) | [1,1'-bis(diphenylphosphino)ferrocene]dichloro-palladium(II) |
| PE | petroleum ether |
| RT | room temperature |
| SFC | supercritical fluidic chromatography |
| t-Bu, tBu | tert-butyl |
| t-BuOH | tert-butanol |
| TBS | tert-butyldimethylsilyl |
| TEA | Triethylamine |
| TFA | trifluoroacetic acid |
| THF | Tetrahydrofuran |

General Synthetic Schemes

Several synthetic routes were employed in the syntheses of the compounds described herein. In one approach, 4,6-dichloropyrimidine-5-amine is elaborated to a common intermediate Gen-1 by addition of an amine (e.g. $R^1$—$NH_2$) followed by cyclization. In one synthesis route, oxidative cyclization with an aldehyde is employed to yield the corresponding purine, Gen-1. Next, Gen-1 is elaborated to Gen-2 by addition of the appropriate bicyclic nucleophile. Illustrative of this sequence is the reaction with a substituted 5,6,7,8-tetrahydro-[1,2,4]triazolo[4,3-a]pyridin-6-amine that yields the corresponding N-(5,6,7,8-tetrahydro-[1,2,4]triazolo[4,3-a]pyridin-6-yl)-9H-purin-6-amine.

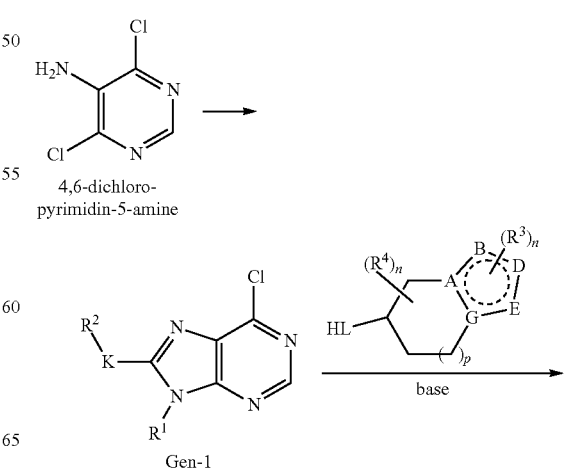

-continued

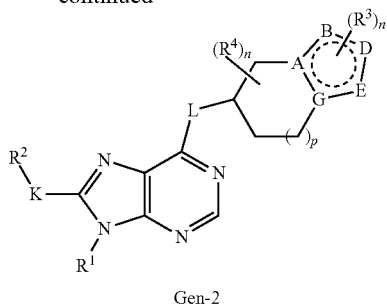

Gen-2

Alternatively, the bicyclic amine or alcohol nucleophile can be incorporated into the structure bearing a protective group, forming an intermediate such as Gen-3. The protective group is then removed and functionalized with diverse $R^3$ to arrive at the final compounds (designated Gen-2). For example, a Boc protective group could be removed by treatment with dilute acid.

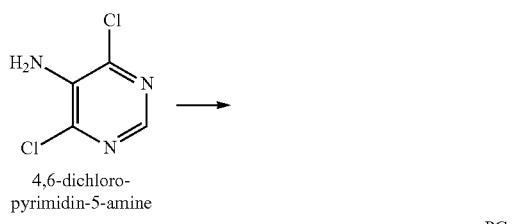

4,6-dichloro-pyrimidin-5-amine

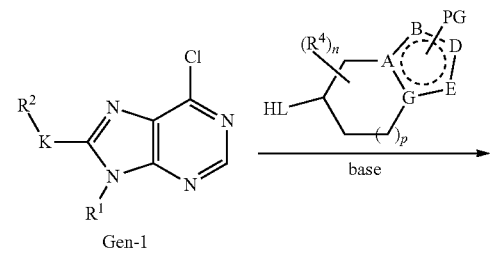

Gen-1

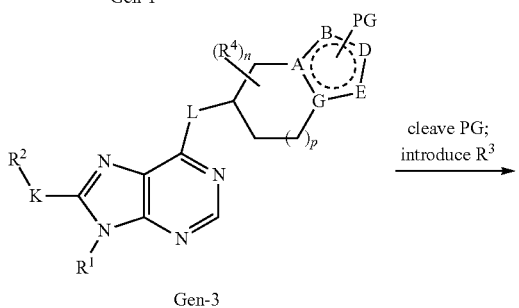

Gen-3 cleave PG; introduce $R^3$

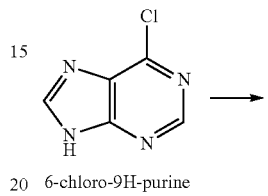

6-chloro-9H-purine

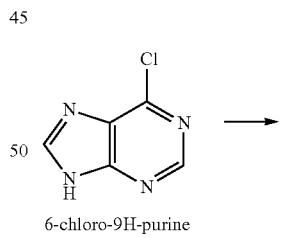

6-chloro-9H-purine

Gen-2

In yet another approach, 6-chloro-9H-purine is elaborated to Gen-4 via alkylation with an alkyl halide, followed by halogenation of the 2-position of the purine (X=Cl, I). Gen-4 can then be elaborated to Gen-via cross-coupling, utilizing techniques, such as a Suzuki coupling with a boronic ester. Alternatively, Gen-4 could be elaborated to Gen-1 via addition of a nucleophile, such as, for example, an amine to form the corresponding 2-aminopurine. In another synthesis route, Gen-4 may be elaborated to Gen-1 via carbonylation to afford the purine carboxylate. Once formed, Gen-1 may be elaborated to Gen-2 by either of the two approaches described above.

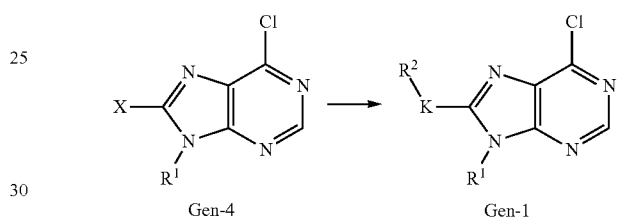

Gen-4                    Gen-1

In yet another synthesis route, Gen-4 is elaborated to Gen-5 by addition of the appropriate amine nucleophile. Gen-5 is subsequently elaborated to Gen-2 via cross-coupling, such as, for example, a Suzuki coupling with a boronic ester. In an alternative route, Gen-5 is elaborated to Gen-2 via addition of a nucleophile. For example, the addition of an amine would form the corresponding 2-aminopurine.

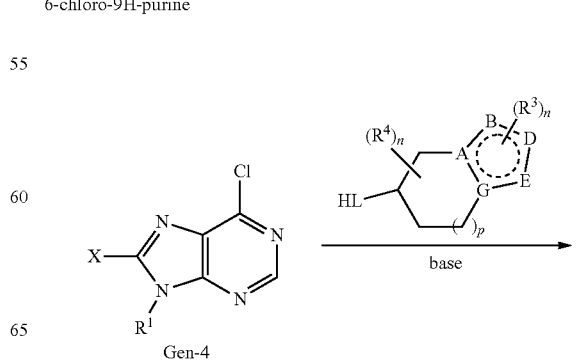

Gen-4

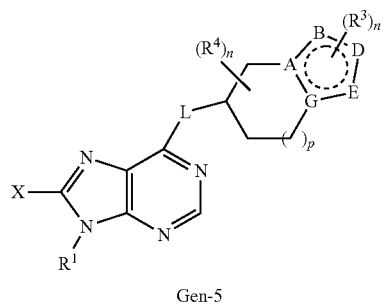

Gen-5

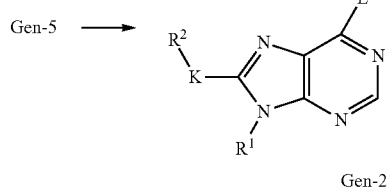

Gen-2

Many synthetic routes were employed to access the bicyclic amine or alcohol nucleophiles employed in the above generic schemes, these synthetic routes are readily accessible and known to those skilled in the art of synthetic chemistry. Such routes include, but are not limited to, the following schemes.

Beginning from a commercially available or known substituted piperidone, Gen-7 may be formed by the addition of a protective group followed by formation of a thioether. For example, if L is O, then a TBS group could be introduced and a corresponding thioether can be formed through the use of Lawesson's reagent. From this point, Gen-7 is then taken to Gen-8 via the addition of a hydrazide and removal of the protective group (PG). Illustrative of this route is the addition of cyclopropanecarbohydrazide to Gen-7 followed by cleavage of the TBS protecting group via standard methods to afford the corresponding 3-cyclopropyl-5,6,7,8-tetrahydro-[1,2,4]triazolo[4,3-a]pyridinol, which then can be employed in any of the generic coupling methods with the purine as described above.

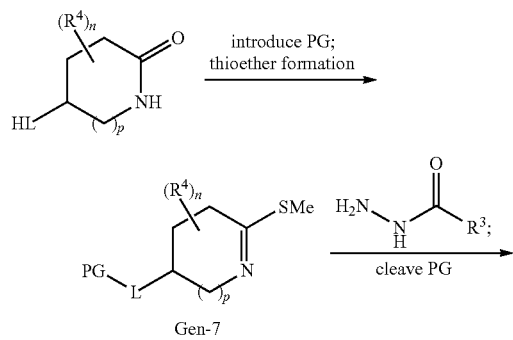

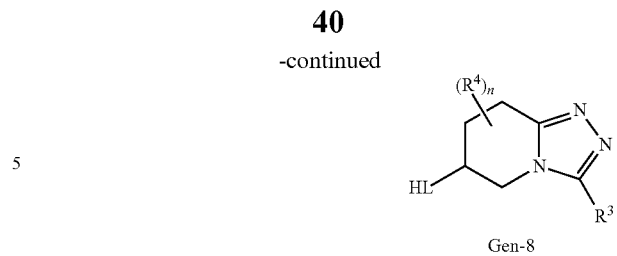

Gen-8

In an alternative route, a commercial or known oxopiperidine carboxylic acid may be used instead of a piperidone amine or alcohol, which could then be elaborated to Gen-9 via the use of Lawesson's Reagent followed by hydrazide addition. The resulting substituted 5,6,7,8-tetrahydro-[1,2,4]triazolo[4,3-a]pyridine-6-carboxylic acid could then undergo a Curtius rearrangement and Cbz group removal to afford Gen-10. Gen-10 could then engage in any of the generic coupling methods with the purine as described previously.

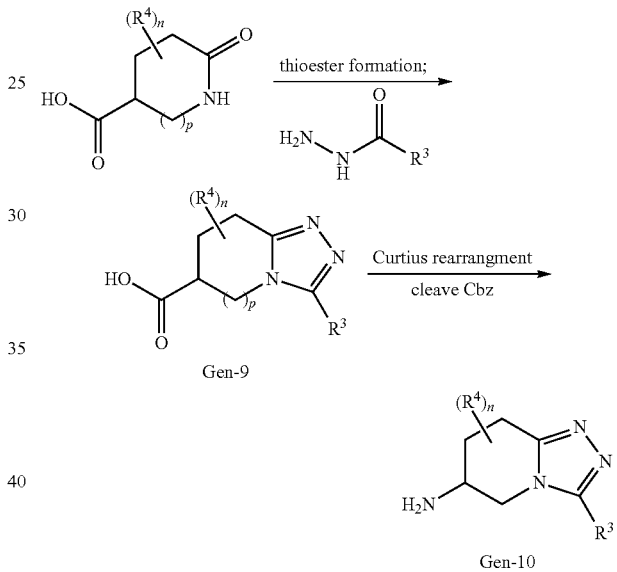

In some cases, a commercial or known cyclic ketone carboxylic acid may be acylated using standard enolate acylation procedures to form Gen-11, after which hydrazine is added and subsequently a protecting group, such as for example, a Boc group, is introduced to provide Gen-12. Gen-12 then can be elaborated to Gen-13 by a Curtius rearrangement followed by removal of the protective groups under standard conditions. For example, the Cbz group resulting from the Curtius rearrangement could be cleaved via hydrogenation and the Boc group removed via treatment with dilute acid. Gen-13 could then engage in any of the generic coupling methods with the purine as described above.

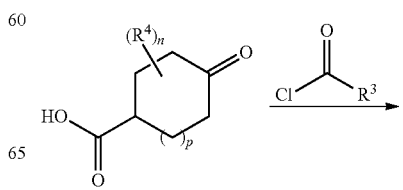

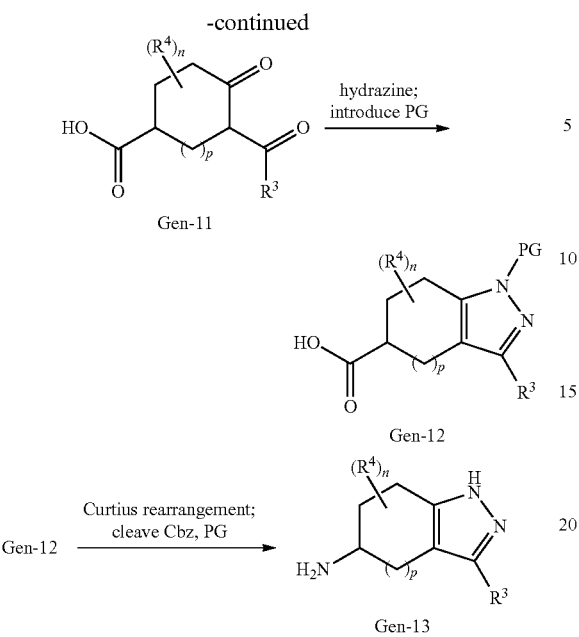

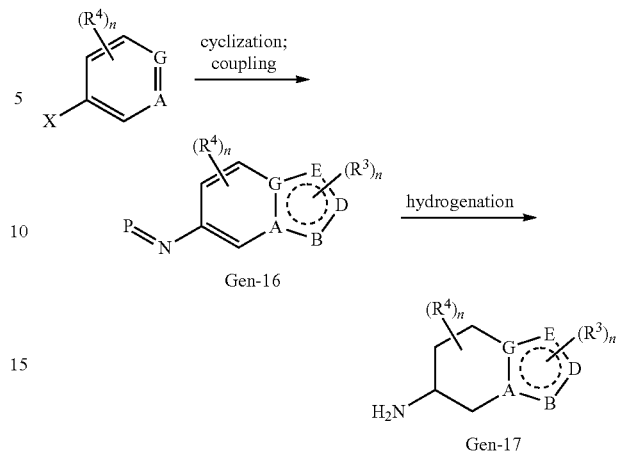

In some cases, the bicycle may be formed from a known or commercial functionalized nitro-arene where G or A is N or a functionalized carbon. For example, in some cases A=N and G=C—NH$_2$. This precursor is then cyclized to form the fully aromatized heterocyclic biaryl Gen-14. For example, the addition of a functionalized alpha-chloro aldehyde would give the corresponding imidazo[1,2-a]pyridine. Gen-14 is then subjected to hydrogenation conditions to provide Gen-15, which could then engage in any of the generic coupling methods with the purine as described above.

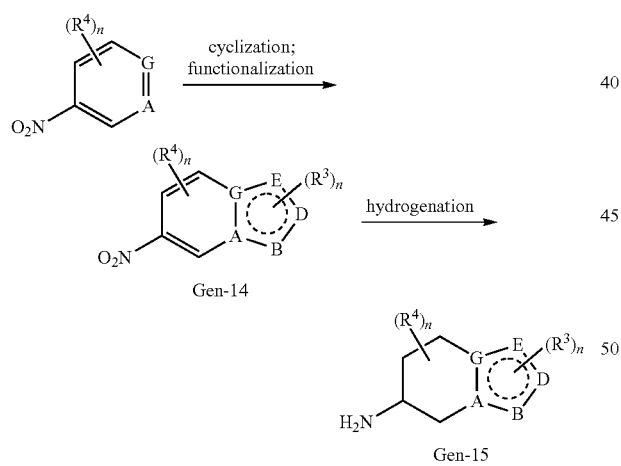

In another variant synthesis route, a commercial or known halo-arene precursor is used in place of a nitro-arene precursor. This precursor may be cyclized as described above, after which the functionalized, fully aromatized heterocyclic biaryl halide undergoes cross-coupling to provide Gen-16, which contains an amine precursor. Gen-16 can then be elaborated to Gen-17 using hydrogenation conditions, such as, for example, P=N=N, and under hydrogenation conditions this azide substitution could be reduced to the alkyl amine. Once formed, Gen-17 could then engage in any of the generic coupling methods with the purine as described above.

Specific illustrations of these general synthetic approaches can be found in the descriptions of the syntheses of several examples enclosed herein.

Compound Examples of Table 1

Example 1: Preparation of Intermediate C

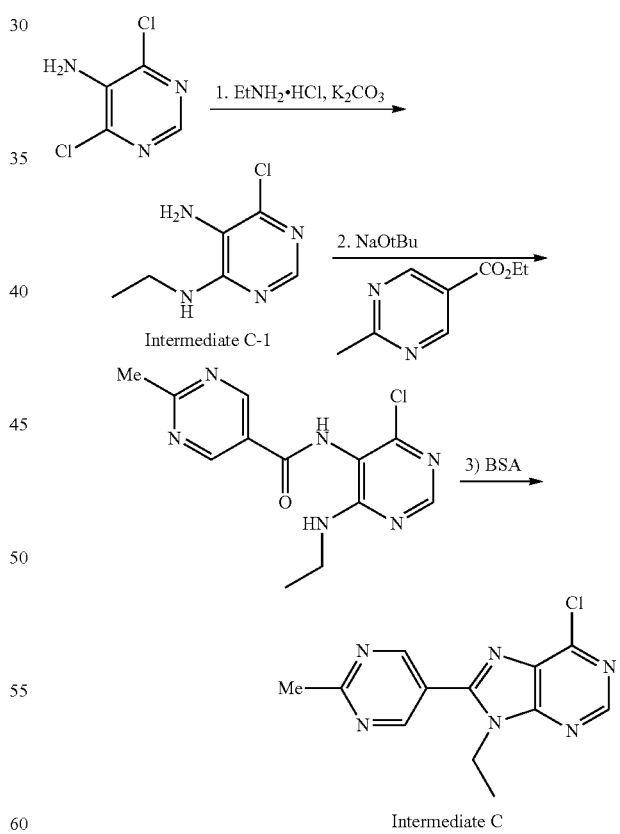

Step 1: Preparation of 6-chloro-N$^4$-ethylpyrimidine-4,5-diamine

A mixture of 4,6-dichloropyrimidin-5-amine (20.0 g, 122 mmol), ethanamine hydrochloride (19.9 g, 243 mmol), and potassium carbonate (50.7 g, 367 mmol) in ethanol (100 ml) was heated to 50° C. for 39 h. The reaction mixture was then cooled to RT, after which it was diluted with DCM (750 ml) and filtered. The filter cake was washed with DCM (250 ml). The combined filtrate was concentrated to dryness to provide 6-chloro-N$^4$-ethylpyrimidine-4,5-diamine. MS (ESI) Calc'd for $C_6H_{10}ClN_4$ [M+H]+: 173; found: 173.

Step 2: Preparation of N-(4-chloro-6-(ethylamino) pyrimidin-5-yl)-2-methylpyrimidine-5-carboxamide To a mixture of 6-chloro-N$^4$-ethylpyrimidine-4,5-diamine (16 g, 91 mmol) and ethyl-2-methylpyrimidine-5-carboxylate (15 g, 90 mmol) in 50 ml of dimethyl ether at RT, a slurry of sodium tert-butoxide (NaOtBu) (9.1 g, 92 mmol) in DME (25 ml) was added over the course of 1 min (reaction internal temperature rose to 43° C.). The reaction mixture was then stirred at RT for 2 h, after which it was quenched by the addition of water (75 ml) and EtOAc (75 ml). The reaction mixture was extracted with EtOAc (75 ml×2). The aqueous layer was then charged with acetic acid (5.3 ml, 92 mmol) and a slurry formed. The solid was collected by filtration, then washed with 75 ml of 1:1 DME: water, after which it was dried under vacuum at 35° C. for 16 h to provide N-(4-chloro-6-(ethylamino)pyrimidin-5-yl)-2-methylpyrimidine-5-carboxamide. MS (ESI) Calc'd for $C_{12}H_{14}ClN_6O$ [M+H]+: 293, found: 293.

Step 3: Preparation of 6-chloro-9-ethyl-8-(2-methyl-pyrimidin-5-yl)-9H-purine (Intermediate C)

A vial was charged with N-trimethylsilyl-1-trimethylsily-loxyethanimine (22. ml, 91 mmol), after which N-(4-chloro-6-(ethylamino)pyrimidin-5-yl)-2-methylpyrimidine-5-carboxamide (5.0 g, 17 mmol) was added in portions. The reaction solution was then heated to 55° C. for 1 h, after which it was cooled down to RT. The formed solid was collected by filtration and washed with heptane (15 ml). The solid was then dried under vacuum at 50° C. for 16 h to provide 6-chloro-9-ethyl-8-(2-methylpyrimidin-5-yl)-9H-purine (Intermediate C). MS (ESI) Calc'd for $C_{12}H_{12}ClN_6$ [M+H]+: 275, found: 275.

Example 2: Preparation of Compounds 1-1 and 1-2

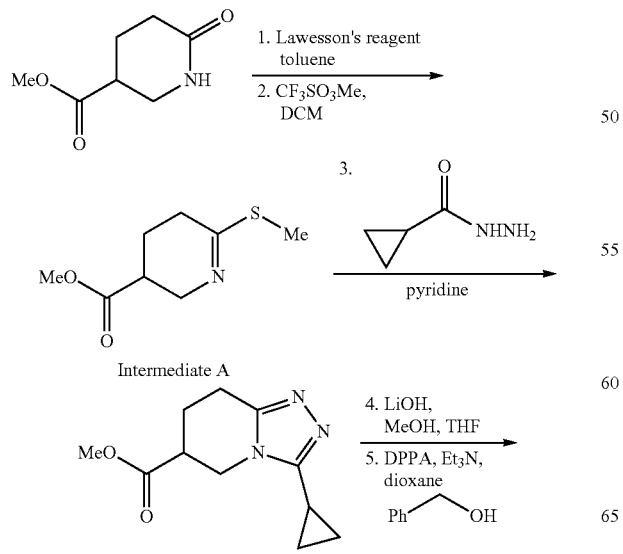

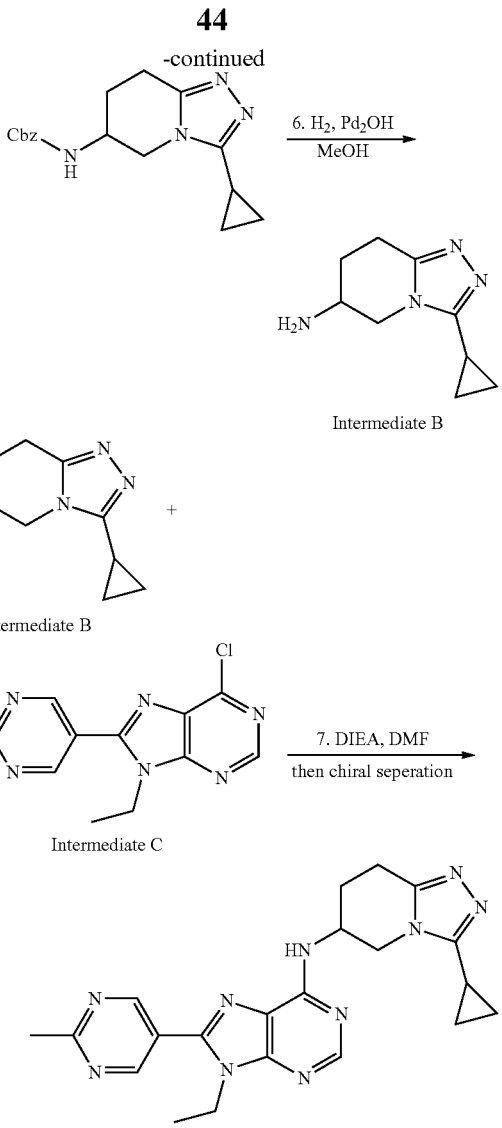

Step 1: Preparation of methyl 6-thioxopiperidine-3-carboxylate

A round-bottom flask was charged with methyl 6-oxopiperidine-3-carboxylate (2.0 g, 12.7 mmol) and Lawesson's Reagent (2.83 g, 7.00 mmol), after which toluene (25.5 ml) was added. The mixture was heated to reflux for 2 h, after which the solution was cooled and subsequently concentrated to dryness in vacuo. The residue was then dissolved in DCM and purified via flash chromatography (silica gel, eluting with a 5-10% gradient of EtOAc in DCM) to afford methyl 6-thioxopiperidine-3-carboxylate. MS (EI) Calc'd for $C_7H_{12}NO_2S$ [M+H]$^+$, 174; found 174.

Step 2: Preparation of methyl 6-(methylthio)-2,3,4,5-tetrahydropyridine-3-carboxylate (Intermediate A)

To a solution of methyl 6-thioxopiperidine-3-carboxylate (0.959 g, 5.53 mmol) in DCM (22 ml) was added methyl trifluoromethanesulfonate (1.15 g, 7.01 mmol). The mixture was stirred at RT for 1.5 h. The solvent was then removed in vacuo to afford methyl 6-(methylthio)-2,3,4,5-tetrahydropyridine-3-carboxylate (Intermediate A), which was used directly in the next step without further purification. MS (EI) Calc'd for $C_8H_{14}NO_2S$ [M+H]$^+$, 188; found 188.

Step 3: Preparation of (S and R)-methyl 3-cyclopropyl-5,6,7,8-tetrahydro-[1,2,4]triazolo[4,3-a]pyridine-6-carboxylate To a solution of (S and R)-methyl 6-(methylthio)-2,3,4,5-tetrahydropyridine-3-carboxylate (1.03 g, 5.50 mmol) in pyridine (3.5 ml) was added cyclopropanecarbohydrazide (0.578 g, 5.78 mmol). The mixture was stirred at RT for 1 h, after which it was heated to 60° C. for 20 min. The mixture was then cooled and concentrated in vacuo. The residue was then dissolved in DCM, and a 1:1 mixture of saturated aqueous sodium hydrogen carbonate and 10% aqueous potassium carbonate was added. The organic layer was separated and the aqueous layer was extracted with additional DCM. The organic phase was then washed with brine and dried with sodium sulfate. The solution was filtered and the filtrate was concentrated in vacuo to afford 1.5 g of methyl 3-cyclopropyl-5,6,7,8-tetrahydro-[1,2,4]triazolo[4,3-a]pyridine-6-carboxylate which was used without further purification. MS (EI) Calc'd for $C_{11}H_{16}N_3O_2$ [M+H]$^+$, 222; found 222.

Step 4: Preparation of (S and R)-3-cyclopropyl-5,6,7,8-tetrahydro-[1,2,4]triazolo[4,3-a]pyridine-6-carboxylic acid To a solution of (S and R)-methyl 3-cyclopropyl-5,6,7,8-tetrahydro-[1,2,4]triazolo[4,3-a]pyridine-6-carboxylate (1.2 g, 5.4 mmol) in THF (16 ml) were added LiOH (0.136 g, 5.69 mmol) and water (5.0 ml). MeOH (3.0 ml) was then added, and the mixture was stirred at RT for 6 h. At this time NaOH was added (5 ml, 5.00 mmol, 1M), and the reaction was allowed to stir 1 h. The solution pH was then adjusted to approximately (~)4 by the addition of 2M HCl, after which the solvent was removed to afford 3-cyclopropyl-5,6,7,8-tetrahydro-[1,2,4]triazolo[4,3-a]pyridine-6-carboxylic acid, which was used in next step without further purification. MS (EI) Calc'd for $C_{10}H_{14}N_3O_2$ [M+H]$^+$, 208; found 208.

Step 5: Preparation of (S and R)-benzyl (3-cyclopropyl-5,6,7,8-tetrahydro-[1,2,4]triazolo[4,3-a]pyridin-6-yl)carbamate A vial was charged with (S and R)-3-cyclopropyl-5,6,7,8-tetrahydro-[1,2,4]triazolo[4,3-a]pyridine-6-carboxylic acid (0.85 g, 4.1 mmol), dioxane (16 ml), diphenylphosphoryl azide (1.5 g, 5.5 mmol) and triethylamine (2.7 ml, 19.4 mmol). The resultant slurry was stirred at 50° C. for 3 h. To this slurry was then added benzyl alcohol (0.9 ml, 8.7 mmol), and the mixture was heated at 70° C. for 16 h. The solvent was then removed in vacuo and the residue was dissolved in DCM. The organic layer was washed with a saturated solution of sodium bicarbonate (×3), after which the organic layer was dried over sodium sulfate, filtered, and the filtrate was concentrated in vacuo. The residue was dissolved in DCM and purified via flash chromatography (silica gel, eluting 1:9 2N ammonia solution in MeOH:DCM) to afford benzyl (3-cyclopropyl-5,6,7,8-tetrahydro-[1,2,4]triazolo[4,3-a]pyridin-6-yl)carbamate. MS (EI) Calc'd for $C_{17}H_{21}N_4O_2$ [M+H]+, 313; found 313.

Step 6: Preparation of 3-cyclopropyl-5,6,7,8-tetrahydro-[1,2,4]triazolo[4,3-a]pyridin-6-amine (Intermediate B)

To a solution of (S and R)-benzyl (3-cyclopropyl-5,6,7,8-tetrahydro-[1,2,4]triazolo[4,3-a]pyridin-6-yl)carbamate (0.521 g, 1.22 mmol) in MeOH (10 ml), was added palladium hydroxide (50 mg, 0.07 mmol). The mixture was stirred at RT under $H_2$ for 1 h. The mixture was then filtered through a Whatman™ Autovial™ Syringeless Filter, PTFE (GE Healthcare Bio-Sciences, Pittsburgh, Pa., USA), (0.45 t and concentrated to afford 3-cyclopropyl-5,6,7,8-tetrahydro-[1,2,4]triazolo[4,3-a]pyridin-6-amine (Intermediate B), which was used in the next step directly without further purification.

Step 7: Preparation of Compounds 1-1 and 1-2

A vial was charged with (S and R)-3-cyclopropyl-5,6,7,8-tetrahydro-[1,2,4]triazolo[4,3-a]pyridin-6-amine (52 mg, 0.29 mmol), 6-chloro-9-ethyl-8-(2-methylpyrimidin-5-yl)-9H-purine (Intermediate C)[1] (88 mg, 0.32 mmol), DMA (2 ml) and DIEA (0.15 ml, 0.86 mmol). The mixture was stirred at 100° C. for 18 h, after which it was further heated to 110° C. for 24 h. The mixture was then filtered through a Whatman™ Autovial™ Syringeless Filter, PTFE; 0.45µ and purified by reverse-phase preparative HPLC (0:100 to 95:5 MeCN:water: 0.1% v/v TFA modifier) to afford N-(3-cyclopropyl-5,6,7,8-tetrahydro-[1,2,4]triazolo[4,3-a]pyridin-6-yl)-9-ethyl-8-(2-methylpyrimidin-5-yl)-9H-purin-6-amine as the TFA salt. Chiral resolution of the racemic compound was achieved via chiral preparative SFC (Chiralcel OJ-H® (Chiral Technologies, Inc., West Chester, Pa., USA), 21×250 (mm), 10% (Methanol+0.25% Dimethyl Ethyl Amine) in $CO_2$, 70 ml/min) to provide 1-1 (faster eluting enantiomer, 5.5 min): $^1$H NMR (600 MHz, DMSO-d6) δ 9.08 (s, 2H), 8.32 (s, 1H), 8.27 (s, 1H), 4.85-4.70 (m, 1H), 4.40-4.20 (m, 3H), 4.00-3.85 (m, 1H), 3.00-2.88 (m, 1H), 2.88-2.78 (m, 1H), 2.70 (s, 3H), 2.20-2.00 (m, 2H), 1.90-1.80 (m, 1H), 1.28 (t, J=7.2 Hz, 3H), 0.92-0.75 (m, 4H); MS (EI) Calc'd for $C_{21}H_{25}N_{10}$ [M+H]$^+$, 417; found 417. The slower-eluting enantiomer (6.2 min) was further purified by reverse-phase preparative HPLC (0:100 to 95:5 MeCN:water: 0.1% v/v TFA modifier) to afford 1-2N-(3-cyclopropyl-5,6,7,8-tetrahydro-[1,2,4]triazolo[4,3-a]pyridin-6-yl)-9-ethyl-8-(2-methylpyrimidin-5-yl)-9H-purin-6-amine as the TFA salt: $^1$H NMR (600 MHz, DMSO-d6) δ 9.08 (s, 2H), 8.45 (s, 1H), 8.35 (s, 1H), 5.05-4.94 (m, 1H), 4.54-4.44 (m, 1H), 4.28 (q, J=7.2 Hz, 2H), 4.23-4.16 (m, 1H), 3.16-3.00 (m, 2H), 2.70 (s, 3H), 2.32-2.22 (m, 1H), 2.22-2.04 (m, 2H), 1.28 (t, J=7.2 Hz, 3H), 1.20-1.10 (m, 2H), 1.10-0.94 (m, 2H); MS (EI) Calc'd for $C_{21}H_{25}N_{10}$ [M+H]$^+$, 417; found 417.

Example 3: Preparation of Compound 1-10

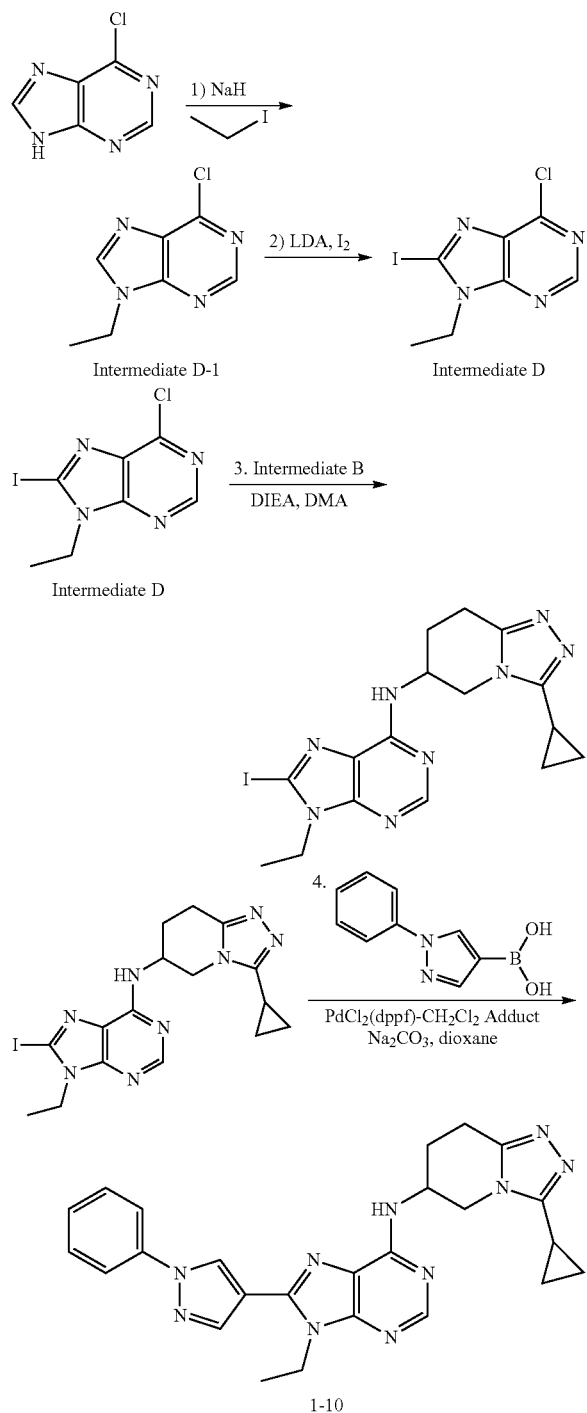

Step 1: Preparation of 6-chloro-9-ethyl-9H-purine (Intermediate D-1)

To a solution of 6-chloro-9H-purine (31 g, 0.20 mol) dissolved in DMF (200 ml) was added NaH (60% w/t in mineral oil, 8.8 g, 0.22 mol) at 0° C. under nitrogen in portions. The mixture was warmed up to RT and stirred for 1 h, after which it was cooled to 0° C. and CH₃CH₂I (34 g, 0.22 mol) was added slowly. Then the mixture was stirred at RT for 2 h. The reaction was quenched with saturated aqueous ammonium chloride and was extracted with EtOAc. The organic layer was washed with brine, dried over sodium sulfate, filtered, and concentrated in vacuo. The crude product was then purified by column chromatography on silica gel (eluting PE:EtOAc=3:1) to give 6-chloro-9-ethyl-9H-purine (Intermediate D-1).

Step 2: Preparation of 6-chloro-9-ethyl-8-iodo-9H-purine (Intermediate D)

To a stirred solution of 6-chloro-9-ethyl-9H-purine (10.0 g, 54.9 mmol) in THF (150 ml) cooled to −78° C., LDA (82 ml, 82 mmol) was added slowly under nitrogen. The reaction was stirred at −78° C. for 1.5 h, after which I₂ (21.0 g, 82.4 mol) in THF (100 ml) was added. The reaction was further stirred for 2 h, after which it was quenched with saturated ammonium chloride. The mixture was then extracted with EtOAc and the organic layer was washed with brine, dried over sodium sulfate, filtered, and concentrated in vacuo to obtain 6-chloro-9-ethyl-8-iodo-9H-purine (Intermediate D).

Step 3: Synthesis of N-(3-cyclopropyl-5,6,7,8-tetrahydro-[1,2,4]triazolo[4,3-a]pyridin-6-yl)-9-ethyl-8-iodo-9H-purin-6-amine A vial was charged with Intermediate B (106.6 mg, 0.598 mmol) and 6-chloro-9-ethyl-8-iodo-9H-purine (Intermediate D) (185 mg, 0.598 mmol), DMA (2.5 ml) and DIEA (0.3 ml, 1.718 mmol). The mixture was stirred at 110° C. for 22 h. The mixture was then cooled, filtered through a Whatman™ Autovial™ Syringeless Filter, PTFE; 0.4511, and purified by reverse-phase preparative HPLC and purified by reverse-phase preparative HPLC (0:100 to 95:5 MeCN:water: 0.1% v/v TFA modifier) to afford (S and R)—N-(3-cyclopropyl-5,6,7,8-tetrahydro-[1,2,4]triazolo[4,3-a]pyridin-6-yl)-9-ethyl-8-iodo-9H-purin-6-amine as the TFA salt. MS (EI) Calc'd for C₁₆H₂₀IN₈ [M+H]+, 451; found 451.

Step 4: Synthesis of N-(3-cyclopropyl-5,6,7,8-tetrahydro-[1,2,4]triazol[4,3-a]pyridin-6-yl)-9-ethyl-8-(1-phenyl-1H-pyrazol-4-yl)-9H-purin-6-amine (1-10)

A vial was charged with (1-phenyl-1H-pyrazol-4-yl)boronic acid (13.78 mg, 0.073 mmol), (S and R)—N-(3-cyclopropyl-5,6,7,8-tetrahydro-[1,2,4]triazolo[4,3-a]pyridin-6-yl)-9-ethyl-8-iodo-9H-purin-6-amine, TFA (22 mg, 0.039 mmol), PdCl₂(dppf)-CH₂Cl₂ adduct (5.98 mg, 7.33 μmol), dioxane (400 μl) and Na₂CO₃ (100 μl, 0.20 mmol, 2M aqueous solution). The vial was sealed and the mixture was evacuated and back filled with N₂ (×6), after which it was heated to 80° C. for 3 h. The mixture was then cooled, filtered through a Whatman™ Autovial™ Syringeless Filter, PTFE; 0.45 t, and purified by reverse-phase preparative HPLC (0:100 to 95:5 MeCN:water: 0.1% v/v TFA modifier) to afford (S and R)—N-(3-cyclopropyl-5,6,7,8-tetrahydro-[1,2,4]triazolo[4,3-a]pyridin-6-yl)-9-ethyl-8-(1-phenyl-1H-pyrazol-4-yl)-9H-purin-6-amine as the TFA salt (1-10) ¹H NMR (600 MHz, DMSO-d6) δ 9.02 (s, 1H), 8.34-8.24 (m, 3H), 7.93 (d, J=7.8 Hz, 2H), 7.53 (t, J=7.2 Hz, 2H), 7.36 (t, J=7.8 Hz, 1H), 5.08-4.90 (m, 1H), 4.54-4.46 (m, 1H), 4.44 (q, J=7.2 Hz, 2H), 4.26-4.16 (m, 1H), 3.16-3.00 (m, 2H), 2.35-2.24 (m, 1H), 2.22-2.06 (m, 2H), 1.31 (t, J=7.2 Hz, 3H), 1.20-1.10 (m, 2H), 1.10-0.94 (m, 2H); MS (EI) Calc'd for $C_{25}H_{27}N_{10}$ [M+H]+, 467; found 467.

Example 4: Preparation of Compound 1-18

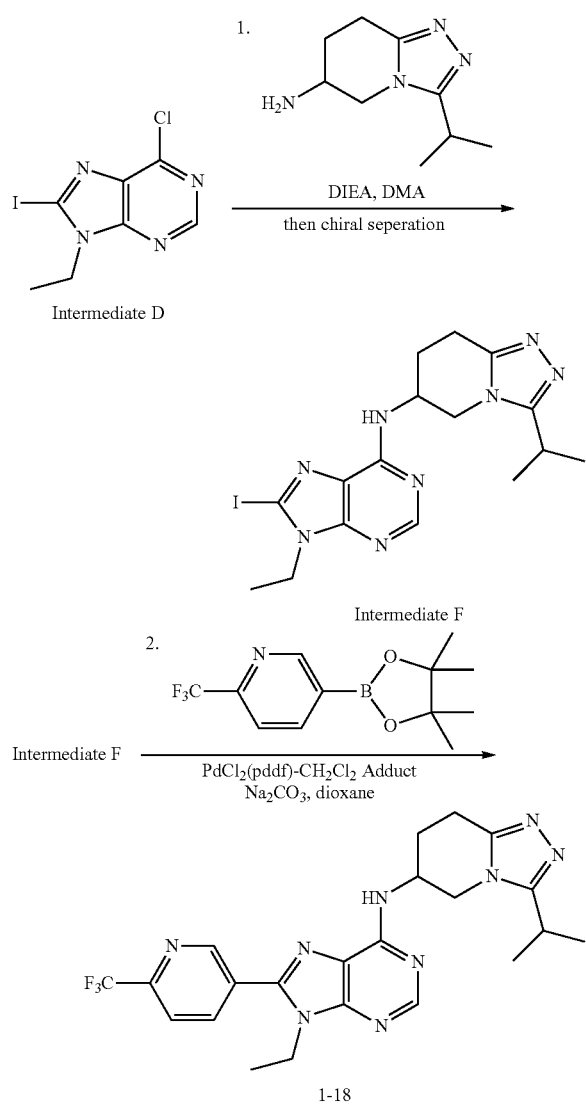

Step 1: Preparation of (S or R)-9-ethyl-8-iodo-N-(3-isopropyl-5,6,7,8-tetrahydro-[1,2,4]triazolo[4,3-a]pyridin-6-yl)-9H-purin-6-amine (Intermediate F)

A vial was charged with (S and R)-3-isopropyl-5,6,7,8-tetrahydro-[1,2,4]triazolo[4,3-a]pyridin-6-amine (1.99 g, 11.0 mmol) (commercially available from Enamine Ltd., Monmouth Junction, N.J., USA) and 6-chloro-9-ethyl-8-iodo-9H-purine (Intermediate D) (3.74 g, 12.11 mmol), DMA (55 ml) and DIEA (5 ml, 28.6 mmol). The vial was sealed and stirred at 110° C. for 21 h, after which the reaction mixture was cooled and the solvent was removed in vacuo. The resulting residue was dissolved in DCM and purified via flash chromatography (silica gel, eluting 9:1 DCM:MeOH) to afford racemic 9-ethyl-8-iodo-N-(3-isopropyl-5,6,7,8-tetrahydro-[1,2,4]triazolo[4,3-a]pyridin-6-yl)-9H-purin-6-amine. Chiral resolution of the racemic compound was achieved via chiral preparative SFC (Chiralpak® IB™, 21×250 (mm) (Chiral Technologies, Inc. West Chester, Pa., USA), 25% (Methanol+0.25% Dimethyl Ethyl Amine) in $CO_2$, 70 ml/min) to provide Intermediate F (faster eluting isomer, 3.3 min): MS (EI) Calc'd for $C_{16}H_{22}IN_8$ [M+H]+, 453; found 453.

Step 2: Preparation of Compound 1-18

A vial was charged with 5-(4,4,5,5-tetramethyl-1,3,2-dioxaborolan-2-yl)-2-(trifluoromethyl)pyridine (180 mg, 0.66 mmol), (S or R)-9-ethyl-8-iodo-N-(3-isopropyl-5,6,7,8-tetrahydro-[1,2,4]triazolo[4,3-a]pyridin-6-yl)-9H-purin-6-amine (Intermediate F) (200 mg, 0.44 mmol), and PdCl2 (dppf)-$CH_2Cl_2$ Adduct (54 mg, 0.066 mmol), after which the vial was sealed and dioxane (2.5 ml) and $Na_2CO_3$ (0.8 ml, 1.6 mmol, 2M aquoues solution). The mixture was evacuated and back-filled with nitrogen (×3), after which the reaction was heated to 80° C. for 3 h. The reaction mixture was then filtered and concentrated in vacuo. The residue was purified via flash chromatography (silica gel, eluting with a 0-8% MeOH in DCM gradient). The product thus obtained was purified by reverse-phase preparative HPLC (0:100 to 95:5 MeCN:water: 0.1% v/v TFA modifier). The liquid fractions were combined and neutralized with saturated aqueous $NaHCO_3$ and the product was extracted with a mixture of 3:1 chloroform:IPA. The organic layer was dried over sodium sulfate and the solvent was removed in vacuo to provide (S or R)-9-ethyl-N-(3-isopropyl-5,6,7,8-tetrahydro-[1,2,4]triazolo[4,3-a]pyridin-6-yl)-8-(6-(trifluoromethyl)pyridin-3-yl)-9H-purin-6-amine (1-18). $^1$H NMR (600 MHz, DMSO-d6) δ 9.15 (s, 1H), 8.54-8.40 (m, 2H), 8.36 (s, 1H), 8.10 (d, J=8.4 Hz, 1H), 5.06-4.90 (m, 1H), 4.50-4.40 (m, 1H), 4.31 (q, J=7.2 Hz, 2H), 4.24-4.12 (m, 1H), 3.32-3.20 (m, 1H), 3.20-3.02 (m, 2H), 2.30-2.20 (m, 1H), 2.20-2.04 (m, 1H), 1.34-1.12 (m, 9H); MS (EI) Calc'd for $C_{22}H_{25}F_3N_9$ [M+H]+, 472; found 472.

Example 5: Preparation of Compound 25

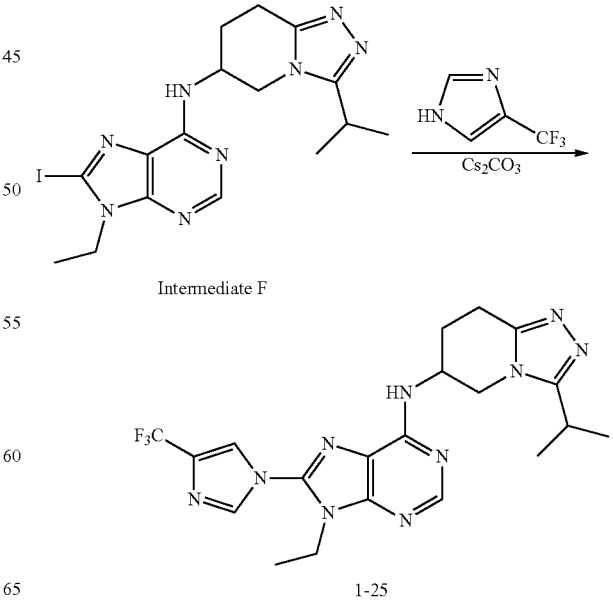

A microwave vial was charged with Intermediate F (20 mg, 0.044 mmol), 4-(trifluoromethyl)-1H-imidazole (20 mg, 0.15 mmol), Cs$_2$CO$_3$ (43.2 mg, 0.133 mmol) and DMA (500 µl). The mixture was heated at 150° C. under microwave irradiation for 3 h. The mixture was then purified by reverse-phase preparative HPLC (0:100 to 95:5 MeCN:water: 0.1% v/v TFA modifier) to afford 1-25 as the TFA salt. $^1$H NMR (500 MHz, DMSO-d6) δ=8.68-8.20 (m, 4H), 5.00 (s, 1H), 4.55-4.38 (m, 1H), 4.22-4.16 (m, 1H), 4.12 (q, J=7.4, 2H), 3.35-3.24 (m, 1H), 3.22-3.01 (m, 2H), 2.33-2.21 (m, 1H), 2.21-2.09 (m, 1H), 1.30 (d, J=6.9, 5H), 1.24 (t, J=7.2, 3H). MS (EI) Calc'd for C$_{20}$H$_{24}$F$_3$N$_{10}$ [M+H]$^+$, 461; found 461.

Example 6: Preparation of Compounds 1-31 and 1-32

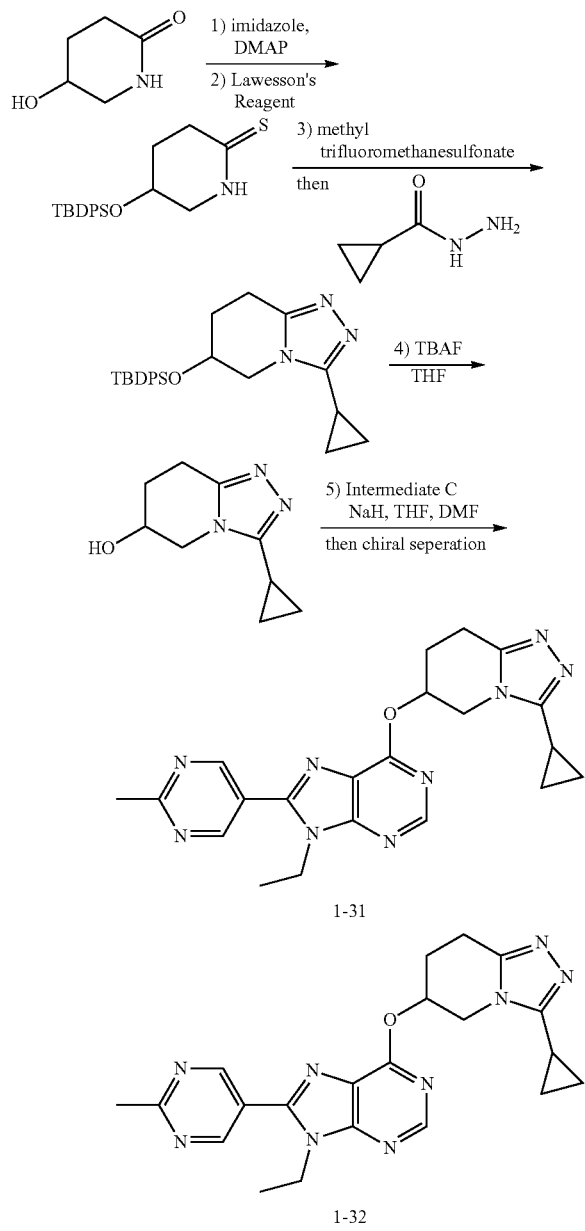

Step 1: Preparation of 5-((tert-butyldiphenylsilyl)oxy)piperidin-2-one

To a solution of 5-hydroxypiperidin-2-one (1 g, 8.69 mmol) in DMF (10 ml) was added imidazole (0.887 g, 13.03 mmol) and DMAP (0.106 g, 0.869 mmol). Tert-butyl (chloro)diphenylsilane (2.71 ml, 10.42 mmol) was then added, and reaction was allowed to stir at RT for 18 h. Water was then added, resulting in the formation of a solid precipitate. The solid was collected and was redissolved in EtOAc, after which it was washed sequentially with 1N HCl, saturated sodium bicarbonate, and brine. The organic layer was then concentrated in vacuo and the residue thus obtained was purified via flash chromatography (silica gel, eluting with 100% EtOAc) to afford the (R and S)-5-((tert-butyldiphenylsilyl)oxy)piperidin-2-one. MS (ESI) Calc'd for (C$_{21}$H$_{28}$NO$_2$Si) [M+H]$^+$, 354; found, 354.

Step 2: Preparation of (R and S)-5-((tert-butyldiphenylsilyl)oxy)piperidine-2-thione To a solution of 5-((tert-butyldiphenylsilyl)oxy)piperidin-2-one (2.2 g, 6.2 mmol) in toluene (20 ml) was added 2,4-bis(4-methoxyphenyl)-2,4-dithioxo-1,3,2,4-dithiadiphosphetane (Lawesson's Reagent) (1.4 g, 3.4 mmol). The reaction was heated to reflux and stirred for 2 h. The solution was then cooled and the solvent was removed in vacuo. The residue thus obtained was purified via flash chromatography (silica gel, eluting 1:1 EtOAc:Hexanes) to afford (R and S)-5-((tert-butyldiphenylsilyl)oxy)piperidine-2-thione. MS (ESI) Calc'd for (C$_{21}$H$_{28}$NOSSi) [M+H]$^+$, 370; found, 370.

Step 3: Preparation of (R and S)-3-((tert-butyldiphenylsilyl)oxy)-6-(methylthio)-2,3,4,5-tetrahydropyridine To a solution of 5-((tert-butyldiphenylsilyl)oxy)piperidine-2-thione (2.4 g, 6.5 mmol) in DCM (25 ml) was added methyl trifluoromethanesulfonate (1.5 ml, 6.5 mmol). The reaction was allowed to stir for 2 h at RT, after which the volatiles were removed in vacuo and the residue was redissolved in pyridine (5 ml). Cyclopropanecarboxylic acid hydrazide (137 mg, 1.37 mmol) (commercially available from Matrix Scientific) was added, and the solution was heated to 80° C. for 16 h. The volatiles were then removed in vacuo and the residue was purified by flash chromatography (silica gel, eluting with 10% MeOH in DCM) to provide (R and S)-6-((tert-butyldiphenylsilyl)oxy)-3-cyclopropyl-5,6,7,8-tetrahydro-[1,2,4]triazolo[4,3-a]pyridine. MS (ESI) Calc'd for (C$_{25}$H$_{32}$N$_3$OSi) [M+H]$^+$, 418; found, 418.

Step 4: Preparation of 3-cyclopropyl-5,6,7,8-tetrahydro-[1,2,4]triazolo[4,3-a]pyridin-6-ol To a solution of 6-((tert-butyldiphenylsilyl)oxy)-3-cyclopropyl-5,6,7,8-tetrahydro-[1,2,4]triazolo[4,3-a]pyridine (380 mg, 0.91 mmol) was added a solution of tetrabutylammonium fluoride (TBAF) in THF (1 ml of 1.0 M solution, 1 mmol). The reaction was allowed to stir at RT for 1 h, after which the reaction was concentrated in vacuo and the residue thus obtained was purified by reverse-phase, mass-triggered HPLC purification (Xbridge Prep C18 10 µm OBD, 19×250 mm; Mobile phase: A: water (10 mM NH$_4$HCO$_3$), B: MeCN; Flow rate: 30 ml/min) to afford (R and S)-3-cyclopropyl-5,6,7,8-tetrahydro-[1,2,4]triazolo[4,3-a]pyridin-6-ol. MS (ESI) Calc'd for ($C_9H_{14}N_3O$) [M+H]$^+$, 180; found, 180.

Step 5: Preparation of Compounds 1-31 and 1-32

A vial was charged with 3-cyclopropyl-5,6,7,8-tetrahydro-[1,2,4]triazolo[4,3-a]pyridin-6-ol (33 mg, 0.184 mmol), THF (600 µl) and DMF (300 µl). To this mixture was added NaH (22 mg, 0.550 mmol), and the reaction mixture was allowed to stir for 1 h. A solution of 6-chloro-9-ethyl-8-(2-methylpyrimidin-5-yl)-9H-purine (Intermediate C) (60.7 mg, 0.221 mmol) in DMF (500 dl) was then added, and the reaction mixture was stirred at RT for 1.5 h. The mixture was then filtered through a Whatman™ Autovial™ Syringeless Filter, PTFE; 0.45µ and purified by reverse-phase preparative HPLC (0:100 to 95:5 MeCN:water: 0.1% v/v TFA modifier) to afford 6-((3-cyclopropyl-5,6,7,8-tetrahydro-[1,2,4]triazolo[4,3-a]pyridin-6-yl)oxy)-9-ethyl-8-(2-methylpyrimidin-5-yl)-9H-purine as the TFA salt. Chiral resolution of the racemic material was achieved via chiral preparative SFC (Phenomenex Cellulose Lux-4, 21×250 (mm), 40% (Methanol+0.25% Dimethyl Ethyl Amine) in $CO_2$, 70 ml/min) to provide 1-31 (faster eluting enantiomer, 7.33 min): $^1$H NMR (600 MHz, DMSO-d6) δ 9.08 (s, 2H), 8.62 (s, 1H), 6.10-6.00 (m, 1H), 4.42-4.28 (m, 4H), 3.00-2.90 (m, 1H), 2.90-2.80 (m, 1H), 2.71 (s, 3H), 2.44-2.36 (m, 1H), 2.20-2.10 (m, 1H), 1.94-1.84 (m, 1H), 1.30 (t, J=7.2 Hz, 3H), 0.95-0.70 (m, 4H); MS (EI) Calc'd for $C_{21}H_{24}N_9O$ [M+H]+, 418; found 418; and 1-32 (slower eluting enantiomer, 8.56 min): $^1$H NMR (600 MHz, DMSO-d6) δ 9.08 (s, 2H), 8.62 (s, 1H), 6.10-6.00 (m, 1H), 4.42-4.28 (m, 4H), 3.00-2.90 (m, 1H), 2.90-2.80 (m, 1H), 2.71 (s, 3H), 2.44-2.36 (m, 1H), 2.20-2.10 (m, 1H), 1.94-1.84 (m, 1H), 1.30 (t, J=7.2 Hz, 3H), 0.95-0.70 (m, 4H); MS (EI) Calc'd for $C_{21}H_{24}N_9O$ [M+H]+, 418; found 418.

Example 7: Preparation of Compound 1-37

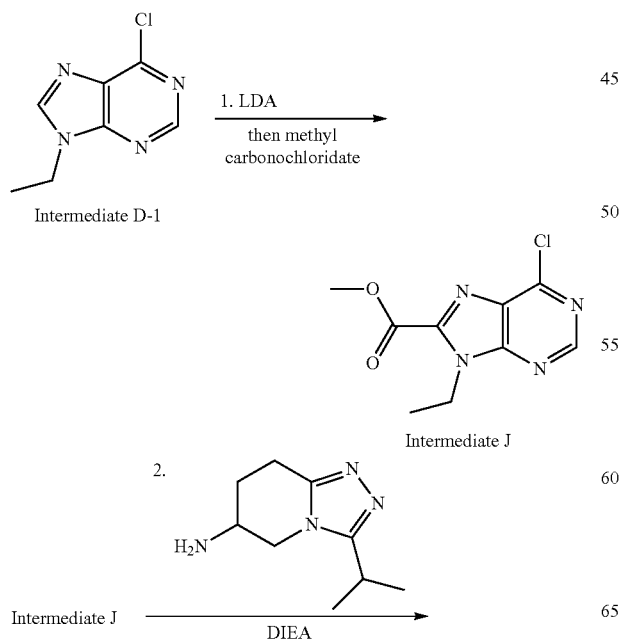

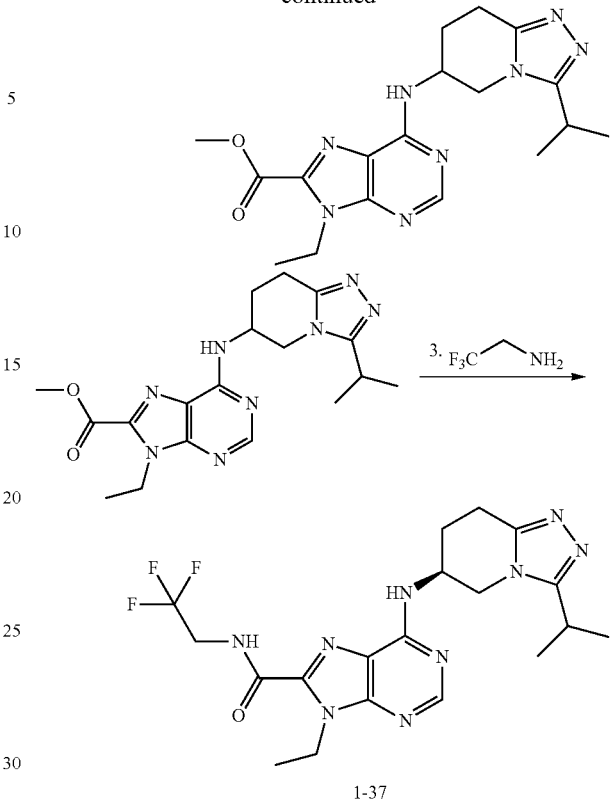

Step 1: Preparation of methyl 6-chloro-9-ethyl-9H-purine-8-carboxylate (Intermediate J)

To a solution of lithium diisopropylamide (LDA) (32.5 ml, 32.5 mmol) in THF (30 ml) was added Intermediate D-1 (5.0 g, 27.5 mmol) in THF (50 ml) drop-wise with stirring at −78° C. The mixture was stirred for 2 h at −78° C. The reaction mixture was then transferred to a solution of methyl carbonochloridate (5.2 g, 55 mmol) in THF (50 ml) at −78° C. and the reaction mixture was maintained at −78° C. for 3 h. The reaction mixture was quenched by saturated aqueous ammonium chloride (100 ml) and extracted with EA (3×100 ml). The combined organic layers were washed with brine, dried over anhydrous sodium sulfate, and filtered. The filtrate was concentrated under vacuum to give a residue, which was purified by silica gel column chromatography eluting with 6% EA in PE to afford methyl 6-chloro-9-ethyl-9H-purine-8-carboxylate (Intermediate J). MS (ESI) Calc'd for ($C_9H_{10}ClN_4O_2$) [M+H]$^+$, 241; found, 241.

Step 2: Preparation of (S and R)-methyl 9-ethyl-6-((3-isopropyl-5,6,7,8-tetrahydro-[1,2,4]triazolo[4,3-a]pyridin-6-yl)amino)-9H-purine-8-carboxylate A vial was charged with methyl 6-chloro-9-ethyl-9H-purine-8-carboxylate (Intermediate J) (33.9 mg, 0.141 mmol), 3-isopropyl-5,6,7,8-tetrahydro-[1,2,4]triazolo[4,3-a]pyridin-6-amine (50.8 mg, 0.282 mmol) (commercially available from Enamine Ltd.), DMA (1 ml) and DIEA (100 µl, 0.573 mmol. The mixture was heated to 90° C. overnight. The mixture was then cooled and purified by reverse-phase preparative HPLC (0:100 to 95:5 MeCN:water: 0.1% v/v TFA modifier) to afford (S and R)-methyl 9-ethyl-6-((3-isopropyl-5,6,7,8-tetrahydro-[1,2,4]triazolo[4,3-a]pyridin-6-yl)amino)-9H-purine-8-carboxylate as the TFA salt. MS (EI) Calc'd for $C_{18}H_{25}N_8O_2$ [M+H]+, 385; found 385.

Step 3: Preparation of Compound 1-37

A microwave vial was charged with (S and R)-methyl 9-ethyl-6-((3-isopropyl-5,6,7,8-tetrahydro-[1,2,4]triazolo[4,3-a]pyridin-6-yl)amino)-9H-purine-8-carboxylate, TFA (24 mg, 0.048 mmol) and 2,2,2-trifluoroethylamine (0.5 ml, 6.37 mmol). The mixture was heated to 120° C. under microwave irradiation for 10 h. The solvent was then removed in vacuo and the residue thus obtained was dissolved in MeOH and purified by reverse-phase preparative HPLC (0:100 to 95:5 MeCN:water: 0.1% v/v TFA modifier) to afford (S and R)-9-ethyl-6-((3-isopropyl-5,6,7,8-tetrahydro-[1,2,4]triazolo[4,3-a]pyridin-6-yl)amino)-N-(2,2,2-trifluoroethyl)-9H-purine-8-carboxamide as the TFA salt (1-37) $^1$H NMR (600 MHz, CD$_3$OD) δ 9.02 (br s, 1H), 8.39 (s, 1H), 5.10-4.75 (m, 2H), 4.68 (q, J=7.2 Hz, 2H), 4.64-4.56 (m, 1H), 4.26-4.18 (m, 1H), 4.16-4.04 (m, 2H), 3.38-3.20 (m, 2H), 2.46-2.30 (m, 2H), 1.48-1.32 (m, 9H); MS (EI) Calc'd for $C_{19}H_{25}F_3N_9O$ [M+H]+, 452; found 452.

Example 8: Preparation of Compound 1-38

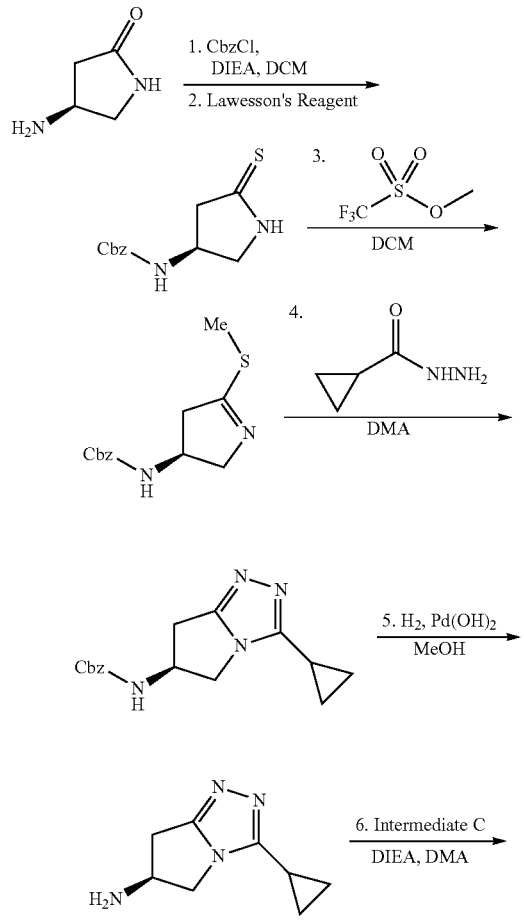

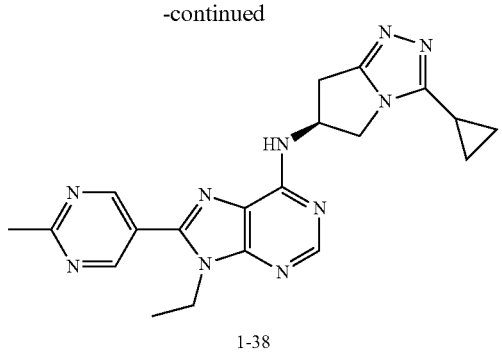

1-38

Step 1: Preparation of (S)-benzyl (5-oxopyrrolidin-3-yl)carbamate (S)-4-aminopyrrolidin-2-one (213 mg, 2.127 mmol) was suspended in DCM (15 ml) and DIEA (0.8 ml, 4.58 mmol) was added. The solution was cooled to 0° C. Benzyl chloroformate (0.35 ml, 2.452 mmol) was added drop-wise and the solution was warmed to RT and stirred for 16 h. The mixture was washed with saturated aqueous NaHCO$_3$ and brine, dried over Na$_2$SO$_4$, and filtered. The filtrate was concentrated in vacuo and the residue was purified via flash chromatography (silica gel, eluting 0-8% DCM in MeOH) to afford (S)-benzyl (5-oxopyrrolidin-3-yl)carbamate. MS (EI) Calc'd for $C_{12}H_{15}N_2O_3$ [M+H]$^+$, 235; found 235.

Step 2: Preparation of (S)-benzyl (5-thioxopyrrolidin-3-yl)carbamate

To a solution of (S)-benzyl (5-oxopyrrolidin-3-yl)carbamate (247.6 mg, 1.057 mmol) in toluene (25 ml) was added Lawesson's Reagent (428 mg, 1.057 mmol). The resulting mixture was heated under reflux for 2 h. The reaction mixture was then cooled to RT and the volatiles were removed in vacuo. The resulting residue was purified by flash chromatography (silica gel, eluting with a 0 to 6% MeOH in DCM gradient) to afford (S)-benzyl (5-thioxopyrrolidin-3-yl)carbamate. MS (EI) Calc'd for $C_{12}H_{15}N_2O_2S$ [M+H]$^+$, 251; found 251.

Step 3: Preparation of (S)-benzyl (5-(methylthio)-3,4-dihydro-2H-pyrrol-3-yl)carbamate To the solution of (S)-benzyl (5-thioxopyrrolidin-3-yl)carbamate (265 mg, 1.06 mmol) in DCM (3 ml) was added methyl trifluoromethanesulfonate (120 μL, 1.09 mmol). The mixture was stirred at RT for 2 h, after which the volatiles were removed in vacuo to afford (S)-benzyl (5-(methylthio)-3,4-dihydro-2H-pyrrol-3-yl)carbamate, which was used in the next step without further purification. MS (EI) Calc'd for $C_{13}H_{17}N_2O_2S$ [M+H]$^+$, 265; found 265.

Step 4: Preparation of (S)-benzyl (3-cyclopropyl-6,7-dihydro-5H-pyrrolo[2,1-c][1,2,4]triazol-6-yl)carbamate A microwave vial was charged with cyclopropanecarbohydrazide (159 mg, 1.59 mmol), (S)-benzyl (5-(methylthio)-3,4-dihydro-2H-pyrrol-3-yl)carbamate (280 mg, 1.06 mmol) and DMA (2.5 ml). The mixture was then heated under microwave irradiation at 150° C. for 2 h. The reaction was then cooled and the volatiles were removed in vacuo. The residue was purified via flash chromatography (silica gel, eluting DCM:MeOH:Et$_3$N=90:9:1) to afford (S)-benzyl (3-cyclopropyl-6,7-dihydro-5H-pyrrolo[2,1-c][1,2,4]triazol-6-yl)carbamate. MS (EI) Calc'd for $C_{16}H_{19}N_4O_2$ [M+H]$^+$, 299; found 299.

Step 5: Preparation of (S)-3-cyclopropyl-6,7-dihydro-5H-pyrrolo[2,1-c][1,2,4]triazol-6-amine To the solution of (S)-benzyl (3-cyclopropyl-6,7-dihydro-5H-pyrrolo[2,1-c][1,2,4]triazol-6-yl)carbamate (316 mg, 1.059 mmol) in MeOH (8 ml), was added palladium hydroxide on carbon (20% Wt, 30 mg, 0.043 mmol). The mixture was stirred under hydrogen (1 atm) for 20 h, after which the mixture was filtered and concentrated in vacuo to afford a residue, which was re-dissolved in MeOH (3 ml). To this solution was added palladium hydroxide on carbon (20% Wt) (80 mg, 0.11 mmol). The mixture was again stirred under hydrogen (1 atm) for 2 h. The mixture was then filtered through Celite (trademarked version of diatomaceous earth) and concentrated in vacuo to afford (S)-3-cyclopropyl-6,7-dihydro-5H-pyrrolo[2,1-c][1,2,4]triazol-6-amine, which was used in next step without further purification. MS (EI) Calc'd for $C_8H_{13}N_4$[M+H]$^+$, 165; found 165.

Step 6: Preparation of Compound 1-38

A vial was charged with (S)-3-cyclopropyl-6,7-dihydro-5H-pyrrolo[2,1-c][1,2,4]triazol-6-amine (30 mg, 0.183 mmol), 6-chloro-9-ethyl-8-(2-methylpyrimidin-5-yl)-9H-purine (Intermediate C) (55.2 mg, 0.201 mmol), DMA (1.2 ml) and DIEA (0.1 ml, 0.573 mmol). The mixture was stirred at 100° C. for 20 h. The mixture was then cooled, filtered through a Whatman™ Autovial™ Syringeless Filter, PTFE; 0.45 t, and purified by reverse-phase preparative HPLC (0:100 to 95:5 MeCN:water: 0.1% v/v TFA modifier) to afford (S)—N-(3-cyclopropyl-6,7-dihydro-5H-pyrrolo[2,1-c][1,2,4]triazol-6-yl)-9-ethyl-8-(2-methylpyrimidin-5-yl)-9H-purin-6-amine as the TFA salt (1-38). $^1$H NMR (600 MHz, CD$_3$OD) δ 9.10 (s, 2H), 8.35 (s, 1H), 4.80-4.72 (m, 1H), 4.46-4.32 (m, 3H), 3.74-3.62 (m, 1H), 3.36-3.25 (m, 2H), 2.79 (s, 3H), 2.30-2.20 (m, 1H), 1.42 (t, J=7.2 Hz, 3H), 1.38-1.30 (m, 2H), 1.26-1.18 (m, 2H); MS (EI) Calc'd for $C_{20}H_{23}N_{10}$ [M+H]+, 403; found 403.

Example 9: Preparation of Intermediate K

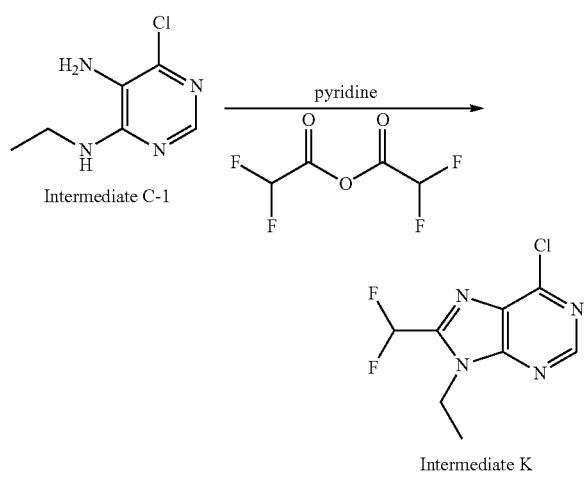

Intermediate C-1 (5 g, 30 mmol) was dissolved in dry DCM (120 ml) then pyridine (47 ml, 58 mmol) and 2,2-difluoroacetic anhydride (10 g, 58 mmol) were added sequentially. The mixture was stirred for 16 h. After this time, another portion of 2,2-difluoroacetic anhydride (10 g, 58 mmol) was added and the reaction was stirred for an additional 4 h, after which the solvent was removed in vacuo. The residue was then partitioned between DCM (50 ml) and water (40 ml), the layers were separated and the aqueous layer was extracted with DCM (2×40 ml). The combined organic layers were dried over anhydrous sodium sulfate and filtered, and the filtrate was concentrated under reduced pressure. The residue was purified by chromatography on silica gel (eluting with EA/PE=1/5) to provide Intermediate K. MS (ESI) Calc'd for $(C_8H_8ClF_2N_4)$ [M+H]$^+$, 233; found, 233.

Compounds 1-1 through 1-38 are listed in Table 1 and have be made in analogous fashion to those compounds illustrated in Examples 1-9 and as outlined below.

Compound 1-3 was prepared in an analogous fashion to Example 2, using benzohydrazide in place of cyclopropanecarbohydrazide. Chiral resolution of the racemic final compound was achieved via chiral preparative SFC (Chiralpak®, AS-H™, 21×250 (mm), 10% (Methanol+0.25% Dimethyl Ethyl Amine) in CO$_2$, 70 ml/min) to provide 1-3 (slower eluting enantiomer, 4.4 min).

Compounds 1-4 and 1-5 were prepared according to Example 2, step 7 using 3-isopropyl-5,6,7,8-tetrahydro-[1,2,4]triazolo[4,3-a]pyridin-6-amine (commercially available from Enamine Ltd.). Chiral resolution of the racemic final compound was achieved via chiral preparative SFC (Phenomenex, Lux-4, 21×250 (mm), 40% (Methanol+0.25% Dimethyl Ethyl Amine) in CO$_2$, 70 ml/min) to provide 1-4 (faster eluting enantiomer, 5.5 min) and 1-5 (slower eluting enantiomer, 6.5 min).

Compounds 1-6 and 1-7 were prepared according to Example 2, step 7 using 3-ethyl-5,6,7,8-tetrahydro-[1,2,4]triazolo[4,3-a]pyridin-6-amine (commercially available from Enamine Ltd.). Chiral resolution of the racemic final compound was achieved via chiral preparative SFC (Chiralpak® IB™, 21×250 (mm), 15% (Methanol+0.25% Dimethyl Ethyl Amine) in CO$_2$, 70 ml/min) to provide 1-6 (faster eluting enantiomer, 8.8 min) and 1-7 (slower eluting enantiomer, 9.9 min).

Compounds 1-8 and 1-9 were prepared according to Example 2, step 7 using 3-isopropyl-5,6,7,8-tetrahydro-[1,2,4]triazolo[4,3-a]pyridin-6-amine (commercially available from Enamine Ltd.) and Intermediate K. Chiral resolution of the racemic final compound was achieved via chiral preparative SFC (Phenomenex, Lux-4, 21×250 (mm), 30% (Methanol+0.25% Dimethyl Ethyl Amine) in CO$_2$, 70 ml/min) to provide 1-8 (faster eluting enantiomer, 3.9 min) and 1-9 (slower eluting enantiomer, 5.2 min).

Compounds 1-11 through 1-17 were prepared in an analogous fashion to Example 3 using the corresponding boronic acids or esters.

Compounds 1-19 through 1-24 were prepared in an analogous fashion to Example 4 using the corresponding boronic acids or esters.

Compounds 1-26 and 1-27 were prepared in an analogous fashion to Example 4, Step 1, using Intermediate B in place of 3-isopropyl-5,6,7,8-tetrahydro-[1,2,4]triazolo[4,3-a]pyridin-6-amine. Chiral resolution of the racemic final compound was achieved via chiral preparative SFC (Chiralpak® IA™, 21×250 (mm), 30% (Methanol+0.25% Dimethyl Ethyl Amine) in CO$_2$, 70 ml/min) to provide 1-26 (faster eluting enantiomer, 5.4 min) and 1-27 (slower eluting enantiomer, 6.1 min).

Compounds 1-28 through 1-30 were prepared in an analogous fashion to Example 4, Step 2 using compound 1-26 in place of Intermediate F.

Compounds 1-33 and 1-34 were prepared in an analogous fashion to Example 6. Chiral resolution of the racemic final compound was achieved via chiral preparative SFC (Phenomenex-Lux-2, 21×250 (mm), 35% (Methanol+0.25% Dimethyl Ethyl Amine) in CO$_2$, 70 ml/min) to provide 1-33 (faster eluting enantiomer, 8.8 min) and 1-34 (slower eluting enantiomer, 10 min).

Compounds 1-35 and 1-36 were prepared in an analogous fashion to Example 6. Chiral resolution of the racemic final compound was achieved via chiral preparative SFC (Phenomenex-Lux-2, 21×250 (mm), 45% (Methanol+0.25% Dimethyl Ethyl Amine) in CO$_2$, 70 ml/min) to provide 1-35 (faster eluting enantiomer, 8.0 min) and 1-36 (slower eluting enantiomer, 9.2 min).

TABLE 1

| Compound Number | Structure | IUPAC Name | Exact Mass [M + H]+ |
| --- | --- | --- | --- |
| 1-1 | 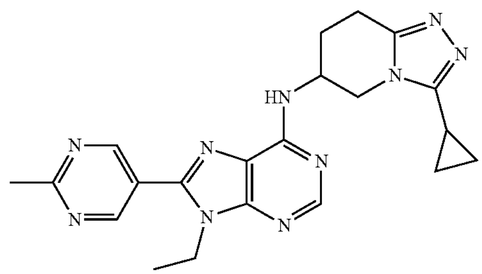 [SMILES: CCn1c(-c2cnc(C)nc2)nc2c(NC3CCc4nnc(C5CC5)n4C3)ncnc21] | (S or R)-N-(3-cyclopropyl-5,6,7,8-tetrahydro[1,2,4]triazolo[4,3-a]pyridin-6-yl)-9-ethyl-8-(2-methylpyrimidin-5-yl)-9H-purin-6-amine | Calc'd 417, found 417 |
| 1-2 | 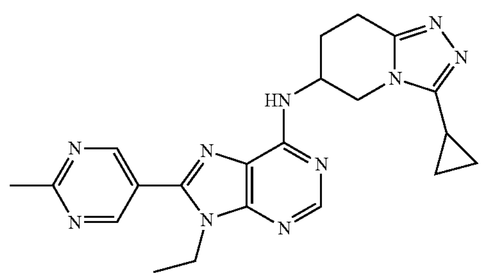 [SMILES: CCn1c(-c2cnc(C)nc2)nc2c(NC3CCc4nnc(C5CC5)n4C3)ncnc21] | (S or R)-N-(3-cyclopropyl-5,6,7,8-tetrahydro[1,2,4]triazolo[4,3-a]pyridin-6-yl)-9-ethyl-8-(2-methylpyrimidin-5-yl)-9H-purin-6-amine | Calc'd 417, found 417 |
| 1-3 | 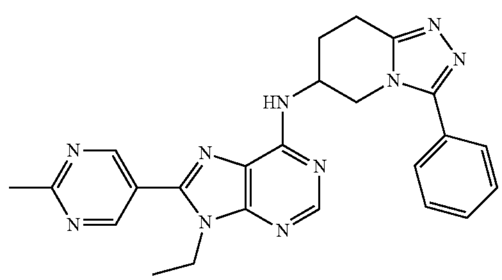 [SMILES: CCn1c(-c2cnc(C)nc2)nc2c(NC3CCc4nnc(-c5ccccc5)n4C3)ncnc21] | (S or R)-9-ethyl-8-(2-methylpyrimidin-5-yl)-N-[3-phenyl-5,6,7,8-tetrahydro[1,2,4]triazolo[4,3-a]pyridin-6-yl]-9H-purin-6-amine | Calc'd 453, found 453 |
| 1-4 | 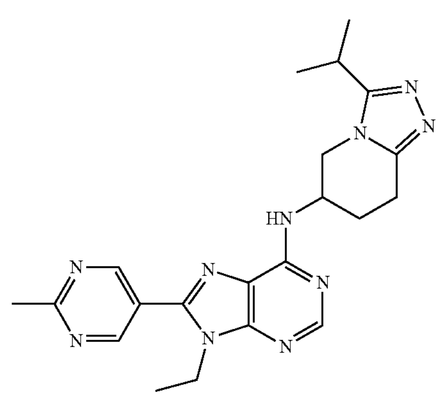 [SMILES: CCn1c(-c2cnc(C)nc2)nc2c(NC3CCc4nnc(C(C)C)n4C3)ncnc21] | (S or R)-9-ethyl-N-[3-(1-methylethyl)-5,6,7,8-tetrahydro[1,2,4]triazolo[4,3-a]pyridin-6-yl]-8-(2-methylpyrimidin-5-yl)-9H-purin-6-amine | Calc'd 419, found 419 |

TABLE 1-continued

| Compound Number | Structure | IUPAC Name | Exact Mass [M + H]+ |
| --- | --- | --- | --- |
| 1-5 | 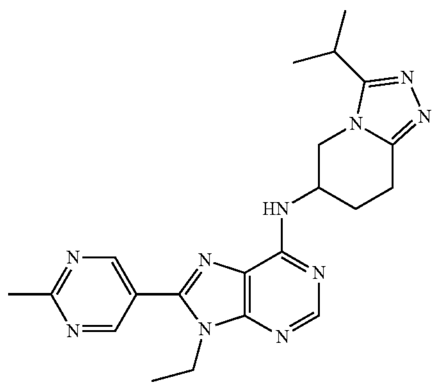 [SMILES: CCn1c(-c2cnc(C)nc2)nc2c(NC3CCc4nnc(C(C)C)n4C3)ncnc21] | (S or R)-9-ethyl-N-[3-(1-methylethyl)-5,6,7,8-tetrahydro[1,2,4]triazolo[4,3-a]pyridin-6-yl]-8-(2-methylpyrimidin-5-yl)-9H-purin-6-amine | Calc'd 419, found 419 |
| 1-6 | 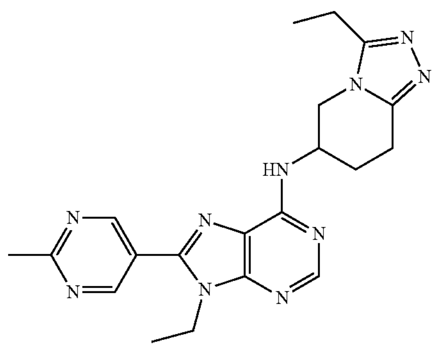 [SMILES: CCc1nnc2n1CC(Nc1ncnc3c1nc(-c1cnc(C)nc1)n3CC)CC2] | (S or R)-9-ethyl-N-[3-ethyl-5,6,7,8-tetrahydro[1,2,4]triazolo[4,3-a]pyridin-6-yl]-8-(2-methylpyrimidin-5-yl)-9H-purin-6-amine | Calc'd 405, found 405 |
| 1-7 | 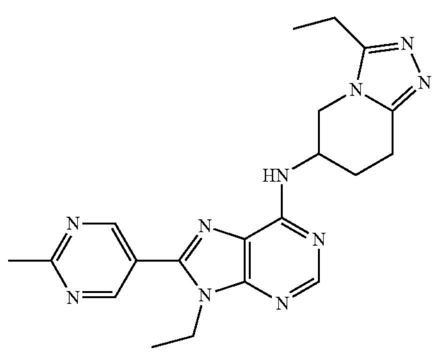 [SMILES: CCc1nnc2n1CC(Nc1ncnc3c1nc(-c1cnc(C)nc1)n3CC)CC2] | (S or R)-9-ethyl-N-[3-ethyl-5,6,7,8-tctrahydro[1,2,4]triazolo[4,3-a]pyridin-6-yl]-8-(2-methylpyrimidin-5-yl)-9H-purin-6-amine | Calc'd 405, found 405 |
| 1-8 | 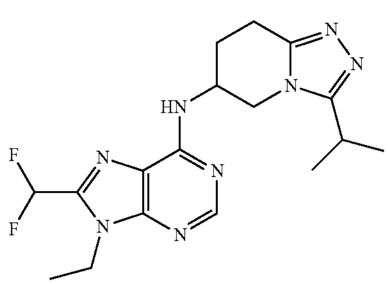 [SMILES: CCn1c(C(F)F)nc2c(NC3CCc4nnc(C(C)C)n4C3)ncnc21] | (S or R)-8-(difluoromethyl)-9-ethyl-N-[3-(1-methylethyl)-5,6,7,8-tetrahydro[1,2,4]triazolo[4,3-a]pyridin-6-yl]-9H-purin-6-amine | Calc'd 377, found 377 |

TABLE 1-continued

| Compound Number | Structure | IUPAC Name | Exact Mass [M + H]+ |
|---|---|---|---|
| 1-9 | 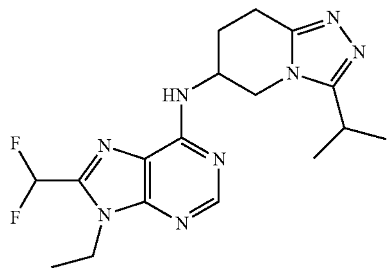 [SMILES: CCn1c(C(F)F)nc2c(NC3CCc4nnc(C(C)C)n4C3)ncnc21] | (S or R)-8-(difluoromethyl)-9-ethyl-N-[3-(1-methylethyl)-5,6,7,8-tetrahydro[1,2,4]triazolo[4,3-a]pyridin-6-yl]-9H-purin-6-amine | Calc'd 377, found 377 |
| 1-10 | 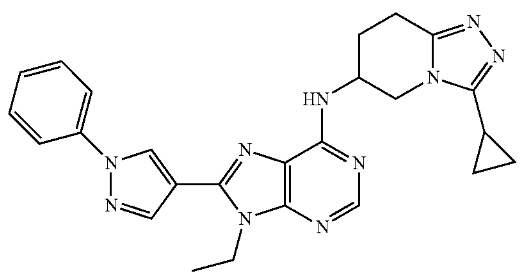 [SMILES: CCn1c(-c2cnn(-c3ccccc3)c2)nc2c(NC3CCc4nnc(C5CC5)n4C3)ncnc21] | (S and R)-N-(3-cyclopropyl-5,6,7,8-tetrahydro[1,2,4]triazolo[4,3-a]pyridin-6-yl)-9-ethyl-8-(1-phenyl-1H-pyrazol-4-yl)-9H-purin-6-amine | Calc'd 467, found 467 |
| 1-11 | 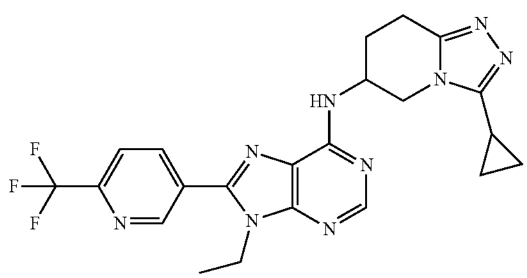 | (S and R)-N-(3-cyclopropyl-5,6,7,8-tetrahydro[1,2,4]triazolo[4,3-a]pyridin-6-yl)-9-ethyl-8-[6-(trifluoromethyl)pyridin-3-yl]-9H-purin-6-amine | Calc'd 470, found 470 |
| 1-12 | 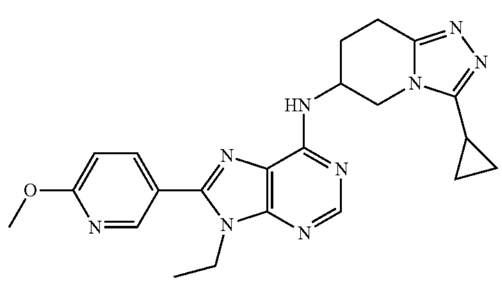 [SMILES: CCn1c(-c2ccc(OC)nc2)nc2c(NC3CCc4nnc(C5CC5)n4C3)ncnc21] | (S and R)-N-(3-cyclopropyl-5,6,7,8-tetrahydro[1,2,4]triazolo[4,3-a]pyridin-6-yl)-9-ethyl-8-(6-methoxypyridin-3-yl)-9H-purin-6-amine | Calc'd 432, found 432 |
| 1-13 | 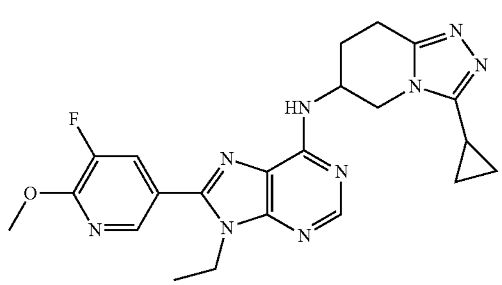 [SMILES: CCn1c(-c2cnc(OC)c(F)c2)nc2c(NC3CCc4nnc(C5CC5)n4C3)ncnc21] | (S and R)-N-(3-cyclopropyl-5,6,7,8-tetrahydro[1,2,4]triazolo[4,3-a]pyridin-6-yl)-9-ethyl-8-(5-fluoro-6-methoxypyridin-3-yl)-9H-purin-6-amine | Calc'd 450, found 450 |

TABLE 1-continued

| Compound Number | Structure | IUPAC Name | Exact Mass [M + H]+ |
|---|---|---|---|
| 1-14 | 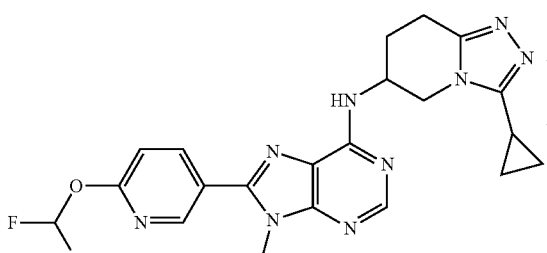 | (S and R)-N-(3-cyclopropyl-5,6,7,8-tetrahydro[1,2,4]triazolo[4,3-a]pyridin-6-yl)-8-[6-(difluoromethoxy)pyridin-3-yl]-9-ethyl-9H-purin-6-amine | Calc'd 468, found 468 |
| 1-15 | 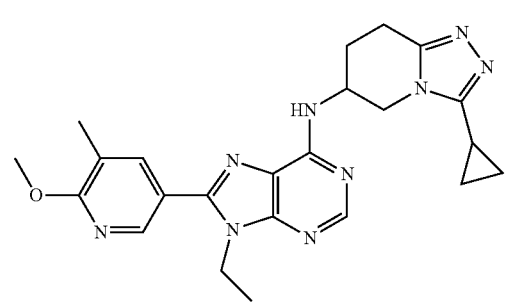 [SMILES: CCn1c(-c2cnc(OC)c(C)c2)nc2c(NC3CCc4nnc(C5CC5)n4C3)ncnc21] | (S and R)-N-(3-cyclopropyl-5,6,7,8-tetrahydro[1,2,4]triazolo[4,3-a]pyridin-6-yl)-9-ethyl-8-(6-methoxy-5-methylpyridin-3-yl)-9H-purin-6-amine | Calc'd 446, found 446 |
| 1-16 | 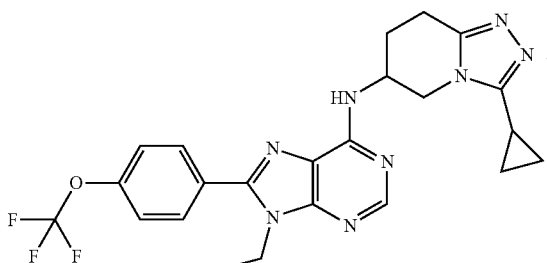 | (S and R)-N-(3-cyclopropyl-5,6,7,8-tetrahydro[1,2,4]triazolo[4,3-a]pyridin-6-yl)-9-ethyl-8-[4-(trifluoromethoxy)phenyl]-9H-purin-6-amine | Calc'd 485, found 485 |
| 1-17 | 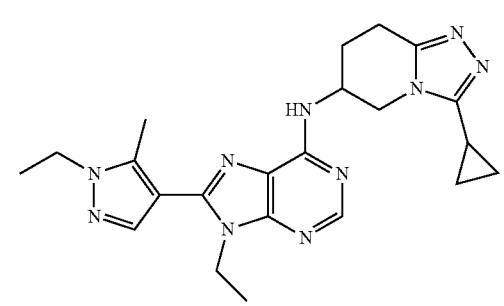 [SMILES: CCn1ncc(-c2nc3c(NC4CCc5nnc(C6CC6)n5C4)ncnc3n2CC)c1C] | (S and R)-N-(3-cyclopropyl-5,6,7,8-tetrahydro[1,2,4]triazolo[4,3-a]pyridin-6-yl)-9-ethyl-8-(1-ethyl-5-methyl-1H-pyrazol-4-yl)-9H-purin-6-amine | Calc'd 433, found 433 |
| 1-18 | 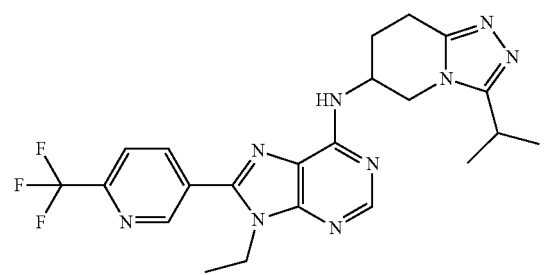 [SMILES: CCn1c(-c2ccc(C(F)(F)F)nc2)nc2c(NC3CCc4nnc(C(C)C)n4C3)ncnc21] | (S or R)-9-ethyl-N-[3-(1-methylethyl)-5,6,7,8-tetrahydro[1,2,4]triazolo[4,3-a]pyridin-6-yl]-8-[6-(trifluoromethyl)pyridin-3-yl]-9H-purin-6-amine | Calc'd 472, found 472 |

TABLE 1-continued

| Compound Number | Structure | IUPAC Name | Exact Mass [M + H]+ |
|---|---|---|---|
| 1-19 | 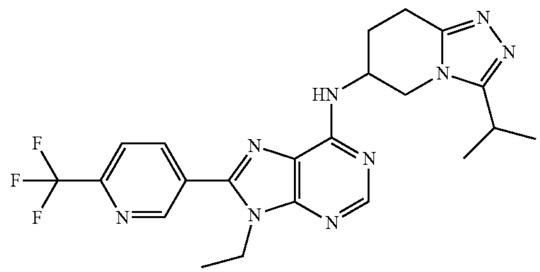 | (S or R)-9-ethyl-N-[3-(1-methylethyl)-5,6,7,8-tetrahydro[1,2,4]triazolo[4,3-a]pyridin-6-yl]-8-(6-(trifluoromethyl)pyridin-3-yl]-9H-purin-6-amine | Calc'd 472, found 472 |
| 1-20 | 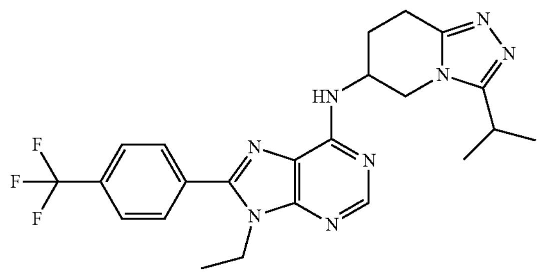 [SMILES: CCn1c(-c2ccc(C(F)(F)F)cc2)nc2c(NC3CCc4nnc(C(C)C)n4C3)ncnc21] | (S or R)-9-ethyl-N-[(6S)-3-(1-methylethyl)-5,6,7,8-tetrahydro[1,2,4]triazolo[4,3-a]pyridin-6-yl]-8-[4-(trifluoromethyl)phenyl]-9H-purin-6-amine | Calc'd 471, found 471 |
| 1-21 | 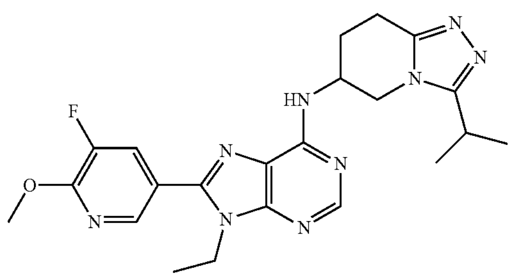 [SMILES: CCn1c(-c2cnc(OC)c(F)c2)nc2c(NC3CCc4nnc(C(C)C)n4C3)ncnc21] | (S or R)-9-ethyl-8-(5-fluoro-6-methoxypyridin-3-yl)-N-[3-(1-methylethyl)-5,6,7,8-tetrahydro[1,2,4]triazolo[4,3-a]pyridin-6-yl]-9H-purin-6-amine | Calc'd 452, found 452 |
| 1-22 | 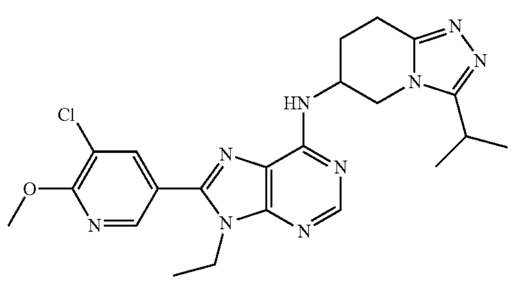 [SMILES: CCn1c(-c2cnc(OC)c(Cl)c2)nc2c(NC3CCc4nnc(C(C)C)n4C3)ncnc21] | (S or R)-8-(5-chloro-6-methoxypyridin-3-yl)-9-ethyl-N-[3-(1-methylethyl)-5,6,7,8-tetrahydro[1,2,4]triazolo[4,3-a]pyridin-6-yl]-9H-purin-6-amine | Calc'd 468, found 468 |
| 1-23 | 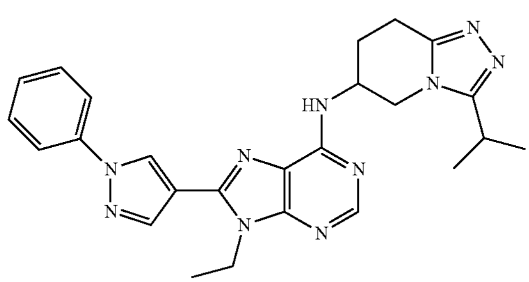 [SMILES: CCn1c(-c2cnn(-c3ccccc3)c2)nc2c(NC3CCc4nnc(C(C)C)n4C3)ncnc21] | (S or R)-9-ethyl-N-[3-(1-mtthylethyl)-5,6,7,8-tetrahydro[1,2,4]triazolo[4,3-a]pyridin-6-yl]-8-(1-phenyl-1H-pyrazol-4-yl)-9H-purin-6-amine | Calc'd 469, found 469 |

TABLE 1-continued

| Compound Number | Structure | IUPAC Name | Exact Mass [M + H]+ |
|---|---|---|---|
| 1-24 | 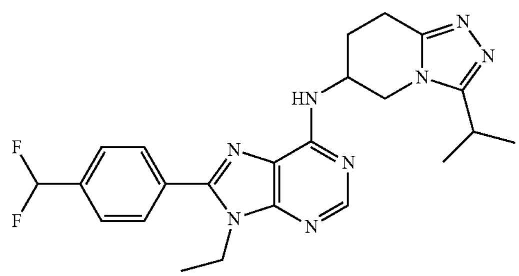 [SMILES: CCn1c(-c2ccc(C(F)F)cc2)nc2c(NC3CCc4nnc(C(C)C)n4C3)ncnc21] | 8-[4-(difluoromethyl)phenyl]-9-ethyl-N-[(6(S or R))-3-(1-methylethyl)-5,6,7,8-tetrahydro[1,2,4]triazolo[4,3-a]pyridin-6-yl]-9H-purin-6-amine | Calc'd 453, found 453 |
| 1-25 | 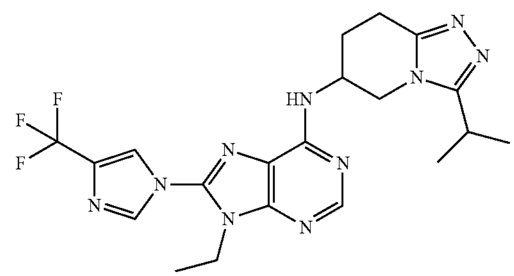 [SMILES: CCn1c(-n2cnc(C(F)(F)F)c2)nc2c(NC3CCc4nnc(C(C)C)n4C3)ncnc21] | 9-ethyl-N-[(6(S or R))-3-(1-methylethyl)-5,6,7,8-tetrahydro[1,2,4]triazolo[4,3-a]pyridin-6-yl]-8-[4-(trifluoromethyl)-1H-imidazol-1-yl]-9H-purin-6-amine | Calc'd 461, found 461 |
| 1-26 | 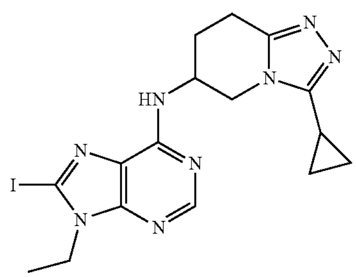 [SMILES: CCn1c(I)nc2c(NC3CCc4nnc(C5CC5)n4C3)ncnc21] | (S or R)-N-[3-cyclopropyl-5,6,7,8-tetrahydro[1,2,4]triazolo[4,3-a]pyridin-6-yl]-9-ethyl-8-iodo-9H-purin-6-amine | Calc'd 451, found 451 |
| 1-27 | 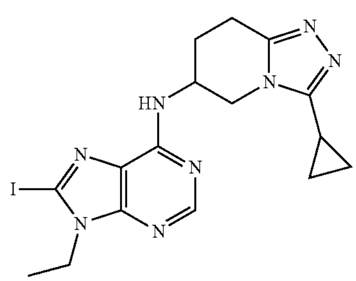 [SMILES: CCn1c(I)nc2c(NC3CCc4nnc(C5CC5)n4C3)ncnc21] | (S or R)-N-[3-cyclopropyl-5,6,7,8-tetrahydro[1,2,4]triazolo[4,3-a]pyridin-6-yl]-9-ethyl-8-iodo-9H-purin-6-amine | Calc'd 451, found 451 |
| 1-28 | 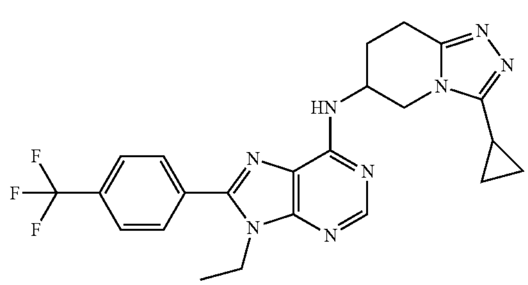 | (S or R)-N-(3-cyclopropyl-5,6,7,8-tetrahydro[1,2,4]triazolo[4,3-a]pyridin-6-yl)-9-ethyl-8-[4-(trifluoromethyl)phenyl]-9H-purin-6-amine | Calc'd 469, found 469 |

TABLE 1-continued

| Compound Number | Structure | IUPAC Name | Exact Mass [M + H]+ |
|---|---|---|---|
| 1-29 | 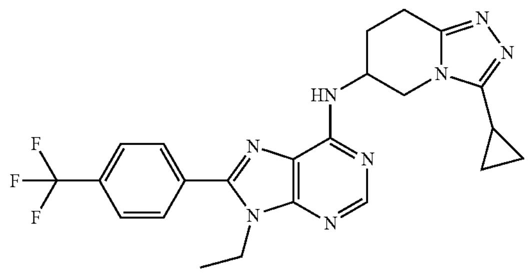 [SMILES: CCn1c(-c2ccc(C(F)(F)F)cc2)nc2c(NC3CCc4nnc(C5CC5)n4C3)ncnc21] | (S or R)-N-(3-cyclopropyl-5,6,7,8-tetrahydro[1,2,4]triazolo[4,3-a]pyridin-6-yl)-9-ethyl-8-[4-(trifluoromethyl)phenyl]-9H-purin-6-amine | Calc'd 469, found 469 |
| 1-30 | 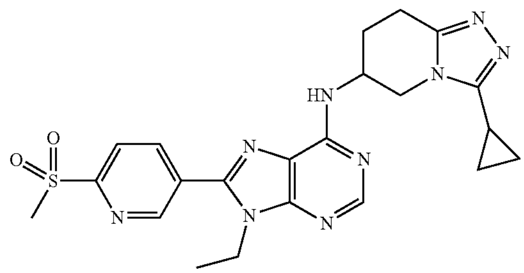 [SMILES: CCn1c(-c2ccc(S(C)(=O)=O)nc2)nc2c(NC3CCc4nnc(C5CC5)n4C3)ncnc21] | (S or R)-N-[(6S)-3-cyclopropyl-5,6,7,8-tetrahydro[1,2,4]triazolo[4,3-a]pyridin-6-yl]-9-ethyl-8-[6-(methylsulfonyl)pyridin-3-yl]-9H-purin-6-amine | Calc'd 480, found 480 |
| 1-31 | 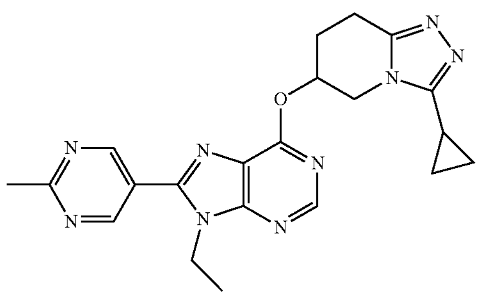 [SMILES: CCn1c(-c2cnc(C)nc2)nc2c(OC3CCc4nnc(C5CC5)n4C3)ncnc21] | (S or R)-6-{[3-cyclopropyl-5,6,7,8-tetrahydro[1,2,4]triazolo[4,3-a]pyridin-6-yl]oxy}-9-ethyl-8-(2-methylpyrimidin-5-yl)-9H-purine | Calc'd 418, found 418 |
| 1-32 | 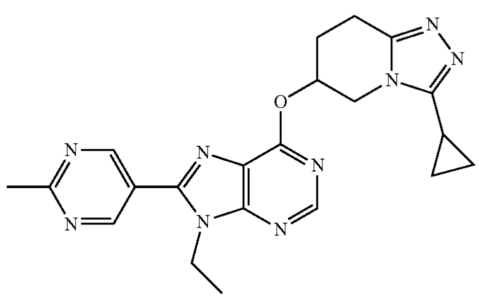 [SMILES: CCn1c(-c2cnc(C)nc2)nc2c(OC3CCc4nnc(C5CC5)n4C3)ncnc21] | (S or R)-6-{[3-cyclopropyl-5,6,7,8-tetrahydro[1,2,4]triazolo[4,3-a]pyridin-6-yl]oxy}-9-ethyl-8-(2-methylpyrimidin-5-yl)-9H-purine | Calc'd 418, found 418 |
| 1-33 | 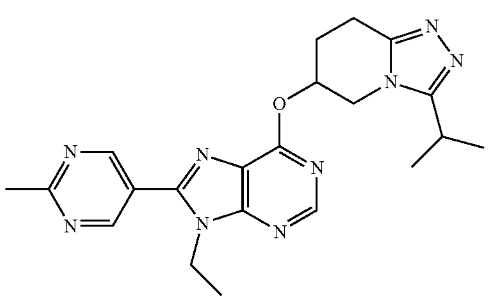 [SMILES: CCn1c(-c2cnc(C)nc2)nc2c(OC3CCc4nnc(C(C)C)n4C3)ncnc21] | (S or R)-9-ethyl-6-{[3-(1-methylethyl)-5,6,7,8-tetrahydro[1,2,4]triazolo[4,3-a]pyridin-6-yl]oxy}-8-(2-methylpyrimidin-5-yl)-9H-purine | Calc'd 420, found 420 |

TABLE 1-continued

| Compound Number | Structure | IUPAC Name | Exact Mass [M + H]+ |
|---|---|---|---|
| 1-34 | 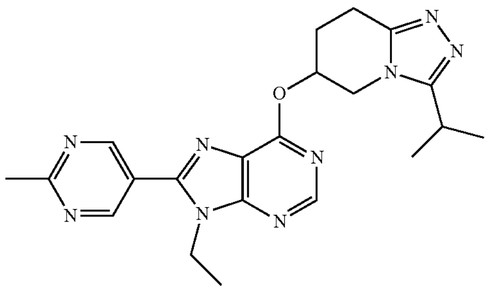 [SMILES: CCn1c(-c2cnc(C)nc2)nc2c(OC3CCc4nnc(C(C)C)n4C3)ncnc21] | (S or R)-9-ethyl-6-{[3-(1-methylethyl)-5,6,7,8-tetrahydro[1,2,4]triazolo[4,3-a]pyridin-6-yl]oxy}-8-(2-methylpyrimidin-5-yl)-9H-purine | Calc'd 420, found 420 |
| 1-35 | 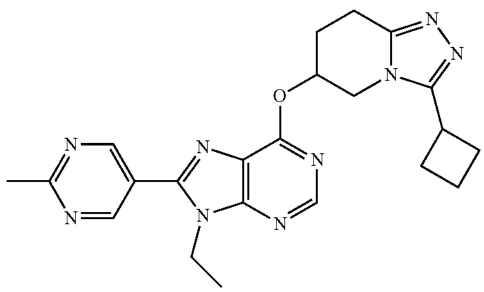 [SMILES: CCn1c(-c2cnc(C)nc2)nc2c(OC3CCc4nnc(C5CCC5)n4C3)ncnc21] | (S or R)-6-{[3-cyclobutyl-5,6,7,8-tetrahydro[1,2,4]triazolo[4,3-a]pyridin-6-yl]oxy}-9-ethyl-8-(2-methylpyrimidin-5-yl)-9H-purine | Calc'd 432, found 432 |
| 1-36 | 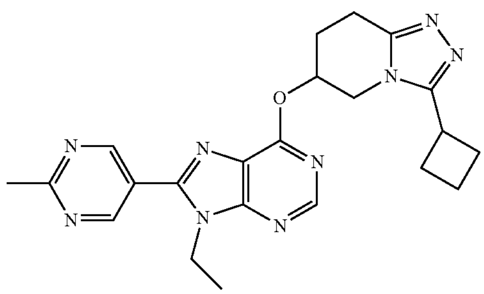 [SMILES: CCn1c(-c2cnc(C)nc2)nc2c(OC3CCc4nnc(C5CCC5)n4C3)ncnc21] | (S or R)-6-{[3-cyclobutyl-5,6,7,8-tetrahydro[1,2,4]triazolo[4,3-a]pyridin-6-yl]oxy}-9-ethyl-8-(2-methylpyrimidin-5-yl)-9H-purine | Calc'd 432, found 432 |
| 1-37 | 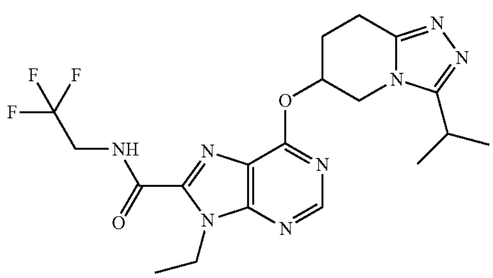 [SMILES: CCn1c(C(=O)NCC(F)(F)F)nc2c(OC3CCc4nnc(C(C)C)n4C3)ncnc21] | (S and R)-9-ethyl-6-{[3-(1-methylethyl)-5,6,7,8-tetrahydro[1,2,4]triazolo[4,3-a]pyridin-6-yl]amino}-N-(2,2,2-trifluoroethyl)-9H-purine-8-carboxamide | Calc'd 452, found 452 |
| 1-38 | 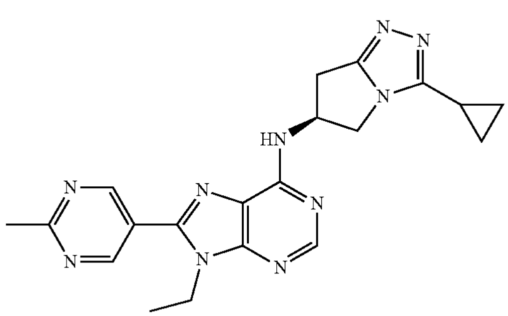 [SMILES: CCn1c(-c2cnc(C)nc2)nc2c(N[C@H]3Cc4nnc(C5CC5)n4C3)ncnc21] | N-[(6S)-3-cyclopropyl-6,7-dihydro-5H-pyrrolo[2,1-c][1,2,4]triazol-6-yl]-9-ethyl-8-(2-methylpyrimidin-5-yl)-9H-purin-6-amine | Calc'd 403, found 403 |

Compound Examples of Table 2

Example 10: Preparation of Compounds 2-1 and 2-2

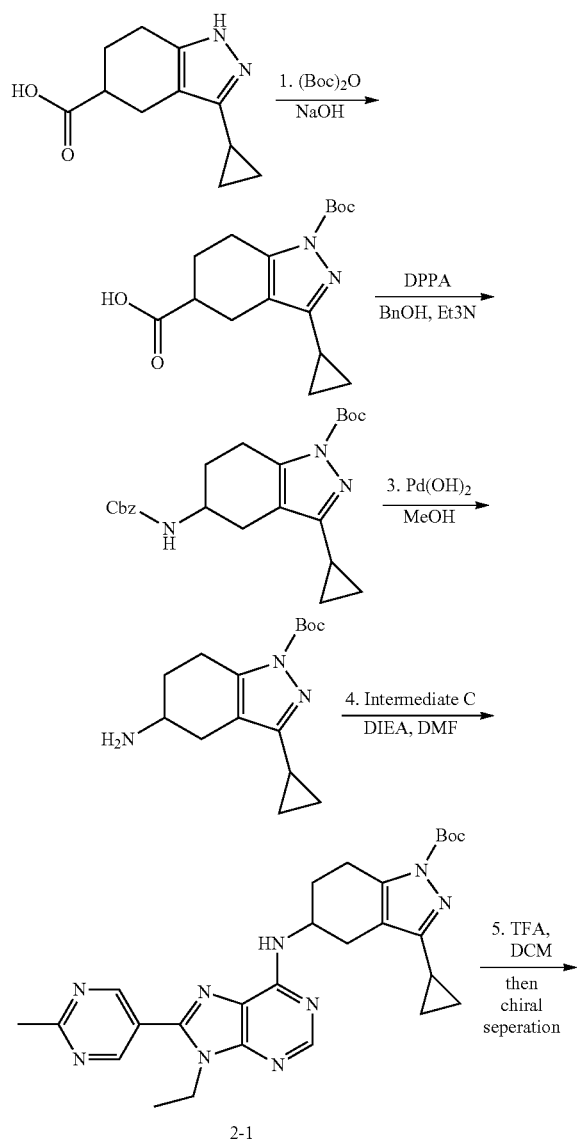

2-1

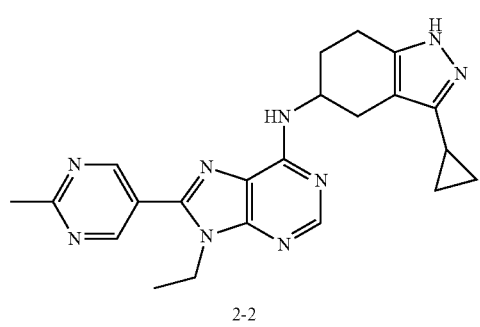

2-2

Step 1: Preparation of (S and R)-1-(tert-butoxycarbonyl)-3-cyclopropyl-4,5,6,7-tetrahydro-1H-indazole-5-carboxylic acid To a slurry of 3-cyclopropyl-4,5,6,7-tetrahydro-1H-indazole-5-carboxylic acid (1 g, 4.85 mmol) (commercially available from Ark Pharm, Inc.) in THF:water (1:1, 10 ml) was added NaOH (0.26 g, 6.50 mmol). The slurry became a solution, after which di-tert-butyl dicarbonate (1.689 ml, 7.27 mmol) was added portion-wise. The mixture was stirred at RT for 48 h, after which the volatiles were removed in vacuo. The residual solution was washed with DCM (×3), after which the pH of the aqueous layer was adjusted to pH4 by the addition of HCl (6M). The aqueous layer was then extracted with EtOAc(×3). The combined organic layers were washed with brine, dried over $Na_2SO_4$, filtered, and concentrated in vacuo to afford (S and R)-1-(tert-butoxycarbonyl)-3-cyclopropyl-4,5,6,7-tetrahydro-1H-indazole-5-carboxylic acid which was used without further purification. MS (EI) Calc'd for $C_{12}H_{15}N_2O_4$ [M+H-t-Bu]+, 251; found 251.

Step 2: Preparation of (S and R)-tert-butyl 5-(((benzyloxy)carbonyl)amino)-3-cyclopropyl-4,5,6,7-tetrahydro-1H-indazole-1-carboxylate A vial was charged with 1-(tert-butoxycarbonyl)-3-cyclopropyl-4,5,6,7-tetrahydro-1H-indazole-5-carboxylic acid (1.17 g, 3.82 mmol), to which dioxane (15 ml), diphenylphosphoryl azide (1.236 g, 4.49 mmol) and $Et_3N$ (2.0 ml, 14.35 mmol) were added. The mixture was stirred at 50° C. for 4 h, after which benzyl alcohol (BnOH) (0.8 ml, 7.73 mmol) was added. The resulting mixture was allowed to stir for 18 h at 70° C., after which it was cooled and the volatiles were removed in vacuo. The residue thus obtained was re-dissolved in EtOAc and the organic layer was washed with saturated aqueous $NaHCO_3$, then brine, after which it was dried over $Na_2SO_4$ and filtered. The solution was then concentrated in vacuo and the resulting residue was dissolved in DCM and filtered. The filtrate was purified via flash chromatography (silica gel, eluting with a gradient of 0-40% EtOAc in hexanes) to afford (S and R)-tert-butyl 5-(((benzyloxy)carbonyl)amino)-3-cyclopropyl-4,5,6,7-tetrahydro-1H-indazole-1-carboxylate. MS (EI) Calc'd for $C_{18}H_{22}N_3O_2$ [M+H-Boc]+, 312; found 312.

Step 3: Preparation of (S and R)-tert-butyl 5-amino-3-cyclopropyl-4,5,6,7-tetrahydro-1H-indazole-1-carboxylate To the solution of (S and R)-tert-butyl 5-(((benzyloxy)carbonyl)amino)-3-cyclopropyl-4,5,6,7-tetrahydro-1H-indazole-1-carboxylate (1.02 g, 2.49 mmol) in MeOH (10 ml), was added $Pd(OH)_2$ (100 mg, 0.142 mmol). The mixture was stirred at RT under $H_2$ for 5 h, after which it was filtered and concentrated in vacuo to afford (S and R)-tert-butyl 5-amino-3-cyclopropyl-4,5,6,7-tetrahydro-1H-indazole-1-carboxylate which was used in the next step without further purification. MS (EI) Calc'd for $C_{15}H_{24}N_3O_2$ [M+H]+, 278; found 278.

Step 4: Preparation of Compound 2-1

To a solution of (S and R)-tert-butyl 5-amino-3-cyclopropyl-4,5,6,7-tetrahydro-1H-indazole-1-carboxylate (184.5 mg, 0.665 mmol) in DMF (4 ml) was added 6-chloro-9-ethyl-8-(2-methylpyrimidin-5-yl)-9H-purine (Intermediate C) (200 mg, 0.73 mmol) and DIEA (0.4 ml, 2.3 mmol). The mixture was stirred at 80° C. for 18 h, after which a second portion of DIEA (0.1 ml) was added and the reaction was further stirred at 90° C. for 20 h. The reaction was then cooled and the solvent was removed in vacuo to afford a residue, which was purified via flash chromatography (silica gel, eluting with a gradient 0-4% MeOH in EtOAc) to afford (S and R)-tert-butyl 3-cyclopropyl-5-((9-ethyl-8-(2-methylpyrimidin-5-yl)-9H-purin-6-yl)amino)-4,5,6,7-tetrahydro-1H-indazole-1-carboxylate (2-1) $^1$H NMR (600 MHz, DMSO-d6) δ 9.08 (s, 2H), 8.28 (s, 1H), 7.97 (d, J=7.8 Hz, 1H), 4.54-4.42 (m, 1H), 4.26 (q, J=7.2 Hz, 2H), 3.06-2.94 (m, 1H), 2.88-2.74 (m, 2H), 2.70 (s, 3H), 2.60-2.50 (m, 1H), 2.08-1.98 (m, 1H), 1.98-1.82 (m, 1H), 1.78-1.68 (m, 1H), 1.50 (s, 9H), 1.27 (t, J=7.2 Hz, 3H), 0.88-0.70 (m, 4H); MS (EI) Calc'd for $C_{27}H_{34}N_9O_2$ [M+H]+, 516; found 516.

Step 5: Preparation of Compound 2-2

To the solution of (S and R)-tert-butyl 3-cyclopropyl-5-((9-ethyl-8-(2-methylpyrimidin-5-yl)-9H-purin-6-yl)amino)-4,5,6,7-tetrahydro-1H-indazole-1-carboxylate (2-1) (224 mg, 0.434 mmol) in DCM (2 ml) was added TFA (0.2 ml, 2.60 mmol). The mixture was stirred at RT for 18 h, after which another portion of TFA (0.5 ml) was added, and the solution was further stirred at RT for 3 h. The solvent was then removed in vacuo and the resulting residue was dissolved into MeOH purified by reverse-phase preparative HPLC (0:100 to 95:5 MeCN:water: 0.1% v/v TFA modifier) to afford N-(3-cyclopropyl-4,5,6,7-tetrahydro-1H-indazol-5-yl)-9-ethyl-8-(2-methylpyrimidin-5-yl)-9H-purin-6-amine as the TFA salt. Chiral resolution of the racemic material was achieved via chiral preparative SFC (Phenomenex Cellulose Lux-4, 21×250 (mm), 40% (Methanol+ 0.25% Dimethyl Ethyl Amine) in $CO_2$, 70 ml/min) to provide 2-2 (faster eluting enantiomer, 7.33 min)$^1$H NMR (600 MHz, DMSO-d6) δ 9.08 (s, 2H), 8.26 (s, 1H), 7.90 (d, J=6.6 Hz, 1H), 4.50-4.40 (m, 1H), 4.26 (q, J=7.2 Hz, 2H), 2.84-2.73 (m, 1H), 2.70 (s, 3H), 2.68-2.48 (m, 4H), 2.05-1.90 (m, 1H), 1.90-1.75 (m, 1H), 1.75-1.60 (m, 1H), 1.27 (t, J=7.2 Hz, 3H), 0.85-0.55 (m, 4H); MS (EI) Calc'd for $C_{22}H_{26}N_9$ [M+H]+, 416; found 416.

Example 11: Preparation of Intermediate M

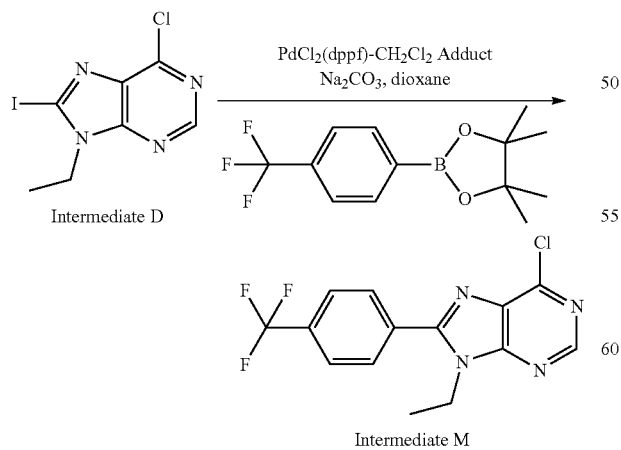

A vial was charged with 4,4,5,5-tetramethyl-2-(4-(trifluoromethyl)phenyl)-1,3,2-dioxaborolane (212 mg, 0.778 mmol), 6-chloro-9-ethyl-8-iodo-9H-purine (Intermediate D) (200 mg, 0.648 mmol), $PdCl_2$(dppf) (23.72 mg, 0.032 mmol), dioxane (5 ml) and $Na_2CO_3$ (0.7 ml, 1.400 mmol, 2M aquoues solution). The vial was sealed and the mixture was evacuated and backfilled with nitrogen (×3), after which it was heated at 80° C. for 4 h. The solution was then cooled and the solvent was removed in vacuo to afford a residue which was purified via column chromatography (silica gel, eluting 0-30% EtOAc in Hexanes) to afford 6-chloro-9-ethyl-8-(4-(trifluoromethyl)phenyl)-9H-purine (Intermediate M). MS (EI) Calc'd for $C_{14}H_{11}ClF_3N_4$[M+H]$^+$, 327; found 327.

Example 12: Preparation of Compound 2-3

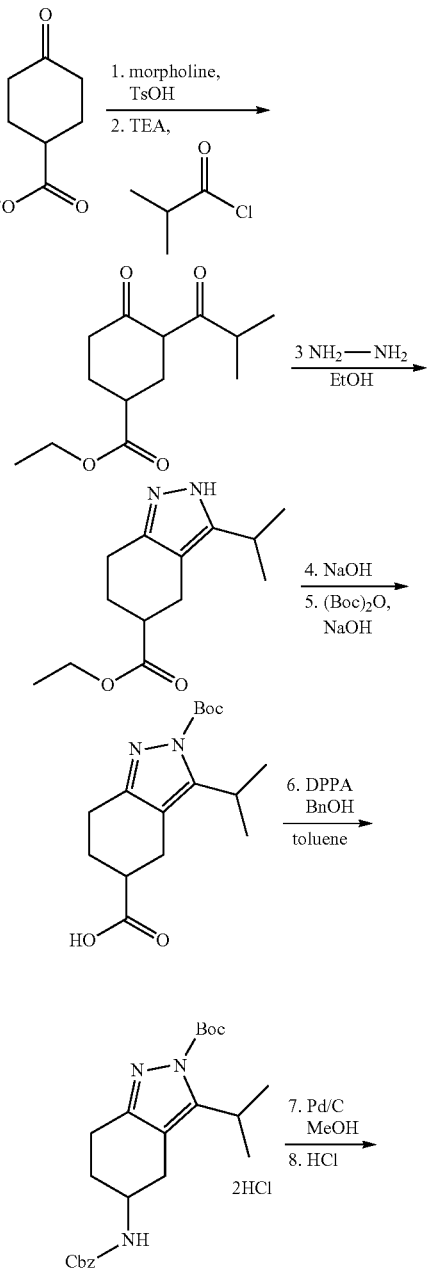

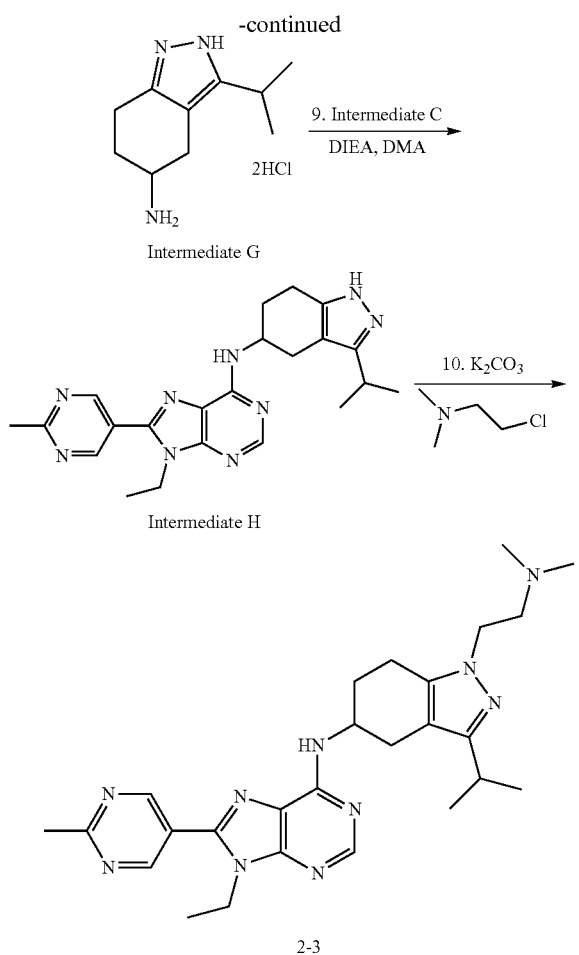

Step 1: Preparation of ethyl 4-morpholinocyclohex-3-enecarboxylate

A 2 L round bottom flask was charged with ethyl 4-oxo-cyclohexane-1-carboxylate (100 g, 590 mmol) in toluene (1 L) and para-toluenesulfonic acid (TsOH) (2.0 g, 11 mmol) and morpholine (57 g, 650 mmol) were added. The resulting solution was stirred at 130° C. for 16 h. The reaction mixture was then cooled to 40° C. and the volatiles were removed in vacuo to afford ethyl 4-morpholinocyclohex-3-enecarboxylate which was used in the next step without further purification.

Step 2: Preparation of (S and R)-ethyl 3-isobutyryl-4-oxocyclohexanecarboxylate A 2 L 3-necked round-bottom, flask purged and maintained with an inert atmosphere of nitrogen, was charged with 4-morpholinocyclohex-3-enecarboxylate (126 g, 527 mmol), and THF (1.3 L) and TEA (133 g, 1.31 mol) were added. The reaction mixture was cooled to 0° C. 2-methyl-propanoyl chloride (55 g. 516 mmol) was added drop-wise with stirring. The resulting solution was allowed to come to RT and stirred 16 h, after which HCl (6 M, 600 ml) was added. The resulting solution was stirred at RT for 3 h, after which ice water (600 ml) was added. The resulting solution was then extracted with EA (3×500 ml). The combined organic extracts were washed with brine (800 ml), dried over anhydrous sodium sulfate, filtered, and the filtrate was concentrated in vacuo to afford (S and R)-ethyl 3-isobutyryl-4-oxocyclohexanecarboxylate, which was used in the next step without further purification.

Step 3: Preparation of (S and R)-ethyl 3-isopropyl-4,5,6,7-tetrahydro-2H-indazole-5-carboxylate A 2 L 4-necked round-bottom flask, purged and maintained with an inert atmosphere of nitrogen, was charged with (S and R)-ethyl 3-isobutyryl-4-oxocyclohexanecar-boxylate (140 g, 583 mmol), ethanol (1.3 L), and hydrazine hydrate (85 wt %, 68 g, 1.46 mol). The resulting solution was stirred overnight at 80° C., after which the solution was cooled to 30° C. and the volatiles were removed in vacuo. The resulting solution was diluted with ice water (600 ml), and the solution was extracted with EA (3×800 ml). The combined organic layers was dried over anhydrous sodium sulfate, filtered, and concentrated in vacuo to afford (S and R)-ethyl 3-isopropyl-4,5,6,7-tetrahydro-2H-indazole-5-car-boxylate which was used in the next step without further purification. MS (EI) Calc'd for $C_{13}H_{20}N_2O_2$ [M+H]+, 237; found 237.

Step 4: Preparation of (S and R)-3-isopropyl-4,5,6,7-tetrahydro-2H-indazole-5-carboxylic acid A 2 L round-bottom flask was charged with ethyl 3-iso-propyl-4,5,6,7-tetrahydro-2H-indazole-5-carboxylate (140 g, 592 mmol) and a mixture of THF:water (400:700 ml) was added, followed by the drop-wise addition of a solution of sodium hydroxide (36 g, 900 mmol) in water (150 ml). The resulting solution was stirred at RT 18 h, after which the volatiles were removed in vacuo and the resulting solution was washed with DCM (2×500 ml). The pH value of the combined aqueous layers was adjusted to 3 with via the addition of aqueous HCl (10 M). The solids which precipitated out of solution were collected by filtration to afford (S and R)-3-isopropyl-4,5,6,7-tetrahydro-2H-indazole-5-carboxylic acid which was used in the next step without further purification. MS (EI) Calc'd for $C_{11}H_{16}N_2O_2$ [M+H]+, 209; found 209.

Step 5: Preparation of (S and R)-2-(tert-butoxycar-bonyl)-3-isopropyl-4,5,6,7-tetrahydro-2H-indazole-5-carboxylic acid A 2 L 3-necked round-bottom flask was charged with 3-isopropyl-4,5,6,7-tetrahydro-2H-indazole-5-carboxylic acid (100 g, 480 mmol) and a mixture of THF:water (500:500 ml) was added, followed by the addition of sodium hydroxide (20 g, 500 mmol) in several batches. Di-tert-butyl dicarbonate (150 g, 720 mmol) was then added in several batches, and the resulting solution was stirred at RT for 48 h, after which the volatiles were removed in vacuo. The resulting solution was extracted with DCM (2×300 ml), and the pH value of the combined aqueous layers was adjusted to 4 with aqueous HCl (6 M). The resulting solution was extracted with EtOAc (3×600 ml) and the combined organic layers were washed with brine (1 L), dried over anhydrous sodium sulfate and filtered. The filtrate was concentrated in vacuo to afford (S and R)-2-(tert-butoxycarbonyl)-3-isopro-pyl-4,5,6,7-tetrahydro-2H-indazole-5-carboxylic acid which was used without further purification in the next step. MS (EI) Calc'd for $C_{16}H_{24}N_2O_4$ [M+H]+, 309; found 309.

Step 6: Preparation of (S and R)-tert-butyl 5-(((benzyloxy)carbonyl)amino)-3-isopropyl-4,5,6,7-tetrahydro-2H-indazole-2-carboxylate A 2 L 4-necked round-bottom flask, purged and maintained with an inert atmosphere of nitrogen, was charged with (S and R)-2-(tert-butoxycarbonyl)-3-isopropyl-4,5,6,7-tetrahydro-2H-indazole-5-carboxylic acid (100 g, 324 mmol), and 1,4-dioxane (1 L), triethylamine (82 g, 810 mmol), and DPPA (98 g, 356 mmol) were added. The resulting solution was stirred for 4 h at 50° C., after which benzyl alcohol (42 g, 389 mmol) was added and the solution was allowed to stir at 70° C. 18 h. The reaction mixture was then cooled to 25° C. and was diluted with water (1 L). The resulting solution was extracted with EtOAc (2×1 L) and the combined organic layers were washed with brine (2×1 L), over anhydrous sodium sulfate, and concentrated in vacuo. The residue thus obtained was purified via flash chromatography (silica gel, eluting with a gradient of 1:20 to 1:10 EtOAc:PE) to provide (S and R)-tert-butyl 5-(((benzyloxy)carbonyl)amino)-3-isopropyl-4,5,6,7-tetrahydro-2H-indazole-2-carboxylate. MS (EI) Calc'd for $C_{23}H_{31}N_3O_4$ [M+H]+, 414; found 414.

Step 7: Preparation of (S and R)-3-isopropyl-4,5,6,7-tetrahydro-2H-indazol-5-amine, 2HCl (Intermediate G)

A 100-mL round-bottom flask, purged and maintained with an inert atmosphere of nitrogen, was charged with (S and R)-tert-butyl 5-(((benzyloxy)carbonyl)amino)-3-isopropyl-4,5,6,7-tetrahydro-2H-indazole-2-carboxylate (1 g, 2.4 mmol), and MeOH (15 ml) and palladium on carbon (500 mg, 10% wt) was added. Hydrogen was then introduced into the system, and the resulting solution was stirred at RT for 18 h. The solids were then filtered, and to the filtrate was added HCl. The resulting solution was stirred overnight at 36° C., after which the solution was concentrated in vacuo. The crude product was purified by re-crystallization from diethyl ether to provide 3-isopropyl-4,5,6,7-tetrahydro-2H-indazol-5-amine, 2HCl (Intermediate G). MS (EI) Calc'd for $C_{10}H_{17}N_3[M+H]^+$, 180; found 180.

Step 8: Preparation of 9-ethyl-N-(3-isopropyl-4,5,6,7-tetrahydro-1H-indazol-5-yl)-8-(2-methylpyrimidin-5-yl)-9H-purin-6-amine (Intermediate H)

A vial was charged with 3-isopropyl-4,5,6,7-tetrahydro-1H-indazol-5-amine, 2HCl (1.61 g, 6.38 mmol) and 6-chloro-9-ethyl-8-(2-methylpyrimidin-5-yl)-9H-purine (Intermediate C) (1.99 g, 7.24 mmol) and DMA (50 ml) and DIEA (5.0 ml, 28.6 mmol) were added. The mixture was stirred at 90° C. for 18 h, after which the temperature was increased to 100° C. for another 7 h. The solvent was then removed in vacuo to afford a residue, which was purified via flash chromatography (silica gel, eluting 3N ammonia in 8:92 MeOH:DCM) to afford (S and R)-9-ethyl-N-(3-isopropyl-4,5,6,7-tetrahydro-1H-indazol-5-yl)-8-(2-methylpyrimidin-5-yl)-9H-purin-6-amine (Intermediate H). MS (EI) Calc'd for $C_{22}H_{28}N_9$ [M+H]+, 418; found 418.

Step 9: Preparation of Compound 2-3

A vial was charged with (S and R)-9-ethyl-N-(3-isopropyl-4,5,6,7-tetrahydro-1H-indazol-5-yl)-8-(2-methylpyrimidin-5-yl)-9H-purin-6-amine (30 mg, 0.072 mmol), 2-chloro-N,N-dimethylethanamine, HCl (10.35 mg, 0.072 mmol), $K_2CO_3$ (34.8 mg, 0.251 mmol) and MeCN (500 µL). The mixture was heated under microwave irradiation at 150° C. for 2 h. The mixture was then cooled, filtered through a Whatman™ Autovial™ Syringeless Filter, PTFE; 0.45µ, and purified by reverse-phase preparative HPLC (0:100 to 95:5 MeCN:water: 0.1% v/v TFA modifier) to afford (S and R)—N-(1-(2-(dimethylamino)ethyl)-3-isopropyl-4,5,6,7-tetrahydro-1H-indazol-5-yl)-9-ethyl-8-(2-methylpyrimidin-5-yl)-9H-purin-6-amine as the TFA salt (2-3). $^1$H NMR (600 MHz, DMSO-d6) δ 9.43 (s, 1H), 9.09 (s, 2H), 8.30 (s, 1H), 8.25 (s, 1H), 4.50-4.38 (m, 1H), 4.34-4.18 (m, 4H), 3.48-3.38 (m, 2H), 2.86-2.74 (m, 9H), 2.74-2.64 (m, 4H), 2.60-2.50 (m, 1H), 2.10-2.00 (m, 1H), 1.94-1.80 (m, 1H), 1.28 (t, J=7.2 Hz, 3H), 1.20-1.06 (m, 6H); MS (EI) Calc'd for $C_{26}H_{37}N_{10}[M+H]+$, 489; found 489.

Example 13: Preparation of Intermediate L

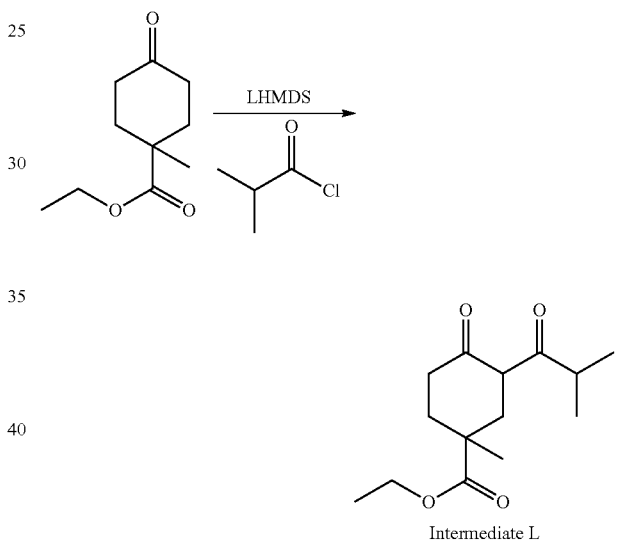

Intermediate L

Into a 5-L 4-necked round-bottom flask, purged and maintained with an inert atmosphere of nitrogen, was placed ethyl 1-methyl-4-oxocyclohexane-1-carboxylate (188 g, 1.02 mol, commercially available from Ark Pharm, Inc.) and toluene (2 L). To this mixture was then added LHMDS (1.02 L, 1.02 mol) drop-wise with stirring at −10° C. The reaction mixture was stirred for 30 min at −10° C., after which a solution of 2-methylpropanoyl chloride (55 g, 516 mmol) in toluene (200 ml) was added drop-wise with stirring at 0° C. The resulting solution was allowed to come to RT and was stirred overnight. The reaction was then quenched by addition of saturated aqueous $NH_4Cl$ (1 L). The resulting solution was extracted with EA (3×300 ml). The combined organic layers were dried over anhydrous sodium sulfate, filtered, and concentrated in vacuo. The resulting residue was purified via flash chromatography (silica gel, eluting with EA:PE (1:30)) to provide (S and R)-ethyl 1-methyl-3-(2-methylpropanoyl)-4-oxocyclohexane-1-carboxylate (Intermediate L).

Example 14: Preparation of Compound 2-12

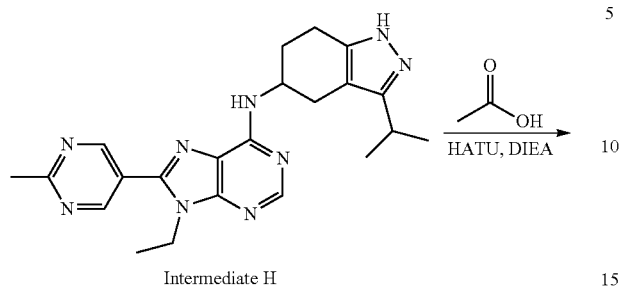

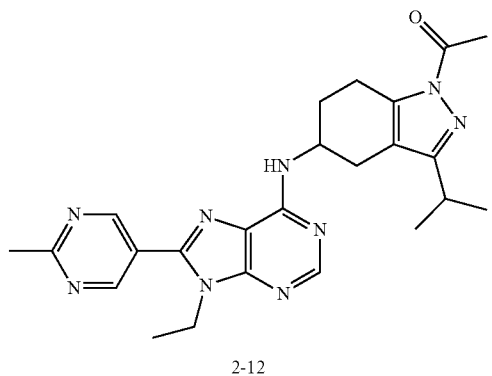

A vial was charged with (S and R)-9-ethyl-N-(3-isopropyl-4,5,6,7-tetrahydro-1H-indazol-5-yl)-8-(2-methylpyrimidin-5-yl)-9H-purin-6-amine (Intermediate H) (25 mg, 0.060 mmol), HATU (25.04 mg, 0.066 mmol), DMF (0.5 ml), acetic acid (25 mg, 0.416 mmol), and DIEA (50 µl, 0.286 mmol). The mixture was stirred at RT for 17 h, after which the mixture was filtered through a Whatman™ Autovial™ Syringeless Filter, PTFE; 0.45 t, and purified by reverse-phase preparative HPLC (0:100 to 95:5 MeCN:water: 0.1% v/v TFA modifier) to afford 1-(5-((9-ethyl-8-(2-methylpyrimidin-5-yl)-9H-purin-6-yl)amino)-3-isopropyl-4,5,6,7-tetrahydro-1H-indazol-1-yl)ethanone as the TFA salt (2-12). $^1$H NMR (600 MHz, DMSO-d6) δ 9.09 (s, 2H), 8.46 (s, 1H), 8.34 (s, 1H), 4.50-4.36 (m, 1H), 4.28 (q, J=7.2 Hz, 2H), 3.18-3.08 (m, 1H), 3.04-2.76 (m, 3H), 2.71 (s, 3H), 2.64-2.55 (m, 1H), 2.52 (s, 3H), 2.10-2.00 (m, 1H), 1.94-1.80 (m, 1H), 1.28 (t, J=7.2 Hz, 3H), 1.22-1.10 (m, 6H); MS (EI) Calc'd for $C_{24}H_{30}N_9O$ [M+H]+, 460; found 460.

Example 15: Preparation of Compound 2-15

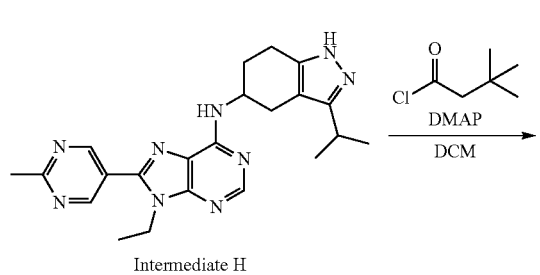

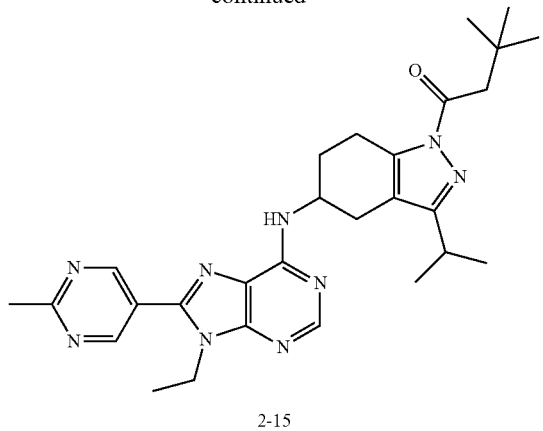

A mixture of (S and R)-9-ethyl-N-(3-isopropyl-4,5,6,7-tetrahydro-1H-indazol-5-yl)-8-(2-methylpyrimidin-5-yl)-9H-purin-6-amine (Intermediate H) (15 mg, 0.036 mmol), tert-butylacetyl chloride (5.80 mg, 0.043 mmol) and DMAP (6.58 mg, 0.054 mmol) in DCM (400 µl) was stirred at RT for 16 h. The solvent was then removed in vacuo and the residue was redissolved into MeOH and purified by reverse-phase preparative HPLC (0:100 to 95:5 MeCN:water: 0.1% v/v TFA modifier) to afford 1-(5-((9-ethyl-8-(2-methylpyrimidin-5-yl)-9H-purin-6-yl)amino)-3-isopropyl-4,5,6,7-tetrahydro-1H-indazol-1-yl)-3,3-dimethylbutan-1-one as the TFA salt (2-15). $^1$H NMR (600 MHz, DMSO-d6) δ 9.09 (s, 2H), 8.43 (s, 1H), 8.33 (s, 1H), 4.48-4.36 (m, 1H), 4.28 (d, J=7.2 Hz, 2H), 3.20-3.10 (m, 1H), 3.00-2.76 (m, 5H), 2.71 (s, 3H), 2.64-2.54 (m, 1H), 2.08-2.00 (m, 1H), 1.96-1.80 (m, 1H), 1.28 (s, J=7.2 Hz, 3H), 1.22-1.10 (m, 6H), 0.98 (s, 9H); MS (EI) Calc'd for $C_{28}H_{38}N_9O$ [M+H]+, 516; found 516.

Example 16: Preparation of Compound 2-16

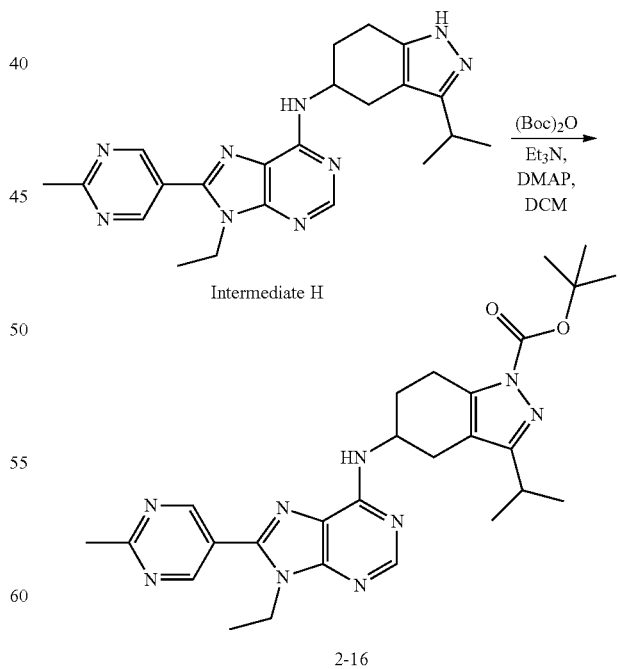

To the solution of (S and R)-9-ethyl-N-(3-isopropyl-4,5,6,7-tetrahydro-1H-indazol-5-yl)-8-(2-methylpyrimidin-5-yl)-9H-purin-6-amine (Intermediate H) (22 mg, 0.052 mmol) in DCM (209 µl) were added Et₃N (10 µl, 0.072 mmol), di-tert-butyl dicarbonate (17 µl, 0.073 mmol) and DMAP (1 mg, 8.2 µmol). The mixture was stirred at RT for 18 h, after which an additional amount of di-tert-butyl dicarbonate (18 mg, 0.082 mmol) and TEA (10 µl, 0.072 mmol) were added. The mixture was heated to 40° C. for 1 h. The resulting mixture was purified by flash chromatography (silica gel, eluting EtOAc:MeOH=8:92) to afford tert-butyl 5-((9-ethyl-8-(2-methylpyrimidin-5-yl)-9H-purin-6-yl)amino)-3-isopropyl-4,5,6,7-tetrahydro-1H-indazole-1-carboxylate (2-16). ¹H NMR (600 MHz, DMSO-d6) δ 9.08 (s, 2H), 8.28 (s, 1H), 8.01 (s, 1H), 4.50-4.40 (m, 1H), 4.26 (q, J=7.2 Hz, 2H), 3.10-2.98 (m, 1H), 2.90-2.74 (m, 3H), 2.70 (s, 3H), 2.64-2.52 (m, 1H), 2.08-1.98 (m, 1H), 1.94-1.80 (m, 1H), 1.51 (s, 9H), 1.28 (t, J=7.2 Hz, 3H), 1.20-1.04 (m, 6H); MS (EI) Calc'd for $C_{27}H_{36}N_9O_2$ [M+H], 518; found 518.

Example 17: Synthesis of Compound 2-20

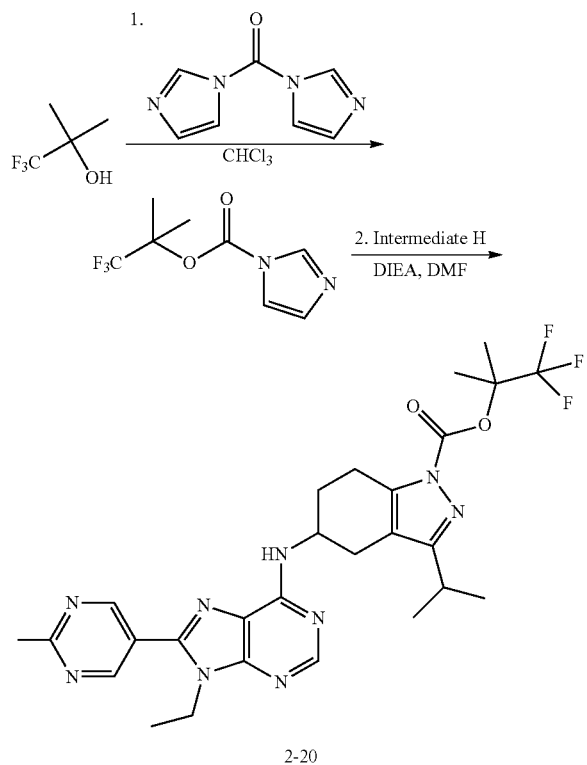

2-20

Step 1: Preparation of 1,1,1-trifluoro-2-methylpropan-2-yl 1H-imidazole-1-carboxylate A solution of carbonyldiimide (1.10 g, 6.78 mmol) in chloroform (10 ml) was charged with 1,1,1-trifluoro-2-methylpropan-2-ol (780 µl, 7.12 mmol) and stirred at RT for 88 h. The crude reaction mixture was then dried onto silica gel in vacuo and was purified via flash column chromatography (silica gel, eluting 0-100% EtOAc in Hexanes) to provide 1,1,1-trifluoro-2-methylpropan-2-yl 1H-imidazole-1-carboxylate. MS (EI) Calc'd for $C_8H_{10}NF_3N_2O_2$ [M+H]⁺, 222; found 222.

Step 2: Preparation of Compound 2-20

A vial was charged with (S and R)-9-ethyl-N-(3-isopropyl-4,5,6,7-tetrahydro-1H-indazol-5-yl)-8-(2-methylpyrimidin-5-yl)-9H-purin-6-amine (Intermediate H) (50 mg, 0.12 mmol), 1,1,1-trifluoro-2-methylpropan-2-yl 1H-imidazole-1-carboxylate (31.9 mg, 0.144 mmol), DIEA (41.8 µl, 0.240 mmol) and DMF (500 µl). The mixture was heated to 70° C. for 24 h, after which the temperature was increased to 90° C. for 20 h. The reaction mixture was then cooled, filtered through a Whatman™ Autovial™ Syringeless Filter, PTFE; 0.45µ, and purified by reverse-phase preparative HPLC (0:100 to 95:5 MeCN:water: 0.1% v/v TFA modifier) to afford (S and R)-1,1,1-trifluoro-2-methylpropan-2-yl 5-((9-ethyl-8-(2-methylpyrimidin-5-yl)-9H-purin-6-yl)amino)-3-isopropyl-4,5,6,7-tetrahydro-1H-indazole-1-carboxylate as the TFA salt (2-20)). ¹H NMR (600 MHz, DMSO-d6) δ 9.09 (s, 2H), 8.41 (s, 1H), 8.34 (s, 1H), 4.50-4.36 (m, 1H), 4.28 (q, J=7.2 Hz, 2H), 3.06-2.92 (m, 1H), 2.92-2.75 (m, 3H), 2.71 (s, 3H), 2.66-2.54 (m, 1H), 2.10-2.00 (m, 1H), 1.96-1.82 (m, 1H), 1.75 (s, 6H), 1.28 (t, J=7.2 Hz, 3H), 1.22-1.06 (m, 6H); MS (EI) Calc'd for $C_{27}H_{33}F_3N_9O_2$[M+H]+, 572; found 572.

Example 18: Synthesis of Compound 2-21

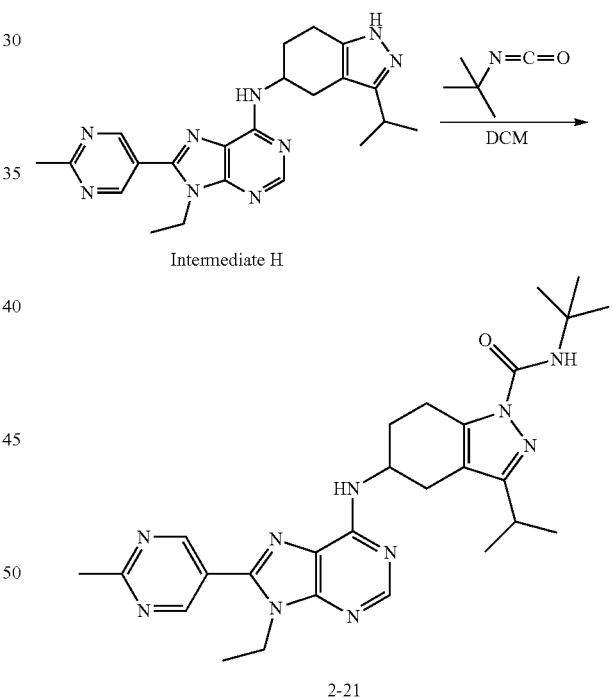

To the solution of 2-isocyanato-2-methylpropane (10 mg, 0.101 mmol) in DCM (200 µl) was added (S and R)-9-ethyl-N-(3-isopropyl-4,5,6,7-tetrahydro-1H-indazol-5-yl)-8-(2-methylpyrimidin-5-yl)-9H-purin-6-amine (Intermediate H) (25 mg, 0.060 mmol). The mixture was stirred at RT for 6 h, after which the solvent was removed in vacuo and the residue was redissolved in MeOH and purified by reverse-phase preparative HPLC (0:100 to 95:5 MeCN:water: 0.1% v/v TFA modifier) afford (S and R)—N-(tert-butyl)-5-((9-ethyl-8-(2-methylpyrimidin-5-yl)-9H-purin-6-yl)amino)-3-isopropyl-4,5,6,7-tetrahydro-1H-indazole-1-carboxamide as the TFA salt (2-21). ¹H NMR (600 MHz, DMSO-d6) δ 9.09 (s, 2H), 8.38 (s, 1H), 8.33 (s, 1H), 7.15 (s, 1H), 4.48-4.36 (m, 1H), 4.28 (q, J=7.2 Hz, 2H), 3.20-3.10 (m, 1H), 2.96-2.76 (m, 3H), 2.71 (s, 3H), 2.64-2.52 (m, 1H), 2.08-1.98 (m, 1H), 1.94-1.80 (m, 1H), 1.34 (s, 9H), 1.28 (t, J=7.2 Hz, 3H); 1.20-1.08 (m, 6H); MS (EI) Calc'd for $C_{27}H_{37}N_{10}O$ [M+H]+, 517; found 517.

Example 19: Synthesis of Compound 2-22

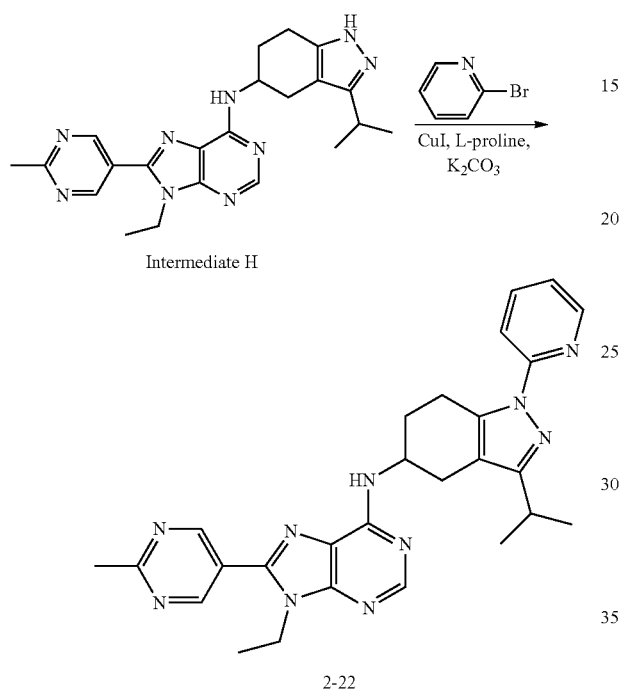

2-22

A vial was charged with (S and R)-9-ethyl-N-(3-isopropyl-4,5,6,7-tetrahydro-1H-indazol-5-yl)-8-(2-methylpyrimidin-5-yl)-9H-purin-6-amine (Intermediate H) (20 mg, 0.048 mmol), copper (I) iodide (0.912 mg, 4.79 μmol), L-proline (1.10 mg, 9.58 μmol), $K_2CO_3$ (19 mg, 0.14 mmol), DMSO (200 μl) and 2-bromopyridine (9.1 mg, 0.057 mmol). The vial was sealed and the mixture was evacuated and back filled with nitrogen (×4), after which it was heated at 100° C. for 24 h. The reaction mixture was then cooled and an additional amount of 2-bromopyridine (20 mg, 130 mmol), CuI (4 mg, 21 μmol), L-proline (4 mg, 35 μmol), and $K_2CO_3$ (15 mg, 0.11 mmol) was added. The mixture was again heated to 100° C. for 24 h, after which the solution was cooled and mixture was filtered through a Whatman™ Autovial™ Syringeless Filter, PTFE; 0.45μ, and purified by reverse-phase preparative HPLC (0:100 to 95:5 MeCN:water: 0.1% v/v TFA modifier) to afford (S and R)-9-ethyl-N-(3-isopropyl-1-(pyridin-2-yl)-4,5,6,7-tetrahydro-1H-indazol-5-yl)-8-(2-methylpyrimidin-5-yl)-9H-purin-6-amine as the TFA salt (2-22). ¹H NMR (600 MHz, DMSO-d6) δ 9.10 (s, 2H), 8.72 (s, 1H), 8.39 (s, 1H), 8.36 (d, J=3.6 Hz, 1H), 7.88 (dd, J=6.6, 1.8 Hz, 1H), 7.80 (d, J=7.8 Hz, 1H), 7.21 (dd, J=7.2, 1.8 Hz, 1H), 4.50-4.40 (m, 1H), 4.30 (q, J=7.2 Hz, 2H), 3.40-3.30 (m, 1H), 3.18-3.06 (m, 1H), 2.98-2.84 (m, 2H), 2.71 (s, 3H), 2.72-2.60 (m, 1H), 2.14-2.04 (m, 1H), 2.00-1.90 (m, 1H), 1.29 (t, J=7.2 Hz, 3H), 1.26-1.14 (m, 6H); MS (EI) Calc'd for $C_{27}H_{31}N_{10}$ [M+H]+, 495; found 495.

Example 20: Synthesis of Compound 2-23

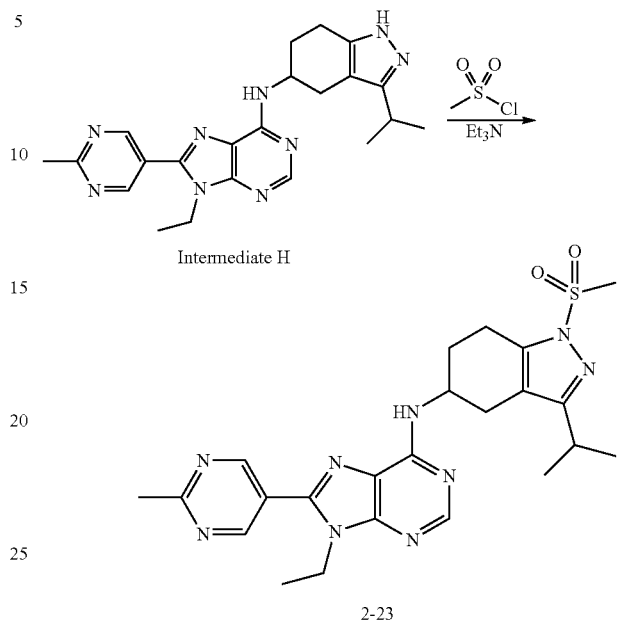

2-23

To a solution of (S and R)-9-ethyl-N-(3-isopropyl-4,5,6,7-tetrahydro-1H-indazol-5-yl)-8-(2-methylpyrimidin-5-yl)-9H-purin-6-amine (37.8 mg, 0.091 mmol) in DCM (700 μl) was added $Et_3N$ (30 μl, 0.215 mmol) and methanesulfonyl chloride (7.01 μl, 0.091 mmol). The mixture was stirred at RT for 16 h, after which the solvent was removed in vacuo and the residue was purified via reverse-phase preparative HPLC (0:100 to 95:5 MeCN:water: 0.1% v/v TFA modifier), which provided the desired compound together with its regioisomer. The compound mixture was then further purified by SFC (ES Industries Pyridyl Amide column, 10% (Methanol+0.25% Dimethyl Ethyl Amine) in $CO_2$, 70 ml/min) to afford desired isomer (S and R)-9-ethyl-N-(3-isopropyl-1-(methylsulfonyl)-4,5,6,7-tetrahydro-1H-indazol-5-yl)-8-(2-methylpyrimidin-5-yl)-9H-purin-6-amine (1-23). ¹H NMR (600 MHz, DMSO-d6) δ 9.08 (s, 2H), 8.27 (s, 1H), 8.03 (d, J=7.2 Hz, 1H), 4.56-4.44 (m, 1H), 4.26 (q, J=7.2 Hz, 2H), 3.34 (s, 3H), 3.08-2.74 (m, 4H), 2.70 (s, 3H), 2.64-2.52 (m, 1H), 2.08-1.98 (m, 1H), 1.96-1.84 (m, 1H), 1.27 (t, J=7.2 Hz, 3H), 1.22-1.10 (m, 6H); MS (EI) Calc'd for $C_{23}H_{30}N_9O_2S$ [M+H]+, 496; found 496.

Example 21: Synthesis of Compounds 2-24 and 2-25

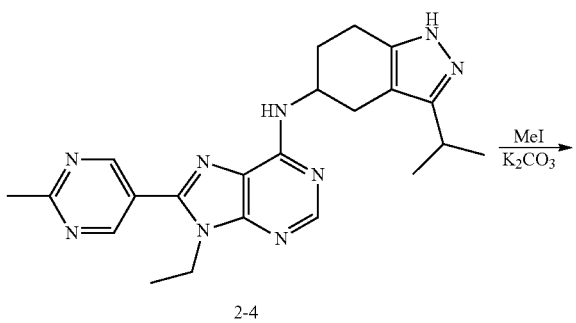

2-4

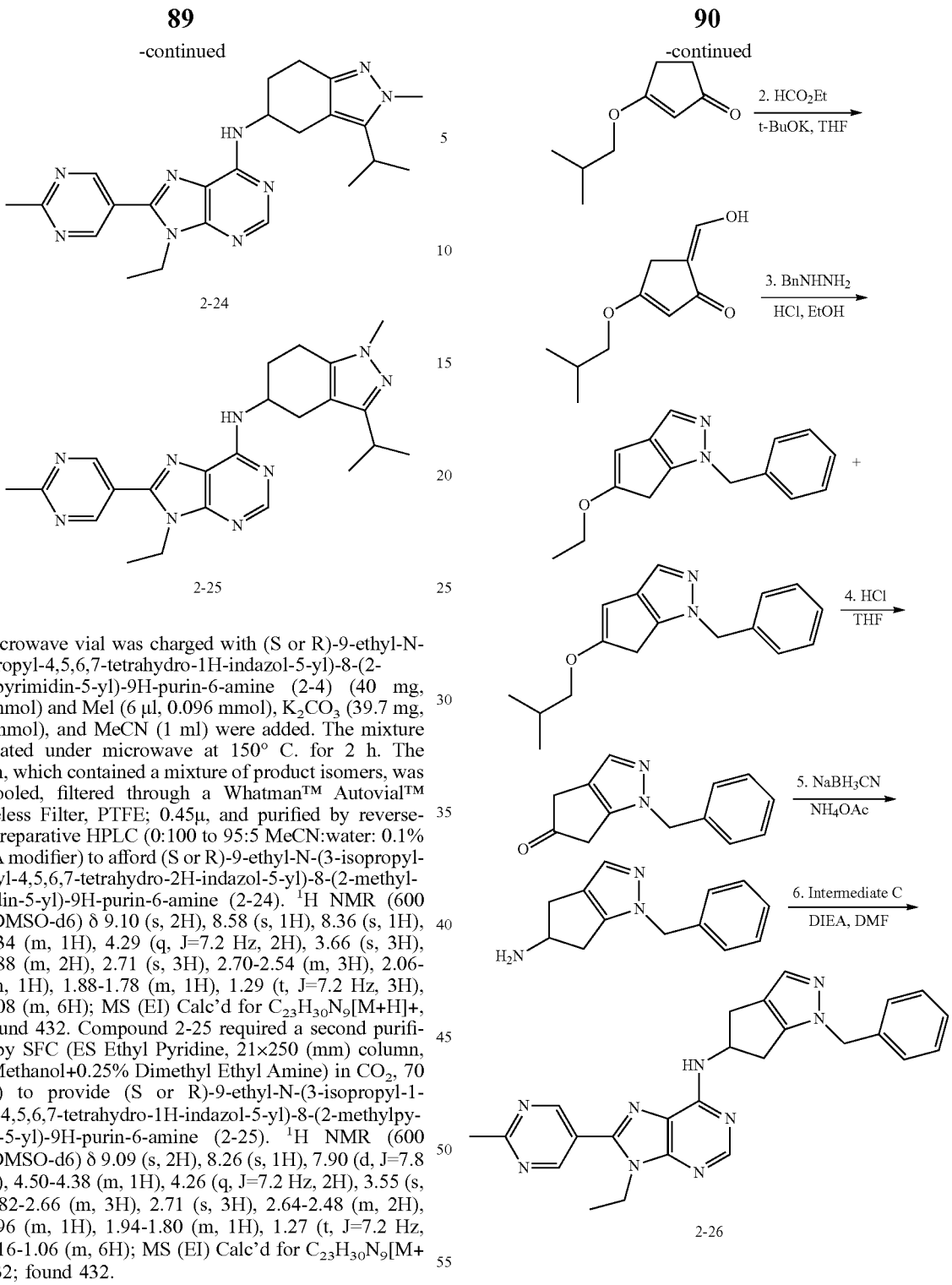

2-24

2-25

A microwave vial was charged with (S or R)-9-ethyl-N-(3-isopropyl-4,5,6,7-tetrahydro-1H-indazol-5-yl)-8-(2-methylpyrimidin-5-yl)-9H-purin-6-amine (2-4) (40 mg, 0.096 mmol) and MeI (6 μl, 0.096 mmol), $K_2CO_3$ (39.7 mg, 0.287 mmol), and MeCN (1 ml) were added. The mixture was heated under microwave at 150° C. for 2 h. The reaction, which contained a mixture of product isomers, was then cooled, filtered through a Whatman™ Autovial™ Syringeless Filter, PTFE; 0.45μ, and purified by reverse-phase preparative HPLC (0:100 to 95:5 MeCN:water: 0.1% v/v TFA modifier) to afford (S or R)-9-ethyl-N-(3-isopropyl-2-methyl-4,5,6,7-tetrahydro-2H-indazol-5-yl)-8-(2-methyl-pyrimidin-5-yl)-9H-purin-6-amine (2-24). $^1$H NMR (600 MHz, DMSO-d6) δ 9.10 (s, 2H), 8.58 (s, 1H), 8.36 (s, 1H), 4.46-4.34 (m, 1H), 4.29 (q, J=7.2 Hz, 2H), 3.66 (s, 3H), 3.10-2.88 (m, 2H), 2.71 (s, 3H), 2.70-2.54 (m, 3H), 2.06-1.96 (m, 1H), 1.88-1.78 (m, 1H), 1.29 (t, J=7.2 Hz, 3H), 1.22-1.08 (m, 6H); MS (EI) Calc'd for $C_{23}H_{30}N_9$[M+H]+, 432; found 432. Compound 2-25 required a second purification by SFC (ES Ethyl Pyridine, 21×250 (mm) column, 35% (Methanol+0.25% Dimethyl Ethyl Amine) in $CO_2$, 70 ml/min) to provide (S or R)-9-ethyl-N-(3-isopropyl-1-methyl-4,5,6,7-tetrahydro-1H-indazol-5-yl)-8-(2-methylpyrimidin-5-yl)-9H-purin-6-amine (2-25). $^1$H NMR (600 MHz, DMSO-d6) δ 9.09 (s, 2H), 8.26 (s, 1H), 7.90 (d, J=7.8 Hz, 1H), 4.50-4.38 (m, 1H), 4.26 (q, J=7.2 Hz, 2H), 3.55 (s, 3H), 2.82-2.66 (m, 3H), 2.71 (s, 3H), 2.64-2.48 (m, 2H), 2.06-1.96 (m, 1H), 1.94-1.80 (m, 1H), 1.27 (t, J=7.2 Hz, 3H), 1.16-1.06 (m, 6H); MS (EI) Calc'd for $C_{23}H_{30}N_9$[M+H]+, 432; found 432.

Example 22: Synthesis of Compound 2-26

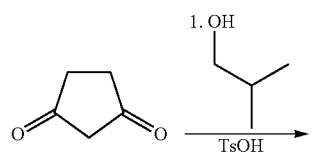

Step 1: Preparation of 3-isobutoxycyclopent-2-enone

To a solution of cyclopentane-1,3-dione (120 g, 1.2 mol) in toluene (300 ml) was added isobutanol (270 g, 3.7 mol) and TsOH (12 g). The reaction solution was heated to reflux overnight. The solution was then cooled and the solvent removed in vacuo. The resulting residue was neutralized via the addition of saturated aqueous sodium bicarbonate. The mixture was then extracted with EtOAc (3×1000 ml). The combined organic layers were washed with brine (500 ml), dried over sodium sulfate, filtered, and concentrated in vacuo. The resulting residue was purified by column chromatography (silica gel) to afford 3-isobutoxycyclopent-2-enone. MS (EI) Calc'd for $C_9H_{15}O_2[M+H]^+$, 155; found 155.

Step 2: Preparation of 5-(hydroxymethylene)-3-isobutoxycyclopent-2-enone

To a solution of 5-(hydroxymethylene)-3-isobutoxycyclopent-2-enone (40.0 g, 260 mmol) in THF (800 ml) was added propionic acid (23.2 g, 311 mmol) followed by potassium tert-butoxide (34.8 g, 311 mmol). The resulting reaction solution was stirred at RT overnight, after which the mixture was quenched with 2N HCl and the organic layer was separated and concentrated in vacuo. The resulting residue was used directly to the next step without further purification.

Step 3: Preparation of 1-benzyl-5-ethoxy-1,6-dihydrocyclopenta[c]pyrazole and 1-benzyl-5-isobutoxy-1,6-dihydrocyclopenta[c]pyrazole To a solution of 5-(hydroxymethylene)-3-isobutoxycyclopent-2-enone (crude from the previous step) was added 2-phenylacetohydrazide, 2HCl (50.6 g, 260 mmol) in EtOH. The reaction solution was allowed to stir at RT overnight, after which the reaction mixture was concentrated in vacuo and the resulting solution was extracted with EtOAc (3×500 ml). The combined organic layers were washed with brine (300 ml), dried over sodium sulfate, filtered, and concentrated in vacuo. The resulting residue was purified by column chromatography (silica gel) to afford a mixture of 1-benzyl-5-ethoxy-1,6-dihydrocyclopenta[c]pyrazole and 1-benzyl-5-isobutoxy-1,6-dihydrocyclopenta[c]pyrazole which was used in the next step without further purification.

Step 4: Preparation of 1-benzyl-4,6-dihydrocyclopenta[c]pyrazol-5(1H)-one, HCl

To a solution of 1-benzyl-5-ethoxy-1,6-dihydrocyclopenta[c]pyrazole and 1-benzyl-5-isobutoxy-1,6-dihydrocyclopenta[c]pyrazole (11.5 g) in EtOH (60 ml) was added HCl (60 ml, 12N), and the resulting solution was stirred at RT overnight. The mixture was then concentrated in vacuo and the residue thus obtained was washed with EtOAc to afford 1-benzyl-4,6-dihydrocyclopenta[c]pyrazol-5(1H)-one as the HCl salt. MS (EI) Calc'd for $C_9H_{13}N_2O$ [M+H]+, 213; found 213.

Step 5: Preparation of (S and R)-1-benzyl-1,4,5,6-tetrahydrocyclopenta[c]pyrazol-5-amine A mixture of 1-benzyl-4,6-dihydrocyclopenta[c]pyrazol-5(1H)-one, HCl (16 g, 0.076 mol), ammonium acetate (232 g, 3 mol) and sodium cyanoborohydride (47.5 g, 0.76 mol) in MeOH (500 ml) was heated to 60° C. for 2 h. The mixture was then cooled and concentrated in vacuo, and the resulting residue was partitioned between EtOAc (100 ml) and H$_2$O (100 ml). The aqueous layer was extracted with EtOAc (100 ml×3), and the combined organic layers were washed with brine (100 ml), dried over sodium sulfate, and concentrated in vacuo. The resulting residue was purified by preparative HPLC to afford (S and R)-1-benzyl-1,4,5,6-tetrahydrocyclopenta[c]pyrazol-5-amine. MS (EI) Calc'd for $C_{13}H_{16}N_3$ [M+H]+, 214; found 214.

Step 6: Preparation of Compound 2-26

A vial was charged with (S and R)-1-benzyl-1,4,5,6-tetrahydrocyclopenta[c]pyrazol-5-amine (58.2 mg, 0.273 mmol), 6-chloro-9-ethyl-8-(2-methylpyrimidin-5-yl)-9H-purine (Intermediate C) (50 mg, 0.18 mmol), DMF (1.4 ml), and DIEA (0.1 ml, 0.573 mmol). The mixture was stirred at 80° C. for 18 h. The reaction mixture was then cooled, filtered through a Whatman™ Autovial™ Syringeless Filter, PTFE; 0.45μ, and purified by reverse-phase preparative HPLC (0:100 to 95:5 MeCN:water: 0.1% v/v TFA modifier) to afford N-(1-benzyl-1,4,5,6-tetrahydrocyclopenta[c]pyrazol-5-yl)-9-ethyl-8-(2-methylpyrimidin-5-yl)-9H-purin-6-amine as the TFA salt (2-26)). $^1$H NMR (600 MHz, DMSO-d6) δ 9.08 (s, 2H), 8.75 (s, 1H), 8.33 (s, 1H), 7.34-7.36 (m, 2H), 7.26-7.21 (m, 1H), 7.18 (d, J=7.2 Hz, 2H), 7.15 (s, 1H), 5.40-5.26 (m, 1H), 5.22-5.14 (m, 2H), 4.27 (q, J=7.2 Hz, 2H), 3.16-3.04 (m, 1H), 3.04-2.94 (m, 1H), 2.74-2.60 (m, 2H), 2.71 (s, 3H), 1.28 (t, J=7.2 Hz, 3H); MS (EI) Calc'd for $C_{25}H_{26}N_9$ [M+H]+, 452; found 452.

Example 23: Preparation of Compound 2-27

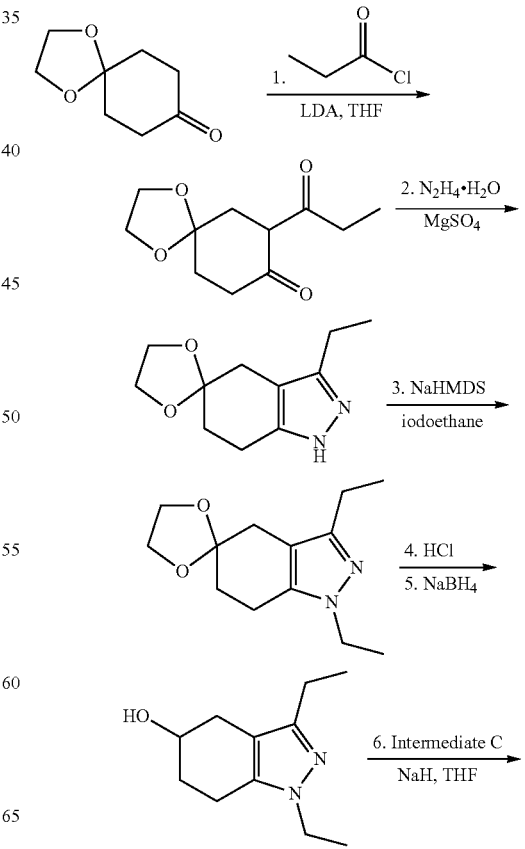

-continued

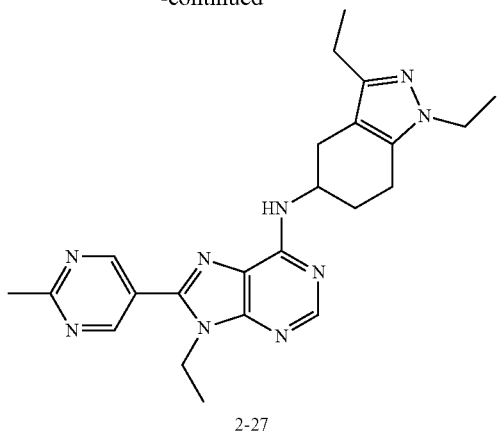

2-27

Step 1: Preparation of 7-propionyl-1,4-dioxaspiro[4.5]decan-8-one

To a solution of 1,4-dioxaspiro[4.5]decan-8-one (5 g, 32 mmol) in THF (50 ml) was added LDA (24 ml, 48.0 mmol, 1M in THF) at −20° C. After stirring for 1 h, propionyl chloride (3.5 g, 37.8 mmol) was added to the reaction mixture. The mixture was then allowed to come to RT and was stirred overnight, after which the mixture was quenched with saturated aqueous $NH_4Cl$ (50 ml) and extracted with EtOAc (3×100 ml). The combined organic layers were dried over $Na_2SO_4$, filtered and concentrated in vacuo. The resulting product was purified by column chromatography (silica gel, eluting with PE:EtOAc=3:1) to give 7-propionyl-1,4-dioxaspiro[4.5]decan-8-one. MS (ESI) Calc'd for $(C_{11}H_{17}O_4)$ [M+H]$^+$, 213; found, 213.

Step 2: Preparation of 3'-ethyl-1',4',6',7'-tetrahydrospiro[[1,3]dioxolane-2,5'-indazole]

A mixture of 85% hydrazine hydrate (5.0 ml, 87 mmol), $MgSO_4$ (8.0 g, 67 mmol) and 7-propionyl-1,4-dioxaspiro[4.5]decan-8-one (4.5 g, 21 mmol) in $CHCl_3$ (50 ml) was stirred at reflux for 3 h. The reaction mixture was then cooled, filtered, and concentrated in vacuo. The resulting residue was purified by reverse phase chromatography (mobile phase: MeOH/(10 mM $NH_4HCO_3$)) to give 3'-ethyl-1',4',6',7'-tetrahydrospiro[[1,3]dioxolane-2,5'-indazole]. MS (ESI) Calc'd for $(C_{11}H_{17}N_2O_2)$ [M+H]$^+$, 209; found, 209.

Step 3: Preparation of 1',3'-diethyl-1',4',6',7'-tetrahydrospiro[[1,3]dioxolane-2,5'-indazole]

To a solution of 3'-ethyl-1',4',6',7'-tetrahydrospiro[[1,3]dioxolane-2,5'-indazole](1.0 g, 4.8 mmol) in THF (10 ml) at 0° C. was added NaHMDS (7 ml, 7 mmol, 1M in THF). After stirring for 1 h, iodoethane (2.2 g, 14 mmol) was added to the mixture, and the reaction mixture was stirred overnight at RT. The reaction was then quenched with saturated aqueous $NH_4Cl$ (20 ml) and extracted with EtOAc (3×50 ml). The combined organic layers were dried over $Na_2SO_4$, filtered and concentrated in vacuo. The residue thus obtained was purified by column chromatography (silica gel, eluting PE:EtOAc=2:1) to afford 1',3'-diethyl-1',4',6',7'-tetrahydrospiro[[1,3]dioxolane-2,5'-indazole] (faster eluting isomer). MS (ESI) Calc'd for $(C_{13}H_{21}N_2O_2)$ [M+H]$^+$, 237; found, 237.

Step 4: Preparation of 1,3-diethyl-6,7-dihydro-1H-indazol-5(4H)-one

To a solution of 1',3'-diethyl-1',4',6',7'-tetrahydrospiro[[1,3]dioxolane-2,5'-indazole] (550 mg, 2.33 mmol) in THF (5 ml) and EtOH (10 ml) was added 3 N HCl (6 ml, 18 mmol). The reaction mixture was heated to 60° C. for 48 h. The reaction was then cooled and concentrated in vacuo, and the residue was purified by reverse phase chromatography (mobile phase: MeOH/water (10 mM $NH_4HCO_3$)) to give 1,3-diethyl-6,7-dihydro-1H-indazol-5(4H)-one. MS (ESI) Calc'd for $(C_{11}H_{17}N_2O)$ [M+H]$^+$, 193; found, 193.

Step 5: Preparation of 1,3-diethyl-4,5,6,7-tetrahydro-1H-indazol-5-ol

To a solution of 1,3-diethyl-6,7-dihydro-1H-indazol-5(4H)-one (150 mg, 0.780 mmol) in MeOH (2 ml) at 0° C. was added sodium borohydride (59.0 mg, 1.56 mmol). The reaction mixture was then allowed to come to RT where it was stirred for 1 h, after which the mixture was concentrated in vacuo and the residue was purified by reverse phase chromatography (mobile phase: MeOH/(10 mM $NH_4HCO_3$)) to give 1,3-diethyl-4,5,6,7-tetrahydro-1H-indazol-5-ol. MS (ESI) Calc'd for $(C_{11}H_{19}N_2O)$ [M+H]$^+$, 195; found, 195.

Step 6: Preparation of Compound 2-27

To a solution of 1,3-diethyl-4,5,6,7-tetrahydro-1H-indazol-5-ol (20 mg, 0.10 mmol) in THF (2 ml) was added sodium hydride (5 mg, 0.21 mmol, 60% in oil) at 0° C. Intermediate C (30 mg, 0.11 mmol) was then added to the reaction, and the solution was allowed to stir at RT overnight. The reaction was then quenched with MeOH (2 ml), and the solvent was removed in vacuo. The residue thus obtained was purified by reverse phase chromatography (mobile phase: MeOH/(10 mM $NH_4HCO_3$)) to give 2-27. $^1$H NMR (400 MHz, $CDCl_3$) δ 9.07 (s, 2H), 8.58 (s, 1H), 5.86-5.81 (m, 1H), 4.41 (q, J=7.2 Hz, 2H), 4.03-3.98 (m, 2H), 3.12-3.07 (m, 1H), 2.88-2.77 (m, 6H), 2.56 (q, J=7.6 Hz, 2H), 2.37-2.24 (m, 2H), 1.50 (t, J=7.2 Hz, 3H), 1.39 (t, J=7.2 Hz, 3H), 1.20 (t, J=7.6 Hz, 3H). MS (ESI) Calc'd for $(C_{23}H_{29}N_8O)$ [M+H]$^+$, 433; found, 433.

Compounds 2-1 through 2-27 are listed in Table 2 and have be made in analogous fashion to those compounds illustrated in Examples 10-23 and as outlined below.

Compounds 2-5 and 2-6 were prepared in an analogous fashion to Example 12, beginning at step 2 with Intermediate L in place of 3-isobutyryl-4-oxocyclohexanecarboxylate. Chiral resolution of 9-ethyl-N-(3-isopropyl-5-methyl-4,5,6,7-tetrahydro-1H-indazol-5-yl)-8-(2-methylpyrimidin-5-yl)-9H-purin-6-amine was achieved via chiral preparative SFC (OJ-H, 21×250 (mm), 10% (Methanol+0.25% Dimethyl Ethyl Amine) in $CO_2$, 70 ml/min) to provide 2-5 (faster eluting enantiomer, 2.7 min) and 2-6 (slower eluting enantiomer, 3.1 min).

Compounds 2-7 and 2-8 were prepared in an analogous fashion to Example 12, using Intermediate M in place of Intermediate C. Chiral resolution of 9-ethyl-N-(3-isopropyl-4,5,6,7-tetrahydro-1H-indazol-5-yl)-8-(4-(trifluoromethyl)phenyl)-9H-purin-6-amine was achieved via chiral preparative SFC (AZ-H, 21×250 (mm), 40% (Methanol+0.25% Dimethyl Ethyl Amine) in $CO_2$, 70 ml/min) to provide 2-7

(faster eluting enantiomer, 2.6 min) and 2-8 (slower eluting enantiomer, 3.9 min).

Compound 2-9 was prepared in an analogous fashion to Example 12, using Intermediate K in place of Intermediate C.

Compounds 2-10 and 2-11 were prepared in an analogous manner to Example 12, step 9 from compound 2-4 in place of Intermediate H, using the corresponding alkyl halides.

Compounds 2-13 and 2-14 were prepared in an analogous manner to Example 14 using the corresponding carboxylic acids.

Compounds 2-17 and 2-18 were prepared in an analogous fashion to Example 16 using the corresponding carbonochloridates in place of Boc anhydride.

Compound 2-19 was prepared in an analogous fashion to Example 16 from compound 2-4 in place of Intermediate H, and using methyl chloroformate in place of Boc anhydride.

TABLE 2

| Compound Number | Structure | IUPAC Name | Exact Mass [M + H]+ |
| --- | --- | --- | --- |
| 2-1 | 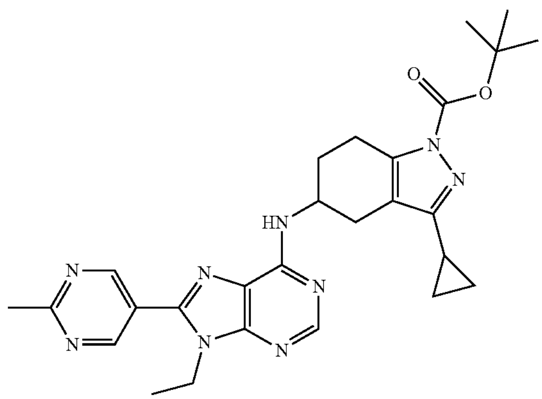 [SMILES: CCn1c(-c2cnc(C)nc2)nc2c(NC3CCc4c(c(C5CC5)nn4C(=O)OC(C)(C)C)C3)ncnc21] | (S and R)-tert-butyl 3-cyclopropyl-5-{[9-ethyl-8-(2-methylpyrimidin-5-yl)-9H-purin-6-yl]amino}-4,5,6,7-tetrahydro-1H-indazole-1-carboxylate | Calc'd 516, found 516 |
| 2-2 | 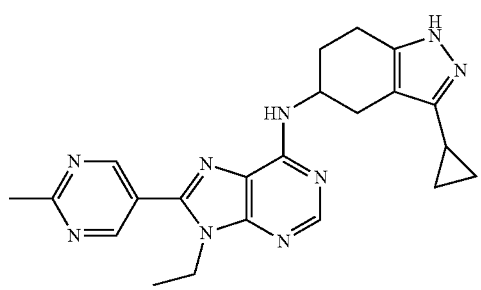 [SMILES: CCn1c(-c2cnc(C)nc2)nc2c(NC3CCc4[nH]nc(C5CC5)c4C3)ncnc21] | (S or R)-N-[3-cyclopropyl-4,5,6,7-tetrahydro-1H-indazol-5-yl]-9-ethyl-8-(2-methylpyrimidin-5-yl)-9H-purin-6-amine | Calc'd 416, found 416 |
| 2-3 | 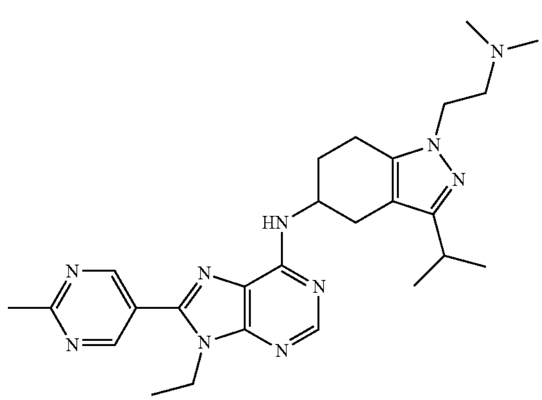 | (S and R)-N-{1-[2-(dimethylamino)ethyl]-3-(1-methylehyl)-4,5,6,7-tetrahydro-1H-indazol-5-yl}-9-ethyl-8-(2-methylpyrimidin-5-yl)-9H-purin-6-amine | Calc'd 489, found 489 |

TABLE 2-continued

| Compound Number | Structure | IUPAC Name | Exact Mass [M + H]+ |
|---|---|---|---|
| 2-4 | 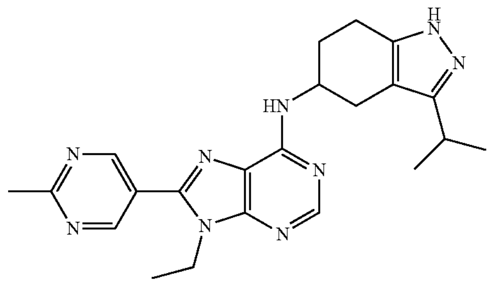 [SMILES: CCn1c(-c2cnc(C)nc2)nc2c(NC3CCc4[nH]nc(C(C)C)c4C3)ncnc21] | (S or R)-9-ethyl-N-[3-(1-methylethyl)-4,5,6,7-tetrahydro-1H-indazol-5-yl]-8-(2-methylpyrimidin-5-yl)-9H-purin-6-amine | Calc'd 418, found 418 |
| 2-5 | 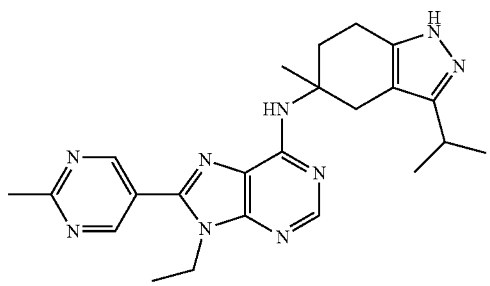 [SMILES: CCn1c(-c2cnc(C)nc2)nc2c(NC3(C)CCc4[nH]nc(C(C)C)c4C3)ncnc21] | (S or R)-9-ethyl-N-[5-methyl-3-(1-methylethyl)-4,5,6,7-tetrahydro-1H-indazol-5-yl]-8-(2-methylpyrimidin-5-yl)-9H-purin-6-amine | Calc'd 432, found 432 |
| 2-6 | 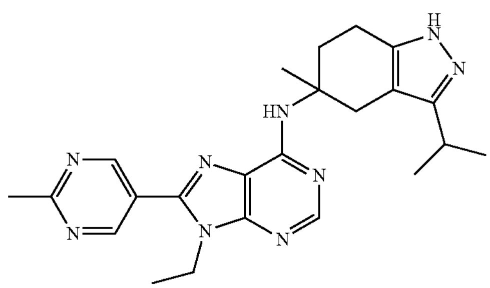 [SMILES: CCn1c(-c2cnc(C)nc2)nc2c(NC3(C)CCc4[nH]nc(C(C)C)c4C3)ncnc21] | (S or R)-9-ethyl-N-[5-methyl-3-(1-methylethyl)-4,5,6,7-tetrahydro-1H-indazol-5-yl]-8-(2-methylpyrimidin-5-yl)-9H-purin-6-amine | Calc'd 432, found 432 |
| 2-7 | 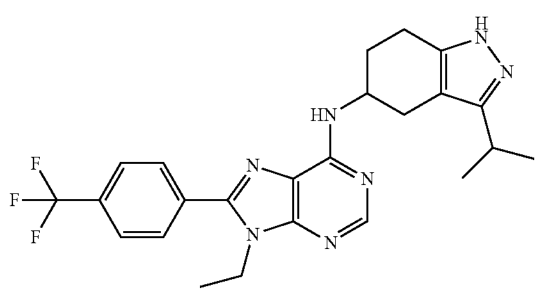 [SMILES: CCn1c(-c2ccc(C(F)(F)F)cc2)nc2c(NC3CCc4[nH]nc(C(C)C)c4C3)ncnc21] | (S or R)-9-ethyl-N-[3-(1-methylethyl)-4,5,6,7-tetrahydro-1H-indazol-5-yl]-8-[4-(trifluoromethyl)phenyl]-9H-purin-6-amine | Calc'd 470, found 470 |
| 2-8 | 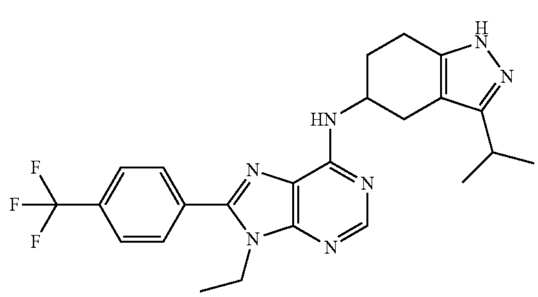 [SMILES: CCn1c(-c2ccc(C(F)(F)F)cc2)nc2c(NC3CCc4[nH]nc(C(C)C)c4C3)ncnc21] | (S or R)-9-ethyl-N-[3-(1-methylethyl)-4,5,6,7-tetrahydro-1H-indazol-5-yl]-8-[4-(trifluoromethyl)phenyl]-9H-purin-6-amine | Calc'd 470, found 470 |

TABLE 2-continued

| Compound Number | Structure | IUPAC Name | Exact Mass [M + H]+ |
|---|---|---|---|
| 2-9 | 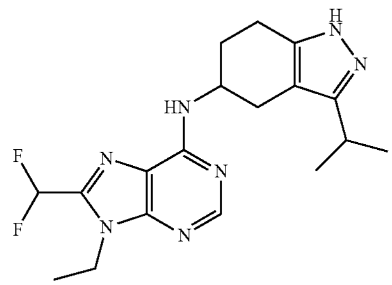 [SMILES: CCn1c(C(F)F)nc2c(NC3CCc4[nH]nc(C(C)C)c4C3)ncnc21] | (S and R)-8-(difluoromethyl)-9-ethyl-N-[3-(1-methylethyl)-4,5,6,7-tetrahydro-1H-indazol-5-yl]-9H-purin-6-amine | Calc'd 376, found 376 |
| 2-10 | 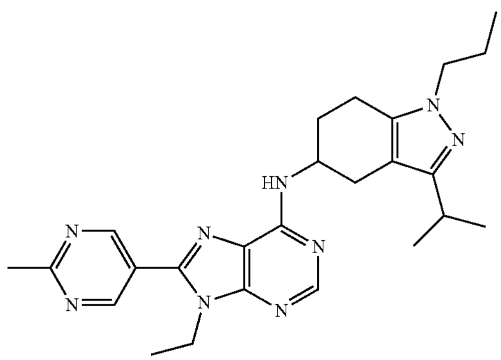 [SMILES: CCCn1nc(C(C)C)c2c1CCC(Nc1ncnc3c1nc(-c1cnc(C)nc1)n3CC)C2] | (S or R)-9-ethyl-N-[3-(1-methylethyl)-1-propyl-4,5,6,7-tetrahydro-1H-indazol-5-yl]-8-(2-methylpyrimidin-5-yl)-9H-purin-6-amine | Calc'd 460, found 460 |
| 2-11 | 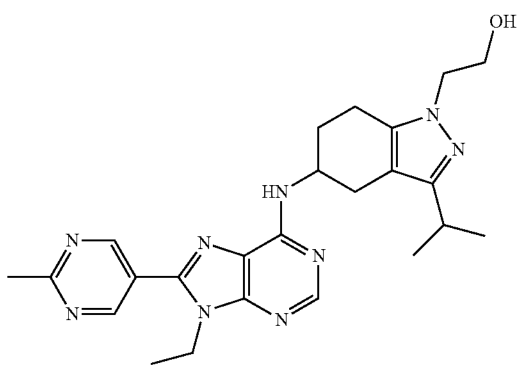 [SMILES: CCn1c(-c2cnc(C)nc2)nc2c(NC3CCc4c(c(C(C)C)nn4CCO)C3)ncnc21] | (S or R)-2-[5-{[9-ethyl-8-(2-methylpyrimidin-5-yl)-9H-purin-6-yl]amino}-3-(1-methylethyl)-4,5,6,7-tetrahydro-1H-indazol-1-yl]ethanol | Calc'd 462, found 462 |
| 2-12 | 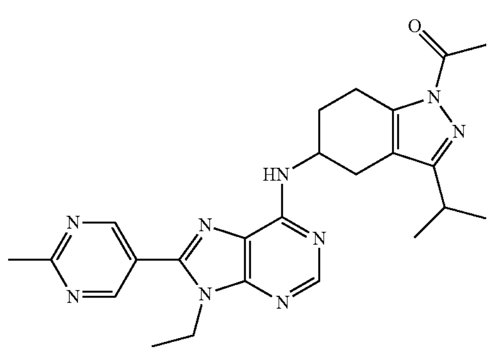 [SMILES: CCn1c(-c2cnc(C)nc2)nc2c(NC3CCc4c(c(C(C)C)nn4C(C)=O)C3)ncnc21] | (S and R)-N-[1-acetyl-3-(1-methylethyl)-4,5,6,7-tetrahydro-1H-indazol-5-yl]-9-ethyl-8-(2-methylpyrimidin-5-yl)-9H-purin-6-amine | Calc'd 460, found 460 |

TABLE 2-continued

| Compound Number | Structure | IUPAC Name | Exact Mass [M + H]+ |
|---|---|---|---|
| 2-13 | 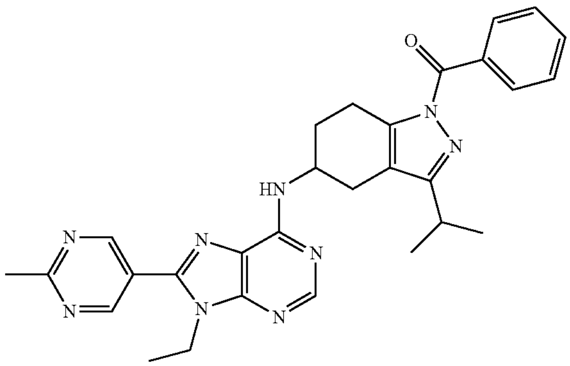 [SMILES: CCn1c(-c2cnc(C)nc2)nc2c(NC3CCc4c(c(C(C)C)nn4C(=O)c4ccccc4)C3)ncnc21] | (S and R)-9-ethyl-N-[3-(1-methylethyl)-1-(phenylcarbonyl)-4,5,6,7-tetrahydro-1H-indazol-5-yl]-8-(2-methylpyrimidin-5-yl)-9H-purin-6-amine | Calc'd 522, found 522 |
| 2-14 | 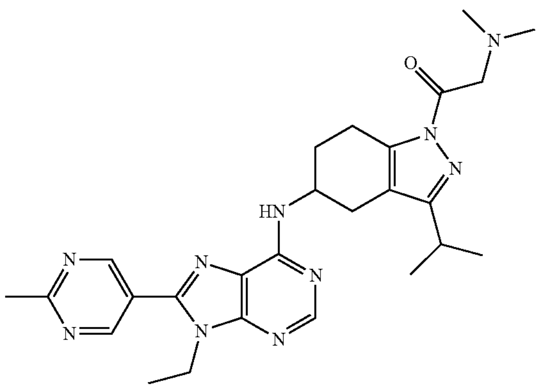 | (S and R)-N-{1-[(dimethylamino)acetyl]-3-(1-methylethyl)-4,5,6,7-tetrahydro-1H-indazol-5-yl}-9-ethyl-8-(2-methylpyrimidin-5-yl)-9H-purin-6-amine | Calc'd 503, found 503 |
| 2-15 | 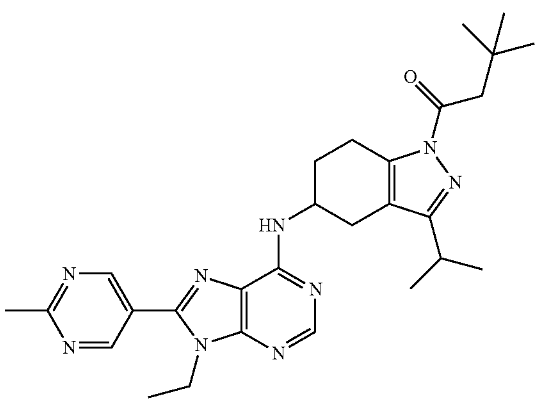 [SMILES: CCn1c(-c2cnc(C)nc2)nc2c(NC3CCc4c(c(C(C)C)nn4C(=O)CC(C)(C)C)C3)ncnc21] | (S and R)-N-[1-(3,3-dimethylbutanoyl)-3-(1-methylethyl)-4,5,6,7-tetrahydro-1H-indazol-5-yl]-9-ethyl-8-(2-methylpyrimidin-5-yl)-9H-purin-6-amine | Calc'd 516, found 516 |
| 2-16 | 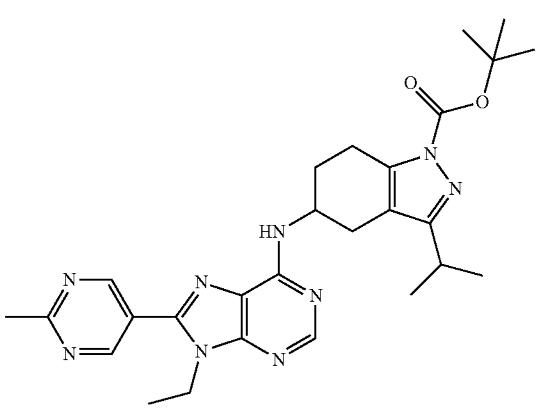 [SMILES: CCn1c(-c2cnc(C)nc2)nc2c(NC3CCc4c(c(C(C)C)nn4C(=O)OC(C)(C)C)C3)ncnc21] | (S and R)-tert-butyl 5-{[9-ethyl-8-(2-methylpyrimidin-5-yl)-9H-purin-6-yl]amino}-3-(1-methylethyl)-4,5,6,7-tetrahydro-1H-indazole-1-carboxylate | Calc'd 518, found 518 |

TABLE 2-continued

| Compound Number | Structure | IUPAC Name | Exact Mass [M + H]+ |
|---|---|---|---|
| 2-17 | 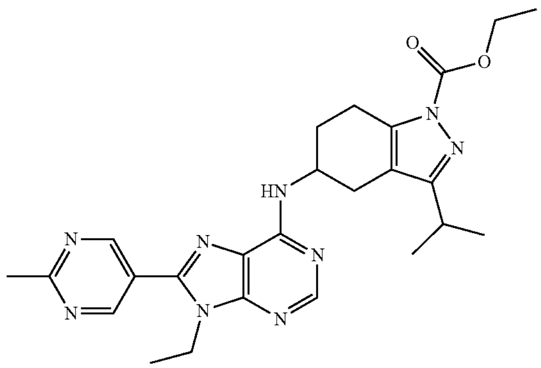 [SMILES: CCOC(=O)n1nc(C(C)C)c2c1CCC(Nc1ncnc3c1nc(-c1cnc(C)nc1)n3CC)C2] | (S and R)-ethyl 5-{[9-ethyl-8-(2-methylpyrimidin-5-yl)-9H-purin-6-yl]amino}-3-(1-methylethyl)-4,5,6,7-tetrahydro-1H-indazole-1-carboxylate | Calc'd 490, found 490 |
| 2-18 | 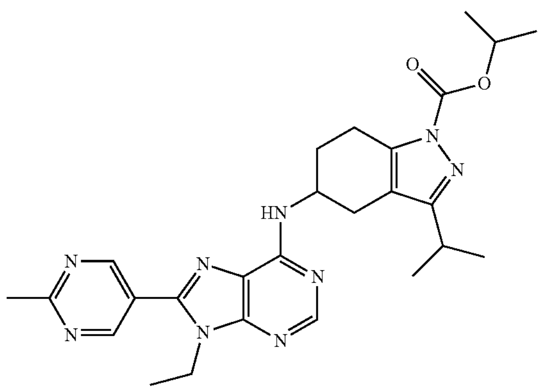 | (S and R)-1-methylethyl 5-{[9-ethyl-8-(2-methylpyrimidin-5-yl)-9H-purin-6-yl]amino}-3-(1-methylethyl)-4,5,6,7-tetrahydro-1H-indazole-1-carboxylate | Calc'd 504, found 504 |
| 2-19 | 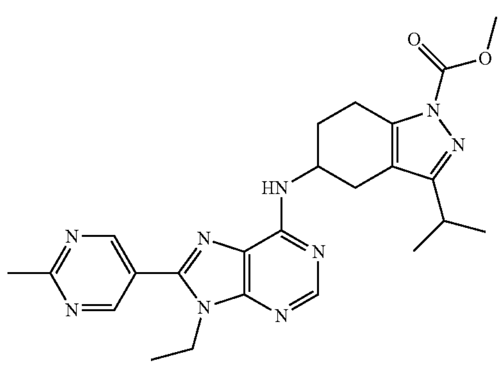 | (S or R)-methyl 5-{[9-ethyl-8-(2-methylpyrimidin-5-yl)-9H-purin-6-yl]amino}-3-(1-methylethyl)-4,5,6,7-tetrahydro-1H-indazole-1-carboxylate | Calc'd 476, found 476 |
| 2-20 | 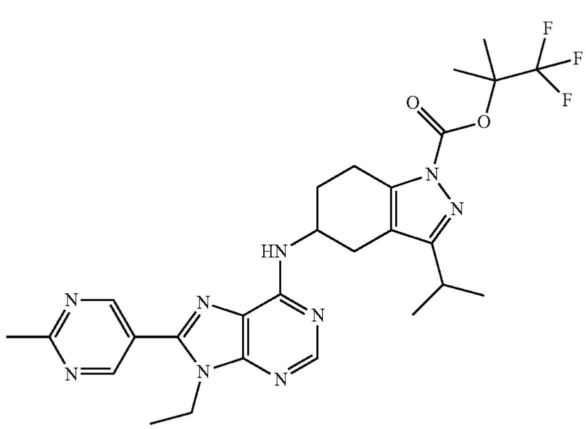 [SMILES: CCn1c(-c2cnc(C)nc2)nc2c(NC3CCc4c(c(C(C)C)nn4C(=O)OC(C)(C)C(F)(F)F)C3)ncnc21] | (S and R)-2,2,2-trifluoro-1,1-dimethylethyl 5-{[9-ethyl-8-(2-methylpyrimidin-5-yl)-9H-purin-6-yl]amino}-3-(1-methylethyl)-4,5,6,7-tetrahydro-1H-indazole-1-carboxylate | Calc'd 572, found 572 |

TABLE 2-continued

| Compound Number | Structure | IUPAC Name | Exact Mass [M + H]+ |
|---|---|---|---|
| 2-21 | 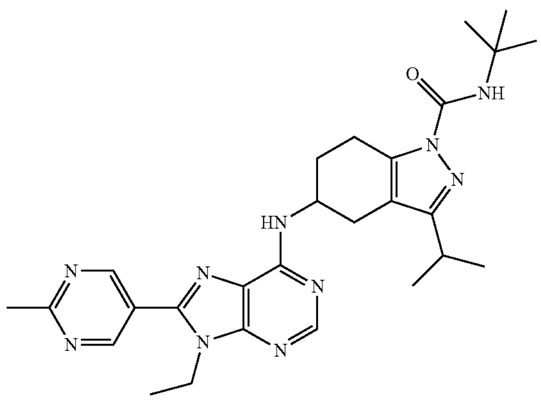 [SMILES: CCn1c(-c2cnc(C)nc2)nc2c(NC3CCc4c(c(C(C)C)nn4C(=O)NC(C)(C)C)C3)ncnc21] | (S and R)-N-tert-butyl-5-{[9-ethyl-8-(2-methylpyrimidin-5-yl)-9H-purin-6-yl]amino}-3-(1-methylethyl)-4,5,6,7-tetrahydro-1H-indazole-1-carboxamide | Calc'd 517, found 517 |
| 2-22 | 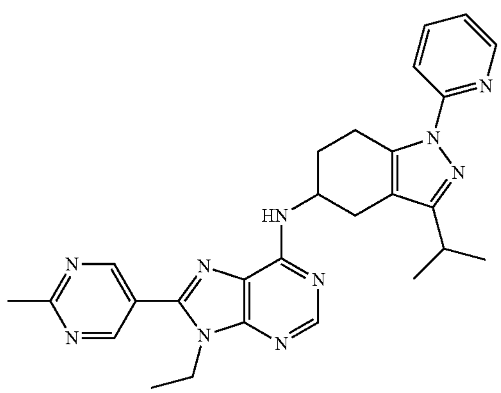 [SMILES: CCn1c(-c2cnc(C)nc2)nc2c(NC3CCc4c(c(C(C)C)nn4-c4ccccn4)C3)ncnc21] | (S and R)-9-ethyl-N-[3-(1-methylethyl)-1-pyridin-2-yl-4,5,6,7-tetrahydro-1H-indazol-5-yl]-8-(2-methylpyrimidin-5-yl)-9H-purin-6-amine | Calc'd 495, found 495 |
| 2-23 | 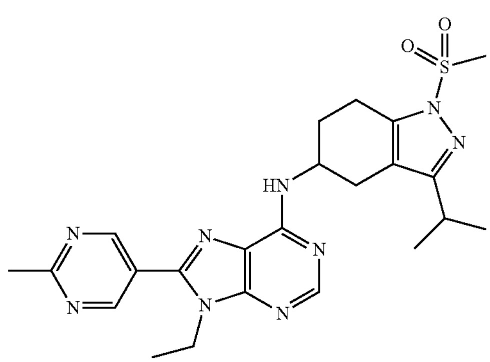 | (S and R)-9-ethyl-N-[3-(1-methylethyl)-1-(methylsulfonyl)-4,5,6,7-tetrahydro-1H-indazol-5-yl]-8-(2-methylpyrimidin-5-yl)-9H-purin-6-amine | Calc'd 496, found 496 |
| 2-24 | 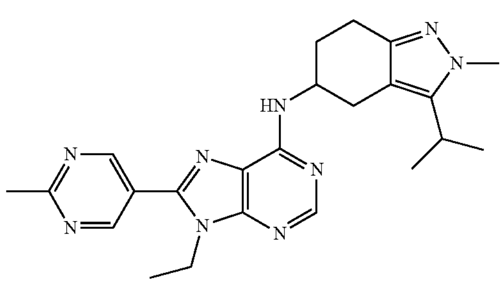 | (S or R)-9-ethyl-N-[(5S)-2-methyl-3-(1-methylethyl)-4,5,6,7-tetrahydro-2H-indazol-5-yl]-8-(2-methylpyrimidin-5-yl)-9H-purin-6-amine | Calc'd 432, found 432 |

TABLE 2-continued

| Compound Number | Structure | IUPAC Name | Exact Mass [M + H]+ |
|---|---|---|---|
| 2-25 | 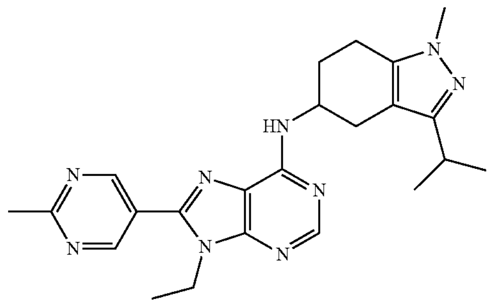 [SMILES: CCn1c(-c2cnc(C)nc2)nc2c(NC3CCc4c(c(C(C)C)nn4C)C3)ncnc21] | (S or R)-9-ethyl-N-[(5S)-1-methyl-3-(1-methylethyl)-4,5,6,7-tetrahydro-1H-indazol-5-yl]-8-(2-methylpyrimidin-5-yl)-9H-purin-6-amine | Calc'd 432, found 432 |
| 2-26 | 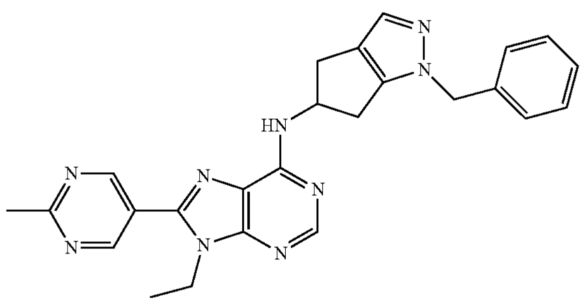 [SMILES: CCn1c(-c2cnc(C)nc2)nc2c(NC3Cc4cnn(Cc5ccccc5)c4C3)ncnc21] | (S and R)-N-(1-benzyl-1,4,5,6-tetrahydrocyclopenta[c]pyrazol-5-yl)-9-ethyl-8-(2-methylpyrimidin-5-yl)-9H-purin-6-amine | Calc'd 452, found 452 |
| 2-27 | 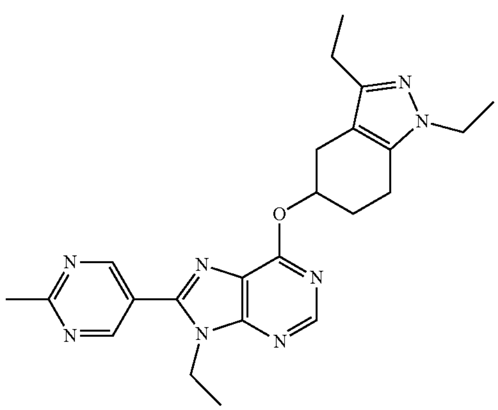 [SMILES: CCc1nn(CC)c2c1CC(Oc1ncnc3c1nc(-c1cnc(C)nc1)n3CC)CC2] | (S and R)-6-[(1,3-diethyl-4,5,6,7-tetrahydro-1H-indazol-5-yl)oxy]-9-ethyl-8-(2-methylpyrimidin-5-yl)-9H-purine | Calc'd 433, found 433 |

Compound Examples of Table 3

Example 24: Preparation of Compound 3-1

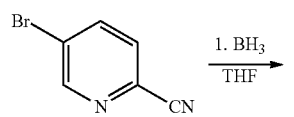

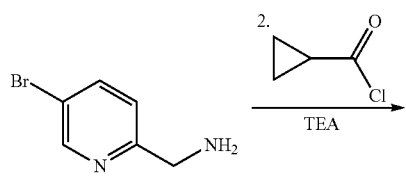

-continued

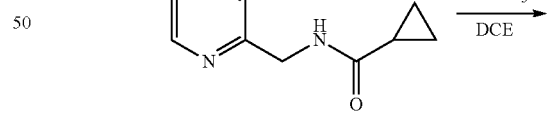

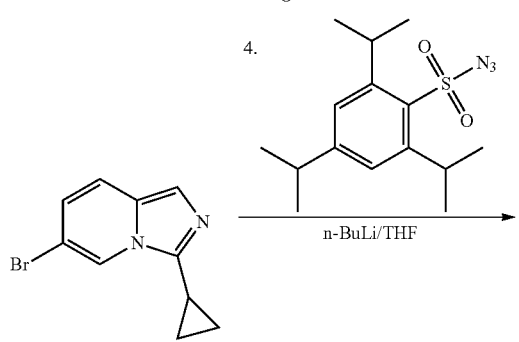

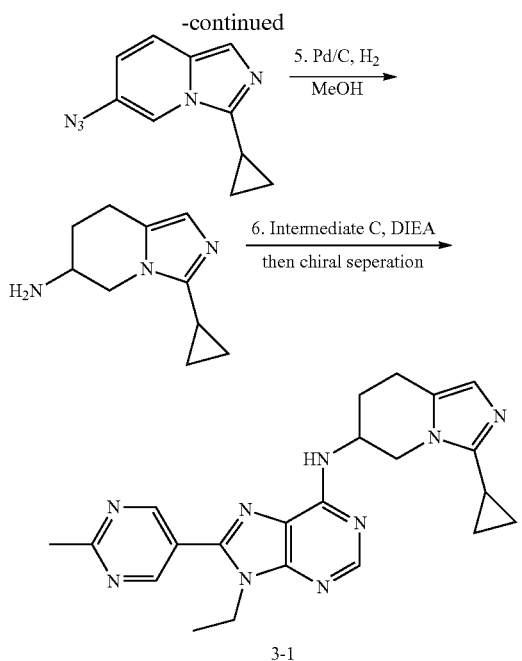

Step 1: Preparation of (5-bromopyridin-2-yl)methanamine[2]

To a solution of borane (400 ml, 400 mmol, 1M in THF) was added 5-bromopicolinonitrile (15 g, 82 mmol, commercial from Shanghai EachChem Co. Ltd.) in portions at 0° C. The resulting solution was stirred at 25° C. for 1 h. The reaction was then quenched by the addition of water (200 ml). The resulting mixture was stirred at 60° C. for 30 min before the addition of hydrochloric acid (50 ml, 100 mmol, 2 M). The pH value of the mixture was adjusted to pH 8 with aqueous sodium hydroxide (2 M). The mixture was stirred at 25° C. for 10 min, after which it was extracted with DCM (3×100 ml). The combined organic fractions was dried over sodium sulfate, filtered and concentrated in vacuo to afford (5-bromopyridin-2-yl)methanamine which was used without further purification. MS (ESI) Calc'd for ($C_6H_8BrN_2$) [M+H]$^+$, 187, 189; found, 187, 189.

Step 2: Preparation of N-((5-bromopyridin-2-yl)methyl)cyclopropanecarboxamide[2]

To a solution of (5-bromopyridin-2-yl)methanamine (15 g, crude material from previous step) and triethylamine (16 g, 160 mmol) in DCM (200 ml) was added drop-wise cyclopropanecarbonyl chloride (13 g, 124 mmol) at 0° C. The resulting solution was stirred for 1 h at 25° C. before the addition of brine (200 ml). The mixture was then extracted with DCM (2×100 ml), and the combined organic layers were dried over anhydrous sodium sulfate, filtered and concentrated in vacuo to give a residue, which was purified by flash column chromatography (silica gel, eluting with 1-2% MeOH in DCM) to afford N-((5-bromopyridin-2-yl)methyl)cyclopropanecarboxamide. MS (ESI) Calc'd for ($C_{10}H_{12}BrN_2O$) [M+H]$^+$, 255, 257; found, 255, 257.

Step 3: Preparation of 6-bromo-3-cyclopropylimidazo[1,5-a]pyridine

To a solution of N-((5-bromopyridin-2-yl)methyl)cyclopropanecarboxamide (8.0 g, 31.3 mmol) in 1,2-dichloroethane (150 ml) was added phosphorus oxychloride (28.9 g, 187 mmol) drop-wise at 0° C. The resulting solution was warmed to 100° C. for 5 h, after which it was cooled to ambient temperature and poured onto ice water (200 ml). The reaction mixture was extracted with DCM (3×100 ml), and the combined organic layers were dried over anhydrous sodium sulfate, filtered and concentrated in vacuo to give a residue, which was purified by flash column chromatography (silica gel, eluting with 1-2% MeOH in DCM) to afford 6-bromo-3-cyclopropylimidazo[1,5-a]pyridine. MS (ESI) Calc'd for ($C_{10}H_{10}BrN_2$) [M+H]$^+$, 237, 239; found, 237, 239.

Step 4: Preparation of 6-azido-3-cyclopropylimidazo[1,5-a]pyridine

To a solution of 6-bromo-3-cyclopropylimidazo[1,5-a]pyridine (1.0 g, 4.22 mmol) in THF (10 ml) was added drop-wise n-butyllithium (4.6 ml, 2.5 M in hexane, 12 mmol) with stirring at −78° C. under a nitrogen atmosphere. The reaction solution was then stirred at −78° C. for 1 h, after which a solution of 2,4,6-triisopropylbenzenesulfonyl azide (1.37 g, 4.42 mmol, commercial from Suzhou Highfine Biotech Co. Ltd.) in THF (5 ml) was added at −78° C. The resulting solution was stirred and the temperature was raised to −65° C. for 30 min. The reaction was then quenched by the addition of water (150 ml) and extracted with DCM (3×100 ml). The combined organic layers were dried over anhydrous sodium sulfate and filtered. The filtrate was concentrated in vacuo to give a residue, which was purified by flash column chromatography (silica gel, eluting with 1% MeOH in DCM) to afford 6-azido-3-cyclopropylimidazo[1,5-a]pyridine. MS (ESI) Calc'd for ($C_{10}H_{10}N_5$) [M+H]$^+$, 200; found, 200.

Step 5: Preparation of (S and R)-3-cyclopropyl-5,6,7,8-tetrahydroimidazo[1,5-a]pyridin-6-amine To a solution of 6-azido-3-cyclopropylimidazo[1,5-a]pyridine (200 mg, 1.00 mmol) in MeOH (5 ml) was added palladium on carbon (100 mg, 10% wt) in portions. The resulting mixture was stirred at 25° C. for 2 h under an atmosphere of hydrogen (2 atm). The reaction mixture was then filtered, and the filtrate was concentrated in vacuo to afford (S and R)-3-cyclopropyl-5,6,7,8-tetrahydroimidazo[1,5-a]pyridin-6-amine which was used in the next step without further purification. MS (ESI) Calc'd for ($C_{10}H_{16}N_3$) [M+H]+, 178; found, 178.

Step 6: Preparation of Compound 3-1

A mixture of 6-chloro-9-ethyl-8-(2-methylpyrimidin-5-yl)-9H-purine (Intermediate C) (100 mg, 0.36 mmol), 3-cyclopropyl-5,6,7,8-tetrahydroimidazo[1,5-a]pyridin-6-amine (120 mg, crude from previous step) and N,N-diisopropylethylamine (142 mg, 1.29 mmol) in t-BuOH (5 ml) was stirred at 85° C. for 16 h. The reaction was then cooled and quenched by the addition of water (100 ml) and extracted with DCM (3×50 ml). The combined organic layers were dried over anhydrous sodium sulfate and filtered. The filtrate was concentrated in vacuo to give a residue, which was purified by reverse phase preparative HPLC (Column: Xbridge Prep C18 5 μm OBD, 19×150 mm; Mobile phase: A: Water (10 mM $NH_4HCO_3$), B: MeCN; Flow rate: 20 ml/min). The racemic (S and R)—N-(3-cyclopropyl-5,6,7,8-tetrahydroimidazo[15-a]pyridin-6-yl)-9-ethyl-8-(2-methylpyrimidin-5-yl)-9H-purin-6-amine was then subjected to preparative chiral HPLC (Column: Chiralpak® AD-H™, 2×25 cm; Mobile phase: 50% 2-propanol in hexane (+0.1% TEA)) to afford compound 3-1 (slower eluting enantiomer, 6.7 min). $^1$H NMR (300 MHz, DMSO-d$_6$) δ9.12 (s, 2H), 8.35 (s, 1H), 8.18 (brs, 1H), 6.45 (s, 1H), 4.77-4.75 (m, 1H), 4.40-4.35 (m, 1H), 4.31 (q, J=7.2 Hz, 2H), 3.85-3.81 (m, 1H), 2.91-2.86 (m, 1H), 2.80-2.74 (m, 1H), 2.74 (s, 3H), 2.03-1.90 (m, 2H), 1.88-1.82 (m, 1H), 1.31 (t, J=7.2 Hz, 3H), 0.82-0.74 (m, 4H). MS (ESI) Calc'd for ($C_{22}H_{26}N_9$) [M+H], 416; found, 416.

Example 25: Preparation of Compound 3-2

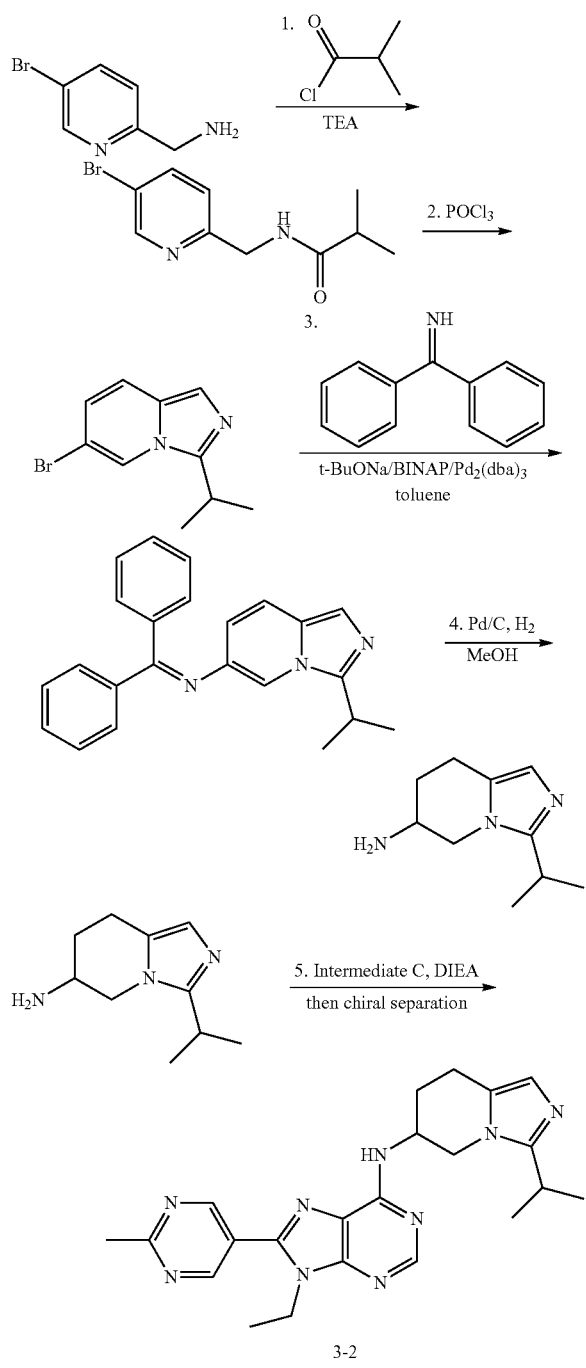

Step 1: Preparation of N-((5-bromopyridin-2-yl)methyl)isobutyramide

To a solution of (5-bromopyridin-2-yl)methanamine (25 g, 13 mmol) in DCM (300 ml) were added triethylamine (55.9 ml, 401 mmol) and isobutyryl chloride (21.4 g, 200 mmol) at 0° C. The resulting solution was stirred at RT for 11 h. The reaction was then quenched by the addition of water (150 ml). The aqueous solution was extracted with DCM (2×200 ml), and the combined organic layers were dried over anhydrous sodium sulfate and filtered. The filtrate was concentrated in vacuo and the resulting residue was purified by flash column chromatography (silica gel, eluting with 1-2% MeOH in DCM) to afford N-((5-bromopyridin-2-yl)methyl)isobutyramide. MS (ESI) Calc'd for ($C_{10}H_{14}BrN_2O$) [M+H]$^+$, 257, 259; found, 257, 259.

Step 2: Preparation of 6-bromo-3-isopropylimidazo[1,5-a]pyridine

To a solution of N-((5-bromopyridin-2-yl)methyl)isobutyramide (3.5 g, 14 mmol) in 1,2-dichloroethane (30 ml) was added phosphoryl trichloride (7.6 ml, 82 mmol). The resulting mixture was stirred for 5 h at 100° C., and then quenched by the slow addition of ice water (150 ml). The aqueous solution was basified to pH=9 with saturated potassium carbonate aqueous solution, after which the aqueous solution was extracted with DCM (3×200 ml). The combined organic layers were dried over anhydrous magnesium sulfate and filtered. The filtrate was concentrated in vacuo and the resulting residue was purified by flash column chromatography (silica gel, eluting with 3-25% EA in n-hexane) to afford 6-bromo-3-isopropylimidazo[1,5-a]pyridine. MS (ESI) Calc'd for ($C_{10}H_{12}BrN_2$) [M+H]$^+$, 239, 241; found, 239, 241.

Step 3: Preparation of N-(diphenylmethylene)-3-isopropylimidazo[1,5-a]pyridin-6-amine A degassed solution of 6-bromo-3-isopropylimidazo[1,5-a]pyridine (2.0 g, 8.4 mmol), diphenylmethanimine (1.82 g, 10.0 mmol), tris(dibenzylideneacetone)dipalladium (Pd$_2$(dba)$_3$) (115 mg, 0.12 mmol), 2,2'-bis(diphenylphosphino)-1,1-binaphthalene (BINAP) (156 mg, 0.25 mmol) and sodium tert-butoxide (1.21 g, 12.6 mmol) in toluene (30 ml) was stirred for 12 h at 80° C. under nitrogen. The mixture was then cooled and concentrated in vacuo. The resulting residue was purified by flash column chromatography (silica gel, eluting with 3-15% EA in n-hexane) to afford N-(diphenylmethylene)-3-isopropylimidazo[1,5-a]pyridin-6-amine. MS (ESI) Calc'd for ($C_{23}H_{22}N_3$) [M+H]$^+$, 340; found, 340.

Step 4: Preparation of (S and R)-3-isopropyl-5,6,7,8-tetrahydroimidazo[1,5-a]pyridin-6-amine To a solution of N-(diphenylmethylene)-3-isopropylimidazo[1,5-a]pyridin-6-amine (1.0 g, 3.0 mmol) in MeOH (20 ml) under nitrogen was added 10% palladium on activated carbon (100 mg). The reaction flask was then evacuated under vacuum and refilled with hydrogen gas (×3). The resulting solution was stirred at 50° C. for 4 h under an atmosphere of hydrogen, after which the solution was cooled and filtered through Celite. The filtrate was concentrated in vacuo to afford (S and R)-3-isopropyl-5,6,7,8-tetrahydroimidazo[1,5-a]pyridin-6-amine, which was directly used in next step without further purification. MS (ESI) Calc'd for ($C_{10}H_{18}N_3$) [M+H]+, 180; found, 180.

Step 5: Preparation of Compound 3-2

A solution of 6-chloro-9-ethyl-8-(2-methylpyrimidin-5-yl)-9H-purine (Intermediate C) (100 mg, 0.36 mmol), (S and R)-3-isopropyl-5,6,7,8-tetrahydroimidazo[1,5-a]pyridin-6-amine (327 mg, crude, ~0.73 mmol) and DIEA (0.19 ml, 1.1 mmol) in t-BuOH (10 ml) was stirred for 12 h at 85° C. The solution was then cooled and diluted with water (50 ml), and the aqueous solution was extracted with DCM (3×100 ml). The organic layers were combined, dried over anhydrous magnesium sulfate, and filtered. The filtrate was concentrated in vacuo, and the resulting residue was purified by preparative reverse-phase HPLC (Xbridge Prep C18 5 μm OBD, 19×150 mm; Mobile phase: 15-35% MeCN in 10 mM ammonium bicarbonate aqueous solution; Flow rate: 20 ml/min) to afford racemic (S and R)-9-ethyl-N-(3-isopropyl-5,6,7,8-tetrahydroimidazo[1,5-a]pyridin-6-yl)-8-(2-methyl-pyrimidin-5-yl)-9H-purin-6-amine, which was further separated by preparative chiral HPLC (Chiralpac® IA-3, 2×25 cm, 3 um; Mobile phase: 30% isopropanol in n-hexane) to afford (S or R)-9-ethyl-N-(3-isopropyl-5,6,7,8-tetrahydroimidazo[1,5-a]pyridin-6-yl)-8-(2-methylpyrimidin-5-yl)-9H-purin-6-amine (3-2) (slower eluting enantiomer, 4.5 min): $^1$H NMR (300 MHz, DMSO-$d_6$) δ 9.12 (s, 2H), 8.34 (s, 1H), 8.14 (brs, 1H), 6.55 (s, 1H), 4.75-4.65 (m, 1H), 4.32 (q, J=7.2 Hz, 2H), 4.34-4.27 (m, 1H), 3.84-3.70 (m, 1H), 3.01-2.88 (m, 2H), 2.80-2.69 (m, 1H), 2.74 (s, 3H), 2.05-1.96 (m, 2H), 1.31 (t, J=7.2 Hz, 3H), 1.17 (d, J=6.9 Hz, 3H), 1.13 (d, J=6.9 Hz, 3H). MS (ESI) Calc'd for ($C_{22}H_{28}N_9$) [M+H]+, 418; found, 418.

Compounds 3-1 and 3-2 are listed in Table 3 and have be made according to the procedures outlined in Examples 24 and 25.

Compound Examples of Table 4

Example 26: Synthesis of Compounds 4-1 and 4-2

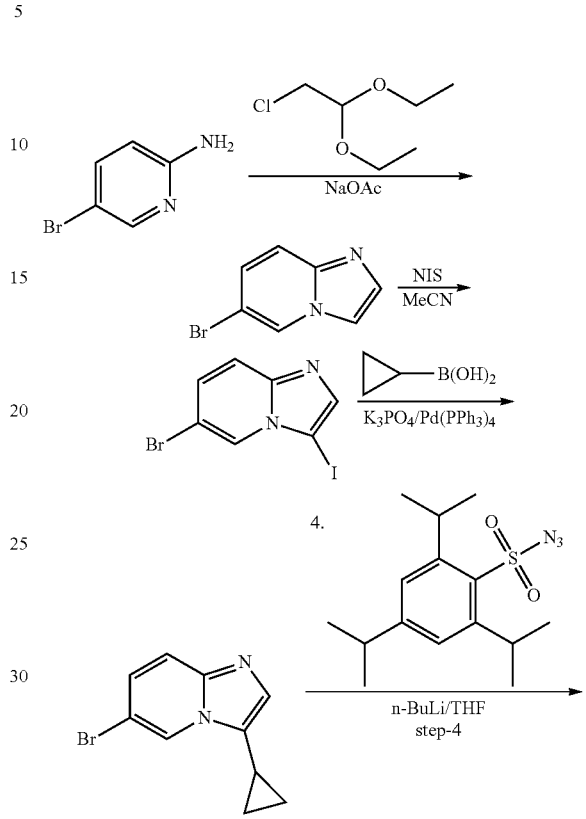

TABLE 3

| Compound Number | Structure | IUPAC Name | Exact Mass [M + H]+ |
|---|---|---|---|
| 3-1 | 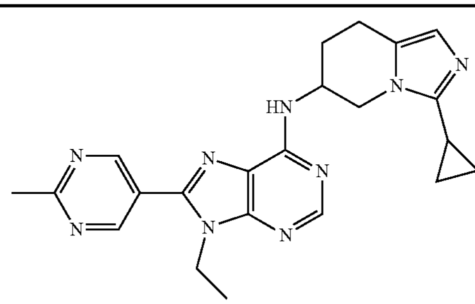 | (S or R)-N-[3-cyclopropyl-5,6,7,8-tetrahydroimidazo[1,5-a]pyridin-6-yl]-9-ethyl-8-(2-methylpyrimidin-5-yl)-9H-purin-6-amine | Calc'd 416, found 416 |
| 3-2 | 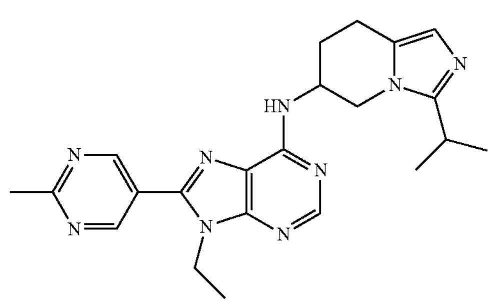 [SMILES: CCn1c(-c2cnc(C)nc2)nc2c(NC3CCc4cnc(C(C)C)n4C3)ncnc21] | (S or R)-9-ethyl-N-[3-(1-methylethyl)-5,6,7,8-tetrahydroimidazo[1,5-a]pyridin-6-yl]-8-(2-methylpyrimidin-5-yl)-9H-purin-6-amine | Calc'd 418, found 418 |

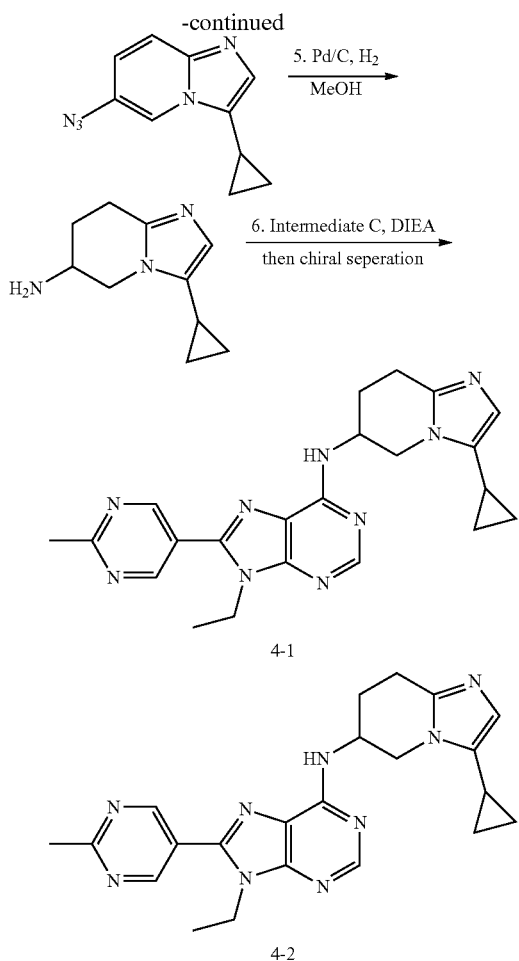

4-1

4-2

Step 1: Preparation of 6-bromoimidazo[1,2-a]pyridine

A mixture of water (75 ml), concentrated hydrochloric acid (5 ml, 37% w/w aqueous solution) and 2-chloro-1,1-diethoxyethane (30 ml) was heated at 90° C. for 10 min. To this mixture was then added sodium acetate (20.0 g, 24.4 mmol), the solution was subsequently poured into a solution of 2-amino-5-bromopyridine (25.0 g, 145 mmol) in 60% ethanol-water (160 ml) containing sodium acetate (10 g, 12.20 mmol). The combined reaction mixture was then heated at reflux for 20 min, after which it was cooled and the solvent was removed in vacuo and the resultant aqueous suspension was extracted with EA (3×300 ml). The combined organic layers were dried over sodium sulfate, filtered, and concentrated in vacuo. The residue was purified by flash column chromatography (silica gel, eluting with 10-20% EA in PE) to afford 6-bromoimidazo[1,2-a]pyridine. MS (ESI) Calc'd for ($C_7H_6BrN_2$) [M+H]$^+$, 197, 199; found, 199, 199.

Step 2: Preparation of 6-bromo-3-iodoimidazo[1,2-a]pyridine

To a solution of 6-bromoimidazo[1,2-a]pyridine (10 g, 51 mmol) in MeCN (100 ml) was added N-iodosuccinimide (10.6 g 61.0 mmol). The reaction was stirred at ambient temperature for 3 h, after which the volatiles were removed in vacuo. The residue thus obtained was dissolved in EA (300 ml) and washed successively with 10% aqueous sodium hydroxide solution (100 ml), saturated aqueous thiosulfate solution (100 ml), and water (100 ml). The organic layer was then dried over sodium sulfate, filtered and concentrated in vacuo. The residue was purified by flash column chromatography (silica gel, eluting with 5%-10% EA in PE) to afford 6-bromo-3-iodoimidazo[1,2-a]pyridine. MS (ESI) Calc'd for ($C_7H_5BrIN_2$) [M+H]$^+$, 323, 325; found, 323, 325.

Step 3: Preparation of 6-bromo-3-cyclopropylimidazo[1,2-a]pyridine

A mixture of 6-bromo-3-iodoimidazo[1,2-a]pyridine (1.0 g, 3.1 mmol), cyclopropylboronic acid (400 mg, 4.6 mmol), potassium phosphate (1.3 g, 6.2 mmol), tetrakis(triphenylphosphine)palladium(0) (Pd(PPh$_3$)$_4$) (35 mg, 0.03 mmol) in toluene (20 ml) and water (2 ml) was stirred at 100° C. for 16 h under a nitrogen atmosphere. The resulting mixture was then cooled and concentrated in vacuo. The resulting residue was purified via flash chromatography (silica gel, eluting with 5-20% EA in PE) to afford 6-bromo-3-cyclopropylimidazo[1,2-a]pyridine. MS (ESI) Calc'd for ($C_{10}H_{10}BrN_2$) [M+H]$^+$, 237, 239; found, 237, 239.

Step 4: Preparation of 6-azido-3-cyclopropylimidazo[1,2-a]pyridine

To a solution of 6-bromo-3-cyclopropylimidazo[1,2-a] pyridine (1.0 g, 4.2 mmol) in THF (10 ml) was added n-butyllithium (4.6 ml, 2.5 M in hexane, 12 mmol) dropwise with stirring at −78° C. under a nitrogen atmosphere. After the reaction solution had stirred at −78° C. for 1 h, a solution of 2,4,6-triisopropylbenzenesulfonyl azide (1.37 g, 4.42 mmol) (Source: Suzhou Highfine Biotech Co., Ltd.) in THF (5 ml) was added at −78° C. The resulting solution was stirred and the temperature was raised to −65° C. for 1 h. The reaction was then quenched by the addition of water (10 ml) and extracted with DCM (3×10 ml). The organic layers was combined and dried over anhydrous sodium sulfate, filtered and concentrated in vacuo. The residue was purified by flash column chromatography (silica gel, eluting with 1% MeOH in DCM) to afford 6-azido-3-cyclopropylimidazo[1,2-a] pyridine. MS (ESI) Calc'd for ($C_{10}H_{10}N_5$) [M+H]$^+$, 200; found, 200.

Step 5: Preparation of (S and R)-3-cyclopropyl-5,6,7,8-tetrahydroimidazo[1,2-a]pyridin-6-amine To a solution of 6-azido-3-cyclopropylimidazo[1,2-a] pyridine (200 mg, 1.00 mmol) in MeOH (5 ml) was added palladium on carbon (10%, 100 mg) in portions, after which the solution was placed under an atmosphere of hydrogen (2 atm). The resulting mixture was stirred at 25° C. for 5 h. The reaction mixture was then filtered, washing the filter cake with MeOH (50 ml). The combined filtrate was concentrated in vacuo to afford 3-cyclopropyl-5,6,7,8-tetrahydroimidazo [1,2-a]pyridin-6-amine which was used in the next step without further purification MS (ESI) Calc'd for ($C_{10}H_{16}N_3$) [M+H]$^+$, 178; found, 178.

Step 6: Preparation of compounds 4-1 and 4-2

A mixture of 6-chloro-9-ethyl-8-(2-methylpyrimidin-5-yl)-9H-purine (Intermediate C) (100 mg, 0.36 mmol), 3-cyclopropyl-5,6,7,8-tetrahydroimidazo[1,5-a]pyridin-6-amine (150 mg, crude from the previous step) and DIEA (142 mg, 1.29 mmol) in t-BuOH (5 ml) was stirred at 85° C. for 16 h. The reaction was then cooled and water (80 ml) was added, after which the reaction mixture was extracted with DCM (3×50 ml). The combined organic layers were dried over anhydrous sodium sulfate, filtered, and concentrated in vacuo. The resulting residue was purified by reverse phase preparative HPLC (Column: Xbridge Prep C18 5 μm OBD, 19×150 mm; Mobile phase: A: Water (10 mM $NH_4HCO_3$), B: MeCN; Flow rate: 20 ml/min). The racemic N-(3-cyclopropyl-5,6,7,8-tetrahydroimidazo[1,2-a]pyridin-6-yl)-9-ethyl-8-(2-methylpyrimidin-5-yl)-9H-purin-6-amine was then subjected to preparative chiral HPLC (Column: Chiralpak® AD-H™, 2×25 cm; Mobile phase: 50% EtOH in hexane (0.1% TEA)) to provide 4-1 (faster eluting enantiomer, 10.6 min): $^1$H NMR (300 MHz, DMSO-$d_6$) δ 9.12 (s, 2H), 8.35 (s, 1H), 8.22 (brs, 1H), 6.52 (s, 1H), 4.90-4.81 (m, 1H), 4.35-4.28 (m, 1H), 4.30 (q, J=7.2 Hz, 2H), 3.93-3.86 (m, 1H), 2.95-2.80 (m, 2H), 2.74 (s, 3H), 2.27-2.00 (m, 2H), 1.63-1.60 (m, 1H), 1.34 (t, J=7.2 Hz, 3H), 0.87-0.76 (m, 2H), 0.52-0.50 (m, 2H). MS (ESI) Calc'd for ($C_{22}H_{26}N_9$) $[M+H]^+$, 416; found, 416; and 4-2 (slower eluting enantiomer, 15.6 min): $^1$H NMR (300 MHz, DMSO-$d_6$) δ 9.12 (s, 2H), 8.35 (s, 1H), 8.23 (brs, 1H), 6.53 (s, 1H), 4.90-4.81 (m, 1H), 4.35-4.28 (m, 1H), 4.30 (q, J=7.2 Hz, 2H), 3.93-3.86 (m, 1H), 2.95-2.80 (m, 2H), 2.74 (s, 3H), 2.27-2.00 (m, 2H), 1.67-1.60 (m, 1H), 1.34 (t, J=7.2 Hz, 3H), 0.87-0.73 (m, 2H), 0.52-0.50 (m, 2H). MS (ESI) Calc'd for ($C_{22}H_{26}N_9$) $[M+H]^+$, 416; found, 416.

Example 27: Synthesis of Compounds 4-3 and 4-4

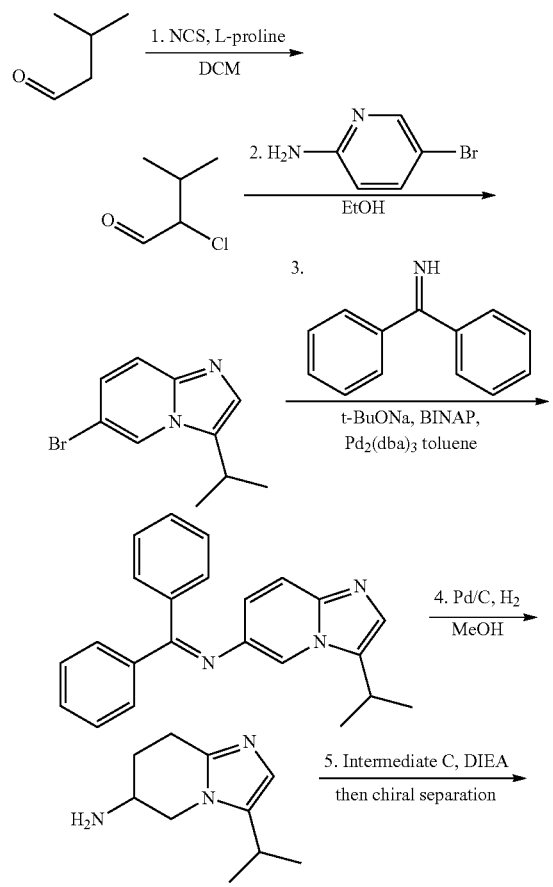

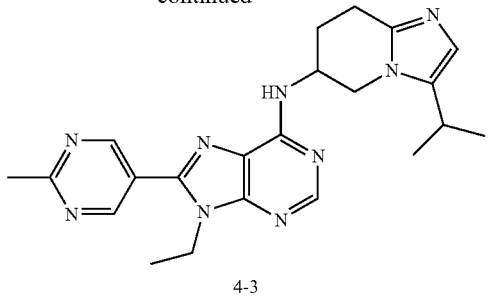

4-3

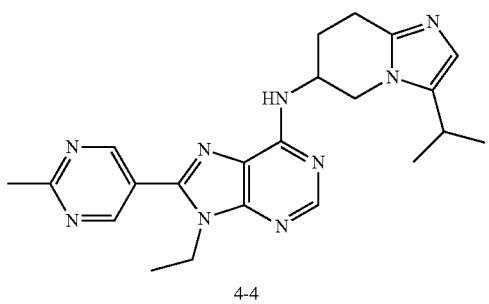

4-4

Step 1: Synthesis of 2-chloro-3-methylbutanal

To a solution of 3-methylbutanal (10.0 g, 0.11 mol) in DCM (100 ml) were added N-chlorosuccinimide (18 g, 0.13 mol) and L-proline (13 g, 0.11 mol). The resulting solution was stirred for 1.5 h at ambient temperature, after which the solution was quenched by the addition of water (30 ml). The resulting mixture was extracted with DCM (3×100 ml), The organic layers were combined and dried over anhydrous sodium sulfate, filtered and the filtrate was concentrated in vacuo to afford 2-chloro-3-methylbutanal, which was used to next step without further purification. $^1$H NMR (300 MHz, $CDCl_3$) δ 9.50 (s, 1H), 4.02 (dd, J=5.4, 3.0 Hz, 1H), 2.33-2.37 (m, 1H), 1.06 (d, J=6.9 Hz, 3H), 1.03 (d, J=6.9 Hz, 3H).

Step-2: Synthesis of 6-bromo-3-isopropylimidazo[1,2-a]pyridine (3)

A mixture of 2-chloro-3-methylbutanal (5.0 g, 42 mmol) and 5-bromopyridin-2-amine (7.3 g, 42 mmol) in ethanol (50 ml) was stirred for 14 h at ambient temperature before the solution was concentrated in vacuo. The resulting residue was diluted by water (50 ml), and the resulting mixture was extracted with DCM (3×100 ml). The organic layers were combined and dried over anhydrous sodium sulfate, filtered and concentrated in vacuo. The residue was then purified by column chromatography (silica gel, eluting with 1-2% MeOH in DCM) to afford 6-bromo-3-isopropylimidazo[1,2-a]pyridine. MS (ESI) Calc'd for ($C_{10}H_{12}BrN_2$) $[M+H]^+$, 239, 241; found, 239, 241.

Step 3: Preparation of N-(diphenylmethylene)-3-isopropylimidazo[1,2-a]pyridin-6-amine To a degassed solution of 6-bromo-3-isopropylimidazo[1,2-a]pyridine (2.0 g, 8.4 mmol) in toluene (30 ml) were added diphenylmethanimine (1.8 g, 10 mmol) sodium tert-butoxide (1.2 g, 12 mmol), tris(dibenzylideneacetone)dipalladium (110 mg, 0.1 mmol) and 2,2-bis(diphenylphosphino)-1,1'-binaphthalene (BINAP) (156 mg, 0.2 mmol). The resulting mixture was stirred for 12 h at 80° C. under an atmosphere of nitrogen, after which the reaction mixture was cooled and concentrated in vacuo. The resulting residue was diluted by water (30 ml), and extracted with DCM (3×50 ml). The organic layers were combined and dried over anhydrous sodium sulfate, filtered and concentrated in vacuo. The residue thus obtained was purified by column chromatography (silica gel, eluting with 3-15% EA in DCM) to afford N-(diphenylmethylene)-3-isopropylimidazo[1,2-a]pyridin-6-amine. MS (ESI) Calc'd for ($C_{23}H_{22}N_3$) [M+H]$^+$, 340; found, 340.

Step 4: Preparation of (S and R)-3-isopropyl-5,6,7,8-tetrahydroimidazo[1,2-a]pyridin-6-amine To a solution of N-(diphenylmethylene)-3-isopropylimidazo[1,2-a]pyridin-6-amine (460 mg, 1.35 mmol) in MeOH (10 ml) under nitrogen was added 10% palladium on activated carbon (100 mg, 0.94 mmol). The resulting solution was stirred for 2 h at ambient temperature under an atmosphere of hydrogen (2 atm), after which the solution was filtered. The filtrate was concentrated in vacuo to afford (S and R)-3-isopropyl-5,6,7,8-tetrahydroimidazo[1,2-a]pyridin-6-amine, which was used to next step without further purification. MS (ESI) Calc'd for ($C_{10}H_{18}N_3$) [M+1]$^+$, 180; found, 180.

Step 5: Preparation of Compounds 4-3 and 4-4

A solution of 3-isopropyl-5,6,7,8-tetrahydroimidazo[1,2-a]pyridin-6-amine (400 mg, 0.81 mmol), 6-chloro-9-ethyl-8-(2-methylpyrimidin-5-yl)-9H-purine (Intermediate C) (153 mg, 0.56 mmol) and DIEA (141 mg, 1.09 mmol) in t-BuOH (4 ml) was stirred at 80° C. for 16 h, after which the solution was cooled and concentrated in vacuo. The resulting residue was purified by flash column chromatography (silica gel, eluting with 8% MeOH in DCM) to afford the racemic (S and R)-9-ethyl-N-(3-isopropyl-5,6,7,8-tetrahydroimidazo[1,2-a]pyridin-6-yl)-8-(2-methylpyrimidin-5-yl)-9H-purin-6-amine. Separation of the enantiomers was achieved by preparative chiral HPLC (Chiralpak® IA-3, 2×25 cm, 5 um, Mobile phase: 30% isopropanol in hexane) to afford 4-3 (faster eluting enantiomer, 10.1 min): $^1$H NMR (300 MHz, DMSO-d$_6$) δ 9.12 (s, 2H), 8.35 (s, 1H), 8.17 (brs, 1H), 6.56 (s, 1H), 4.82-4.74 (m, 1H), 4.32 (q, J=7.2 Hz, 2H), 4.19-4.17 (m, 1H), 3.92-3.80 (m, 1H), 2.92-2.80 (m, 3H), 2.74 (s, 3H), 2.16-2.02 (m, 2H), 1.32 (t, J=7.2 Hz, 3H), 1.17 (d, J=6.9 Hz, 3H), 1.13 (d, J=6.9 Hz, 3H). MS (ESI) Calc'd for ($C_{22}H_{28}N_9$) [M+H]$^+$, 418; found, 418; and 4-4 (slower eluting enantiomer, 13.3 min): $^1$H NMR (300 MHz, DMSO-d$_6$) 9.12 (s, 2H), 8.35 (s, 1H), 8.17 (brs, 1H), 6.56 (s, 1H), 4.82-4.74 (m, 1H), 4.32 (q, J=7.2 Hz, 2H), 4.19-4.17 (m, 1H), 3.92-3.80 (m, 1H), 2.93-2.79 (m, 3H), 2.74 (s, 3H), 2.15-2.02 (m, 2H), 1.32 (t, J=7.2 Hz, 3H), 1.17 (d, J=6.9 Hz, 3H), 1.13 (d, J=6.9 Hz, 3H). MS (ESI) Calc'd for ($C_{22}H_{28}N_9$) [M+H]$^+$, 418; found, 418.

Example 28: Preparation of Compound 4-5

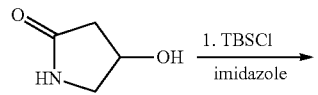

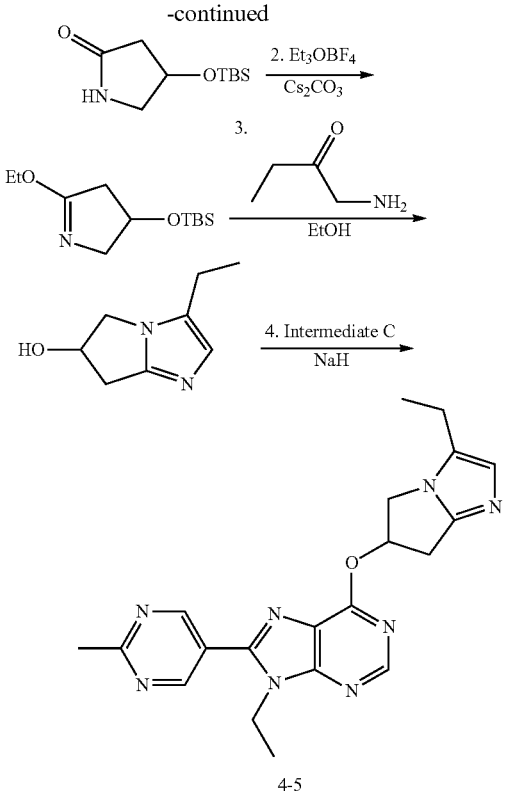

Step 1: Preparation of 4-(tert-butyldimethylsilyloxy)pyrrolidin-2-one

To a solution of 4-hydroxypyrrolidin-2-one (15 g, 150 mmol, commercially available from Ark Pharm, Inc.) in DMF (200 ml) was added imidazole (16 g, 240 mmol) and tert-butylchlorodimethylsilane (27 g, 180 mmol). The mixture was stirred at RT overnight, after which the solution was poured over ice and an aqueous solution of hydrochloric acid (2N, 200 ml) was added. The mixture was stirred at RT for 10 min., after which it was extracted with EtOAc (3×500 ml). The combined organic layers were dried over anhydrous Na$_2$SO$_4$, filtered, and concentrated in vacuo to give a residue, which was purified by column chromatography (silica gel, eluting with a gradient of 20:1 to 1:1 PE:EtOAc) to give the 4-((tert-butyldimethylsilyl)oxy)pyrrolidin-2-one. MS (ESI) Calc'd for ($C_{10}H_{22}NO_2Si$) [M+H]$^+$, 216; found, 216.

Step 2: Preparation of 3-(tert-butyldimethylsilyloxy)-5-ethoxy-3,4-dihydro-2H-pyrrole To a solution of 4-((tert-butyldimethylsilyl)oxy)pyrrolidin-2-one (1.2 g, 5.6 mmol) in DCM (20 ml) was added cesium carbonate (5.5 g, 17 mmol) and triethyloxonium tetrafluoroborate (1.1 g, 5.8 mmol). The reaction mixture was stirred at RT overnight, after which it was quenched with water (50 ml). The mixture was extracted with DCM (3×200 ml), and the combined organic layers were dried over anhydrous Na$_2$SO$_4$, filtered, and concentrated in vacuo to give a residue, which was purified by column chromatography (silica gel, eluting with a gradient of 20:1 to 1:1 PE:EtOAc) to give 3-((tert-butyldimethylsilyl)oxy)-5-ethoxy-3,4-dihydro-2H-pyrrole.

Step 3: Preparation of (S and R)-3-ethyl-6,7-dihydro-5H-pyrrolo[1,2-a]imidazol-6-ol A solution of 3-((tert-butyldimethylsilyl)oxy)-5-ethoxy-3,4-dihydro-2H-pyrrole (120 mg, 0.493 mmol) and 1-aminobutan-2-one (42.9 mg, 0.493 mmol, commerically available from Enamine Building Blocks) in EtOH (1 ml) was stirred for 18 h at 82° C. under an atmosphere of nitrogen. Then the mixture was then cooled and concentrated in vacuo to a residue, which was purified by reverse phase chromatography (mobile phase: MeOH/(10 mM NH$_4$HCO$_3$)) to afford (S and R)-3-ethyl-6,7-dihydro-5H-pyrrolo[1,2-a]imidazol-6-ol. MS (ESI) Calc'd for (C$_8$H$_{13}$N$_2$O) [M+H]$^+$, 153; found, 153.

Step 4: Preparation of Compound 4-5

A solution of 6-chloro-9-ethyl-8-(2-methylpyrimidin-5-yl)-9H-purine (Intermediate C) (35 mg, 0.13 mmol), (S and R)-3-ethyl-6,7-dihydro-5H-pyrrolo[1,2-a]imidazol-6-ol (19 mg, 0.13 mmol) and sodium hydride (30 mg, 0.75 mmol, 60% in oil) in dry THF (2 ml) was stirred at RT overnight. The reaction mixture was then quenched with water (10 ml), and the reaction mixture was extracted with DCM (3×50 ml). The combined organic layers were concentrated in vacuo, and the residue thus obtained purified by reverse phase chromatography (mobile phase: MeOH/(10 mM NH$_4$HCO$_3$)) to give 4-5: $^1$H NMR (CD$_3$OD, 400 MHz): δ 8.99 (s, 2H), 8.51 (s, 1H), 6.59 (s, 1H), 6.37 (s, 1H), 4.39-4.43 (m, 1H), 4.35 (q, J=7.2 Hz, 2H), 4.15-4.18 (m, 1H), 3.35-3.39 (m, 1H), 3.01-3.05 (m, 1H), 2.70 (s, 3H), 2.49 (q, J=7.6 Hz, 2H), 1.35 (t, J=7.2 Hz, 3H), 1.13 (t, J=7.6 Hz, 3H). MS (ESI) Calc'd for (C$_{20}$H$_{23}$N$_8$O) [M+H]$^+$, 391; found, 391.

Compounds 4-1 through 4-5 are listed in Table 1 and have be made in accordance to procedures illustrated in Examples 26-28.

TABLE 4

| Compound Number | Structure | IUPAC Name | Exact Mass [M + H]+ |
|---|---|---|---|
| 4-1 | 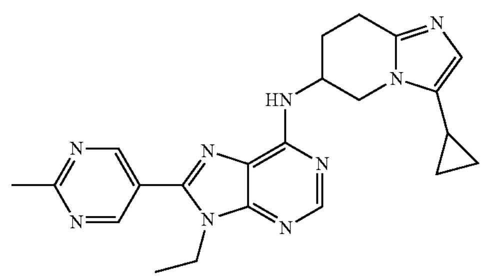 [SMILES: CCn1c(-c2cnc(C)nc2)nc2c(NC3CCc4ncc(C5CC5)n4C3)ncnc21] | (S or R)-N-(3-cyclopropyl 5,6,7,8-tetrahydroimidazo[1,2-a]pyridin-6-yl)-9-ethyl-8-(2-methylpyrimidin-5-yl)-9H-purin-6-amine | Calc'd 416, found 416 |
| 4-2 | 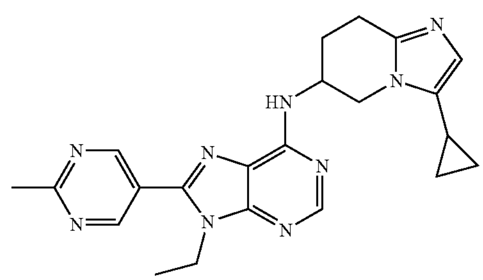 [SMILES: CCn1c(-c2cnc(C)nc2)nc2c(NC3CCc4ncc(C5CC5)n4C3)ncnc21] | (S or R)-N-(3-cyclopropyl-5,6,7,8-tetrahydroimidazo[1,2-a]pyridin-6-yl)-9-ethyl-8-(2-methylpyrimidin-5-yl)-9H-purin-6-amine | Calc'd 416, found 416 |
| 4-3 | 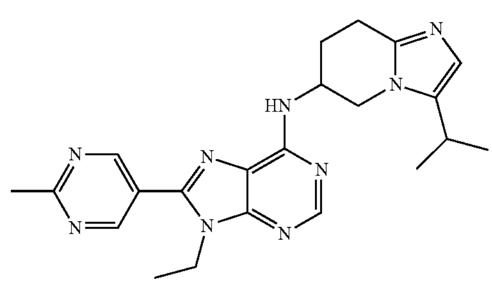 [SMILES: CCn1c(-c2cnc(C)nc2)nc2c(NC3CCc4ncc(C(C)C)n4C3)ncnc21] | (S or R)-9-ethyl-N-[3-(1-methylethyl)-5,6,7,8-tetrahydroimidazo[1,2-a]pyridin-6-yl]-8-(2-methylpyrimidin-5-yl)-9H-purin-6-amine | Calc'd 418, found 418 |

TABLE 4-continued

| Compound Number | Structure | IUPAC Name | Exact Mass [M + H]+ |
|---|---|---|---|
| 4-4 | 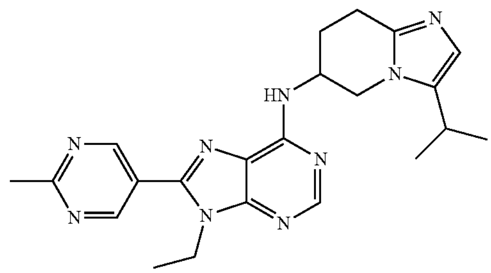 [SMILES: CCn1c(-c2cnc(C)nc2)nc2c(NC3CCc4ncc(C(C)C)n4C3)ncnc21] | (S or R)-9-ethyl-N-[3-(1-methylethyl)-5,6,7,8-tetrahydroimidazo[1,2-a]pyridin-6-yl]-8-(2-methylpyrimidin-5-yl)-9H-purin-6-amine | Calc'd 418, found 418 |
| 4-5 | 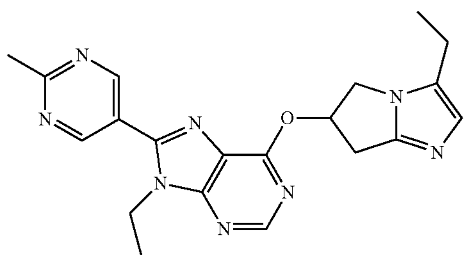 [SMILES: CCc1cnc2n1CC(Oc1ncnc3c1nc(-c1cnc(C)nc1)n3CC)C2] | (S and R)-9-ethyl-6-[(3-ethyl-6,7-dihydro-5H-pyrrolo[1,2-a]imidazol-6-yl)oxy]-8-(2-methylpyrimidin-5-yl)-9H-purine | Calc'd 391, found 391 |

Compound Examples of Table 5

Example 29: Preparation of Compound 5-1

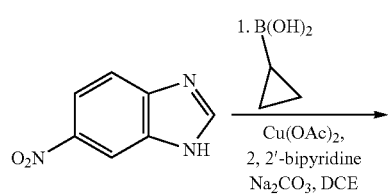

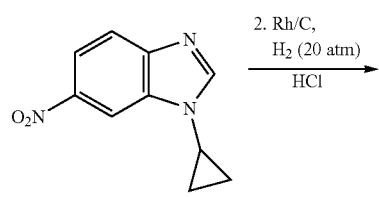

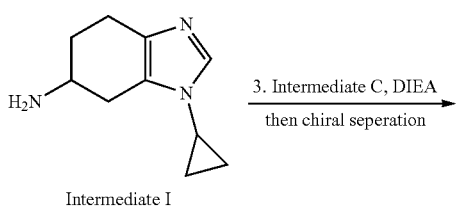

Intermediate I

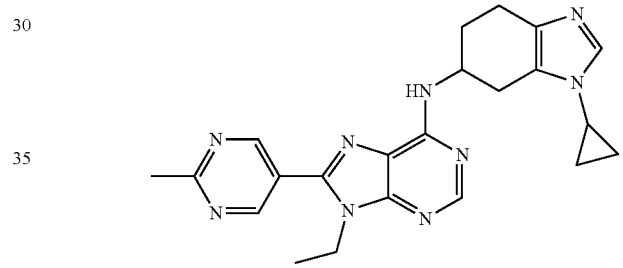

5-1

Step 1: Preparation of 1-cyclopropyl-6-nitro-1H-benzo[d]imidazole

A mixture of 6-nitro-1H-benzo[d]imidazole (5.0 g, 30.6 mmol), cyclopropylboronic acid (5.3 g, 61.3 mmol), copper (II) acetate (1.7 g, 9.2 mmol), 2,2'-bipyridine (1.4 g, 9.2 mmol) and sodium carbonate (9.8 g, 92.2 mmol) in DCE (100 ml) was stirred for 16 h at 70° C. The reaction mixture was then cooled to ambient temperature and concentrated in vacuo. The residue was purified by flash column chromatography (silica gel, eluting with 1-5% MeOH in DCM), after which the product was further purified via preparative reverse-phase HPLC: (Column:Xbridge Prep C18, 19×150 mm; Mobile phase: 10-35% MeCN in water with 0.1% TFA) to afford 1-cyclopropyl-6-nitro-1H-benzo[d]imidazole. MS (ESI)Calc'd for ($C_{10}H_{10}N_3O_2$) [M+H]+, 204; found, 204.

Step 2: Preparation of (S and R)-1-cyclopropyl-4,5,6,7-tetrahydro-1H-benzo[d]imidazol-6-amine (Intermediate I)

A mixture of 1-cyclopropyl-6-nitro-1H-benzo[d]imidazole (200 mg, 0.98 mmol) and 10% rhodium on carbon (20 mg) in hydrochloric acid (3 N aqueous solution, 3 ml) was stirred at 80° C. for 4 h under a hydrogen atmosphere (20 atm). The resulting mixture was then treated with ammonia (4 ml, 7 N aqueous solution), and extracted with chloroform (8×30 ml). The combined organic layers were dried over anhydrous sodium sulfate, filtered, and concentrated in vacuo to afford (S and R)-1-cyclopropyl-4,5,6,7-tetrahydro-1H-benzo[d]imidazol-6-amine (Intermediate I), which was used directly in the next step without further purification. MS (ESI)Calc'd for ($C_{10}H_{16}N_3$) [M+H]+, 178; found, 178.

Step 3: Preparation of Compound 5-1

A solution of (S and R)-1-cyclopropyl-4,5,6,7-tetrahydro-1H-benzo[d]imidazol-6-amine (Intermediate I) (90 mg, 0.51 mmol), 6-chloro-9-ethyl-8-(2-methylpyrimidin-5-yl)-9H-purine (Intermediate C) (153 mg, 0.56 mmol) and DIEA (197 mg, 1.52 mmol) in t-BuOH (7 ml) was stirred at 80° C. for 16 h, after which the solution was cooled and concentrated in vacuo. The residue was purified by flash column chromatography (silica gel, eluting 8% MeOH in DCM) to afford the racemic (S and R)—N-(1-cyclopropyl-4,5,6,7-tetrahydro-1H-benzo[d]imidazol-6-yl)-9-ethyl-8-(2-methylpyrimidin-5-yl)-9H-purin-6-amine. Separation of the enantiomers was achieved via chiral preparative chiral HPLC (Chiralpak® IA™, 2×25 cm; Mobile phase: 50% ethanol in n-hexane containing 0.1% trifluoroacetic acid) to afford 5-1 (faster eluting enantiomer, 2.9 min): $^1$H NMR (300 MHz, CD$_3$OD) δ 9.13 (s, 2H), 8.36 (s, 1H), 7.53 (s, 1H), 4.83-4.74 (m, 1H), 4.42 (q, J=7.2 Hz, 2H), 3.29-3.20 (m, 2H), 2.84 (s, 3H), 2.83-2.70 (m, 3H), 2.22-2.05 (m, 2H), 1.45 (t, J=7.2 Hz, 3H), 1.07-0.92 (m, 4H). MS (ESI) Calc'd for ($C_{22}H_{26}N_9$) [M+H]+, 416; found, 416.

Example 30: Preparation of Compound 5-9

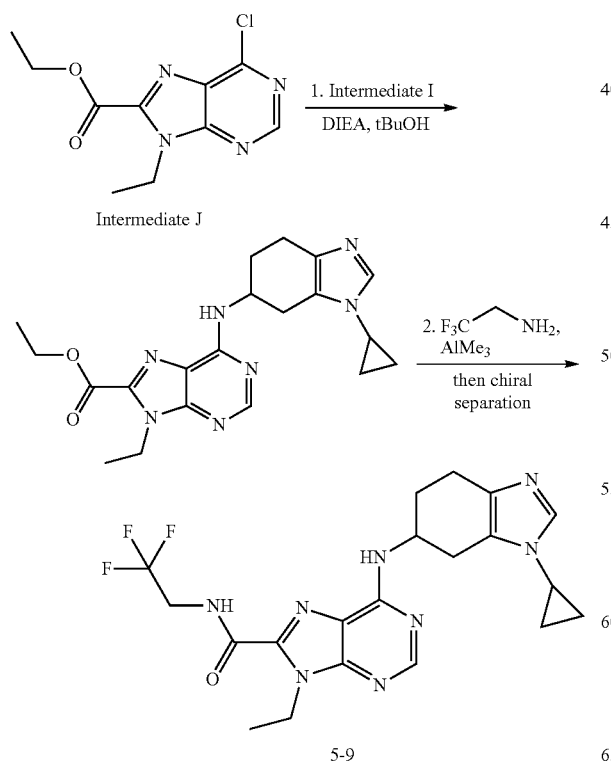

Step 1: Preparation of (S and R)-ethyl 6-((1-cyclopropyl-4,5,6,7-tetrahydro-1H-benzo[d]imidazol-6-yl)amino)-9-ethyl-9H-purine-8-carboxylate A mixture of ethyl 6-chloro-9-ethyl-9H-purine-8-carboxylate (Intermediate J) (100 mg, 0.39 mmol), (S and R)-1-cyclopropyl-4,5,6,7-tetrahydro-1H-benzo[d]imidazol-6-amine (Intermediate I) (84 mg, 0.47 mmol) and DIEA (152 mg, 1.2 mmol) in isobutanol (5 ml) was stirred at 80° C. for 18 h, after which the solution was cooled and concentrated in vacuo. The resulting residue was purified by flash column chromatography (silica gel, eluting with 1-10% MeOH in DCM) to afford (S and R)-ethyl 6-((1-cyclopropyl-4,5,6,7-tetrahydro-1H-benzo[d]imidazol-6-yl)amino)-9-ethyl-9H-purine-8-carboxylate. MS (ESI) Calc'd for ($C_{20}H_{26}N_7O_2$) [M+H]+, 396; found, 396.

Step 2: Preparation of Compound 5-9

To a solution of 2,2,2-trifluoroethanamine (200 mg, 2.0 mmol) in DCM (5 ml) was added trimethylaluminum (1.5 ml, 3.0 mmol, 2 N solution in toluene) drop-wise at 0° C. The resulting solution was stirred at 0° C. for 1 h before the addition of (S and R)-ethyl 6-((1-cyclopropyl-4,5,6,7-tetrahydro-1H-benzo[d]imidazol-6-yl)amino)-9-ethyl-9H-purine-8-carboxylate (40 mg, 0.10 mmol). The resulting mixture was warmed to 20° C. and stirred for 4 h before the reaction was quenched with water (30 ml). The aqueous solution was then extracted with DCM (4×80 ml). The organic layers were combined, dried over anhydrous sodium sulfate, and filtered. The filtrate was concentrated in vacuo and the residue was purified flash column chromatography (silica gel, eluting with 1-10% MeOH in DCM) to afford (S and R)-6-((1-cyclopropyl-4,5,6,7-tetrahydro-1H-benzo[d]imidazol-6-yl)amino)-9-ethyl-N-(2,2,2-trifluoroethyl)-9H-purine-8-carboxamide. Separation of the enantiomers was achieved via chiral preparative HPLC (Chiralpak® IC-3, 2×25 cm; Mobile phase: 25% ethanol in n-hexane, Flow rate: 20 ml/min) to afford 5-9 (faster eluting enantiomer, 3.9 min): $^1$H NMR (400 MHz, CD$_3$OD): δ 8.36 (s, 1H), 7.55 (s, 1H), 4.70 (q, J=7.2 Hz, 2H), 4.69-4.67 (m, 1H), 4.14 (q, J=9.2 Hz, 2H), 3.29-3.21 (m, 2H), 2.81-2.68 (m, 3H), 2.19-2.02 (m, 2H), 1.45 (t, J=7.2 Hz, 3H), 1.05-0.94 (m, 4H). MS (ESI) Calc'd for ($C_{20}H_{24}F_3N_8O$) [M+H]+, 449; found, 449.

Example 31: Synthesis of Intermediate N

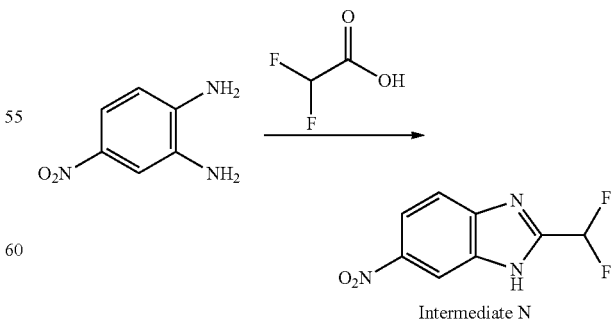

A mixture of 4-nitrobenzene-1,2-diamine (5.0 g, 33 mmol, commercially available from BePharm Ltd.) in 2,2-difluoroacetic acid (30 ml) was stirred at 70° C. for 16 h before the volatiles were removed in vacuo. The resulting residue was purified by flash column chromatography (silica gel, eluting with 8-50% EA in PE) to afford 2-(difluoromethyl)-6-nitro-1H-benzo[d]imidazole (Intermediate N). MS (ESI) Calc'd for ($C_8H_6F_2N_3O_2$) [M+H]$^+$, 214; found, 214.

Example 32: Synthesis of Compound 5-12

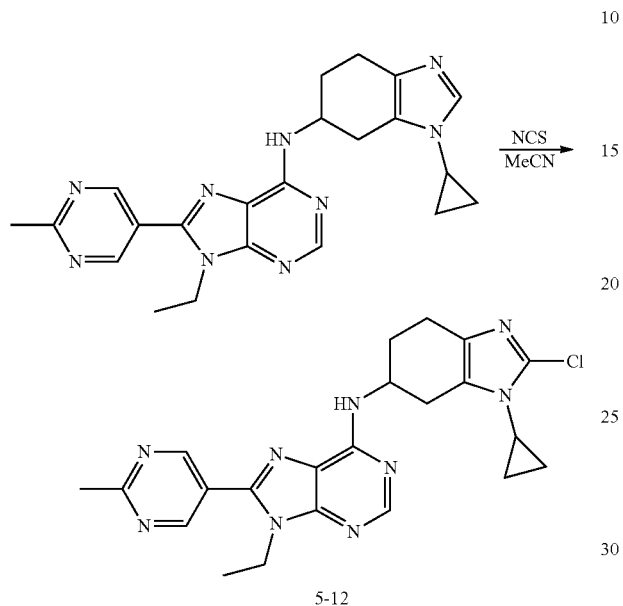

To a mixture of (R and S)—N-(1-cyclopropyl-4,5,6,7-tetrahydro-1H-benzo[d]imidazol-6-yl)-9-ethyl-8-(2-methyl-pyrimidin-5-yl)-9H-purin-6-amine (180 mg, 0.43 mmol, prepared as in Example 17) in MeCN (5 ml) was added N-chlorosuccinimide (104 mg, 0.78 mmol). The resulting solution was stirred for 30 min at 40° C., after which the volatiles were removed in vacuo. The resulting mixture was diluted with water (10 ml), and extracted with EA (2×30 ml). The combined organic layers were dried over anhydrous sodium sulfate, filtered, and concentrated in vacuo. The crude residue was purified by preparative reverse-phase HPLC (Column: X Bridge C18, 19×150 mm, 5 μm; Mobile Phase: 40-60% MeCN in 10 mM ammonium bicarbonate aqueous solution) to afford 5-12. $^1$H NMR (300 MHz, CD$_3$OD): δ 9.01 (s, 2H), 8.31 (s, 1H), 4.85-4.70 (m, 1H), 4.42 (q, J=7.2 Hz, 2H), 3.29-3.20 (m, 2H), 2.84 (s, 3H), 2.83-2.70 (m, 3H), 2.22-2.05 (m, 2H), 1.45 (t, J=7.2 Hz, 3H), 1.20-1.10 (m, 2H), 1.09-1.01 (m, 2H). MS (ESI) Calc'd for ($C_{22}H_{25}C_1N_9$) [M+H]$^+$, 450; found, 450.

Example 33: Preparation of Compounds 5-13 and 5-14

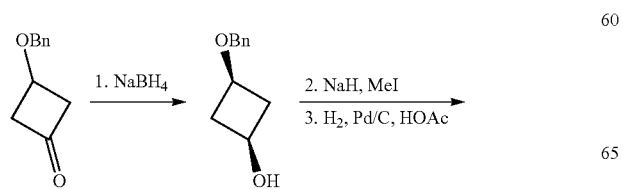

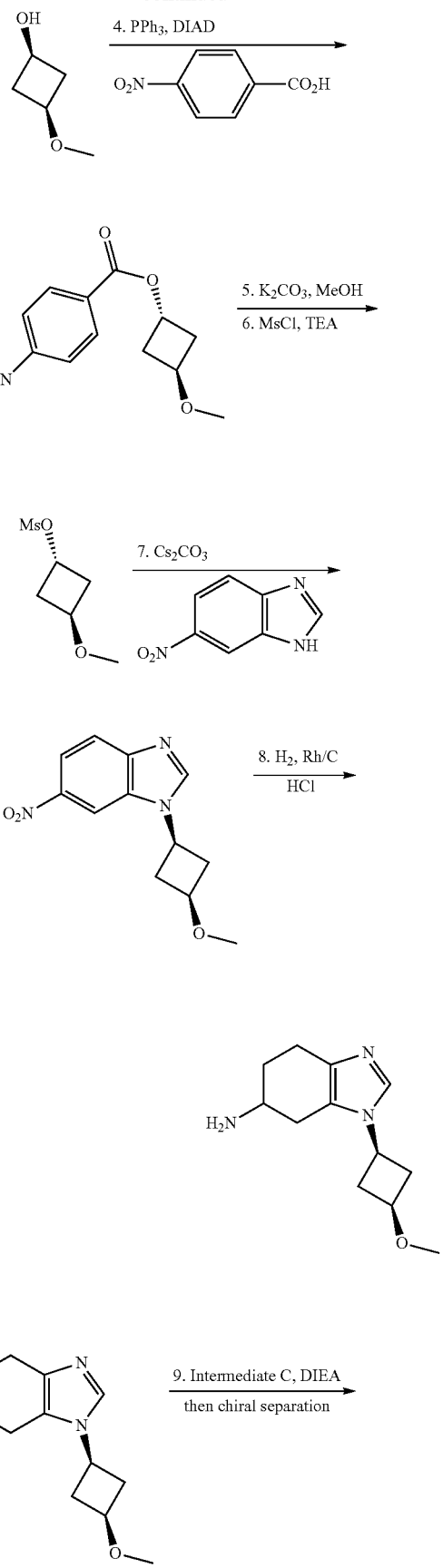

-continued

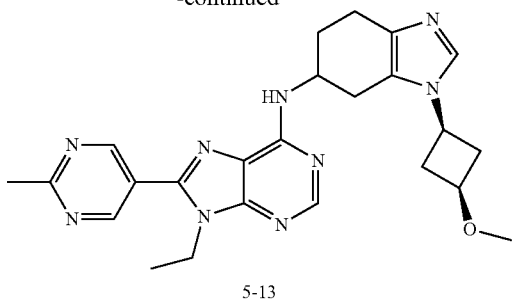

5-13

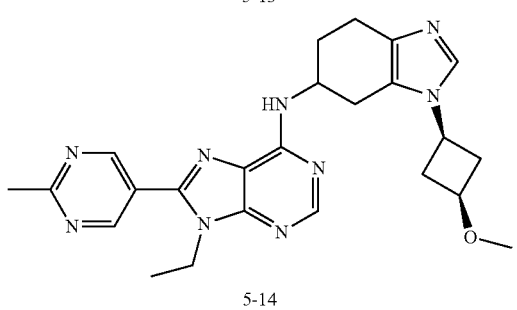

5-14

Step 1: Preparation of
cis-3-(benzyloxy)cyclobutanol

To a mixture of 3-(benzyloxy)cyclobutanone (10 g, 57 mmol, commercially available from Shanghai Epochem Co., Ltd) in MeOH (100 ml) was added sodium borohydride (6.4 g, 170 mmol) in several portions. The resulting mixture was stirred at RT for 2 h, after which the reaction was quenched with water (100 ml). The aqueous solution was then extracted with EA (3×200 ml), and the combined organic layers were dried over anhydrous sodium sulfate and filtered. The filtrate was concentrated in vacuo to afford cis-3-(benzyloxy)cyclobutanol, which was used in the next step without further purification. MS (ESI) Calc'd for ($C_{11}H_{15}O_2$) [M+H]$^+$, 179; found, 179.

Step 2: Preparation of
((cis-3-methoxycyclobutoxy)methyl)benzene

To a solution of cis-3-(benzyloxy)cyclobutanol (10.0 g, 56 mmol) in THF (100 ml) was added sodium hydride (3.4 g, 84 mmol, 60% w/w in mineral oil) at 0° C. The resulting solution was stirred for 15 min, after which iodomethane (9.6 g, 67 mmol) was added. The resulting solution was stirred for 1 h at 25° C. before the reaction was carefully quenched with water (50 ml). The aqueous solution was then extracted with EA (3×200 ml), and the combined organic layers were dried over anhydrous sodium sulfate, filtered, and concentrated in vacuo to afford ((cis-3-methoxycyclobutoxy)methyl)benzene, which was used in the next step without further purification. MS (ESI) Calc'd for ($C_{12}H_{17}O_2$) [M+H]$^+$, 193; found, 193.

Step 3: Preparation of cis-3-methoxycyclobutanol

A mixture of ((cis-3-methoxycyclobutoxy)methyl)benzene (3.0 g, 15.6 mmol), palladium on carbon (1.7 g, wet, 10% w/w) and acetic acid (0.9 ml, 15.6 mmol, 47% w/w) in MeOH (50 ml) was stirred at 80° C. for 14 h under an atmosphere of hydrogen (20 atm) in a pressure tank reactor. The resulting mixture was cooled, filtered, and washed with MeOH (3×20 ml). The combined filtrate was concentrated to afford cis-3-methoxycyclobutanol (0.5 g, crude) as colorless oil, which was used in the next step without further purification.

Step 4: Preparation of trans-3-methoxycyclobutyl
4-nitrobenzoate

To a mixture of cis-3-methoxycyclobutanol (1.0 g, 9.8 mmol), 4-nitrobenzoic acid (1.6 g, 9.8 mmol) and triphenylphosphine (3.08 g, 11.8 mmol) in DCM (10 ml) was added diisopropyl azodicarboxylate (2.3 ml, 11.8 mmol) at 0° C. The resulting solution was stirred for 2 h at 25° C., after which the reaction mixture was concentrated in vacuo. The resulting residue was purified by column chromatography (silica gel, eluting with 10-50% EA in PE) to afford cis-3-methoxycyclobutyl 4-nitrobenzoate.

Step 5: Preparation of trans-3-methoxycyclobutanol

To a solution of trans-3-methoxycyclobutyl 4-nitrobenzoate (0.6 g, 2.4 mmol) in MeOH (5 ml) and water (1 ml) was added potassium carbonate (0.7 g, 4.8 mmol). The resulting solution was stirred for 2 h, after which the mixture was diluted with water (10 ml). The aqueous solution was then extracted with EtOAc (3×20 ml). The combined organic layers were dried over anhydrous sodium sulfate and filtered. The filtrate was concentrated under vacuum to afford trans-3-methoxycyclobutanol, which was used in the next step without further purification.

Step 6: Preparation of trans-3-methoxycyclobutyl
methanesulfonate

To a solution of trans-3-methoxycyclobutanol (200 mg, 1.96 mmol) and triethylamine (396 mg, 3.92 mmol) in DCM (2 ml) was added methanesulfonyl chloride (MsCl) (0.17 ml, 2.2 mmol) at 0° C. The resulting solution was stirred for 1 h at 25° C. before the reaction was quenched with water (10 ml). The aqueous solution was then extracted with EtOAc (3×20 ml), and the combined organic layers were dried over anhydrous sodium sulfate and filtered. The filtrate was concentrated in vacuo to afford trans-3-methoxycyclobutyl methanesulfonate, which was used in the next step without further purification.

Step 7: Preparation of 1-(cis-3-methoxycyclobutyl)-
6-nitro-1H-benzo[d]imidazole To a solution of trans-3-methoxycyclobutyl methanesulfonate (243 mg, 1.35 mmol) and 6-nitro-1H-benzo[d]imidazole (200 mg, 1.23 mmol) in N,N-dimethylformamide (5 ml) was added cesium carbonate (799 mg, 2.45 mmol). The resulting mixture was stirred for 12 h at 110° C. The reaction mixture was then cooled and diluted with water (15 ml), after which it was extracted with EtOAc (3×30 ml). The combined organic layers were then dried over anhydrous sodium sulfate, filtered, and concentrated in vacuo. The resulting residue was purified via preparative reverse-phase HPLC (Column: Sunfire C18, 19×150 mm, 5 μm; Mobile Phase: 30-50% MeCN in 10 mM trifluoroacetic acid aqueous solution) to afford 1-(cis-3-methoxycyclobutyl)-6-nitro-1H-benzo[d]imidazole. MS (ESI) Calc'd for ($C_{12}H_{14}N_3O_3$) [M+H]$^+$, 248; found, 248.

Step 8: Preparation of (S and R)-3-(cis-3-methoxy-cyclobutyl)-4,5,6,7-tetrahydro-3H-benzo[d]imidazol-5-amine A mixture of 1-(cis-3-methoxycyclobutyl)-6-nitro-1H-benzo[d]imidazole (50 mg, 0.20 mmol), rhodium on carbon (20 mg) and hydrochloric acid (1 ml, 37% w/w aqueous solution) in MeOH (7 ml) and water (1 ml) was stirred at 80° C. for 4 h under an atmosphere of hydrogen (30 atm) in a pressure tank reactor. The resulting mixture was cooled and filtered, washing with MeOH (3×20 ml). The combined filtrate was concentrated in vacuo to afford (S and R)-3-(cis-3-methoxycyclobutyl)-4,5,6,7-tetrahydro-3H-benzo[d]imidazol-5-amine, which was used in the next step without further purification. MS (ESI) Calc'd for ($C_{12}H_{20}N_3O$) [M+H]$^+$, 222; found, 222.

Step 9: Preparation of Compounds 5-13 and 5-14

To a mixture of (S and R)-3-(cis-3-methoxycyclobutyl)-4,5,6,7-tetrahydro-3H-benzo[d]imidazol-5-amine (20 mg, 0.09 mmol) and 6-chloro-9-ethyl-8-(2-methylpyrimidin-5-yl)-9H-purine Intermediate C (30 mg, 0.11 mmol) in t-BuOH (3 ml) was added DIEA (0.02 ml, 0.11 mmol). The resulting solution was stirred at 80° C. for 24 h, after which it was cooled and concentrated in vacuo. The resulting residue was purified by column chromatography (silica gel, eluting with 1-10% MeOH in DCM) to afford racemic (R and S)-9-ethyl-N-(3-((1s,3s)-3-methoxycyclobutyl)-4,5,6,7-tetrahydro-3H-benzo[d]imidazol-5-yl)-8-(2-methylpyrimidin-5-yl)-9H-purin-6-amine. Separation of the enantiomers was achieved via preparative chiral HPLC (Column: Chiralpak® IB2, 2×25 cm, 5 μm; Mobile phase: 20% ethanol in n-hexane, Flow rate: 20 ml/min) to afford 5-13 (faster eluting enantiomer, 3.1 min): $^1$H NMR (400 MHz, CD$_3$OD) δ 9.12 (s, 2H), 8.36 (s, 1H), 7.67 (s, 1H), 4.80-4.70 (m, 1H), 4.43 (q, J=6.8 Hz, 2H), 4.21-4.18 (m, 1H), 3.82-3.79 (m, 1H), 3.29 (s, 3H), 3.20-3.10 (m, 1H), 2.90-2.85 (m, 2H), 2.83 (s, 3H), 2.78-2.70 (m, 3H), 2.20-2.02 (m, 4H), 1.46 (t, J=6.8 Hz, 3H). MS (ESI) Calc'd for ($C_{24}H_{30}N_9O$) [M+H]$^+$, 460; found, 460; and 5-14 (slower eluting enantiomer, 5.2 min): $^1$H NMR (400 MHz, CD$_3$OD) δ 9.12 (s, 2H), 8.36 (s, 1H), 7.67 (s, 1H), 4.80-4.70 (m, 1H), 4.43 (q, J=6.8 Hz, 2H), 4.21-4.18 (m, 1H), 3.82-3.79 (m, 1H), 3.29 (s, 3H), 3.20-3.10 (m, 1H), 2.90-2.85 (m, 2H), 2.83 (s, 3H), 2.78-2.70 (m, 3H), 2.20-2.02 (m, 4H), 1.46 (t, J=6.8 Hz, 3H). MS (ESI) Calc'd for ($C_{24}H_{30}N_9O$) [M+H]$^+$, 460; found, 460.

Example 34: Preparation of Compounds 5-15 and 5-16

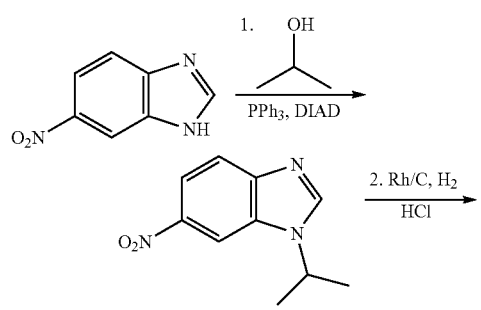

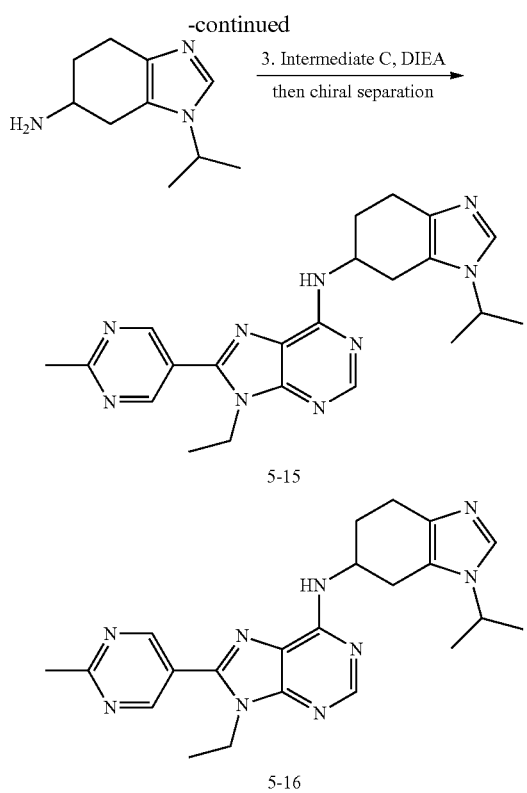

Step 1: Preparation of 1-isopropyl-6-nitro-1H-benzo[d]imidazole

To a solution of 6-nitro-1H-benzo[d]imidazole (1.0 g, 6.1 mmol), propan-2-ol (0.57 ml, 7.4 mmol) and triphenylphosphine (1.93 g, 7.4 mmol) in DCM (20 ml) was added diisopropyl azodicarboxylate (1.46 ml, 7.4 mmol) drop-wise at 0° C. The resulting solution was stirred for 12 h at RT, after which the solution was concentrated in vacuo. The residue was purified by flash column chromatography (silica gel, eluting with 0-10% MeOH in DCM) to afford a mixture containing the desired 1-isopropyl-6-nitro-1H-benzo[d]imidazole along with regioisomer 1-isopropyl-5-nitro-1H-benzo[d]imidazole. The mixture was further separated by preparative reverse-phase HPLC (X Bridge C18, 19×150 mm, 5 m; Mobile phase: 30-70% MeCN in water containing 0.05% trifluoroacetic acid) to afford 1-isopropyl-6-nitro-1H-benzo[d]imidazole. MS (ESI) Calc'd for ($C_{10}H_{12}N_3O_2$) [M+H]$^+$, 206; found, 206.

Step 2: Synthesis of (S and R)-3-isopropyl-4,5,6,7-tetrahydro-3H-benzo[d]imidazol-5-amine A solution of 1-isopropyl-6-nitro-1H-benzo[d]imidazole (100 mg, 0.49 mmol) and 10% rhodium on carbon (50 mg) in hydrochloric acid aqueous solution (3 N, 3 ml) was stirred at 80° C. for 5 h under an atmosphere of hydrogen (20 atm). The resulting solution was cooled and filtered through Celite. The filtrate was concentrated in vacuo to afford (S and R)-3-isopropyl-4,5,6,7-tetrahydro-3H-benzo[d]imidazol-5-amine as the HCl salt which was used in the next reaction without further purification. MS (ESI) Calc'd for ($C_{10}H_{18}N_3$) [M+H]$^+$, 180; found, 180.

Step 3: Preparation of Compounds 5-15 and 5-16

A solution of 6-chloro-9-ethyl-8-(2-methylpyrimidin-5-yl)-9H-purine (Intermediate C) (46 mg, 0.17 mmol), (S and R)-3-isopropyl-4,5,6,7-tetrahydro-3H-benzo[d]imidazol-5-amine, HCl (50 mg, crude from previous step) and DIEA (110 mg, 0.85 mmol) in t-BuOH (5 ml) was stirred at 80° C. for 15 h, after which the reaction was cooled to RT and then diluted with water (15 ml). The aqueous solution was extracted with DCM (3×50 ml), and the combined organic layers were dried over anhydrous magnesium sulfate, filtered, and the filtrate was concentrated in vacuo. The resulting residue was purified by preparative thin layer chromatography (silica gel, eluting with 10% MeOH in DCM) to afford racemic (S and R)-9-ethyl-N-(3-isopropyl-4,5,6,7-tetrahydro-3H-benzo[d]imidazol-5-yl)-8-(2-methylpyrimidin-5-yl)-9H-purin-6-amine. Separation of the enantiomers was achieved via preparative chiral HPLC (Column: OD-H 2×25 cm, 5 μm; Mobile phase: 20% ethanol in n-hexane; Flow rate: 20 ml/min) to afford 5-15 (faster eluting enantiomer, 9.0 min): $^1$H NMR (400 MHz, CD$_3$OD) δ 9.16 (s, 2H), 8.35-8.34 (m, 1H), 7.64 (s, 1H), 4.85-4.75 (m, 1H), 4.42 (q, J=6.8 Hz, 2H), 4.37-4.31 (m, 1H), 3.22-3.15 (m, 1H), 2.88 (s, 3H), 2.86-2.77 (m, 3H), 2.19-2.05 (m, 2H), 1.51-1.43 (m, 9H). MS (ESI) Calc'd for (C$_{22}$H$_{28}$N$_9$) [M+H]$^+$, 418; found, 418; and 5-16 (slower eluting enantiomer, 13.5 min): $^1$H NMR (400 MHz, CD$_3$OD) δ 9.16 (s, 2H), 8.35-8.34 (m, 1H), 7.64 (s, 1H), 4.85-4.75 (m, 1H), 4.42 (q, J=6.8 Hz, 2H), 4.37-4.31 (m, 1H), 3.22-3.15 (m, 1H), 2.88 (s, 3H), 2.86-2.77 (m, 3H), 2.19-2.05 (m, 2H), 1.51-1.43 (m, 9H). MS (ESI) Calc'd for (C$_{22}$H$_{28}$N$_9$) [M+H]$^+$, 418; found, 418.

Example 35: Preparation of Compounds 5-17 and 5-18

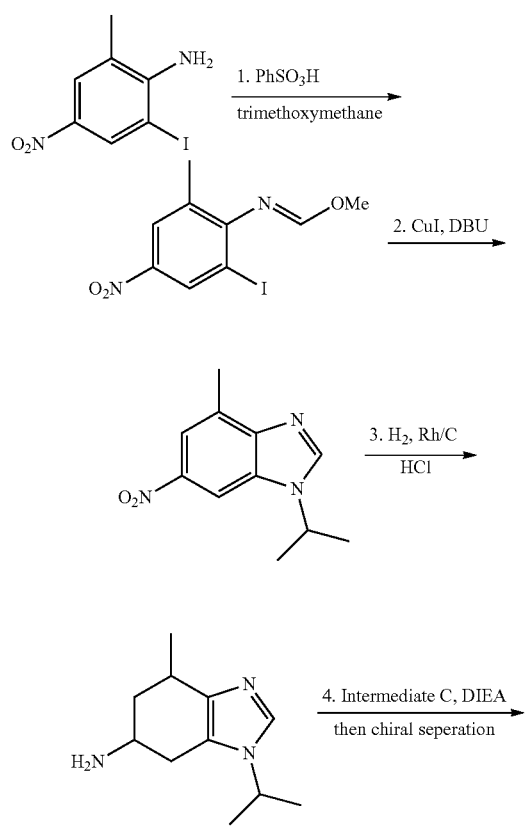

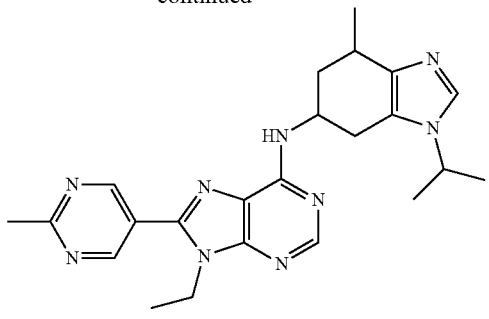

5-17

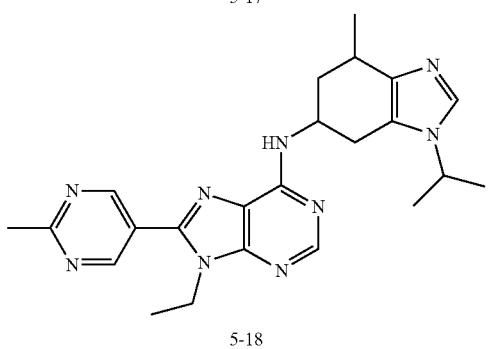

5-18

Step 1: Preparation of (E)-methyl N-(2-iodo-6-methyl-4-nitrophenyl)formimidate

A mixture of 2-iodo-6-methyl-4-nitroaniline (2.0 g, 7.2 mmol) and benzenesulfonic acid (0.11 g, 0.72 mmol) in trimethoxymethane (5 mL) was stirred for 5 h at 95° C. The reaction mixture was then cooled and concentrated in vacuo. The crude residue was purified by flash column chromatography (silica gel, eluting with 0-5% EtOAc in PE to afford (E)-methyl N-(2-iodo-6-methyl-4-nitrophenyl)formimidate. MS (ESI) Calc'd for (C$_9$H$_{10}$IN$_2$O$_3$) [M+H]+, 321; found, 321.

Step 2: Preparation of 1-isopropyl-4-methyl-6-nitro-1H-benzo[d]imidazole

To a degassed mixture of (E)-methyl N-(2-iodo-6-methyl-4-nitrophenyl)formimidate (1.8 g, 5.6 mmol), DBU (1.7 g, 11 mmol), and isopropylamine (8 mL) in dimethyl sulfoxide (8 mL) was added copper(I) iodide (0.11 g, 0.56 mmol) under nitrogen. The resulting mixture was stirred for 5 h at 100° C., after which water (15 mL) was added, and the solution was extracted with DCM (3×30 mL). The organic layers were combined, washed with brine, dried over anhydrous magnesium sulfate, and filtered. The filtrate was concentrated in vacuo, and the residue was purified by flash column chromatography (silica gel, eluting with 3-5% MeOH in DCM to afford 1-isopropyl-4-methyl-6-nitro-1H-benzo[d]imidazole. MS (ESI) Calc'd for (C$_{11}$H$_{14}$N$_3$O$_2$) [M+H]+, 220; found, 220.

Step 3: Synthesis of 1-isopropyl-4-methyl-4,5,6,7-tetrahydro-1H-benzo[d]imidazol-6-amine A mixture of 1-isopropyl-4-methyl-6-nitro-1H-benzo[d]imidazole (120 mg, 0.55 mmol) and rhodium on carbon (10 wt %, 20 mg) in hydrochloric acid (3 N aqueous solution, 3 mL) was stirred at 80° C. for 16 h under an atmosphere of hydrogen (30 atm). The resulting mixture was then cooled and filtered through Celite, after which the pH of the filtrate was adjusted to 11 via the addition of ammonia (4 mL, 7 N aqueous solution). The reaction mixture was then extracted with chloroform (8×20 mL), and the combined organic layers were dried over anhydrous sodium sulfate and filtered. The filtrate was concentrated in vacuo to afford 1-isopropyl-4-methyl-4,5,6,7-tetrahydro-1H-benzo[d]imidazol-6-amine, which was used in next step directly without further purification. MS (ESI) Calc'd for ($C_{11}H_{20}N_3$) [M+H]+, 194; found, 194.

Step 4: Preparation of Compounds 5-17 and 5-18

A solution of 1-isopropyl-4-methyl-4,5,6,7-tetrahydro-1H-benzo[d]imidazol-6-amine (90 mg), Intermediate C (50 mg, 0.18 mmol) and DIEA (118 mg, 0.91 mmol) in t-BuOH (7 mL) was stirred at 80° C. for 16 h, after which the solution was cooled and then concentrated in vacuo. The residue thus obtained was purified by flash column chromatography (silica gel, eluting with 2-8% MeOH in DCM) to afford the racemic 9-ethyl-N-(((5S,7R and 5R,7S) or (5S,7S and 5R,7R))-3-isopropyl-7-methyl-4,5,6,7-tetrahydro-3H-benzo[d]imidazol-5-yl)-8-(2-methylpyrimidin-5-yl)-9H-purin-6-amine. Chiral separation of the enantiomers was achieved via preparative chiral HPLC (Column: Chiralpak® IB™, 2×25 cm, 5 μm; Mobile phase: 7% isopropanol in n-hexane; Flow rate: 20 mL/min] to afford 5-17 (faster eluting enantiomer, 20.1 min): $^1$H NMR (300 MHz, CD$_3$OD) δ 9.14 (s, 2H), 8.24 (s, 1H), 7.60 (s, 1H), 4.63 (br, 1H), 4.40 (q, J=6.9 Hz, 2H), 4.30-4.20 (m, 1H), 3.27-3.15 (m, 1H), 3.03-2.92 (m, 1H), 2.80 (s, 3H), 2.68-2.53 (m, 1H), 2.36-2.26 (m, 1H), 1.66-1.55 (m, 1H), 1.52-1.41 (m, 9H), 1.30 (d, J=6.9 Hz, 3H). MS (ESI) Calc'd for ($C_{23}H_{30}N_9$) [M+H]+, 432; found, 432; and 5-18 (slower eluting enantiomer, 26.8 min): $^1$H NMR (300 MHz, CD$_3$OD) δ 9.15 (s, 2H), 8.22 (s, 1H), 7.62 (s, 1H), 4.63 (br, 1H), 4.41 (q, J=6.9 Hz, 2H), 4.33-4.21 (m, 1H), 3.27-3.15 (m, 1H), 3.02-2.89 (m, 1H), 2.81 (s, 3H), 2.68-2.56 (m, 1H), 2.36-2.25 (m, 1H), 1.66-1.55 (m, 1H), 1.54-1.38 (m, 9H), 1.30 (d, J=6.9 Hz, 3H). MS (ESI) calc'd for ($C_{23}H_{30}N_9$) [M+1]+, 432; found, 432.

Example 36: Preparation of Compounds 5-19 and 5-20

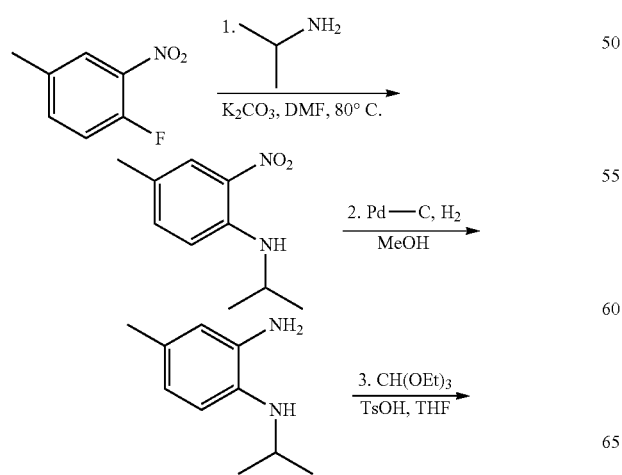

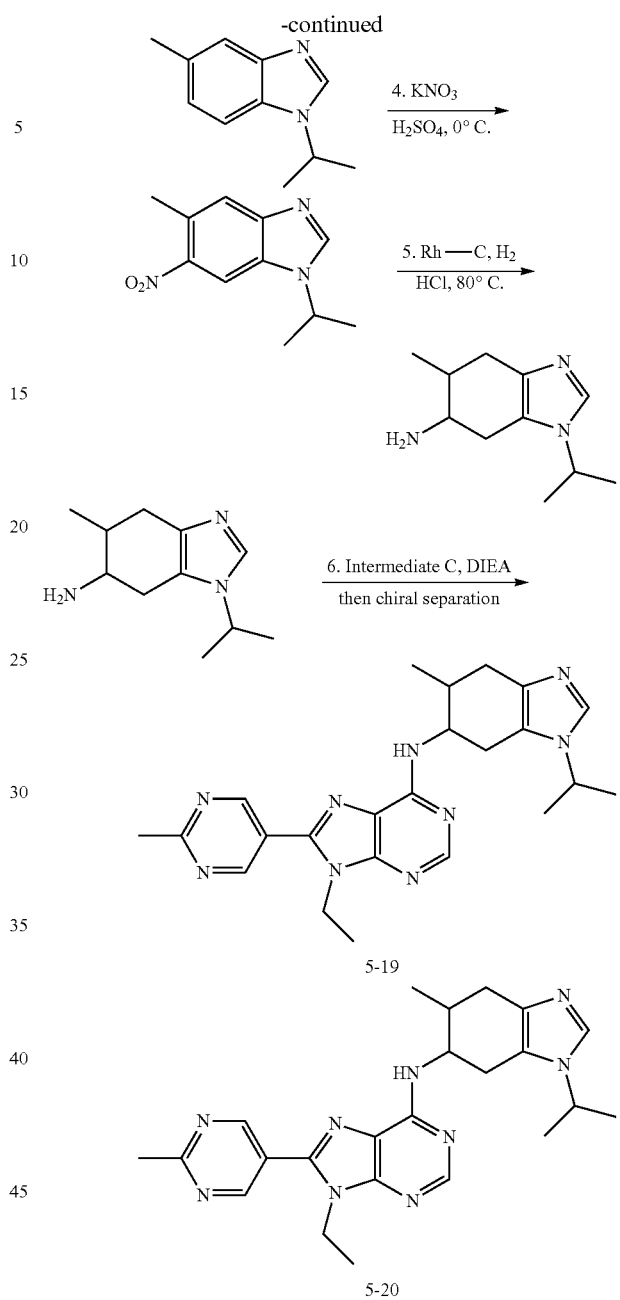

Step 1: Preparation of N-isopropyl-4-methyl-2-nitrobenzenamine

To a solution of 1-fluoro-4-methyl-2-nitrobenzene, (5.0 g, 32 mmol, commercially available from Bepharm) in DMF (50 ml), were added propan-2-amine (3.81 g, 64.5 mmol), and potassium carbonate (8.91 g, 64.5 mmol) at RT. The resulting mixture was then warmed to 80° C. and stirred for 5 h. The reaction mixture was then cooled to RT and was quenched with water (100 mL). The resulting mixture was extracted with EtOAc (3×50 mL). The combined organic layers were washed with brine (100 mL), dried over anhydrous sodium sulfate, and filtered. The filtrate was concentrated under reduced pressure to afford N-isopropyl-4-methyl-2-nitroaniline, which was used for next step directly without further purification. MS (ESI) Calc'd for (C$_{10}$H$_{15}$N$_2$O$_2$) [M+H]$^+$, 195; found, 195.

Step 2: Preparation of N$^1$-isopropyl-4-methylbenzene-1,2-diamine

To a solution of N-isopropyl-4-methyl-2-nitroaniline (5.5 g, 28 mmol) in methanol (100 ml) was added Pd/C (3.01 g, 2.83 mmol, 10%, wet) at RT. The mixture was then stirred under a hydrogen balloon for 12 h. The resulting mixture was then filtered, and the filtrate was concentrated under reduced pressure to afford N$^1$-isopropyl-4-methylbenzene-1,2-diamine, which was used for next step directly without further purification. MS (ESI) Calc'd for (C$_{10}$H$_{17}$N$_2$) [M+H]$^+$, 165; found, 165.

Step 3: Preparation of 1-Isopropyl-5-methyl-1H-benzo[d]imidazole

To a solution of N$^1$-isopropyl-4-methylbenzene-1,2-diamine (4.5 g, 27 mmol) in THF (50 ml) were added triethyl orthoformate (8.12 g, 54.8 mmol) and 4-methylbenzenesulfonic acid (0.521 g, 2.74 mmol) at RT. The reaction mixture was then heated to 70° C. and stirred for 1 h. The mixture was then cooled to RT, and was quenched with water (50 mL). The resulting mixture was extracted with EtOAc (3×50 mL), and the combined organic layers were washed with brine (100 mL), dried over anhydrous sodium sulfate, and filtered. The filtrate was concentrated under reduced pressure, and the residue obtained was purified by column chromatography (silica gel, eluting with 0-30% EtOAc in hexanes) to afford 1-isopropyl-5-methyl-1H-benzo[d]imidazole. MS (ESI) Calc'd for (C$_{11}$H$_{15}$N$_2$) [M+H]+, 175; found, 175.

Step 4: Preparation of 1-Isopropyl-5-methyl-6-nitro-1H-benzo[d]imidazole

To a solution of 1-isopropyl-5-methyl-1H-benzo[d]imidazole (1.0 g, 5.7 mmol) in concentrated sulfuric acid (10 ml) was added potassium nitrate (0.64 g, 6.3 mmol) at 0° C. The mixture was then stirred at 0° C. for 1 h. The reaction mixture was then carefully poured into ice-water (100 mL) and the pH was adjusted to 8 by the addition of potassium hydroxide powder. The resulting mixture was extracted with EtOAc (3×50 mL), and the combined organic layers were washed with brine (100 mL), dried over anhydrous sodium sulfate, and filtered. The filtrate was concentrated under reduced pressure, and the residue obtained was purified by column chromatography (silica gel, eluting 0-30% EtOAc in hexanes) to afford 1-isopropyl-5-methyl-6-nitro-1H-benzo[d]imidazole. MS (ESI) Calc'd for (C$_{11}$H$_{14}$N$_3$O$_2$) [M+H]$^+$, 220; found, 220.

Step 5: Preparation of 3-Isopropyl-6-methyl-4,5,6,7-tetrahydro-3H-benzo[d]imidazol-5-amine To a solution of 1-isopropyl-5-methyl-6-nitro-1H-benzo[d]imidazole (200 mg, 0.91 mmol) in hydrochloric acid (3.0 M, 10 ml) was added rhodium-carbon (94 mg, 0.091 mmol, 10%, dry) at RT. The mixture was then stirred at 80° C. for 20 h under hydrogen (30 atm). The reaction was then cooled to RT, the solution was filtered, and the filtrate concentrated under reduced pressure to afford 1-isopropyl-5-methyl-4,5,6,7-tetrahydro-1H-benzo[d]imidazol-6-amine, HCl, which was used for next step directly without further purification. MS (ESI) Calc'd for (C$_{11}$H$_{20}$N$_3$) [M+H]$^+$, 194; found, 194.

Step 5: Preparation of Compounds 5-19 and 5-20

To a solution of 1-isopropyl-5-methyl-4,5,6,7-tetrahydro-1H-benzo[d]imidazol-6-amine, HCl (180 mg, 0.78 mmol) in 2-propanol (5 ml) were added DIEA (0.136 ml, 0.776 mmol) and Intermediate C (213 mg, 0.776 mmol). The mixture was then heated to 80° C. and stirred for 48 h. After cooling to RT, the reaction mixture was quenched with water (30 mL). The resulting mixture was extracted with EtOAc (3×15 mL), and the combined organic layers were washed with brine (20 mL), dried over anhydrous sodium sulfate, and filtered. The filtrate was concentrated under reduced pressure, and the residue obtained was purified by column chromatography (silica gel, eluting 0-20% MeOH in DCM) to provide the racemic product. The racemic product was then separated by preparatory Chiral HPLC (Chiralpak IB 2×25 cm, 5 um; eluting 30% IPA in Hexanes (isocratic); Flow rate: 20 mL/min) to provide 5-19 (faster eluting enantiomer, 7.6 min): $^1$H NMR (300 MHz, CD$_3$OD) δ: 9.04 (s, 2H), 8.32 (s, 1H), 7.60 (s, 1H), 4.87-4.84 (m, 1H), 4.35 (q, J=7.2 Hz, 2H), 4.30-4.19 (m, 1H), 3.04-2.97 (m, 1H), 2.83-2.75 (m, 5H), 2.58-2.50 (m, 1H), 2.36-2.33 (m, 1H), 1.45-1.39 (m, 9H), 1.05 (d, J=6.9 Hz, 3H). MS (ESI) Calc'd for (C$_{23}$H$_{30}$N$_9$) [M+H]$^+$, 432; found, 432; and 5-20 (slower eluting enantiomer, 12.0 min): $^1$H NMR (300 MHz, CD$_3$OD) δ: 9.05 (s, 2H), 8.33 (s, 1H), 8.21 (s, 1H), 4.92-4.83 (m, 1H), 4.35-4.32 (m, 3H), 3.10-3.03 (m, 1H), 2.91-2.84 (m, 2H), 2.80 (s, 3H), 2.64-2.55 (m, 1H), 2.45-2.40 (m, 1H), 1.47-1.43 (m, 9H), 1.10 (d, J=6.9 Hz, 3H). MS (ESI) Calc'd for (C$_{23}$H$_{30}$N$_9$) [M+H]$^+$, 432; found, 432.

Example 37: Preparation of Compounds 5-21 and 5-22

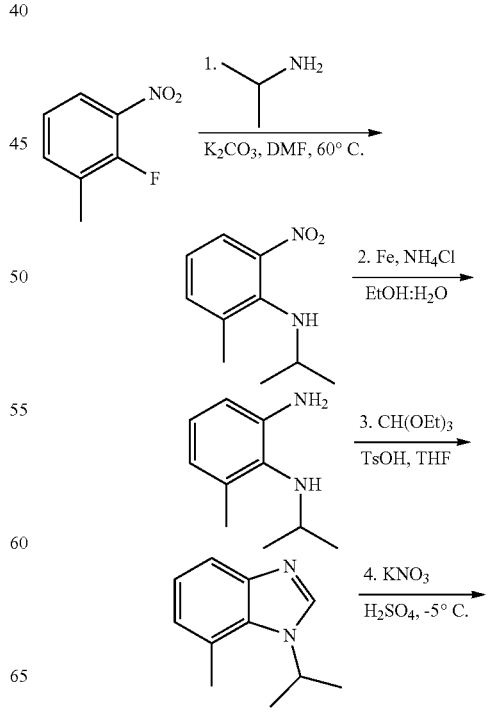

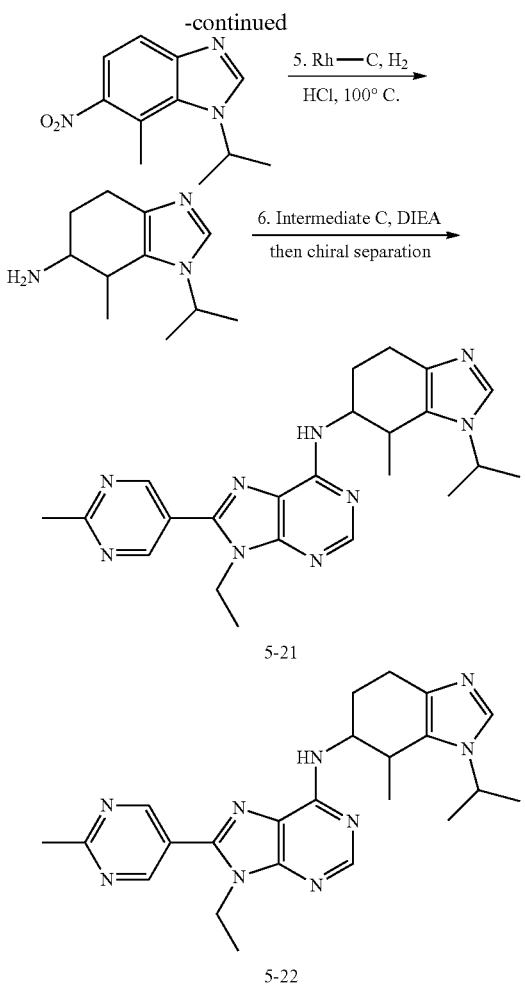

Step 1: Preparation of
N-isopropyl-2-methyl-6-nitroaniline

To a solution of 2-fluoro-1-methyl-3-nitrobenzene (10.0 g, 64.5 mmol) in DMF (50 mL), were added potassium carbonate (8.91 g, 64.5 mmol) and propan-2-amine (4.6 g, 77 mmol). The resulting mixture was heated to 60° C. and stirred for 6 h. The reaction mixture was then cooled to RT and was quenched with water (50 mL). The resulting mixture was extracted with EtOAc (3×100 mL), and the combined organic layers were washed with brine (2×50 mL), dried over anhydrous sodium sulfate, and filtered. The filtrate was concentrated under reduced pressure to afford N-isopropyl-2-methyl-6-nitroaniline which was used directly in the next step without further purification. MS (ESI) Calc'd for ($C_{10}H_{15}N_2O_2$) [M+H]+ 195, found 195.

Step 2: Preparation of
N-isopropyl-6-methylbenzene-1,2-diamine

To a solution of N-isopropyl-2-methyl-6-nitroaniline (12.0 g, 61.8 mmol) in ethanol/water (100/20 mL), were added ammonium chloride (3.97 g, 74.1 mmol) and iron powder (10.35 g, 185 mmol).
The resulting mixture was heated to 80° C. and stirred for 1 h. The reaction mixture was then cooled to RT and filtered. The filtrate was extracted with EtOAc (3×50 mL), and the combined organic layers were washed with brine (2×50 mL), dried over anhydrous sodium sulfate, and filtered. The filtrate was concentrated under reduced pressure, and the residue obtained was purified by column chromatography (silica gel, eluting 0-20% EtOAc in hexane) to afford N-isopropyl-6-methylbenzene-1,2-diamine. MS (ESI) Calc'd for ($C_{10}H_{17}N_2$) [M+H]+, 165, found, 165.

Step 3: Preparation of 1-Isopropyl-7-methyl-1H-
benzo[d]imidazole

To a solution of triethoxymethane (21.7 g, 146 mmol) in THF (100 mL), were added 4-methylbenzene sulfonic acid (0.839 g, 4.87 mmol) and $N^1$-isopropyl-6-methylbenzene-1,2-diamine (8.0 g, 49 mmol). The resulting solution was stirred for 1 h at 60° C. After cooling to RT, the reaction mixture was quenched with water (50 mL). The resulting mixture was extracted with EtOAc (3×50 mL), and the combined organic layers were washed with brine (2×50 mL), dried over anhydrous sodium sulfate, and filtered. The filtrate was concentrated under reduced pressure, and the residue obtained was purified by column chromatography (silica gel, eluting 0%-30% EtOAc in petroleum ether) to afford 1-isopropyl-7-methyl-1H-benzo[d]imidazole. MS (ESI) Calc'd for ($C_{11}H_{15}N_2$) [M+H]+ 175, found 175.

Step 4: Preparation of 1-Isopropyl-7-methyl-6-nitro-
1H-benzo[d]imidazole

To a solution of 1-isopropyl-7-methyl-1H-benzo[d]imidazole (4.0 g, 23 mmol) in sulfuric acid (5 mL) was added potassium nitrate (2.32 g, 23.0 mmol) at −5° C. The resulting solution was stirred for 1 h at −5° C. The reaction solution was then poured into ice-water, and the PH value was adjusted to 9 with aqueous sodium hydroxide (50 mL). The resulting solution was extracted with EtOAc (2×50 mL). The combined organic layers was washed with brine (2×50 mL), dried over anhydrous sodium sulfate, and filtered. The filtrate was concentrated under reduced pressure to afford 1-isopropyl-7-methyl-6-nitro-1H-benzo[d]imidazole, along with 1-isopropyl-7-methyl-4-nitro-1H-benzo[d]imidazole (23:1 ratio). The mixture was used in the next step without further purification; products derived from the undesired isomer were removed in the final purification (step 6). MS (ESI) Calc'd for ($C_{11}H_{14}N_3O_2$) [M+H]+, 220, found, 220.

Step 5: Preparation of 1-Isopropyl-7-methyl-4,5,6,
7-tetrahydro-1H-benzo[d]imidazol-6-amine To a solution of 1-isopropyl-7-methyl-6-nitro-1H-benzo[d]imidazole (1.0 g, 4.6 mmol, crude from step 4) in hydrochloric acid (12 N, 10 mL), was added rhodium on carbon (200 mg, m/m=20%). The resulting mixture was placed in a sealed tube and was stirred for 24 h at 100° C. under an atmosphere of hydrogen (40 atm). The reaction was then cooled, filtered, and the filtrate was concentrated under reduced pressure to afford 1-isopropyl-7-methyl-4,5,6,7-tetrahydro-1H-benzo[d]imidazol-6-amine as the HCl salt, which was used in the next step without further purification. MS (ESI) Calc'd for ($C_{11}H_{20}N_3$) [M+H]+, 194, found 194.

Step 6: Preparation of Compounds 5-19 and 5-20

A mixture of 1-isopropyl-7-methyl-4,5,6,7-tetrahydro-1H-benzo[d]imidazol-6-amine, HCl (209 mg, 0.908 mmol), DIEA (235 mg, 1.82 mmol) and Intermediate C (250 mg, 0.910 mmol) in i-PrOH (10 mL) was stirred for 3 h at 80°

C. After cooling to RT, the reaction mixture was diluted with water (10 mL) and extracted with EtOAc (3×15 mL). The combined organic layers were concentrated under reduced pressure to give a residue which was was purified by Preparatory HPLC (Column: X Bridge C18, 19×150 mm, 5 µm; Mobile Phase: 17-58% MeCN in Water (0.05% TFA); Flow rate: 20 mL/min; 254 nm) to afford 9-Ethyl-N-(3-isopropyl-4-methyl-4,5,6,7-tetrahydro-3H-benzo[d]imidazol-5-yl)-8-(2-methylpyrimidin-5-yl)-9H-purin-6-amine as a mixture of isomers. The isomers were separated by Chiral Preparatory HPLC (Column: Chiralpak IC 2×25 cm, 5 µm; Mobile phase: 40% isocratic EtOH in Hexanes; Flow rate: 18 mL/min; 254/220 nm); to provide 5-19 (faster eluting compound, 5.1 min): $^1$H NMR (400 MHz, CDCl$_3$) δ: 9.04 (s, 2H), 8.43 (s, 1H), 7.64 (s, 1H), 5.83 (s, 1H), 4.70 (s, 1H), 4.38-4.33 (m, 2H), 4.24-4.21 (m, 1H), 3.59-3.52 (m, 1H), 2.87-2.83 (m, 5H), 2.22-2.02 (m, 2H), 1.54-1.48 (m, 9H), 1.15-1.12 (m, 3H). MS (ESI) Calc'd for (C$_{23}$H$_{30}$N$_9$) [M+H]$^+$, 432.0, found, 432; and 5-20 (slower eluting compound, 6.6 min): $^1$H NMR (400 MHz, CDCl$_3$) δ: 9.04 (s, 2H), 8.43 (s, 1H), 7.63 (s, 1H), 5.84 (s, 1H), 4.70 (s, 1H), 4.38-4.33 (m, 2H), 4.22-4.21 (m, 1H), 3.57-3.54 (m, 1H), 2.87-2.82 (m, 5H), 2.22-2.07 (m, 2H), 1.54-1.48 (m, 9H), 1.15-1.12 (m, 3H). MS (ESI) Calc'd for (C$_{23}$H$_{30}$N$_9$) [M+H]$^+$, 432.0, found, 432.

Compounds 5-1 and 5-22 are listed in Table 5 and have be made according to procedures analogous procedures to those outlined in Examples 29 through 37 and those described below.

Compounds 5-2 and 5-3 were prepared in an analogous fashion to Example 29, using 6-chloro-9-ethyl-8-(6-(trifluoromethyl)pyridin-3-yl)-9H-purine, synthesized in an analogous fashion to Intermediate M (Example 10), in place of Intermediate C. Chiral resolution of the racemic final compound was achieved via preparative chiral HPLC (Column: IA 2×25 cm, 5 µm, mobile phase: 30% EtOH in n-hexane, flow rate: 20 ml/min) to afford 5-2 (faster eluting enantiomer, 11.5 min) and 5-3 (slower eluting enantiomer, 16.7 min).

Compounds 5-4 and 5-5 were prepared in an analogous fashion to Example 29, using Intermediate M in place of Intermediate C. Chiral resolution of the racemic final compound was achieved via preparative chiral SFC (Phenomenex Lux 5u Cellulose-4 250×50 mm, mobile phase: 50% MeOH (containing 0.1% diethylamine) in CO$_2$, flow rate: 150 g/min) to afford 5-4 (faster eluting enantiomer, 8.2 min) and 5-5 (slower eluting enantiomer, 9.5 min).

Compound 5-6 was prepared in an analogous fashion to Example 29, using Intermediate K in place of Intermediate C. Chiral resolution of the racemic final compound was achieved via preparative chiral HPLC (Column: AD-H 21.2×150 mm, 5 µm, mobile phase: 30% EtOH in n-hexane, flow rate: 20 ml/min) to afford 5-6 (faster eluting enantiomer, 6.2 min).

Compound 5-7 was prepared in an analogous fashion to Example 29, using 2-methyl-6-nitro-1H-benzo[d]imidazole in place of 6-nitro-1H-benzo[d]imidazole. Chiral resolution of the racemic final compound was achieved via preparative chiral HPLC (Column: OD-H 2×25 cm, 5 µm, mobile phase: 30% ethanol in n-hexane, flow rate: 20 ml/min) to afford 5-7 (faster eluting enantiomer, 5.8 min).

Compound 5-8 was prepared in an analogous fashion to Example 29, using 2-ethyl-6-nitro-1H-benzo[d]imidazole in place of 6-nitro-1H-benzo[d]imidazole. Chiral resolution of the racemic final compound was achieved via preparative chiral HPLC (Column: Phenomenex Lux 5u Cellulose-4, AXIA 250×21.2 mm, 5 µm, mobile phase: 30% ethanol in n-hexane, flow rate: 20 ml/min) to afford 5-8 (faster eluting enantiomer, 31.7 min).

Compounds 5-10 and 5-11 were prepared in an analogous fashion to Example 29, using Intermediate N in place of 6-nitro-1H-benzo[d]imidazole. Chiral resolution of the racemic final compound was achieved via preparative chiral HPLC (Column: Chiralpak® IB™ 2×25 cm, 5 µm, mobile phase: 10% ethanol in n-hexane, flow rate: 20 ml/min) to afford 5-10 (faster eluting enantiomer, 16.5 min) and 5-11 (slower eluting enantiomer, 23.3 min).

TABLE 5

| Compound Number | Structure | IUPAC Name | Exact Mass [M + H]+ |
| --- | --- | --- | --- |
| 5-1 | 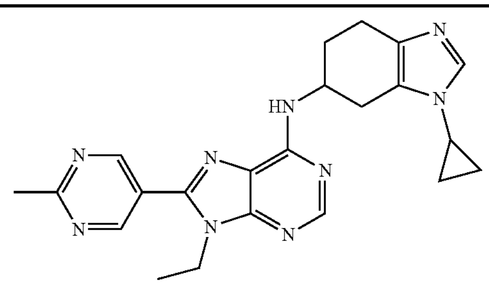 | (S or R)-N-(1-cyclopropyl-4,5,6,7-tetrahydro-1H-benzimidazol-6-yl)-9-ethyl-8-(2-methylpyrimidin-5-yl)-9H-purin-6-amine | Calc'd 416, found 416 |
| 5-2 | 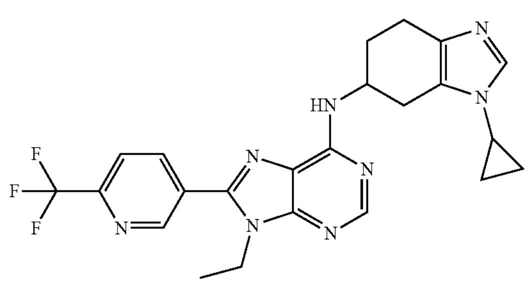 [SMILES: CCn1c(-c2ccc(C(F)(F)F)nc2)nc2c(NC3CCc4ncn(C5CC5)c4C3)ncnc21] | (S or R)-N-(1-cyclopropyl-4,5,6,7-tetrahydro-1H-benzimidazol-6-yl)-9-ethyl-8-[6-(trifluoromethyl)pyridin-3-yl]-9H-purin-6-amine | Calc'd 469, found 469 |

TABLE 5-continued

| Compound Number | Structure | IUPAC Name | Exact Mass [M + H]+ |
|---|---|---|---|
| 5-3 | 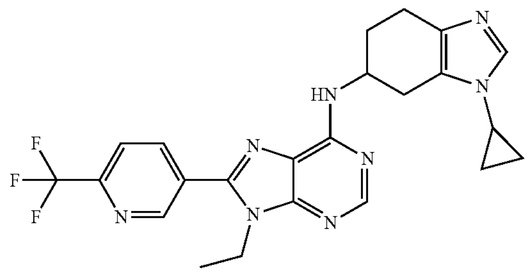 [SMILES: CCn1c(-c2ccc(C(F)(F)F)nc2)nc2c(NC3CCc4ncn(C5CC5)c4C3)ncnc21] | (S or R)-N-(1-cyclopropyl-4,5,6,7-tetrahydro-1H-benzimidazol-6-yl)-9-ethyl-8-[6-(trifluoromethyl)pyridin-3-yl]-9H-purin-6-amine | Calc'd 469, found 469 |
| 5-4 | 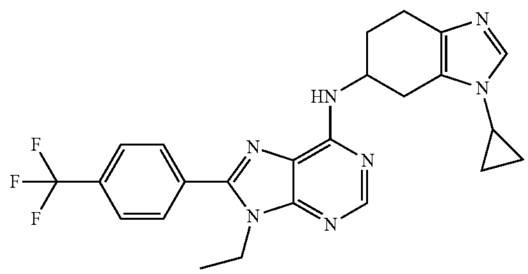 [SMILES: CCn1c(-c2ccc(C(F)(F)F)cc2)nc2c(NC3CCc4ncn(C5CC5)c4C3)ncnc21] | (S or R)-N-(1-cyclopropyl-4,5,6,7-tetrahydro-1H-benzimidazol-6-yl)-9-ethyl-8-[4-(trifluoromethyl)phenyl]-9H-purin-6-amine | Calc'd 468, found 468 |
| 5-5 | 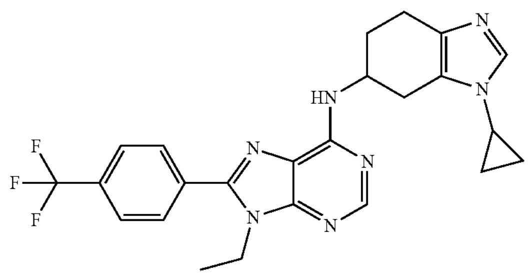 [SMILES: CCn1c(-c2ccc(C(F)(F)F)cc2)nc2c(NC3CCc4ncn(C5CC5)c4C3)ncnc21] | (S or R)-N-(1-cyclopropyl-4,5,6,7-tetrahydro-1H-benzimidazol-6-yl)-9-ethyl-8-[4-(trifluoromethyl)phenyl]-9H-purin-6-amine | Calc'd 468, found 468 |
| 5-6 | 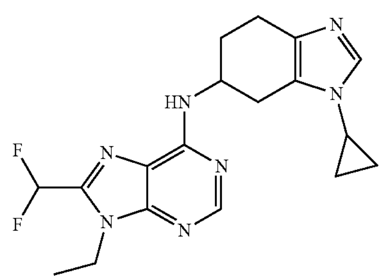 [SMILES: CCn1c(C(F)F)nc2c(NC3CCc4ncn(C5CC5)c4C3)ncnc21] | (S or R)-N-(1-cyclopropyl-4,5,6,7-tetrahydro-1H-benzimidazol-6-yl)-8-(difluoromethyl)-9-ethyl-9H-purin-6-amine | Calc'd 374, found 374 |
| 5-7 | 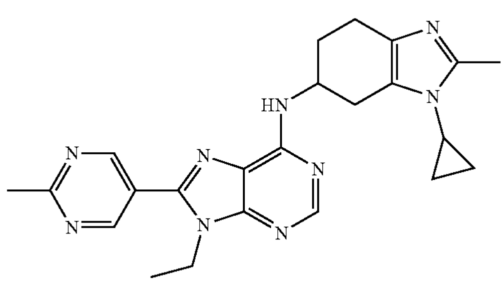 | (S or R)-N-(1-cyclopropyl-2-methyl-4,5,6,7-tetrahydro-1H-benzimidazol-6-yl)-9-ethyl-8-(2-methylpyrimidin-5-yl)-9H-purin-6-amine | Calc'd 430, found 430 |

TABLE 5-continued

| Compound Number | Structure | IUPAC Name | Exact Mass [M + H]+ |
|---|---|---|---|
| 5-8 | 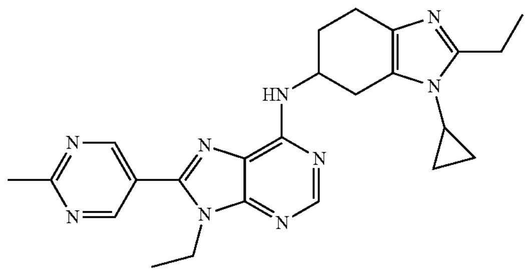 [SMILES: CCc1nc2c(n1C1CC1)CC(Nc1ncnc3c1nc(-c1cnc(C)nc1)n3CC)CC2] | (S or R)-N-(1-cyclopropyl-2-ethyl-4,5,6,7-tetrahydro-1H-benzimidazol-6-yl)-9-ethyl-8-(2-methylpyrimidin-5-yl)-9H-purin-6-amine | Calc'd 444, found 444 |
| 5-9 | 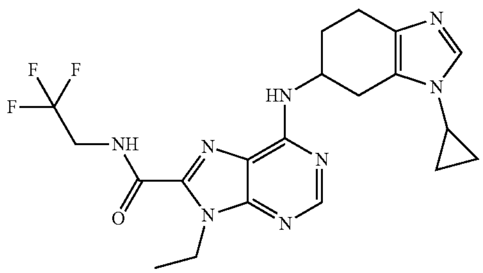 [SMILES: CCn1c(C(=O)NCC(F)(F)F)nc2c(NC3CCc4ncn(C5CC5)c4C3)ncnc21] | (S or R)-6-[(1-cyclopropyl-4,5,6,7-tetrahydro-1H-benzimidazol-6-yl)amino]-9-ethyl-N-(2,2,2-trifluoroethyl)-9H-purine-8-carboxamide | Calc'd 449, found 449 |
| 5-10 | 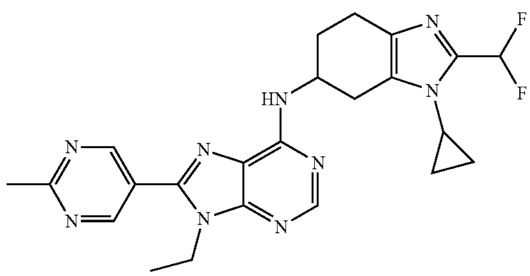 [SMILES: CCn1c(-c2cnc(C)nc2)nc2c(NC3CCc4nc(C(F)F)n(C5CC5)c4C3)ncnc21] | (S or R)-N-[1-cyclopropyl-2-(difluoromethyl)-4,5,6,7-tetrahydro-1H-benzimidazol-6-yl]-9-ethyl-8-(2-methylpyrimidin-5-yl)-9H-purin-6-amine | Calc'd 466, found 466 |
| 5-11 | 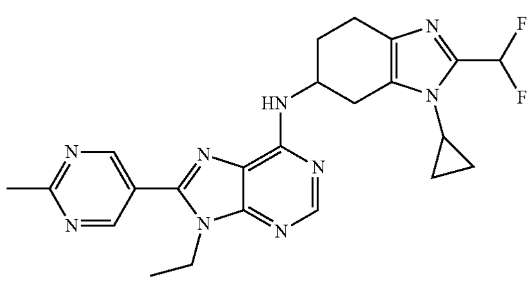 [SMILES: CCn1c(-c2cnc(C)nc2)nc2c(NC3CCc4nc(C(F)F)n(C5CC5)c4C3)ncnc21] | (S or R)-N-[1-cyclopropyl-2-(difluoromethyl)-4,5,6,7-tetrahydro-1H-benzimidazol-6-yl]-9-ethyl-8-(2-methylpyrimidin-5-yl)-9H-purin-6-amine | Calc'd 466, found 466 |
| 5-12 | 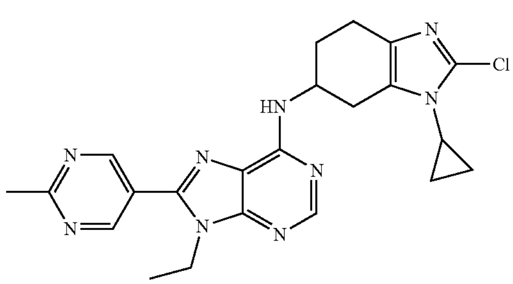 [SMILES: CCn1c(-c2cnc(C)nc2)nc2c(NC3CCc4nc(Cl)n(C5CC5)c4C3)ncnc21] | (S and R)-N-(2-chloro-1-cyclopropyl-4,5,6,7-tetrahydro-1H-benzimidazol-6-yl)-9-ethyl-8-(2-methylpyrimidin-5-yl)-9H-purin-6-amine | Calc'd 450, found 450 |

TABLE 5-continued

| Compound Number | Structure | IUPAC Name | Exact Mass [M + H]+ |
|---|---|---|---|
| 5-13 | 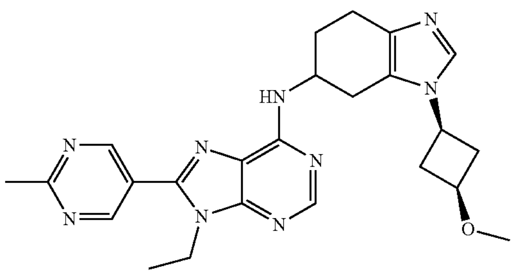 | (S or R)-9-ethyl-N-[1-(cis-3-methoxycyclobutyl)-4,5,6,7-tetrahydro-1H-benzimidazol-6-yl]-8-(2-methylpyrimidin-5-yl)-9H-purin-6-amine | Calc'd 460, found 460 |
| 5-14 | 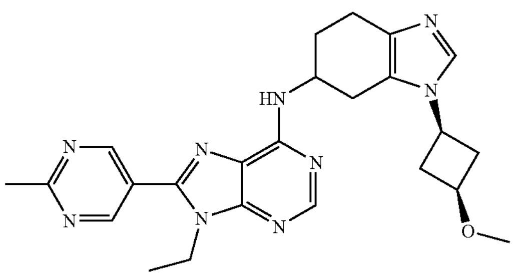 | (S or R)-9-ethyl-N-[1-(cis-3-methoxycyclobutyl)-4,5,6,7-tetrahydro-1H-benzimidazol-6-yl]-8-(2-methylpyrimidin-5-yl)-9H-purin-6-amine | Calc'd 460, found 460 |
| 5-15 | 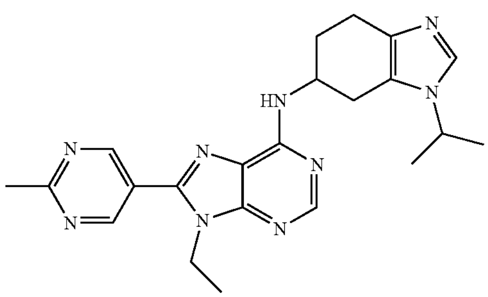 [SMILES: CCn1c(-c2cnc(C)nc2)nc2c(NC3CCc4ncn(C(C)C)c4C3)ncnc21] | (S or R)-9-ethyl-N-[1-(1-methylethyl)-4,5,6,7-tetrahydro-1H-benzimidazol-6-yl]-8-(2-methylpyrimidin-5-yl)-9H-purin-6-amine | Calc'd 418, found 418 |
| 5-16 | 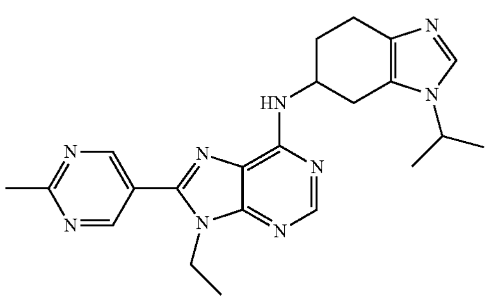 [SMILES: CCn1c(-c2cnc(C)nc2)nc2c(NC3CCc4ncn(C(C)C)c4C3)ncnc21] | (S or R)-9-ethyl-N-[1-(1-methylethyl)-4,5,6,7-tetrahydro-1H-benzimidazol-6-yl]-8-(2-methylpyrimidin-5-yl)-9H-purin-6-amine | Calc'd 418, found 418 |
| 5-17 | 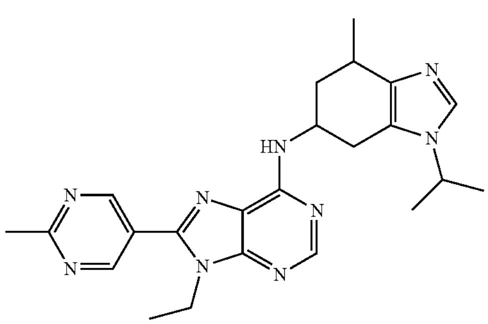 [SMILES: CCn1c(-c2cnc(C)nc2)nc2c(NC3Cc4c(ncn4C(C)C)C(C)C3)ncnc21] | 9-ethyl-N-[(4(S or R), 6(S or R)-4-methyl-1-(1-methylethyl)-4,5,6,7-tetrahydro-1H-benzimidazol-6-yl]-8-(2-methylpyrimidin-5-yl)-9H-purin-6-amine | Calc'd 432, found 432 |

TABLE 5-continued

| Compound Number | Structure | IUPAC Name | Exact Mass [M + H]+ |
|---|---|---|---|
| 5-18 | 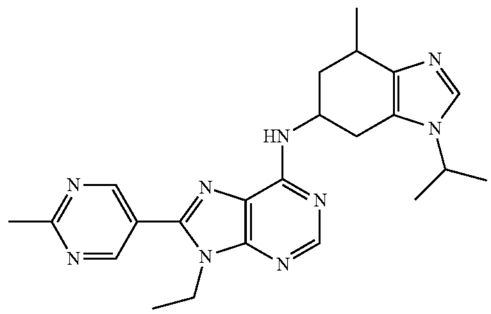 [SMILES: CCn1c(-c2cnc(C)nc2)nc2c(NC3Cc4c(ncn4C(C)C)C(C)C3)ncnc21] | 9-ethyl-N-[(4(S or R), 6(S or R)-4-methyl-1-(1-methylethyl)-4,5,6,7-tetrahydro-1H-benzimidazol-6-yl]-8-(2-methylpyrimidin-5-yl)-9H-purin-6-amine | Calc'd 432, found 432 |
| 5-19 | 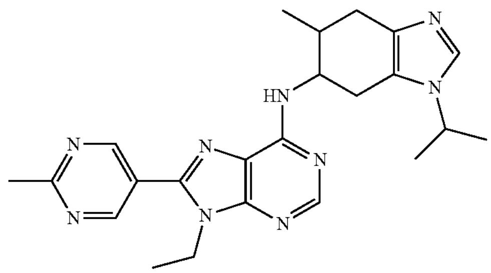 [SMILES: CCn1c(-c2cnc(C)nc2)nc2c(NC3Cc4c(ncn4C(C)C)CC3C)ncnc21] | 9-ethyl-N-[cis-5-methyl-1-(1-methylethyl)-4,5,6,7-tetrahydro-1H-benzimidazol-6-yl]-8-(2-methylpyrimidin-5-yl)-9H-purin-6-amine | Calc'd 432, found 432 |
| 5-20 | 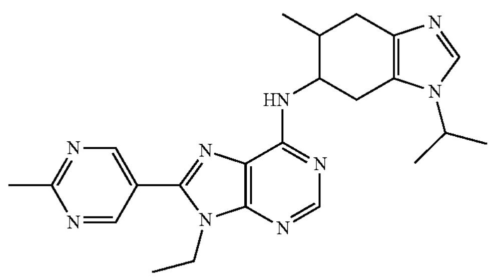 [SMILES: CCn1c(-c2cnc(C)nc2)nc2c(NC3Cc4c(ncn4C(C)C)CC3C)ncnc21] | 9-ethyl-N-[trans-5-methyl-1-(1-methylethyl)-4,5,6,7-tetrahydro-1H-benzimidazol-6-yl]-8-(2-methylpyrimidin-5-yl)-9H-purin-6-amine | Calc'd 432, found 432 |
| 5-21 | 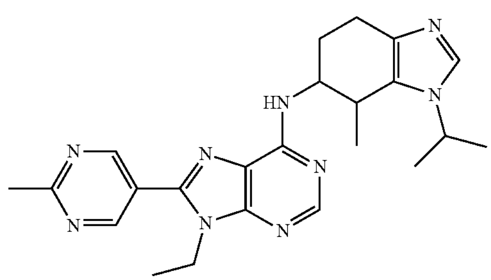 [SMILES: CCn1c(-c2cnc(C)nc2)nc2c(NC3CCc4ncn(C(C)C)c4C3C)ncnc21] | 9-ethyl-N-[((6S, 7S) or (6R, 7R))-7-methyl-1-(1-methylethyl)-4,5,6,7-tetrahydro-1H-benzimidazol-6-yl]-8-(2-methylpyrimidin-5-yl)-9H-purin-6-amine | Calc'd 432, found 432 |
| 5-22 | 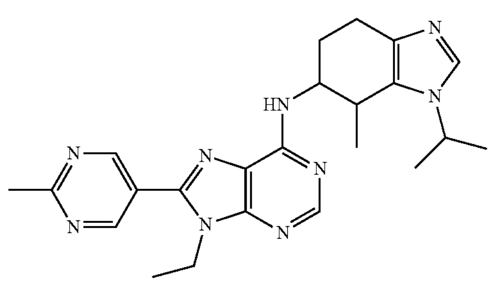 [SMILES: CCn1c(-c2cnc(C)nc2)nc2c(NC3CCc4ncn(C(C)C)c4C3C)ncnc21] | 9-ethyl-N-[((6S, 7S) or (6R, 7R))-7-methyl-1-(1-methylethyl)-4,5,6,7-tetrahydro-1H-benzimidazol-6-yl]-8-(2-methylpyrimidin-5-yl)-9H-purin-6-amine | Calc'd 432, found 432 |

Compound Examples of Table 6

Example 38: Preparation of Compound 6-1

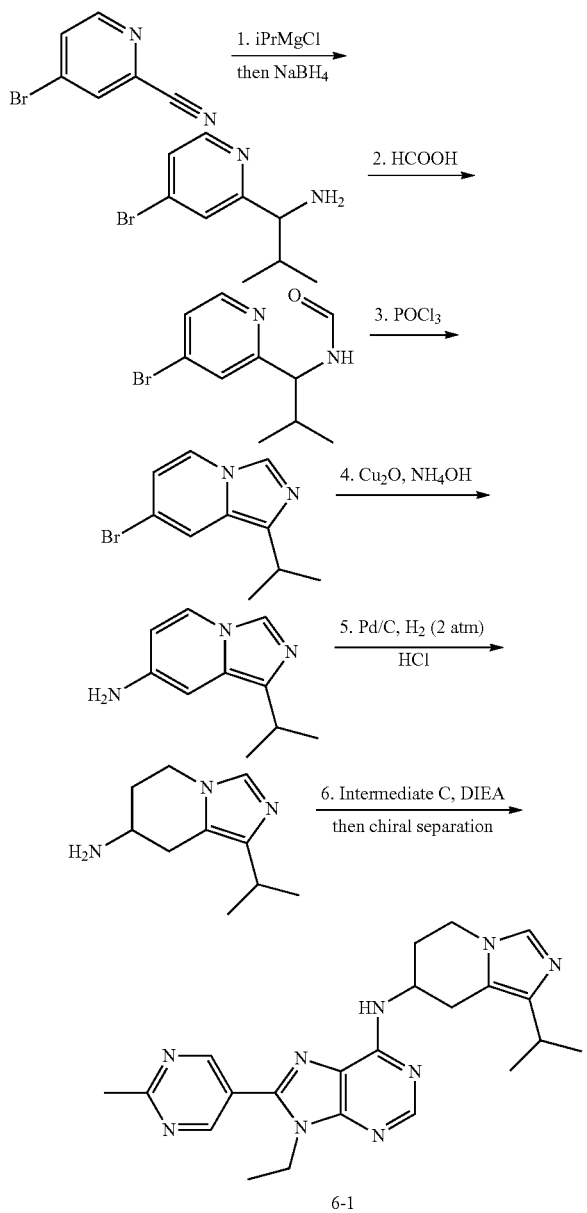

Step 1: Preparation of 1-(4-bromopyridin-2-yl)-2-methylpropan-1-amine

To a solution of 4-bromopicolinonitrile (5.0 g, 27 mmol) in toluene (150 mL) was added isopropylmagnesium chloride (15 mL, 2 N solution in THF, 30 mmol) drop wise at 0° C. The resulting solution was stirred at 0° C. for 1 h, after which MeOH (100 mL) was carefully added. The reaction mixture was then treated with sodium borohydride (1.5 g, 41 mmol) in several portions. The reaction mixture was then allowed to come to RT and was stirred for 3 h, after which it was quenched by the addition of water (50 mL). The aqueous solution was extracted with EtOAc (4×150 mL), and the combined organic layers were washed with brine, dried over anhydrous magnesium sulfate, and filtered. The filtrate was concentrated in vacuo, and the resulting residue was purified by flash column chromatography (silica gel, eluting with 0-6% MeOH in DCM) to afford 1-(4-bromopyridin-2-yl)-2-methylpropan-1-amine. MS (ESI) Calc'd for ($C_9H_{14}BrN_2$) $[M+H]^+$, 229, 231; found, 229, 231.

Step 2: Preparation of N-(1-(4-bromopyridin-2-yl)-2-methylpropyl)formamide

A solution of 1-(4-bromopyridin-2-yl)-2-methylpropan-1-amine (3.0 g, 13 mmol) in formic acid (20 mL, 521 mmol) was stirred at 90° C. for 12 h, after which the solution was cooled and concentrated in vacuo. The residue was then partitioned between EtOAc (50 mL) and saturated aqueous sodium carbonate (50 mL). The aqueous layer was extracted with EtOAc (4×50 mL), and the combined organic layers were washed with brine, dried over anhydrous magnesium sulfate, and filtered. The filtrate was concentrated in vacuo, and the resulting residue was purified by flash column chromatography (silica gel, eluting with 20-80% EtOAc in n-hexane) to afford N-(1-(4-bromopyridin-2-yl)-2-methylpropyl)formamide. MS (ESI) calc'd for ($C_{10}H_{14}BrN_2O$) $[M+H]^+$, 257, 259; found, 257, 259.

Step 3: Preparation of 7-bromo-1-isopropylimidazo[1,5-a]pyridine

To a solution of N-(1-(4-bromopyridin-2-yl)-2-methylpropyl)formamide (2.0 g, 7.8 mmol) in toluene (25 mL) was added phosphoryl trichloride (0.87 mL, 9.3 mmol) under nitrogen. The resulting solution was stirred at 80° C. for 3 h, after which the solution was cooled and concentrated in vacuo. The pH of the residue was then adjusted to 10 by the careful addition of saturated aqueous sodium carbonate (50 mL). The aqueous solution was then extracted with EtOAc (3×100 mL), and the combined organic layers were washed with brine, dried over anhydrous sodium sulfate, and filtered. The filtrate was concentrated in vacuo, and the resulting residue was purified by flash column chromatography (silica gel, eluting with 0-45% EtOAc in n-hexane) to afford 7-bromo-1-isopropylimidazo[1,5-a]pyridine. MS (ESI) calc'd for ($C_{10}H_{12}BrN_2$) $[M+H]^+$, 239, 241; found, 239, 241.

Step 4: Preparation of 1-isopropylimidazo[1,5-a]pyridin-7-amine

To a degassed solution of 7-bromo-1-isopropylimidazo[1,5-a]pyridine (520 mg, 2.2 mmol) in NMP (5 mL) were added ammonia (3.1 mL, 7 N aqueous solution, 22 mmol) and copper (I) oxide (62 mg, 0.44 mmol) under nitrogen. The resulting mixture was stirred for 12 h at 80° C., after which the reaction mixture was cooled and subsequently diluted with water (50 mL). The aqueous solution was then extracted with EtOAc (4×50 mL), and the combined organic layers were washed with brine, dried over anhydrous sodium sulfate, and filtered. The filtrate was concentrated in vacuo, and the resulting residue was purified by flash column chromatography (silica gel, eluting with 0-6% MeOH in DCM) to afford 1-isopropylimidazo[1,5-a]pyridin-7-amine. MS (ESI) Calc'd for ($C_{10}H_{14}N_3$) $[M+H]^+$, 176; found, 176.

Step 5: Preparation of 1-isopropyl-5,6,7,8-tetrahydroimidazo[1,5-a]pyridin-7-amine A mixture of 1-isopropylimidazo[1,5-a]pyridin-7-amine (200 mg, 1.1 mmol) and palladium on carbon (20 mg, 10 wt % wet) in hydrochloric acid (3 N aqueous solution, 0.5 mL) and MeOH (8 mL) was stirred for 12 h under an atmosphere of hydrogen (2 atm). The reaction mixture was then filtered through Celite, and the pH of the filtrate was adjusted to 11 bye the addition of an ammonia solution (1 mL, 7 N aqueous solution). The resulting solution was then extracted with chloroform (8×20 mL), and the combined organic layers were dried over anhydrous sodium sulfate, filtered, and concentrated in vacuo to afford 1-isopropyl-5,6,7,8-tetrahydroimidazo[1,5-a]pyridin-7-amine, which was used in next step directly without further purification. MS (ESI) calc'd for ($C_{10}H_{18}N_3$) [M+H]$^+$, 180; found, 180.

Step 6: Preparation of Compound 6-1

A solution of 1-isopropyl-5,6,7,8-tetrahydroimidazo[1,5-a]pyridine-7-amine (150 mg), Intermediate C (50 mg, 0.18 mmol), and DIEA (0.87 mL, 5.0 mmol) in t-BuOH (10 mL) was stirred at 80° C. for 16 h, after which the solution was cooled and concentrated in vacuo. The resulting residue was purified by flash column chromatography (silica gel, eluting with 2-8% MeOH in DCM) to afford racemic 9-ethyl-N-(1-isopropyl-5,6,7,8-tetrahydroimidazo[1,5-a]pyridin-7-yl)-8-(2-methylpyrimidin-5-yl)-9H-purin-6-amine. Chiral separation of the enantiomers was achieved via preparative chiral HPLC (Column: Chiralpak® IA™, 21.2×150 mm, 5 µm; Mobile phase: 50% EtOH in n-hexane; Flow rate: 20 mL/min) to afford 6-1 (slower eluting enantiomer, 9.3 min): $^1$H NMR (300 MHz, CD$_3$OD) δ 9.11 (s, 2H), 8.35 (s, 1H), 7.53 (s, 1H), 4.80-4.75 (m, 1H), 4.41 (q, J=7.2 Hz, 2H), 4.33-4.25 (m, 1H), 4.18-4.09 (m, 1H), 3.29-3.27 (m, 1H), 2.95-2.77 (m, 2H), 2.81 (s, 3H), 2.39-2.35 (m, 1H), 2.24-2.15 (m, 1H), 1.44 (t, J=7.2 Hz, 3H), 1.23 (d, J=7.2 Hz, 3H), 1.21 (d, J=7.2 Hz, 3H); MS (ESI) calc'd for ($C_{22}H_{28}N_9$) [M+H]$^+$, 418; found, 418.

Table 6 lists a summary of Compounds 6-1.

Fluorescence energy transfer) complex is formed consisting of europium (Eu)-labeled anti-GST, GSTtagged GRP1-PH domain, biotin-PIP3 and streptavidin conjugated APC. The native PIP3 produced by PI3-Kinase activity disrupts in a competitive manner the biotin-PIP3 from the PH domain, resulting in the loss of energy transfer (HTRF complex) and a decrease in the signal. The format of this assay is the same for all 4 isoforms of PI3K; the differences lie in the concentration of enzyme used to achieve robust assay window. The alpha, beta, and delta assays are run at 0.5, 1, and 0.3 nM enzymes and the gamma assay is run at 5 nM enzyme. The ATP concentration is 100 uM in the alpha, beta, and delta assays and 50 uM ATP in the gamma assay. All reactions are run at 5 uM PIP2.

Assay Protocol

Compounds are serially diluted (3-fold in 100% DMSO) across a 384-well polypropylene source plated from column 3 to column 12 and column 13 to column 22, to yield 10 concentration dose response for each test compound. Columns 1, 2, 23 and 24 contain either only DMSO or pharmacological known control inhibitor. Once titrations are made, 2.5 nL of the compounds on 384 well plates are reformatted and transferred by acoustic dispense in quadruplicates to a 1536 assay plate (Greiner) to assay across all four PI3K isoform enzymes.

The PI3-Kinase biochemical assay was optimized using the HTRF kit provided by Upstate (Millipore). The assay kit contains six reagents: 1) 4× Reaction Buffer; 2) native PIP2 (substrate); 3) Stop (EDTA); 4) Detection Mix A (Streptavidin-APC); 5) Detection Mix B (Eu-labeled Anti-GST plus GST-tagged PH-domain); 6) Detection Mix C. In addition, the following items were obtained or purchased; PI3Kinase (alpha 14-602, beta 14-603, gamma 14-558 and delta 14-604 from Upstate; Millipore), dithiothreitol (Sigma, D-5545), Adenosine-5' triphosphate (InVitrogen, Cat#AS001A),

TABLE 6

| Compound Number | Structure | IUPAC Name | Exact Mass [M + H]+ |
|---|---|---|---|
| 6-1 | 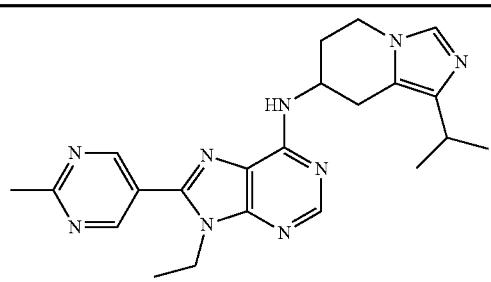 | (S or R)-9-ethyl-N-[1-(1-methylethyl)-5,6,7,8-tetrahydroimidazo[1,5-a]pyridin-7-yl]-8-(2-methylpyrimidin-5-yl)-9H-purin-6-amine | Calc'd 418, found 418 |

HTRF PI3K Biochemical Assay to Measure Intrinsic Potency of Compound Inhibitors

The PI3-Kinase biochemical assays were developed to measure the intrinsic potency and compound dependent inhibition of the alpha, beta, delta, and gamma PI3K isoform enzymes. This assay was developed and further optimized from a kit produced by Upstate (Millipore catalog #33-047) and has been configured for HTS and SAR screening. Briefly, this procedure exploits the exquisite specificity and high affinity binding of enzyme reaction substrate phosphatidyl(3,4,5)triphosphate (PIP3) to the GRP1 pleckstrin homology (PH) domain to generate the signal. In the absence of PIP3, an HTRF (Homogeneous Time-Resolved native PIP3 (PI(3,4,5)P3, diC8, H$^+$, CELLSIGNALS, INC. Cat #907) DMSO (Sigma, 472301).

PI3Kinase Reaction Buffer is prepared by dilution the stock 1:4 with de-ionized water. DTT, PIP2 and Biotin-PIP3 were added to 1536 assay plate at a final concentration of 5 mM, 5 mM and 25 nM on the day of use. Enzyme addition and compound pre-incubation are initiated by the addition of 1.25 ul of PI3K (at twice its final concentration) in the 1× reaction buffer to all wells using a BioRaptor. Plates are incubated at room temperature for 15 minutes. Reactions are initiated by addition of 1.25 ul of 2× substrate solution (PIP2 and ATP in 1× reaction buffer) using BioRaptor. Plates are incubated in humidified chamber at room temperature for one hour. Reactions are quenched by addition of 0.625 uL of stop solution to all wells using the BioRaptor. The quenched reactions are then processed to detect product formation by adding 0.625 uL of Detection Solution to all wells using the BioRaptor (Detection mix C, Detection Mix A, and Detection Mix B combined together in an 18:1:1 ratio prepared 2 hours prior to use). Following a one hour incubation in the dark, the HTRF signal is measured on the Envision plate reader set for 330 nm excitation and dual emission detection at 620 nM (Eu) and 665 nM (APC).

Data Analysis

The loss of the HTRF signal is due to the displacement of biotinylated-PIP3 from the PH domain by the PI3K-dependent conversion of PIP2 to PIP3. This loss of signal is nonlinear with respect to both increasing product and time. This non-linear detection will impact accuracy of $IC_{50}$ calculations; therefore, there is a need for a correction factor to obtain more accurate $IC_{50}$ values. This correction is derived from a PIP3 standard curve run in a separate assay plate. All data were calculated using the ratio of acceptor (APC) to donor (Europium) fluorescence in each well of the assay plate. The percent inhibition for each compound concentration was calculated as follows: % inhibition=100× (fluorescence ratio-CtrlB)/(CtrlA-CtrlB) where CtrlA=PI3Kinase reaction+known reference inhibitor and CtrlB=PI3K+DMSO. An $IC_{50}$ was then calculated fitting the % inhibition data to the equation: % inhibition=min+(Max-min)/1+([inhibitor]/IC50)^n) where min is the % inhibition with inhibitor, max is the signal in DMSO control, and n is the Hill slope.

Biological Data

The following table tabulates the biological data disclosed for the instant invention. The biological data was collected using the methodology described above. For each compound, PI3Kdelta $IC_{50}$ values are listed along with the relative selectivity versus PI3Kalpha, as well as the physical form of the compound dosed in this assay.

The determination of relative selectivity for a given compound is defined as the relative ratio of the (PI3K-alpha$IC_{50}$ value/PI3K-delta $IC_{50}$ value).

| Compound Number | Form Screened | PI3Kdelta IC50 (nM) | Selectivity versus PI3Kalpha |
|---|---|---|---|
| 1-1 | Neutral | 4.2 | >10 |
| 1-2 | TFA salt | 65 | >10 |
| 1-3 | Neutral | 5.9 | >10 |
| 1-4 | Neutral | 46 | >10 |
| 1-5 | Neutral | 1.1 | >10 |
| 1-6 | Neutral | 2.0 | >10 |
| 1-7 | Neutral | 13 | >10 |
| 1-8 | Neutral | 460 | >10 |
| 1-9 | Neutral | 16 | >10 |
| 1-10 | TFA salt | <1.0 | >10 |
| 1-11 | TFA salt | 4.1 | >10 |
| 1-12 | TFA salt | 1.2 | >10 |
| 1-13 | TFA salt | 1.1 | >10 |
| 1-14 | Neutral | 2.1 | >10 |
| 1-15 | TFA salt | <1.0 | >10 |
| 1-16 | TFA salt | 3.9 | >10 |
| 1-17 | TFA salt | <1.0 | >10 |
| 1-18 | TFA salt | <1.0 | >10 |
| 1-19 | TFA salt | 31 | >10 |
| 1-20 | Neutral | <1.0 | >10 |
| 1-21 | TFA salt | <1.0 | >10 |
| 1-22 | TFA salt | 221 | >10 |
| 1-23 | TFA salt | <1.0 | >10 |
| 1-24 | TFA salt | 3.5 | >10 |
| 1-25 | TFA salt | 24 | >10 |
| 1-26 | Neutral | 12 | >10 |
| 1-27 | Neutral | 151 | >10 |
| 1-28 | TFA salt | 1.4 | >10 |
| 1-29 | TFA salt | 49 | >10 |
| 1-30 | TFA salt | 8.3 | >10 |
| 1-31 | Neutral | 220 | >10 |
| 1-32 | Neutral | 4.4 | >10 |
| 1-33 | Neutral | 35 | >10 |
| 1-34 | Neutral | 4.1 | >10 |
| 1-35 | Neutral | 19 | >10 |
| 1-36 | Neutral | 1.1 | >10 |
| 1-37 | TFA salt | 12 | >10 |
| 1-38 | TFA salt | 5.0 | >10 |
| 2-1 | Neutral | <1.0 | >10 |
| 2-2 | Neutral | 2.9 | >10 |
| 2-3 | TFA salt | 7.4 | >10 |
| 2-4 | Neutral | 1.8 | >10 |
| 2-5 | Neutral | 4.1 | >10 |
| 2-6 | Neutral | 21 | >10 |
| 2-7 | Neutral | 1.7 | >10 |
| 2-8 | Neutral | 210 | >10 |
| 2-9 | TFA salt | 60 | >10 |
| 2-10 | TFA salt | 6.1 | >10 |
| 2-11 | Neutral | 2.1 | >10 |
| 2-12 | TFA salt | 15 | >10 |
| 2-13 | TFA salt | 30 | >10 |
| 2-14 | TFA salt | 20 | >10 |
| 2-15 | TFA salt | 78 | >10 |
| 2-16 | Neutral | <1.0 | >10 |
| 2-17 | TFA salt | 2.3 | >10 |
| 2-18 | TFA salt | <1.0 | >10 |
| 2-19 | TFA salt | 1.0 | >10 |
| 2-20 | TFA salt | 2.6 | >10 |
| 2-21 | TFA salt | 16 | >10 |
| 2-22 | TFA salt | 11 | >10 |
| 2-23 | Neutral | <1.0 | >10 |
| 2-24 | Neutral | 41 | >10 |
| 2-25 | Neutral | 14 | >10 |
| 2-26 | TFA salt | 6.1 | >10 |
| 2-27 | Neutral | 25 | >10 |
| 3-1 | Neutral | 11 | >10 |
| 3-2 | Neutral | 5.2 | >10 |
| 4-1 | Neutral | 6.9 | >10 |
| 4-2 | Neutral | 290 | >10 |
| 4-3 | Neutral | 2.8 | >10 |
| 4-4 | Neutral | 210 | >10 |
| 4-5 | Neutral | 550 | >10 |
| 5-1 | Neutral | 5.5 | >10 |
| 5-2 | Neutral | 3.3 | >10 |
| 5-3 | Neutral | 180 | >10 |
| 5-4 | Neutral | 180 | >10 |
| 5-5 | Neutral | 5.1 | >10 |
| 5-6 | Neutral | 170 | >10 |
| 5-7 | Neutral | 19 | >10 |
| 5-8 | Neutral | 21 | >10 |
| 5-9 | Neutral | 51 | >10 |
| 5-10 | Neutral | <1.0 | >10 |
| 5-11 | Neutral | 40 | >10 |
| 5-12 | Neutral | <1.0 | >10 |
| 5-13 | Neutral | 4.7 | >10 |
| 5-14 | Neutral | 230 | >10 |
| 5-15 | Neutral | 4.2 | >10 |
| 5-16 | Neutral | 384 | >10 |
| 5-17 | Neutral | 9.0 | >10 |
| 5-18 | Neutral | 510 | >10 |
| 5-19 | Neutral | 1.7 | >10 |
| 5-20 | Neutral | 120 | >10 |
| 5-21 | Neutral | 5.7 | >10 |
| 5-22 | Neutral | 260 | >10 |
| 6-1 | Neutral | 10 | >10 |

What is claimed is:

1. A compound of formula I or a pharmaceutically acceptable salt or stereoisomer thereof:

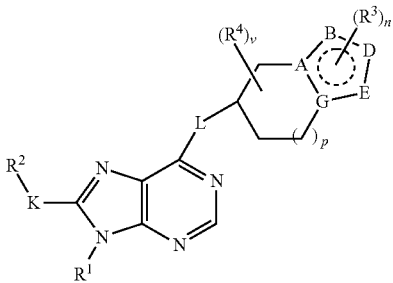

I

A, B, D, E and G are independently selected from carbon and nitrogen, wherein at least two of A, B, D, E and G are carbon and wherein A, B, D, E and G form an aromatic ring;

$R^1$ is selected from hydrogen, $C_{1-5}$alkyl, and —$(C_{0-3}$alkyl$)C_{3-4}$cycloalkyl, wherein $R^1$ is optionally substituted by 0, 1, 2, 3, or 4 groups independently selected from hydrogen, fluoro, chloro, methyl, $C_{1-3}$haloalkyl, amino, O(C=O)$R^a$, O(C=O)O$R^a$ and NH(C=O)$R^a$;

$R^a$ is independently selected from $C_{1-3}$alkyl, $C_{1-3}$haloalkyl and —$(C_{0-3}$alkyl$)C_{3-4}$cycloalkyl;

$R^2$ is selected from pyridinyl, pyrimidinyl, fluoro, pyrazolyl, phenyl, imidazolyl, iodo, and trifluoroethyl, wherein $R^2$ is substituted with 0, 1, 2, 3, or 4 $R^6$ substituents;

$R^4$ is selected from halogen, $C_{1-10}$alkyl, $C_{2-10}$alkynyl, and $C_{1-10}$ alkoxy, wherein $R^4$ is substituted with 0, 1, 2, 3, or 4 substituents selected from OH, halogen, and —CO$_2$H;

n is 0, 1, 2, or 3;

v is 0, 1, 2, or 3;

p is 0 or 1;

L is selected from —O—, —NH—, and —N($C_{1-3}$alkyl)-;

K is selected from a bond, NH, O, C(O), CH$_2$, N(C$_1$s) alkyl, —C(O)N($R^b$)—(CH$_2$)$_m$—, S, SO$_2$, and $C_{2-10}$ alkynylene;

$R^b$ is H or $C_{1-10}$ alkyl, m is 0, 1, 2, or 3;

$R^3$ is independently selected from:
halogen,
$C_{1-10}$ alkyl(oxy)$_{0-1}$(carbonyl)$_{0-1}C_{0-10}$ alkyl,
aryl $C_{0-10}$ alkyl(oxy)$_{0-1}$(carbonyl)$_{0-1}$-$C_{0-10}$ alkyl,
$C_{3-12}$ cycloalkyl$C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{1-10}$ alkyl)$_{1-2}$ amino$C_{0-10}$ alkyl,
$C_{0-10}$ alkylamino(carbonyl)$_{0-1}C_{0-10}$ alkyl,
$(C_{1-10}$ alkyl)$_{1-2}$amino$C_{0-10}$ alkyl carbonyl$C_{0-10}$ alkyl,
$C_{0-10}$ alkylsulfonyl$C_{0-10}$ alkyl,
$(C_{1-10}$ alkyl)OH, and
$C_{1-6}$haloalkyl;

wherein $R^3$ is each substituted with 0, 1, 2, 3, or 4 $R^5$ substituents and each $R^5$ is independently selected from:

halogen, $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, $C_{3-12}$ cycloalkyl $C_{0-10}$ alkyl(oxy)$_{0-1}$(carbonyl)$_{0-1}C_{0-10}$ alkyl, heteroaryl $C_{0-10}$ alkyl(oxy)$_{0-1}$(carbonyl)$_{0-1}C_{0-10}$ alkyl, $(C_{3-12})$heterocycloalkyl $C_{0-10}$ alkyl(oxy)$_{0-1}$(carbonyl)$_{0-1}C_{0-10}$ alkyl, $C_{1-10}$ alkylamino(carbonyl)$_{0-1}C_{0-10}$ alkyl, $C_{3-12}$ cycloalkyl $C_{0-10}$ alkylamino(carbonyl)$_{0-1}C_{0-10}$ alkyl, aryl $C_{0-10}$ alkylamino(carbonyl)$_{0-1}C_{0-10}$ alkyl, heteroaryl $C_{0-10}$ alkylamino(carbonyl)$_{0-1}C_{0-10}$ alkyl, $(C_{3-12})$heterocycloalkyl $C_{0-10}$ alkylamino(carbonyl)$_{0-1}C_{0-10}$ alkyl, $C_{0-10}$ alkylsulfonyl$C_{0-10}$ alkyl, $(C_{3-12})$cycloalkyl$C_{0-10}$alkylsulfonyl $C_{0-10}$ alkyl, $(C_{3-12})$cycloheteroalkyl$C_{0-10}$alkylsulfonyl$C_{0-10}$ alkyl, heteroaryl$C_{0-10}$ alkylsulfonyl$C_{0-10}$ alkyl, aryl$C_{0-10}$ alkylsulfonyl$C_{0-10}$ alkyl, —CO$_2$(C$_{0-10}$ alkyl), —(C$_{0-10}$ alkyl)CO$_2$H, Oxo (=O), —SO$_2$N(C$_{1-6}$alkyl)$_{1-2}$, —SO$_2$C$_{1-6}$alkyl, —SO$_2$CF$_3$, —SO$_2$CF$_2$H, amino, (C$_{0-10}$ alkyl)$_{1-2}$ amino, hydroxy, (C$_{1-10}$ alkyl)OH, C$_{1-10}$ alkoxy, cyano, and C$_{1-6}$haloalkyl;

$R^6$ is independently selected from:
halogen,
$C_{1-10}$ alkyl(oxy)$_{0-1}$(carbonyl)$_{0-1}C_{0-10}$ alkyl,
$C_{1-10}$ haloalkyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
$C_{3-12}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$ (carbonyl)$_{0-1}C_{0-10}$ alkyl,
$(C_{3-12})$heterocycloalkyl $C_{0-10}$ alkyl(oxy)$_{0-1}$ (carbonyl)$_{0-1}C_{0-10}$ alkyl,
$C_{0-10}$ alkyl(oxy)$_{0-1}$carbonylamino$C_{0-10}$ alkyl,
$C_{0-10}$ alkylamino(oxy)$_{0-1}$carbonyl$C_{0-10}$ alkyl,
$(C_{1-10})$heteroalkylamino(oxy)$_{0-1}$ (carbonyl)$_{0-1}C_{0-10}$ alkyl,
$C_{3-12}$ cycloalkylamino(oxy)$_{0-1}$(carbonyl)$_{0-1}C_{0-10}$ alkyl,
aryl $C_{0-10}$ alkylamino(oxy)$_{0-1}$(carbonyl)$_{0-1}C_{10}$ alkyl,
heteroaryl $C_{0-10}$ alkylamino(oxy)$_{0-1}$ (carbonyl)$_{0-1}C_{0-10}$ alkyl,
$(C_{3-12})$heterocycloalkylamino(oxy)$_{0-1}$(carbonyl)$_{0-1}$ $C_{0-10}$ alkyl,
—CO$_2$(C$_{0-10}$ alkyl),
—(C$_{0-10}$ alkyl)CO$_2$H,
oxo (=O),
$C_{0-10}$ alkylsulfonyl$C_{0-10}$ alkyl,
$C_{1-10}$ heteroalkylsulfonyl$C_{0-10}$ alkyl,
$(C_{3-12})$cycloalkyl$C_{0-10}$alkylsulfonyl$C_{0-10}$ alkyl,
$(C_{3-12})$cycloheteroalkyl$C_{0-10}$alkylsulfonyl$C_{0-10}$ alkyl,
heteroaryl$C_{0-10}$ alkylsulfonyl$C_{0-10}$ alkyl,
aryl$C_{0-10}$ alkylsulfonyl$C_{0-10}$ alkyl,
—SO$_2$NH$_2$,
—SO$_2$NH(C$_{1-10}$ alkyl),
—SO$_2$N(C$_{1-10}$ alkyl)$_2$,
—SO$_2$CF$_3$,
—SO$_2$CF$_2$H,
amino,
(C$_{1-10}$ alkyl)$_{1-2}$ amino,
-(oxy)$_{0-1}$(carbonyl)$_{0-1}$N(C$_{0-10}$ alkyl)$_{1-2}$
hydroxy,
(C$_{1-10}$ alkyl)OH,
C$_{1-10}$ alkoxy,
(C$_{1-10}$ alkyl)cyano,
cyano, and
$C_{1-6}$haloalkyl; and wherein $R^5$ and $R^6$ are each independently substituted with 0, 1, 2, or 3 $R^7$ substituents and each $R^7$ substituent is independently selected from hydroxy, (C$_{1-6}$)alkyl, (C$_{1-6}$)alkoxy, (C$_{5-6}$)aryl, (C$_{5-6}$)heteroaryl, (C$_{1-10}$ alkyl)OH, halogen, CO$_2$H, —(C$_{0-6}$)alkylCN, —O(C=O)C$_1$-C$_6$ alkyl, —(C=O)OC$_1$-C$_6$ alkyl, NO$_2$, trifluoromethoxy, trifluoroethoxy, trifluoromethyl, trifluoroethyl, —N—C(O)O(C$_{0-6}$)alkyl, C$_{1-10}$ alkylsulfonyl, oxo (O=), aminosulfonyl, —SO$_2$N(C$_{1-6}$ alkyl)$_{1-2}$, —SO$_2$C$_{1-6}$alkyl, —SO$_2$CF$_3$, —SO$_2$CF$_2$H, —C$_{1-10}$ alkylsulfinyl, —O$_{(0-1)}$(C$_{1-10}$)haloalkyl, amino (C$_{1-6}$alkyl)$_{1-2}$ and NH$_2$.

2. A compound according to claim 1, or a pharmaceutically acceptable salt, or a stereoisomer thereof, wherein $R^1$ is hydrogen or $C_{1-5}$alkyl optionally substituted by 0, 1, 2, 3, or 4 groups independently selected from hydrogen, $C_{1-3}$haloalkyl, fluoro, chloro, methyl, amino, $O(C=O)R^a$, $O(C=O)OR^a$ and $NH(C=O)R^a$.

3. A compound according to claim 2, or a pharmaceutically acceptable salt, or a stereoisomer thereof, wherein

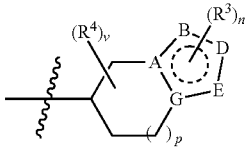

is selected from:

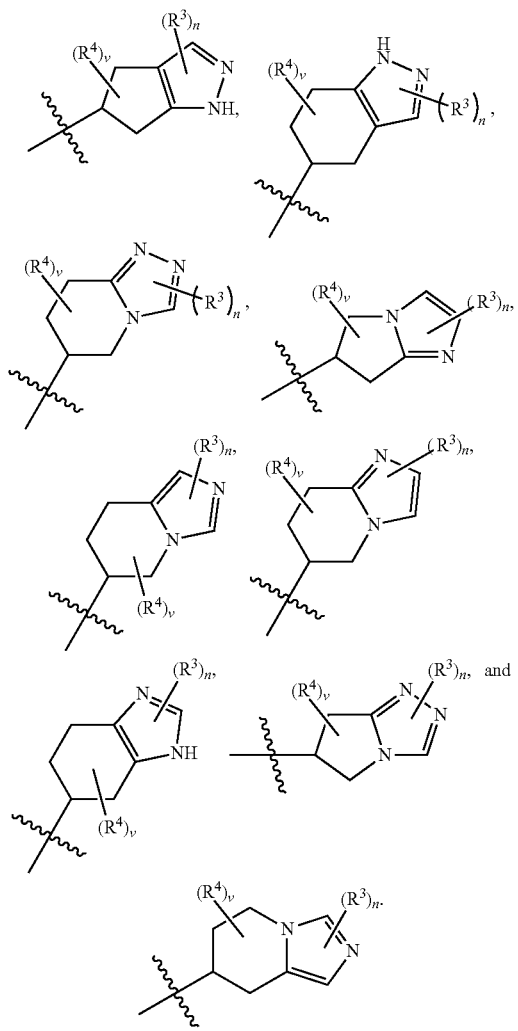

4. A compound according to claim 3, or a pharmaceutically acceptable salt, or a stereoisomer thereof, wherein v is 0 or 1; and n is 0, 1, or 2.

5. A compound according to claim 4, or a pharmaceutically acceptable salt, or a stereoisomer thereof, wherein K is selected from a bond, NH, $CH_2$, and —C(O)N($R^b$)—$(CH_2)_m$—.

6. A compound according to claim 5, or a pharmaceutically acceptable salt, or a stereoisomer thereof, wherein K is a bond.

7. A compound according to claim 6, a pharmaceutically acceptable salt, or a stereoisomer thereof, wherein L is —NH— or —O—.

8. A compound according to claim 7, a pharmaceutically acceptable salt, or a stereoisomer thereof, wherein $R^1$ is methyl, ethyl, propyl, isopropyl, butyl, isobutyl, pentyl, or isopentyl, wherein $R^1$ is substituted by 0, 1, 2, 3, or 4 groups independently selected from hydrogen, fluoro, chloro, methyl, $C_{1-3}$haloalkyl, amino, $O(C=O)R^a$, $O(C=O)OR^a$ and $NH(C=O)R^a$.

9. A compound or a pharmaceutically acceptable salt, or a stereoisomer thereof, wherein said compound is selected from:

N-(3-cyclopropyl-5,6,7,8-tetrahydro[1,2,4]triazolo[4,3-a]pyridin-6-yl)-9-ethyl-8-(2-methylpyrimidin-5-yl)-9H-purin-6-amine;

9-ethyl-8-(2-methylpyrimidin-5-yl)-N-[3-phenyl-5,6,7,8-tetrahydro[1,2,4]triazolo[4,3-a]pyridin-6-yl]-9H-purin-6-amine;

9-ethyl-N-[3-(1-methylethyl)-5,6,7,8-tetrahydro[1,2,4]triazolo[4,3-a]pyridin-6-yl]-8-(2-methylpyrimidin-5-yl)-9H-purin-6-amine;

9-ethyl-N-[3-ethyl-5,6,7,8-tetrahydro[1,2,4]triazolo[4,3-a]pyridin-6-yl]-8-(2-methylpyrimidin-5-yl)-9H-purin-6-amine;

8-(difluoromethyl)-9-ethyl-N-[3-(1-methylethyl)-5,6,7,8-tetrahydro[1,2,4]triazolo[4,3-a]pyridin-6-yl]-9H-purin-6-amine;

N-(3-cyclopropyl-5,6,7,8-tetrahydro[1,2,4]triazolo[4,3-a]pyridin-6-yl)-9-ethyl-8-(1-phenyl-1H-pyrazol-4-yl)-9H-purin-6-amine;

N-(3-cyclopropyl-5,6,7,8-tetrahydro[1,2,4]triazolo[4,3-a]pyridin-6-yl)-9-ethyl-8-[6-(trifluoromethyl)pyridin-3-yl]-9H-purin-6-amine;

N-(3-cyclopropyl-5,6,7,8-tetrahydro[1,2,4]triazolo[4,3-a]pyridin-6-yl)-9-ethyl-8-(5-fluoro-6-methoxypyridin-3-yl)-9H-purin-6-amine;

N-(3-cyclopropyl-5,6,7,8-tetrahydro[1,2,4]triazolo[4,3-a]pyridin-6-yl)-9-ethyl-8-(6-methoxypyridin-3-yl)-9H-purin-6-amine;

N-(3-cyclopropyl-5,6,7,8-tetrahydro[1,2,4]triazolo[4,3-a]pyridin-6-yl)-8-[6-(difluoromethoxy)pyridin-3-yl]-9-ethyl-9H-purin-6-amine;

N-(3-cyclopropyl-5,6,7,8-tetrahydro[1,2,4]triazolo[4,3-a]pyridin-6-yl)-9-ethyl-8-(6-methoxy-5-methylpyridin-3-yl)-9H-purin-6-amine;

N-(3-cyclopropyl-5,6,7,8-tetrahydro[1,2,4]triazolo[4,3-a]pyridin-6-yl)-9-ethyl-8-[4-(trifluoromethoxy)phenyl]-9H-purin-6-amine;

N-(3-cyclopropyl-5,6,7,8-tetrahydro[1,2,4]triazolo[4,3-a]pyridin-6-yl)-9-ethyl-8-(1-ethyl-5-methyl-1H-pyrazol-4-yl)-9H-purin-6-amine;

9-ethyl-N-[3-(1-methylethyl)-5,6,7,8-tetrahydro[1,2,4]triazolo[4,3-a]pyridin-6-yl]-8-[6-(trifluoromethyl)pyridin-3-yl]-9H-purin-6-amine;

9-ethyl-N-[3-(1-methylethyl)-5,6,7,8-tetrahydro[1,2,4]triazolo[4,3-a]pyridin-6-yl]-8-[4-(trifluoromethyl)phenyl]-9H-purin-6-amine;

9-ethyl-8-(5-fluoro-6-methoxypyridin-3-yl)-N-[3-(1-methylethyl)-5,6,7,8-tetrahydro[1,2,4]triazolo[4,3-a]pyridin-6-yl]-9H-purin-6-amine;

8-(5-chloro-6-methoxypyridin-3-yl)-9-ethyl-N-[3-(1-methylethyl)-5,6,7,8-tetrahydro[1,2,4]triazolo[4,3-a]pyridin-6-yl]-9H-purin-6-amine;

9-ethyl-N-[3-(1-methylethyl)-5,6,7,8-tetrahydro[1,2,4]triazolo[4,3-a]pyridin-6-yl]-8-(1-phenyl-1H-pyrazol-4-yl)-9H-purin-6-amine;

8-[4-(difluoromethyl)phenyl]-9-ethyl-N-[-3-(1-methylethyl)-5,6,7,8-tetrahydro[1,2,4]triazolo[4,3-a]pyridin-6-yl]-9H-purin-6-amine;

9-ethyl-N-[-3-(1-methylethyl)-5,6,7,8-tetrahydro[1,2,4]triazolo[4,3-a]pyridin-6-yl]-8-[4-(trifluoromethyl)-1H-imidazol-1-yl]-9H-purin-6-amine;

N-[3-cyclopropyl-5,6,7,8-tetrahydro[1,2,4]triazolo[4,3-a]pyridin-6-yl]-9-ethyl-8-iodo-9H-purin-6-amine;

N-(3-cyclopropyl-5,6,7,8-tetrahydro[1,2,4]triazolo[4,3-a]pyridin-6-yl)-9-ethyl-8-[4-(trifluoromethyl)phenyl]-9H-purin-6-amine;

N-[-3-cyclopropyl-5,6,7,8-tetrahydro[1,2,4]triazolo[4,3-a]pyridin-6-yl]-9-ethyl-8-[6-(methylsulfonyl)pyridin-3-yl]-9H-purin-6-amine;

6-{[3-cyclopropyl-5,6,7,8-tetrahydro[1,2,4]triazolo[4,3-a]pyridin-6-yl]oxy}-9-ethyl-8-(2-methylpyrimidin-5-yl)-9H-purine;

9-ethyl-6-{[3-(1-methylethyl)-5,6,7,8-tetrahydro[1,2,4]triazolo[4,3-a]pyridin-6-yl]oxy}-8-(2-methylpyrimidin-5-yl)-9H-purine;

6-{[3-cyclobutyl-5,6,7,8-tetrahydro[1,2,4]triazolo[4,3-a]pyridin-6-yl]oxy}-9-ethyl-8-(2-methylpyrimidin-5-yl)-9H-purine;

9-ethyl-6-{[3-(1-methylethyl)-5,6,7,8-tetrahydro[1,2,4]triazolo[4,3-a]pyridin-6-yl]amino}-N-(2,2,2-trifluoroethyl)-9H-purine-8-carboxamide;

N-[-3-cyclopropyl-6,7-dihydro-5H-pyrrolo[2,1-c][1,2,4]triazol-6-yl]-9-ethyl-8-(2-methylpyrimidin-5-yl)-9H-purin-6-amine;

tert-butyl 3-cyclopropyl-5-{[9-ethyl-8-(2-methylpyrimidin-5-yl)-9H-purin-6-yl]amino}-4,5,6,7-tetrahydro-1H-indazole-1-carboxylate;

N-[3-cyclopropyl-4,5,6,7-tetrahydro-1H-indazol-5-yl]-9-ethyl-8-(2-methylpyrimidin-5-yl)-9H-purin-6-amine;

N-{1-[2-(dimethylamino)ethyl]-3-(1-methylethyl)-4,5,6,7-tetrahydro-1H-indazol-5-yl}-9-ethyl-8-(2-methylpyrimidin-5-yl)-9H-purin-6-amine;

9-ethyl-N-[3-(1-methylethyl)-4,5,6,7-tetrahydro-1H-indazol-5-yl]-8-(2-methylpyrimidin-5-yl)-9H-purin-6-amine;

9-ethyl-N-[5-methyl-3-(1-methylethyl)-4,5,6,7-tetrahydro-1H-indazol-5-yl]-8-(2-methylpyrimidin-5-yl)-9H-purin-6-amine;

9-ethyl-N-[3-(1-methylethyl)-4,5,6,7-tetrahydro-1H-indazol-5-yl]-8-[4-(trifluoromethyl)phenyl]-9H-purin-6-amine;

8-(difluoromethyl)-9-ethyl-N-[3-(1-methylethyl)-4,5,6,7-tetrahydro-1H-indazol-5-yl]-9H-purin-6-amine;

9-ethyl-N-[3-(1-methylethyl)-1-propyl-4,5,6,7-tetrahydro-1H-indazol-5-yl]-8-(2-methylpyrimidin-5-yl)-9H-purin-6-amine;

2-[5-{[9-ethyl-8-(2-methylpyrimidin-5-yl)-9H-purin-6-yl]amino}-3-(1-methylethyl)-4,5,6,7-tetrahydro-1H-indazol-1-yl]ethanol;

N-[1-acetyl-3-(1-methylethyl)-4,5,6,7-tetrahydro-1H-indazol-5-yl]-9-ethyl-8-(2-methylpyrimidin-5-yl)-9H-purin-6-amine;

9-ethyl-N-[3-(1-methylethyl)-1-(phenylcarbonyl)-4,5,6,7-tetrahydro-1H-indazol-5-yl]-8-(2-methylpyrimidin-5-yl)-9H-purin-6-amine;

N-{1-[(dimethylamino) acetyl]-3-(1-methylethyl)-4,5,6,7-tetrahydro-1H-indazol-5-yl}-9-ethyl-8-(2-methylpyrimidin-5-yl)-9H-purin-6-amine;

N-[1-(3,3-dimethylbutanoyl)-3-(1-methylethyl)-4,5,6,7-tetrahydro-1H-indazol-5-yl]-9-ethyl-8-(2-methylpyrimidin-5-yl)-9H-purin-6-amine;

tert-butyl 5-{[9-ethyl-8-(2-methylpyrimidin-5-yl)-9H-purin-6-yl]amino}-3-(1-methylethyl)-4,5,6,7-tetrahydro-1H-indazole-1-carboxylate;

ethyl 5-{[9-ethyl-8-(2-methylpyrimidin-5-yl)-9H-purin-6-yl]amino}-3-(1-methylethyl)-4,5,6,7-tetrahydro-1H-indazole-1-carboxylate;

1-methylethyl 5-{[9-ethyl-8-(2-methylpyrimidin-5-yl)-9H-purin-6-yl]amino}-3-(1-methylethyl)-4,5,6,7-tetrahydro-1H-indazole-1-carboxylate;

methyl 5-{[9-ethyl-8-(2-methylpyrimidin-5-yl)-9H-purin-6-yl]amino}-3-(1-methylethyl)-4,5,6,7-tetrahydro-1H-indazole-1-carboxylate;

2,2,2-trifluoro-1,1-dimethylethyl 5-{[9-ethyl-8-(2-methylpyrimidin-5-yl)-9H-purin-6-yl]amino}-3-(1-methylethyl)-4,5,6,7-tetrahydro-1H-indazole-1-carboxylate;

N-tert-butyl-5-{[9-ethyl-8-(2-methylpyrimidin-5-yl)-9H-purin-6-yl]amino}-3-(1-methylethyl)-4,5,6,7-tetrahydro-1H-indazole-1-carboxamide;

9-ethyl-N-[3-(1-methylethyl)-1-pyridin-2-yl-4,5,6,7-tetrahydro-1H-indazol-5-yl]-8-(2-methylpyrimidin-5-yl)-9H-purin-6-amine;

9-ethyl-N-[3-(1-methylethyl)-1-(methylsulfonyl)-4,5,6,7-tetrahydro-1H-indazol-5-yl]-8-(2-methylpyrimidin-5-yl)-9H-purin-6-amine;

9-ethyl-N-[-2-methyl-3-(1-methylethyl)-4,5,6,7-tetrahydro-2H-indazol-5-yl]-8-(2-methylpyrimidin-5-yl)-9H-purin-6-amine;

9-ethyl-N-[-1-methyl-3-(1-methylethyl)-4,5,6,7-tetrahydro-1H-indazol-5-yl]-8-(2-methylpyrimidin-5-yl)-9H-purin-6-amine;

N-(1-benzyl-1,4,5,6-tetrahydrocyclopenta[c]pyrazol-5-yl)-9-ethyl-8-(2-methylpyrimidin-5-yl)-9H-purin-6-amine;

6-[(1,3-diethyl-4,5,6,7-tetrahydro-1H-indazol-5-yl)oxy]-9-ethyl-8-(2-methylpyrimidin-5-yl)-9H-purine;

N-[3-cyclopropyl-5,6,7,8-tetrahydroimidazo[1,5-a]pyridin-6-yl]-9-ethyl-8-(2-methylpyrimidin-5-yl)-9H-purin-6-amine;

9-ethyl-N-[3-(1-methylethyl)-5,6,7,8-tetrahydroimidazo[1,5-a]pyridin-6-yl]-8-(2-methylpyrimidin-5-yl)-9H-purin-6-amine;

N-(3-cyclopropyl-5,6,7,8-tetrahydroimidazo[1,2-a]pyridin-6-yl)-9-ethyl-8-(2-methylpyrimidin-5-yl)-9H-purin-6-amine;

9-ethyl-N-[3-(1-methylethyl)-5,6,7,8-tetrahydroimidazo[1,2-a]pyridin-6-yl]-8-(2-methylpyrimidin-5-yl)-9H-purin-6-amine;

9-ethyl-6-[(3-ethyl-6,7-dihydro-5H-pyrrolo[1,2-a]imidazol-6-yl)oxy]-8-(2-methylpyrimidin-5-yl)-9H-purine;

N-(1-cyclopropyl-4,5,6,7-tetrahydro-1H-benzimidazol-6-yl)-9-ethyl-8-(2-methylpyrimidin-5-yl)-9H-purin-6-amine;

N-(1-cyclopropyl-4,5,6,7-tetrahydro-1H-benzimidazol-6-yl)-9-ethyl-8-[6-(trifluoromethyl)pyridin-3-yl]-9H-purin-6-amine;

N-(1-cyclopropyl-4,5,6,7-tetrahydro-1H-benzimidazol-6-yl)-9-ethyl-8-[4-(trifluoromethyl)phenyl]-9H-purin-6-amine;

N-(1-cyclopropyl-4,5,6,7-tetrahydro-1H-benzimidazol-6-yl)-8-(difluoromethyl)-9-ethyl-9H-purin-6-amine;

N-(1-cyclopropyl-2-methyl-4,5,6,7-tetrahydro-1H-benzimidazol-6-yl)-9-ethyl-8-(2-methylpyrimidin-5-yl)-9H-purin-6-amine;

N-(1-cyclopropyl-2-ethyl-4,5,6,7-tetrahydro-1H-benzimidazol-6-yl)-9-ethyl-8-(2-methylpyrimidin-5-yl)-9H-purin-6-amine;

6-[(1-cyclopropyl-4,5,6,7-tetrahydro-1H-benzimidazol-6-yl)amino]-9-ethyl-N-(2,2,2-trifluoroethyl)-9H-purine-8-carboxamide;

N-[1-cyclopropyl-2-(difluoromethyl)-4,5,6,7-tetrahydro-1H-benzimidazol-6-yl]-9-ethyl-8-(2-methylpyrimidin-5-yl)-9H-purin-6-amine;

N-(2-chloro-1-cyclopropyl-4,5,6,7-tetrahydro-1H-benzimidazol-6-yl)-9-ethyl-8-(2-methylpyrimidin-5-yl)-9H-purin-6-amine;

9-ethyl-N-[1-(-3-methoxycyclobutyl)-4,5,6,7-tetrahydro-1H-benzimidazol-6-yl]-8-(2-methylpyrimidin-5-yl)-9H-purin-6-amine;

9-ethyl-N-[1-(1-methylethyl)-4,5,6,7-tetrahydro-1H-benzimidazol-6-yl]-8-(2-methylpyrimidin-5-yl)-9H-purin-6-amine;

9-ethyl-N-[4-methyl-1-(1-methylethyl)-4,5,6,7-tetrahydro-1H-benzimidazol-6-yl]-8-(2-methylpyrimidin-5-yl)-9H-purin-6-amine;

9-ethyl-N-[5-methyl-1-(1-methylethyl)-4,5,6,7-tetrahydro-1H-benzimidazol-6-yl]-8-(2-methylpyrimidin-5-yl)-9H-purin-6-amine;

9-ethyl-N-[7-methyl-1-(1-methylethyl)-4,5,6,7-tetrahydro-1H-benzimidazol-6-yl]-8-(2-methylpyrimidin-5-yl)-9H-purin-6-amine; and 9-ethyl-N-[1-(1-methylethyl)-5,6,7,8-tetrahydroimidazo[1,5-a]pyridin-7-yl]-8-(2-methylpyrimidin-5-yl)-9H-purin-6-amine.

10. A pharmaceutical composition comprising a compound of claim 1 or a pharmaceutically acceptable salt or stereoisomer thereof and a pharmaceutically acceptable carrier.

11. A pharmaceutical composition according to claim 10, further comprising one or more other therapeutic agents.

\* \* \* \* \*